(12) United States Patent
Brown et al.

(10) Patent No.: US 8,968,885 B2
(45) Date of Patent: Mar. 3, 2015

(54) ORGANIC ELECTRONIC DEVICES AND POLYMERS, INCLUDING PHOTOVOLTAIC CELLS AND DIKETONE-BASED POLYMERS

(75) Inventors: Christopher T. Brown, Pittsburgh, PA (US); Christophe René Gaston Grenier, Pittsburgh, PA (US); Chad Landis, Oakmont, PA (US); Elena E. Sheina, Pittsburgh, PA (US); Atta Gueye, Pittsburgh, PA (US)

(73) Assignee: Solvay USA, Inc., Cranbury, NJ (US)

( * ) Notice: Subject to any disclaimer, the term of this patent is extended or adjusted under 35 U.S.C. 154(b) by 285 days.

(21) Appl. No.: 12/874,163

(22) Filed: Sep. 1, 2010

(65) Prior Publication Data

US 2011/0204341 A1 Aug. 25, 2011

Related U.S. Application Data

(60) Provisional application No. 61/240,137, filed on Sep. 4, 2009, provisional application No. 61/241,813, filed on Sep. 11, 2009, provisional application No. 61/248,335, filed on Oct. 2, 2009, provisional application No. 61/289,314, filed on Dec. 22, 2009, provisional application No. 61/290,844, filed on Dec. 29, 2009, provisional application No. 61/307,387, filed on Feb. 23, 2010.

(51) Int. Cl.

| | | |
|---|---|---|
| H01L 51/54 | (2006.01) |
| H01L 51/46 | (2006.01) |
| C08F 228/06 | (2006.01) |
| C08L 41/00 | (2006.01) |
| C08L 65/00 | (2006.01) |
| C07D 487/04 | (2006.01) |
| C07D 495/04 | (2006.01) |
| C07D 519/00 | (2006.01) |
| C07F 7/08 | (2006.01) |
| C08G 61/12 | (2006.01) |
| C09D 165/00 | (2006.01) |
| H01L 51/00 | (2006.01) |
| C09B 57/00 | (2006.01) |
| C09B 69/00 | (2006.01) |

(Continued)

(52) U.S. Cl.

CPC .............. *C08L 65/00* (2013.01); *C07D 487/04* (2013.01); *C07D 495/04* (2013.01); *C07D 519/00* (2013.01); *C07F 7/0816* (2013.01); *C08G 61/12* (2013.01); *C08G 61/126* (2013.01); *C09D 165/00* (2013.01); *H01L 51/0036* (2013.01); *C09B 57/004* (2013.01); *C09B 69/008* (2013.01); *C09B 69/109* (2013.01); *C08G 2261/124* (2013.01); *C08G 2261/18* (2013.01); *C08G 2261/226* (2013.01); *C08G 2261/228* (2013.01); *C08G 2261/334* (2013.01); *C08G 2261/344* (2013.01); *C08G 2261/364* (2013.01); *C08G 2261/414* (2013.01); *H01L 51/0043* (2013.01); *H01L 51/0069* (2013.01); *H01L 51/0077* (2013.01); *H01L 51/4253* (2013.01); *Y02E 10/549* (2013.01); *Y10S 428/917* (2013.01)

USPC ...... 428/690; 428/917; 257/40; 257/E51.024; 524/547; 526/256

(58) Field of Classification Search

None

See application file for complete search history.

(56) References Cited

U.S. PATENT DOCUMENTS

| 2006/0149016 A1* | 7/2006 | O'Dell et al. ..................... 528/8 |
| 2007/0057627 A1* | 3/2007 | Kidu et al. ..................... 313/503 |

(Continued)

FOREIGN PATENT DOCUMENTS

| WO | WO 2007105386 A1 * | 9/2007 | .............. H01L 51/00 |
| WO | WO 2008073149 A2 * | 6/2008 | .............. C08G 61/12 |

(Continued)

OTHER PUBLICATIONS

Jayakannan et al. Journal of Polymer Science Part A: Polymer Chemistry 2002, 40, 251-261. Year of online publication: Dec. 4, 2001.*
Partial International Search Report in corresponding PCT Application PCT/US2010/047565.
Pomerantz, M. et al., "Studies of planar poly(3,4-disubstituted-thiophenes)," 135-136 Synthetic Metals 257 (2003).

(Continued)

*Primary Examiner* — Andrew K Bohaty
(74) *Attorney, Agent, or Firm* — The Marbury Law Group, PLLC

(57) ABSTRACT

Polymers which can be used in p-type materials for organic electronic devices and photovoltaic cells. Compounds, monomers, dimers, trimers, and polymers comprising:

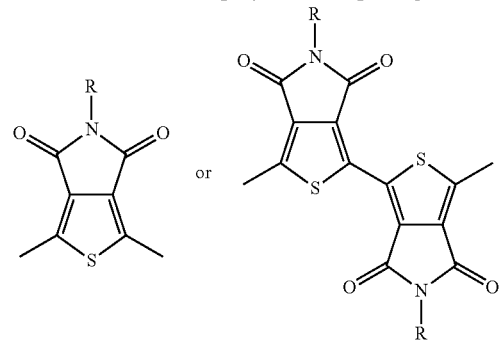

Good photovoltaic efficiency and lifetime can be achieved. The R group can provide solubility, environmental stability, and fine tuning of spectroscopic and/or electronic properties. Different polymer microstructures can be prepared which encourage multiple band gaps and broad and strong absorptions. The carbonyl can interact with adjacent thiophene rings to provide backbone with rigidity, induce planarity, and reduce and/or eliminate intramolecular chain twisting defects. Polymers comprising benzodithiophene and/or benzothiadiazole structures can show particularly high performance.

30 Claims, 14 Drawing Sheets

(51) Int. Cl.
*C09B 69/10* (2006.01)
*H01L 51/42* (2006.01)

(56) References Cited

U.S. PATENT DOCUMENTS

2007/0221916 A1* 9/2007 Shkunov et al. ............... 257/40
2009/0065770 A1* 3/2009 Miura et al. .................... 257/40

FOREIGN PATENT DOCUMENTS

| WO | WO 2008/127029 A1 | 10/2008 |
| WO | WO 2008/144756 A1 | 11/2008 |
| WO | WO 2010/079064 A2 | 7/2010 |
| WO | WO 2010/117449 A2 | 10/2010 |

OTHER PUBLICATIONS

Vala, M. et al., "Novel, soluble diphenyl-diketo-pyrrolopyrroles: Experimental and theoretical study," 84 Dyes and Pigments 176 (2009).

Wienk, M. et al., "Narrow-bandgap diketo-pyrrolo-pyrrole polymer solar cells: the effect of processing on the performance," 20 Adv. Mat. 2556 (2008).

Zhang, G. et al., "Alternating Donor/Acceptor Repeat Units in Polythiophenes: Intramolecular Charge Transfer for Reducing Band Gaps in Fully Substituted Conjugated Polymers," 120 J. Am. Chem. Soc. 5355 (1998).

Zhang, G. et al., "Low Optical Bandgap Polythiophenes by an Alternating Donor/Acceptor Repeat Unit Strategy," 119 J. Am. Chem. Soc. 5065 (1997).

* cited by examiner

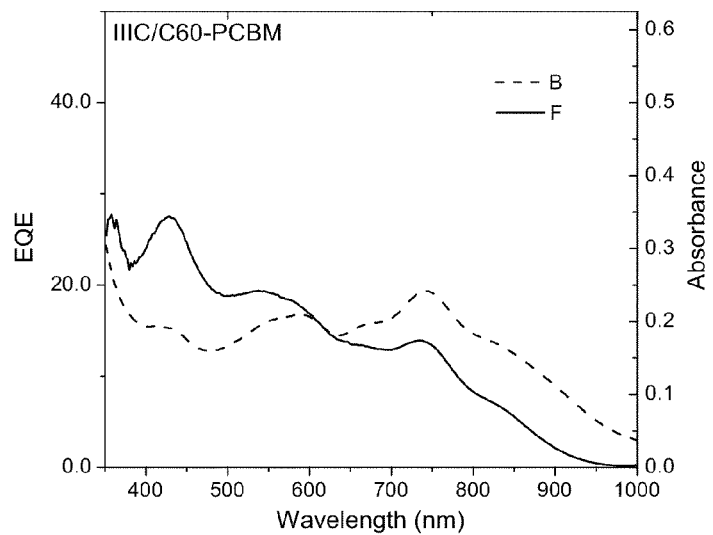
Figure 5
Figure 6A (left); Figure 6B (right).
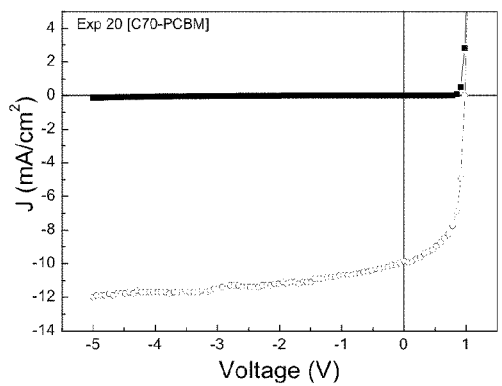 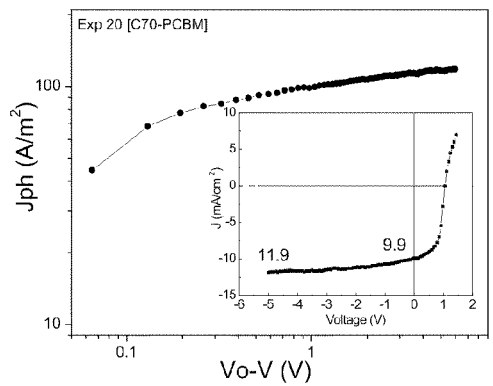

ORGANIC ELECTRONIC DEVICES AND POLYMERS, INCLUDING PHOTOVOLTAIC CELLS AND DIKETONE-BASED POLYMERS

RELATED APPLICATIONS

This application claims priority to U.S. provisional application Ser. Nos. 61/240,137 filed Sep. 4, 2009; 61/241,813 filed Sep. 11, 2009; 61/248,335 filed Oct. 2, 2009; 61/289,314 filed Dec. 22, 2009; 61/290,844 filed Dec. 29, 2009; and 61/307,387 filed Feb. 23, 2010, which are each hereby incorporated by reference in its entirety.

INTRODUCTION

A need exists to provide better electronic and photonic devices including better solar cells or photovoltaic devices. If some aspects of the devices are based on organic materials, including organic polymers, cost reduction can be achieved.

In particular, a need exists to provide better active layers for organic photovoltaic devices. These active layers can comprise a combination of p-type material and n-type material. The p-type material can be a conjugated polymer. The polymer ideally should satisfy a variety of chemico-physical properties, such as solubility, processability, good film formation, proper absorption properties, proper HOMO/LUMO (molecular orbitals and energy levels), bandgap, charge carrier mobility, and other properties. However, achievement of combinations of properties can be difficult, and gaining one property may result in the sacrifice of another.

For a review of organic photovoltaic technology, see, for example, Sun and Saraciftci (Eds.), *Organic Photovoltaics, Mechanisms, Materials, and Devices*, CRC, 2005.

SUMMARY

Embodiments provided herein include, for example, compositions, devices, and methods of making and using the same. Compositions include, for example, monomer, oligomer, and polymer compositions, as well as ink formulations. Compositions also can include those prepared by particular processes. Devices include photovoltaic and/or solar cell devices including modules and devices which comprise a plurality of photovoltaic and/or solar cell devices. Coated substrates can be prepared, wherein the substrate is rigid or flexible.

For example, one embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

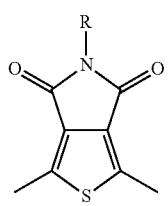

(I)

The structure I can be part of, for example:

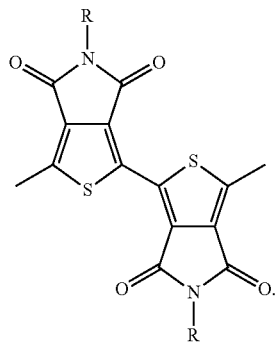

Also, the polymer can comprise, for example:

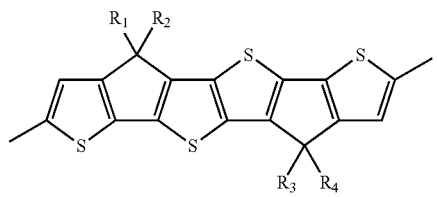

wherein R1, R2, R3, and R4 are independently hydrogen or solubilizing groups.

In another embodiment, the polymer comprises at least one of the following structures:

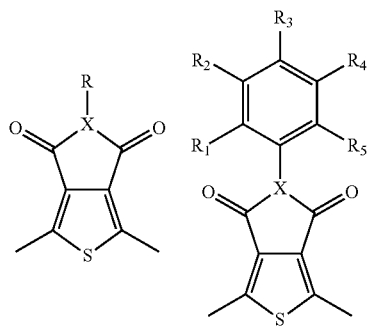

In another embodiment, the polymer comprises at least one of the following structures:

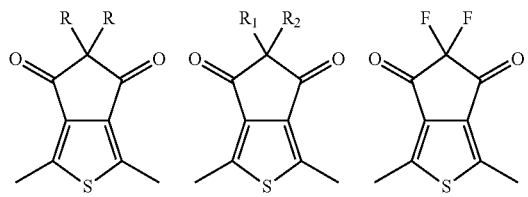

wherein R, R1, and/or R2 independently can be a solubilizing group or hydrogen.

In another embodiment, the polymer comprises at least one of the following structures:

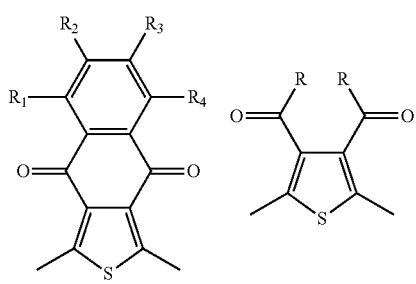
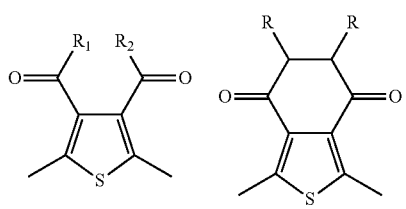
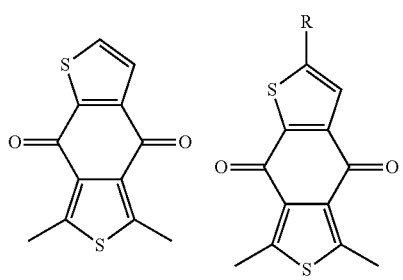
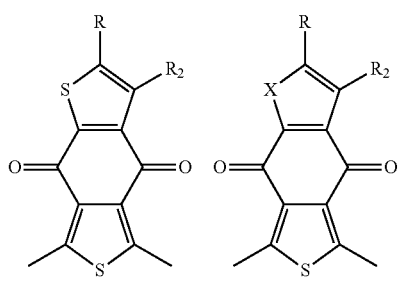
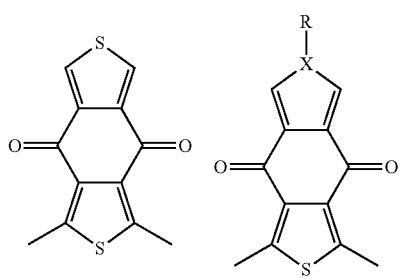
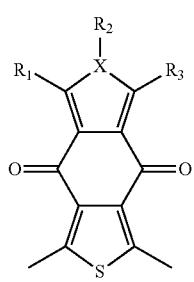
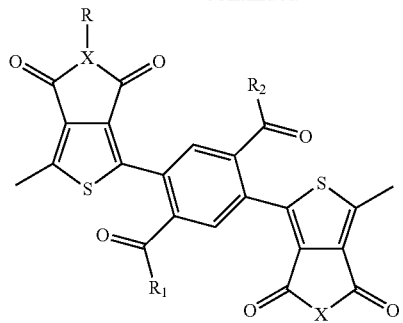
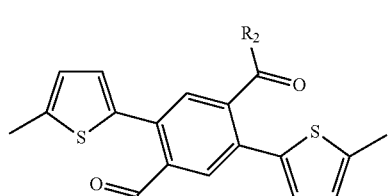
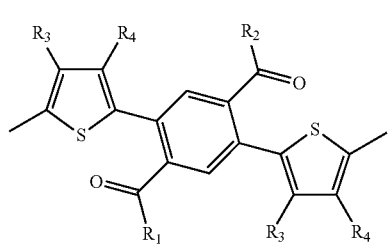
In another embodiment, the polymer comprises at least one of the following structures:
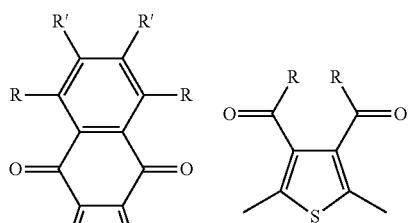
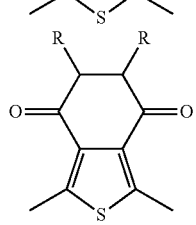
In another embodiment, the p-type material comprises at least one

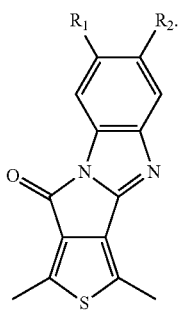

wherein R1 and R2 are independently hydrogen or solubilizing groups.

In another embodiment, the polymer comprises at least one arylamine. In another embodiment, the polymer comprises at least one additional donor or acceptor. The donor-acceptor polymer can have at least three moieties which are donors and/or acceptors.

Another embodiment provides a monomer, oligomer, or polymer comprising:

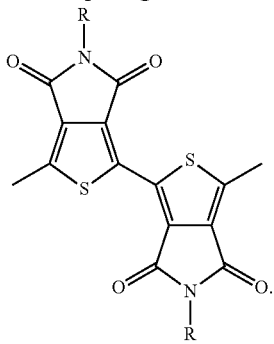

Another embodiment provides a monomer, oligomer, or polymer comprising:

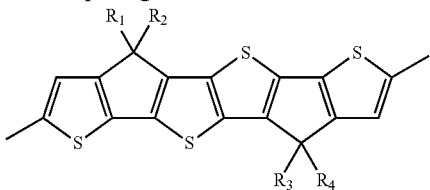

wherein R1, R2, R3, and R4 are independently hydrogen or solubilizing groups.

Another embodiment provides a monomer, oligomer, or polymer comprising:

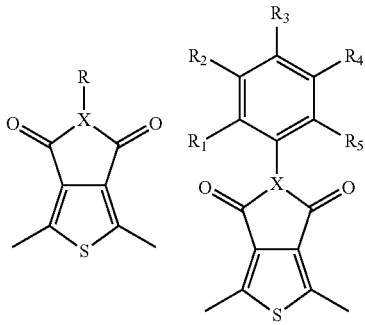

Another embodiment provides a monomer, oligomer, or polymer comprising:

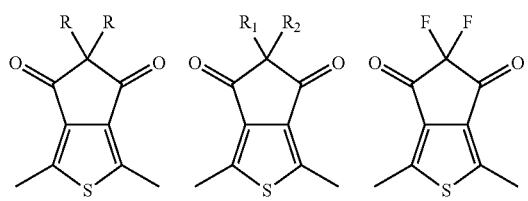

Another embodiment provides a monomer, oligomer, or polymer comprising:

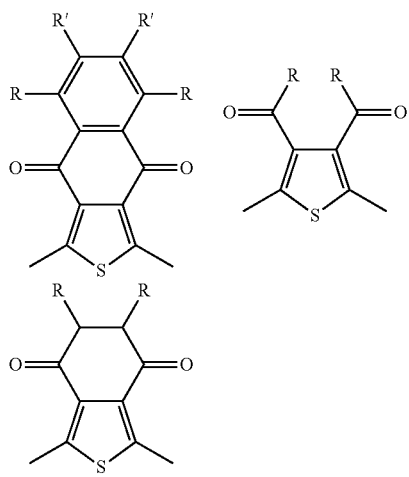

Another embodiment provides a monomer, oligomer, or polymer comprising:

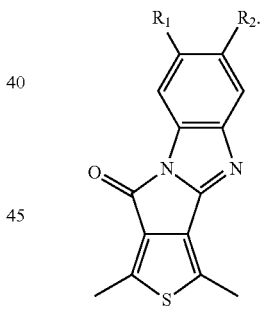

wherein R1 and R2 are independently hydrogen or solubilizing groups.

Another embodiment provides a monomer, oligomer, or polymer comprising:

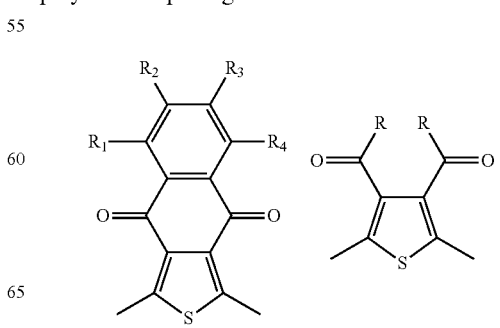

-continued

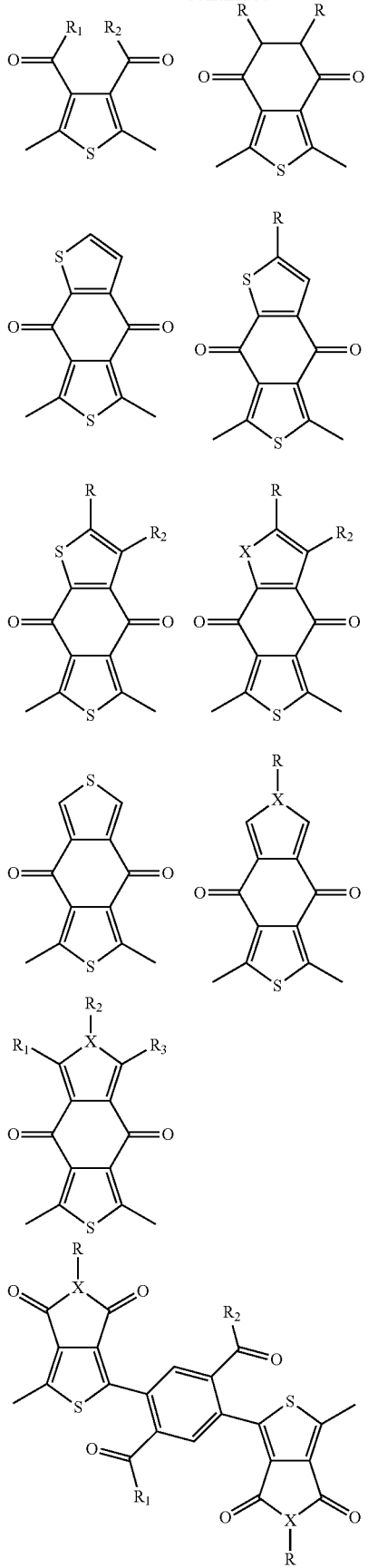

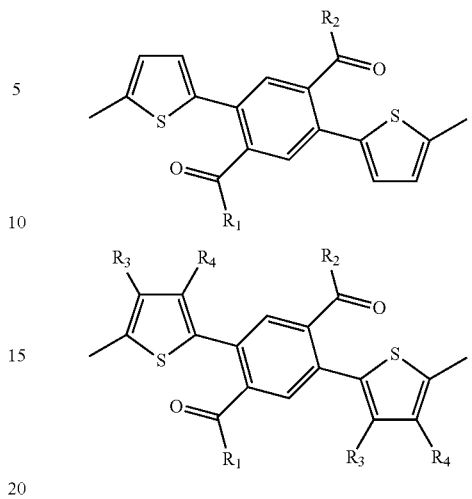

Another embodiment provides a composition comprising at least one donor-acceptor polymer comprising:

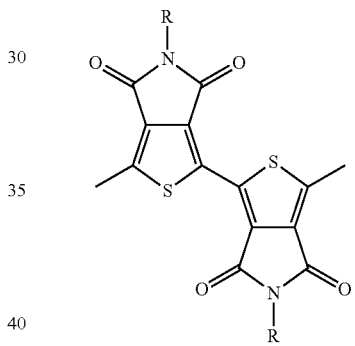

wherein R is a solubilizing group. Another embodiment provides that the polymer further comprises at least one benzodithiophene. Another embodiment provides that the polymer further comprises

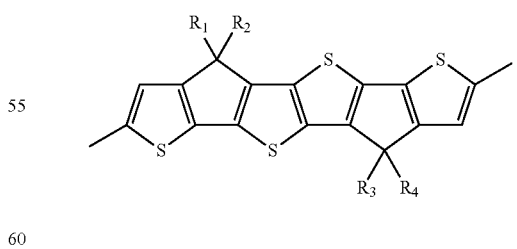

wherein R1, R2, R3, and R4 are independently hydrogen or solubilizing groups.

Another embodiment provides an ink composition comprising at least one oligomer, or polymer comprising:

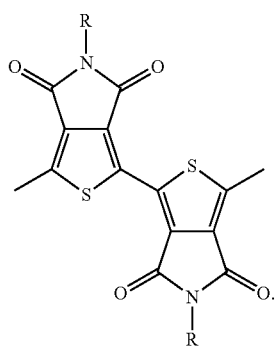

Another embodiment provides an ink composition comprising at least one oligomer, or polymer comprising:

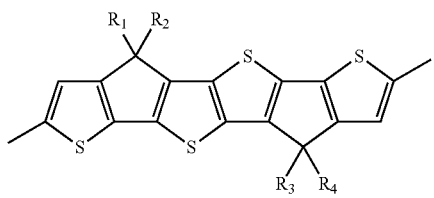

wherein R1, R2, R3, and R4 are independently hydrogen or solubilizing groups.

Another embodiment provides an ink composition comprising at least one oligomer, or polymer comprising:

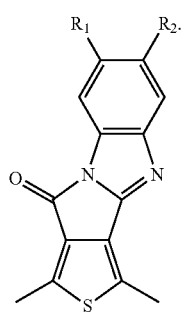

Another embodiment provides an ink composition comprising at least one oligomer, or polymer comprising:

Another embodiment provides an ink composition comprising at least one oligomer, or polymer comprising:

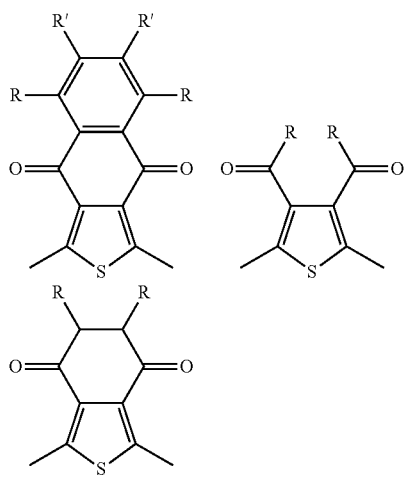

Another embodiment provides an ink composition comprising at least one oligomer, or polymer comprising:

wherein R1 and R2 are independently hydrogen or solubilizing groups.

Another embodiment provides an ink composition comprising at least one oligomer, or polymer comprising:

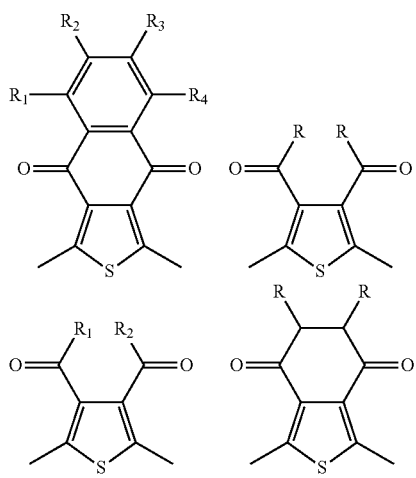

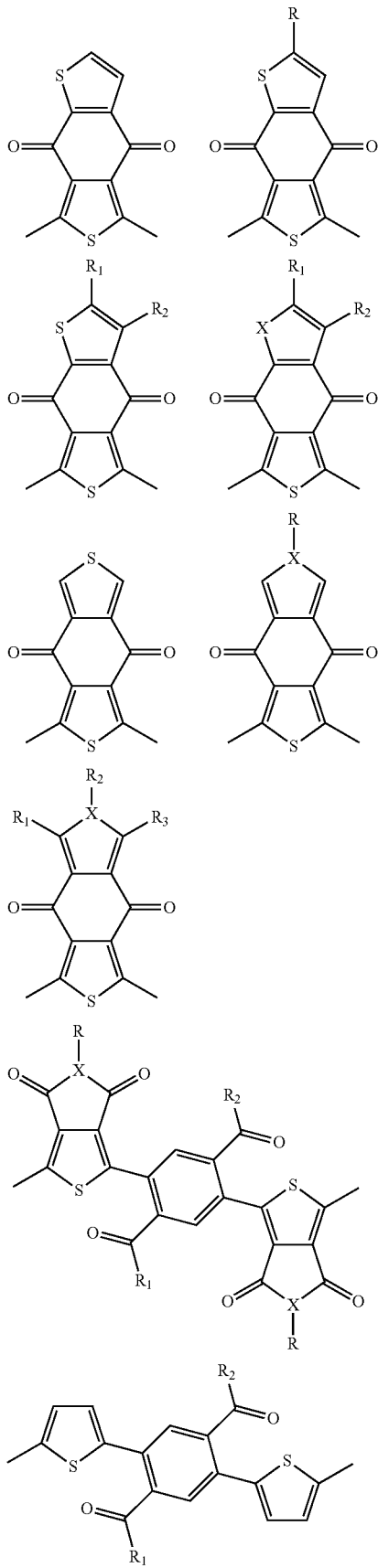

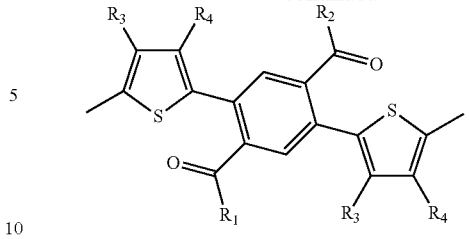

Another embodiment provides that the polymer comprises a donor-acceptor structure, and wherein the polymer comprises the same total amounts of donor and acceptor, but the polymer comprises (i) at least one first acceptor and at least one second acceptor, and the amounts of the first and second acceptors are not the same, or (ii) at least one first donor and at least one second donor, and the amounts of the first and second donors are not the same. Another embodiment provides that the polymer comprises a D1-D1-A1-A1 donor-acceptor structure.

One further embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

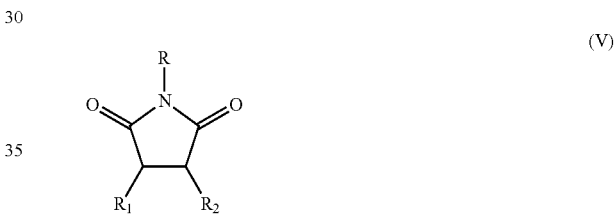

(V)

wherein the moiety V is bivalently linked to the polymer backbone via the $R_1$ and $R_2$ groups, and the $R_1$ and $R_2$ groups form a ring.

One further embodiment provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

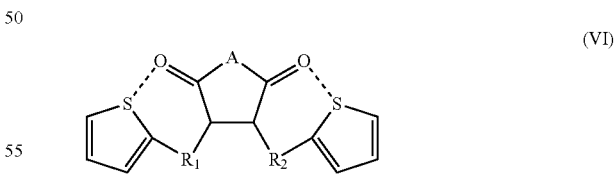

(VI)

wherein A can be a heteroatom, and wherein the moiety VI is bivalently linked to the polymer backbone via the illustrated thiophene rings linked to the $R_1$ and $R_2$ groups, and the $R_1$ and $R_2$ groups form a ring.

One embodiment also provides a device comprising: at least one cathode; at least one anode; and at least one photovoltaic active layer disposed between the cathode and anode and comprising at least one p-type material and at least one n-type material, wherein the p-type material comprises at least one polymer comprising a backbone moiety:

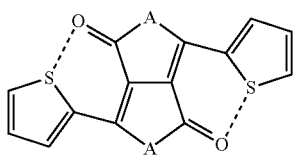

(VII)

wherein A can be a heteroatom, and wherein the moiety VII is linked to the polymer backbone via the illustrated thiophene rings.

At least one more embodiment comprises a device comprising: at least one cathode; at least one anode; at least one photovoltaic active layer disposed between the cathode and anode and comprising at least one p-type material and at least one n-type material, wherein the p-type material comprises at least one polymer comprising a donor-acceptor structure, comprising a first acceptor backbone moiety:

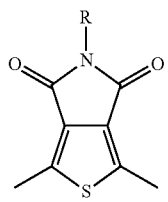

(I)

and wherein the donor comprises at least one benzodithiophene structure, and the polymer comprises at least one second acceptor other than (I).

An additional embodiment comprises a device comprising: at least one cathode; at least one anode; at least one photovoltaic active layer disposed between the cathode and anode and comprising at least one p-type material and at least one n-type material, wherein the p-type material comprises at least one polymer comprising a donor-acceptor structure, comprising a first acceptor backbone moiety:

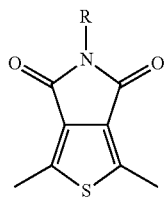

(I)

and the polymer comprises at least one second acceptor other than (I) which comprises a benzothiadiazole structure.

Additional embodiments include compositions and devices, wherein structure I is part of:

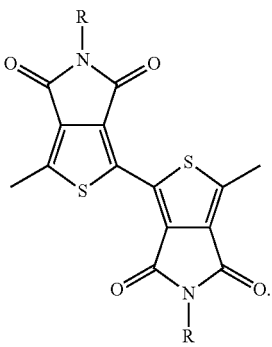

Additional embodiments include the monomer, dimer, trimer, oligomer, and polymer compositions described herein, as well as ink compositions comprising same. Coated substrates can be prepared, wherein the substrate is any solid surface including, for example, glasses, ceramics, metals, and polymers.

Additional embodiments include the methods of making and using the polymer compositions described herein, as well as methods of making and using the devices and other articles described herein.

At least one advantage of at least one embodiment is good photovoltaic performance including efficiency (including power conversion efficiency), fill factor, open circuit voltage, and/or short circuit current, and combinations thereof. At least one additional advantage for at least one embodiment is improved lifetime and environmental stability. At least one additional advantage of at least one embodiment is high molar absorptivity sometimes referred to as Alpha and/or molar absorption/extinction coefficient. At least one additional advantage of at least one embodiment is an absorption profile with vibronic structure or features. This can provide, for example, broader absorption bands. Vibronic structure can be observed in the solid state or in solution. At least one additional advantage of at least one embodiment is good charge mobility. At least one additional advantage of at least one embodiment is good exciton diffusion length. At least one additional advantage of at least one embodiment is extended conjugation length. At least one additional advantage is use of less hindered pendant groups and more rigid donor-chromophores. At least one additional advantage of at least one embodiment is good processability. At least one additional advantage of at least one embodiment is presence of order in the film as detected by, for example, x-ray diffraction. At least one additional advantage of at least one embodiment is improved formation of bulk heterojunction. At least one additional advantage of at least one embodiment is improved polymer solubility, including improved solubility coupled with relatively high molecular weight. Relatively high molecular weight can be achieved despite the rigidity of the polymer backbone. At least one additional advantage of at least one embodiment is ability to improve photovoltaic efficiency by control of copolymer microstructure including ratio of acceptor. At least one additional advantage for at least one embodiment is simultaneously lower LUMO and also deepen HOMO for optimal current and voltage performance. At least one additional advantage for at least one embodiment is the capability for performance tuning with different classes of donors and acceptors.

BRIEF DESCRIPTION OF FIGURES

FIG. 5 shows EQE and absorption spectra for donor-acceptor polymer (Example 9) mixed with n-type material (C60 derivative) in a photovoltaic device active layer.

FIGS. 6A and 6B show electrical testing of devices.

DETAILED DESCRIPTION

Introduction

Figure 1A:
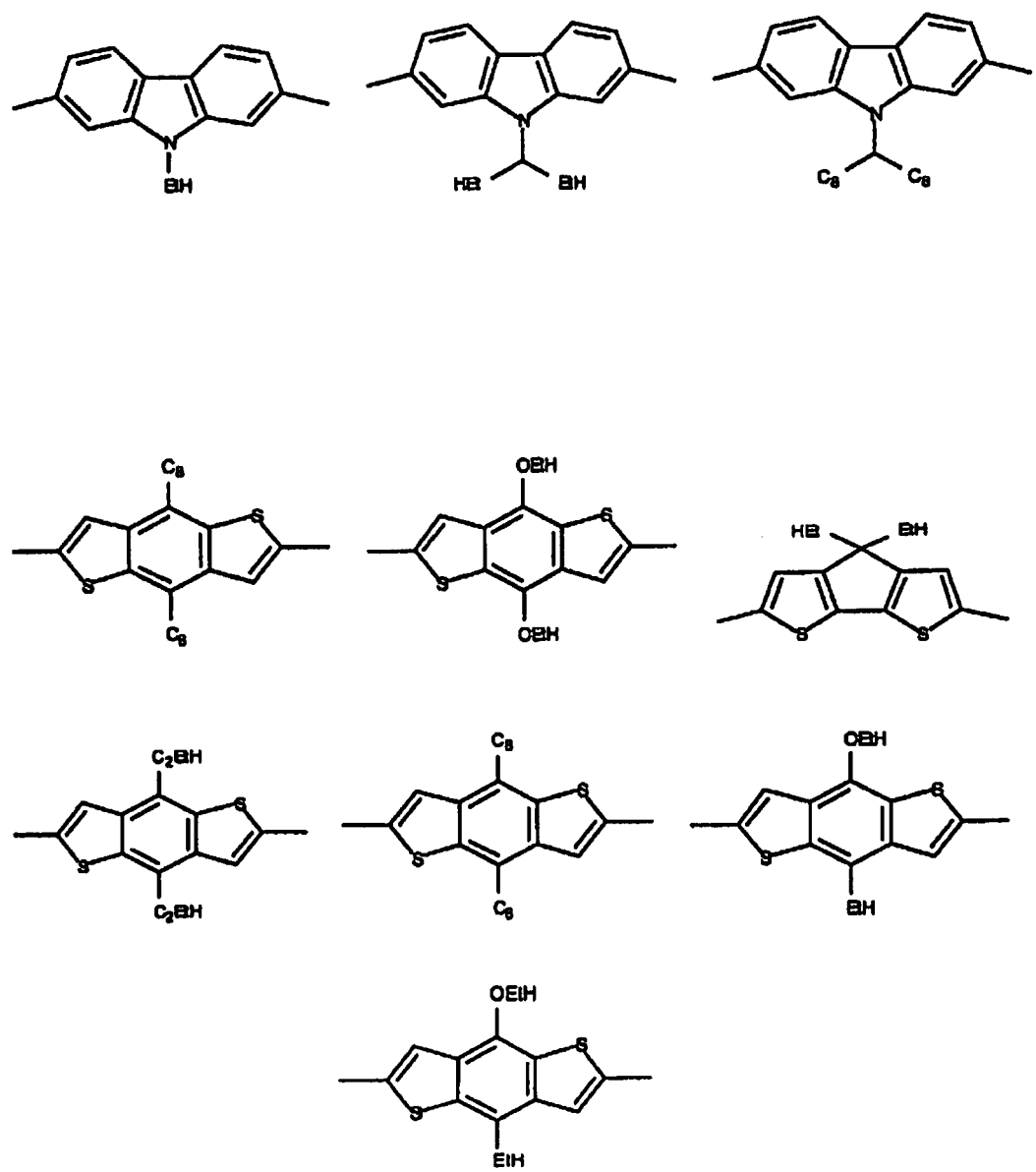
FIGS. 1A-1H provide a listing of exemplary donor moieties, useful for monomers and polymers. The side groups illustrated are representative and can be adjusted to provide, for example, desired electronic, steric, and reactivity effects. The side groups can also function as solubilizing groups. The side groups also can be optionally substituted.
Figure 1B:
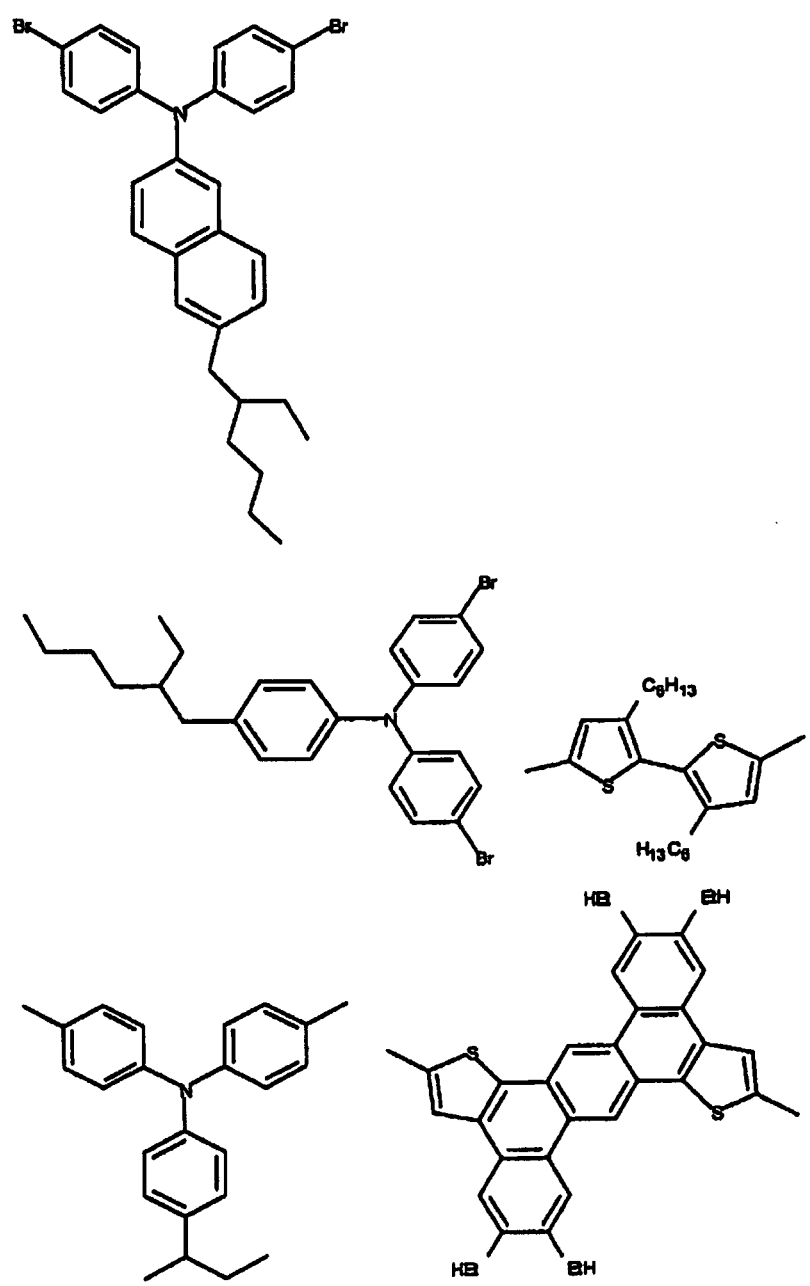
Figure 1C:
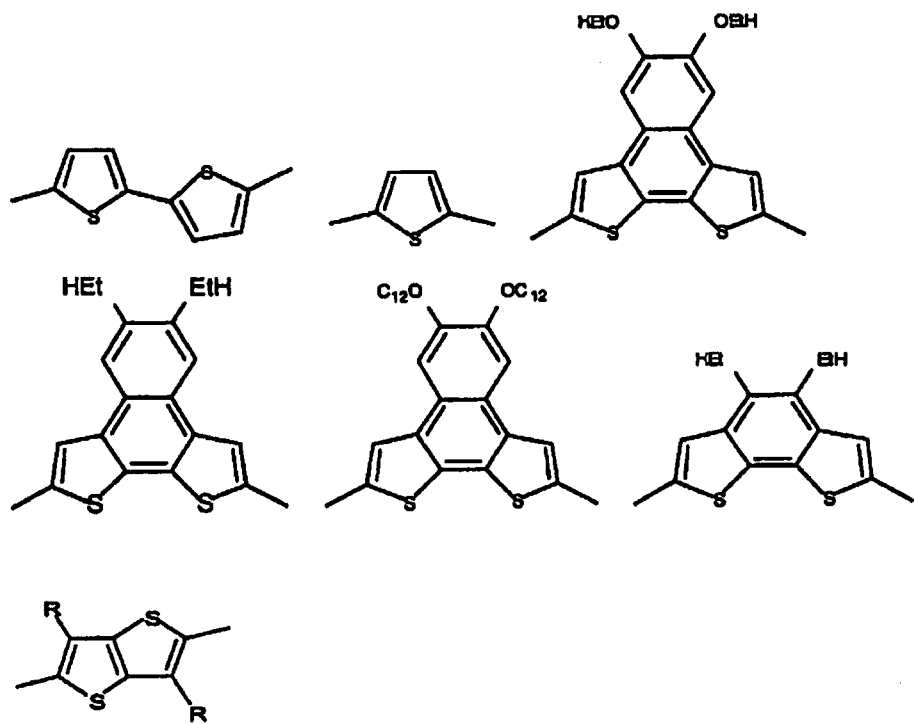
Figure 1D:
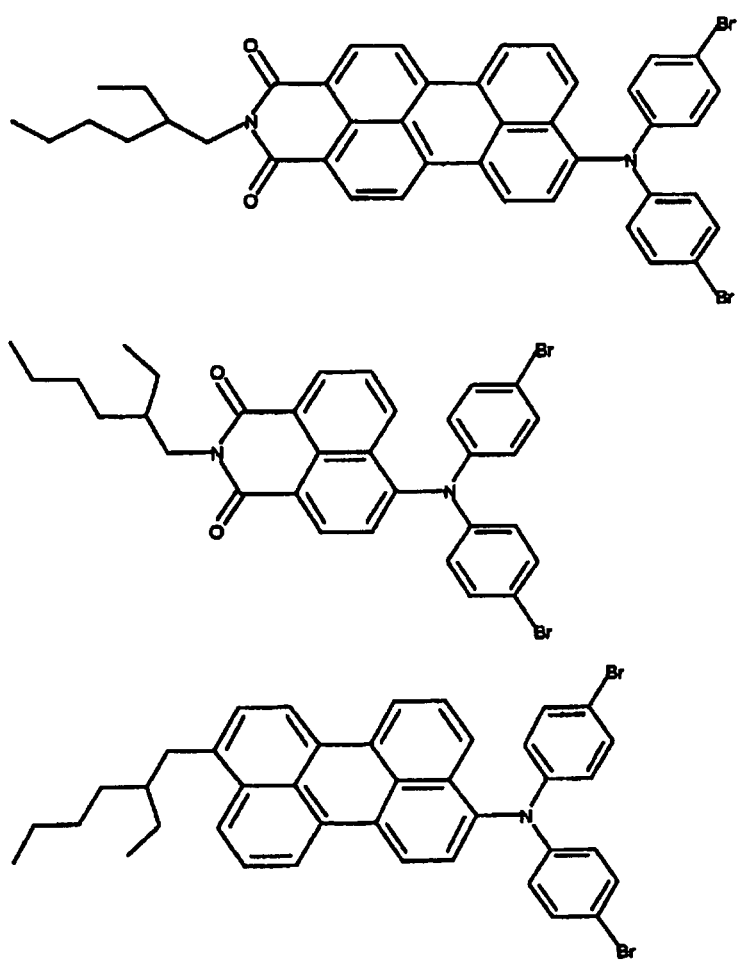
Figure 1E:
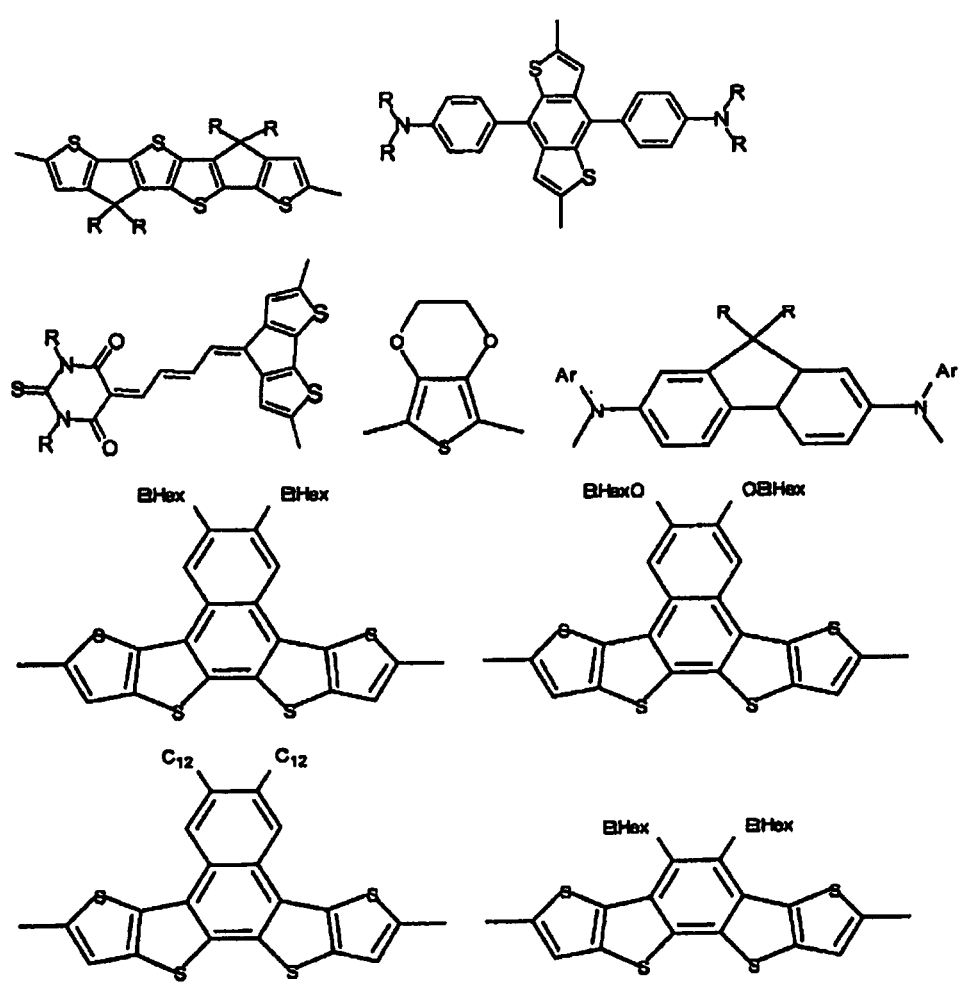
Figure 1F:
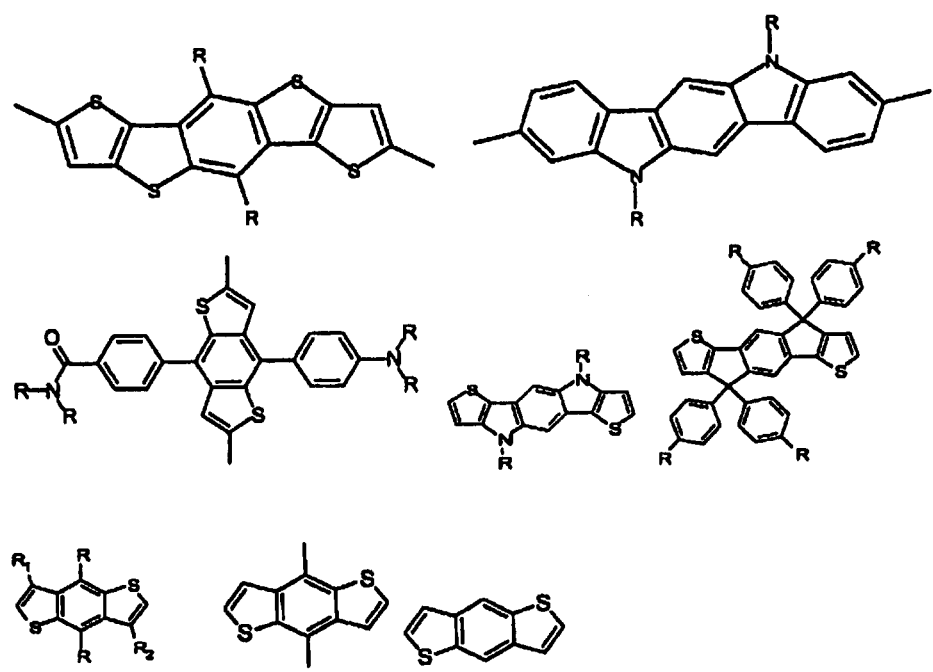
Figure 1G:
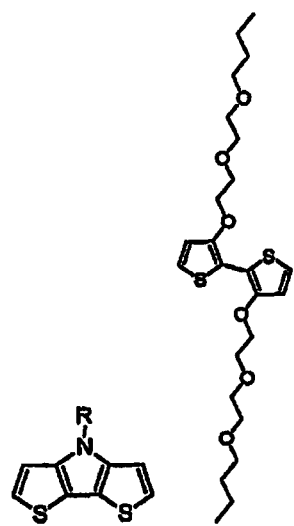
Figure 1H:
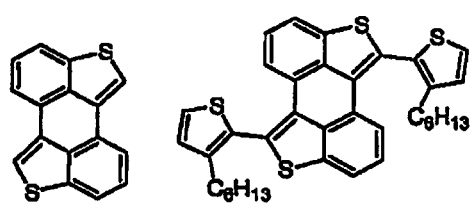

All references cited herein are incorporated by reference in their entirety.

No admission is made that any reference cited in this application is prior art.

The following six U.S. provisional applications are incorporated by reference in their entirety, including incorporated for their monomer and polymer structures, including donor and acceptor structures: (i) 61/240,137 filed Sep. 4, 2009; (ii) 61/241,813 filed Sep. 11, 2009; (iii) 61/248,335 filed Oct. 2, 2009; (iv) 61/289,314 filed Dec. 22, 2009; and (v) 61/290,844 filed Dec. 29, 2009; and (vi) 61/307,387 filed Feb. 23, 2010, which are each hereby incorporated by reference in its entirety.

In addition, patent application U.S. Ser. No. 12/828,121 filed Jun. 30, 2010, is incorporated by reference in its entirety.

In addition, PCT patent applications serial nos. PCT/US2010/037802 and PCT/US2010/037805 each filed Jun. 8, 2010 are each incorporated by reference in their entirety.

Low band gap materials are known in the art. See, for example, Blouin et al., *Accounts of Chemical Research,* 1110-1119, September 2008, 41, 9.

Polymer solar cells are known in the art. See, for example, Chen et al., *Advanced Materials,* 2009, 21, 1-16; Hoppe, *Adv. Polym. Sci.,* 2008, 214, 1-86; Gunes et al., *Chem. Rev.,* 2007, 107, 1324-1338. See also, for example, organic photovoltaic technologies described in, for example, a series of articles in *Accounts of Chemical Research,* 42, 11, November 2009, including Zhu et al. (1779-1787); Bredas et al. (1691-1699); Chen et al. (1709-1718); Heremans et al. (1740-1747); Nelson et al. (1768-1778); Peet et al. (1700-1708); Potscavage et al. (1758-1767); Roncali (1719-1730).

Organic semiconductors including arylamines and TPD are known in the art. See, for example, Walzer et al., *Chem. Rev.,* 2007, 107, 1233-1271.

Polymers used in active layers for solar cells are known in the art. See, for example, PCT/US2009/034157 filed Feb. 13, 2009 to Sheina et al. and U.S. provisional application 61/222, 053 filed Jun. 30, 2009 (both assigned to Plextronics, Inc.).

One exemplary embodiment provides compositions comprising at least one conjugated copolymer, wherein the copolymer backbone comprises at least one donor moiety and at least one acceptor moiety, and wherein the copolymer has at least two high extinction coefficient chromophores thereby covering the high photon flux portion of the solar spectrum which is from about 400-1000 nm and centered at about 750-800 nm. Broad absorption is desired including up to the near-infrared region. Vibronic structure can be detected.

For all structures shown herein, for monomers, oligomers, and polymers, the side groups can be adapted to be solubilizing groups as described further herein.

Part I

Polymers

Polymers and Conjugated Polymers and Copolymers
Polymers can comprise a backbone and side groups as known in the art. See, for example, Billmeyer, *Textbook of Polymer Science,* 1984. Copolymers are known in the art and comprise, for example, terpolymers and block copolymers, as well as alternating and random copolymers. Polymer blends can be prepared.

Conjugated polymers are described in, for example, T. A. Skotheim, *Handbook of Conducting Polymers,* 3$^{rd}$ Ed. (two vol), 2007; Meijer et al., *Materials Science and Engineering,* 32 (2001), 1-40; and Kim, *Pure Appl. Chem.,* 74, 11, 2031-2044, 2002.

Conjugated polymers can be used in photovoltaic active layers as a p-type material. The p-type active material can comprise a member of a family of similar polymers which have a common polymer backbone but are different in the derivatized side groups to tailor the properties of the polymer.

Conjugated polymers can comprise planarized backbone and increasing conjugation length before conjugation is interrupted.

Polymers Comprising Structure (I)
Polymers can be prepared which comprise a backbone moiety represented by (I):

In (I), the lines at the 2- and 5-position of the thiophene ring show where the attachment occurs to another moiety, such as a polymer chain or a reactive group for polymerization or coupling.

An important aspect of polymers which comprise (I) is that they are sufficiently soluble so that inks can be formed and solution processing can be achieved. Solubility can be examined in organic or aqueous solvents. One skilled in the art can adapt the R group and other parts of the polymer chain and side groups, as well as molecular weight, to generate sufficient solubility. Organic solvents can be, for example, halogenated and non-halogenated solvents. The solvent can be a single solvent or a mixture of solvents. An example of halogenated solvent is ortho-dichlorobenzene, and this solvent can be used to measure solubility. Solubility can be measured at 25° C. Solubility can be, for example, at least 1 mg/mL, or at least 20 mg/mL. In some embodiments, solubility can be adapted to provide good bulk heterojunction (BHJ) layer morphology. For example, in some embodiments, if the solubility is high when molecular weight is too low, BHJ formation could be compromised. Higher molecular weight may be preferred to modulate solubility, and molecular weight can be used with other formulation strategies including additives to modulate solubility and/or BHJ formation. In addition, polymers can be both soluble and also functionally dispersible in a solvent so that solution processing can be achieved, whether or not a true solution is formed.

The R group can be adapted to facilitate or provide solubility. The R group can also be adapted to provide desired electronic properties. The R group can be also adapted to provide steric and molecular stacking properties.

The atom in the R group bonding to the polymer chain can be, for example, carbon.

For example, the R group can be optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy. The R group can have, for example, 3-30 carbons, or 4-25 carbons, or 5-15 carbons. Examples include butyl, octyl and dodecyl, as well as ethylhexyl. Different R groups can be used in the same polymer as needed. The R group can be chiral. The R group can be functionalized or substituted as desired. Examples of substituents include amino, carboxylic acid, ester, halogen (including fluoro and chloro), pseudohalogen (e.g., cyano), and other functional groups known in the art.

The R group can comprise a heteroatom, such as oxygen or nitrogen in the carbon chain (e.g., ether or amino linkages, respectively). The R group can comprise C1-C20 alkoxy, or C1-C20 alkyleneoxy, for example. The R group can be an oligoether, such as, for example, alkoxyalkoxy or alkoxyalkoxyalkoxy, such as, for example, methoxyethoxyethoxy.

The polymer comprising structure (I) can be free of protecting groups, and in particular the R group can be free of protecting groups.

The R group can be adapted to modulate or tune the LUMO, including provide a decreasing or increasing LUMO, or provide better solid state packing, or provide improved charge transport, and/or provide environmental stability. For example, the R group can be halogenated including comprise a group comprising chlorine or fluorine. The R group can be, for example, perfluorinated. The R group can be, for example, a perfluoroalkyl group such as, for example, —$C_3F_7$. The R group can be, for example, a perfluoroaryl group, such as, for example, —$C_6F_5$. For use of halogenated substituent groups to modulate LUMO and solid state packing, see, for example, Schmidt et al., *J. Am. Chem. Soc.,* 2009, 131, 6215-6228.

The R group in one or more polymers can be varied, and different R groups can be used, such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Oligomeric and polymeric structures comprising (I) are known in the art. See, for example, Nielsen et al., *Organic Letters,* 2004, 6, 19, 3381-3384 (describing dioxopyrrolofunctionalized polythiophene); Zhang et al., *J. Am. Chem. Soc.,* 120, 22, Jun. 10, 1998 (structures 12 and 21); Zhang et al., *J. Am. Chem. Soc.,* 1997, 119, 5065-5066.

Other references, including references providing theoretical considerations, include Li et al., *Polymeric Materials Science and Engineering (PMSE) Preprints,* 2007, 96, 757-758; Pomerantz et al., *Synthetic Metals,* 2003, 135-136, 257-258; Pomerantz et al., *Tetrahedron Letters,* 2003, 44(8), 1563-1565; and Pomerantz et al., *Tetrahedron Letters,* 40, 1999, 3317-3320.

Polymer comprising (I) can be a random copolymer or a regular alternating copolymer. Polymer comprising (I) can comprise multiple repeat moieties.

Moieties in the polymer chain can provide for carbon-carbon bonding with conjugation, and, in addition, can provide charge transport.

Polymer side groups can provide electron withdrawing or electron accepting character, and the strength of this can be varied, e.g., weak or strong, or from weak to strong. Push-pull electronic effects can be produced. Electron donating side groups can be also used as appropriate.

Polymer side groups can be protected or deprotected. For example, butyloxycarbonyl (BOC) can be used to protect amino side groups. However, an embodiment comprises the polymer being totally free of protecting groups.

Block copolymers can be prepared. Either all blocks can be embodiments as described herein, or only a subset of block(s) can be embodiments described herein. For example, a block copolymer could comprise both a conjugated polymer block and a non-conjugated polymer block, or both a donor-acceptor block, and a non-donor-acceptor block. Also, block copolymers can be prepared comprising blocks of different donors and acceptors, e.g., (D1-A1)-b-(D1-A2), and the like.

In one embodiment, the polymer comprises a number average molecular weight, Mn, of at least 6,000 g/mol, or of at least 7,500 g/mol, or at least 10,000. In another embodiment, the polymer comprises a number average molecular weight, Mn, of at least 20,000, or at least 30,000, or at least 40,000, or at least 50,000.

In another embodiment, the polymer comprises a donor-acceptor structure comprising at least two acceptors, wherein at least one acceptor is represented by structure (I) and at least one acceptor is represented by structure (VII) (below).

In another embodiment, the polymer comprises a donor-acceptor structure, and the donor comprises at least one tricyclic unit comprising three fused rings. The rings can provide conjugation or can be conjugated rings. For example, in one embodiment, the donor comprises a tricyclic ring structure represented by A-B-C, wherein A and C are thiophene rings fused to a central ring B which, optionally, can comprise a heteroatom. The central ring B can be, for example, a five- or six-membered ring. An example of a heteroatom is silicon or nitrogen. In another embodiment, the donor comprises two fused rings. At least one thienothiophene can be used.

In another embodiment, the polymer comprises a donor-acceptor structure, and the donor comprises at least one tricyclic unit comprising three fused rings, wherein two of the rings are thiophene rings and one of the rings is a benzene ring. In another embodiment, the polymer comprises a donor-acceptor structure, and the donor comprises at least one tricyclic unit comprising three fused rings, wherein two of the rings are thiophene rings and one of the rings is a benzene ring, and the benzene ring is in the middle of the three ring structure. In another embodiment, the polymer comprises a donor-acceptor structure, and the donor is a symmetrical moiety. In another embodiment, the polymer comprises a donor-acceptor structure, and the donor comprises at least one tricyclic unit comprising three fused rings, wherein two of the rings are thiophene rings and one of the rings is a benzene ring. If the donor comprises two thiophene rings, the thiophene rings can be cis or trans to each other, as know to those skilled in the art.

In another embodiment, the polymer is free of protecting groups for both the donor and acceptor.

The polymer can exhibit vibronic structure and/or a structured absorption profile as measured by, for example, UV-Vis absorption spectroscopy.

The structure (I), including the R group, can be adapted so the molecular weight is less than, for example, 1,000 g/mole, or even less than 500 g/mole.

Additional polymeric structures comprising (I) are described herein.

Donor-Acceptor Polymers

An important embodiment is the donor-acceptor polymer, which is known in the art. See, for example, Zhang et al., *J. Am. Chem. Soc.*, 1995, 117, 4437-4447; Sun and Sariciftci (Eds.), *Organic Photovoltaics, Mechanisms, Materials, and Devices*, CRC, 2005. The structure (I) can be found in acceptor structures of the donor-acceptor polymer.

Donor-Acceptor (D-A) structures can be alternating or random as known in the art and as determined by the polymer synthesis. For example, an alternating structure can be represented as -(D-A)$_n$- (D-A regular alternating donor-acceptor repeating units) and a random structure can be -(D$_x$A$_y$)- (D and A are randomly dispersed). Segmented copolymers can be made wherein donor and acceptor units are included in dimers, trimers, and oligomers, and these dimers, trimers, and oligomers are subjected to further polymerization.

The donor-acceptor structure can be tuned and adapted to provide lower band gaps and/or better absorption properties. For example, the donor and the acceptor energy levels, e.g., HOMO and LUMO, can be tuned. Use of different donors and acceptors with different HOMOs and LUMOs can be used in the same polymer. The donor can have HOMO of, for example, −4.9-5.6; or −4.9-5.4, or −5.1-5.4, or −5.2-5.3 eV. The polymer structure can be adapted to provide deeper HOMO.

Polymer structure can be adapted to provide for small singlet/triplet splitting including, for example, use of rigid chromophores which can minimize loss pathways.

The donor-acceptor structure can comprise one or more dye structures, and the dye structure can be in the backbone or side group.

The structures can be adapted to provide low and/or multiple band gaps. Examples of band gaps include those less than 2 eV including about 1.4 to about 1.9 eV, or about 1.4 eV to about 1.8 eV. Low band gaps can be associated with high current potential.

Structures can be adapted to avoid recombination sites by, for example, avoiding almost the same or the same LUMOs of the p-type and n-type (e.g., differences of 0.3 eV or less can be avoided).

Structures can be adapted to provide ordered and/or flat assembly. Flat, aromatic-like structures can be used.

Material and/or structural purity can be achieved or improved by use of, for example, crystalline synthetic intermediates.

Molecular weight of the polymer (number average molecular weight, Mn) can be, for example, about 10,000 to about 1,000,000, or about 25,000 to about 500,000, or about 25,000 to about 100,000, or about 25,000 to about 40,000, or about 10,000 to about 25,000. Polydispersity can be, for example, about 1.5 to about 4.0, or about 1.5 to about 3.0, or about 2.0 to about 2.8.

Model spectra can be used to design polymer structures.

Polymer film absorption profiles can be used to compute theoretical photovoltaic cell efficiencies.

Materials can be prepared which provide absorption/extinction coefficients (alpha) on the order of $10^5$ cm$^{-1}$.

Absorption can be balanced between red and blue regions of absorption spectrum.

Use of spacer groups can be minimized or avoided to alter or reduce the dihedral angle of rotation between adjacent rings.

Planarizing non-covalent binding interactions between donor-donor and/or donor-acceptor, and/or acceptor-acceptor can serve to rigidify the chromophore which can help to increase material packing density and/or alpha.

Steric interactions between donor and acceptor can be minimized.

Kits can be produced comprising at least one donor molecule or monomer and at least one acceptor molecule or monomer.

Additional donor-acceptor structures are described herein.

Moieties IIA and IIB

As part of a larger molecule, including a polymer, for example, the structure (I) can be part of another larger moiety such as, for example, IIA or IIB:

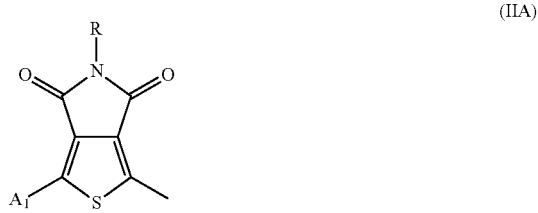

(IIA)

wherein A1 comprises a thiophene ring linked to (I) at the two or five position of the thiophene ring; and

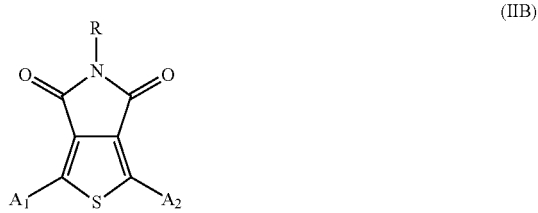

(IIB)

wherein both A1 and A2 comprise thiophene ring linked to (I) at the two or five position of the thiophene ring.

Structures IIA and IIB can be incorporated into the polymer backbone via the A1 and A2 groups. Structures A1 and A2 can be part of a donor moiety, for example. For example, the donor moiety benzodithiophene comprises two thiophene rings, either of which can be an A1 or an A2.

Here, A1 can comprise a thiophene ring linked to (I) at the two or five position of the illustrated thiophene ring. Similarly, A2 (and both A1 and A2) also can comprise a thiophene ring linked to (I) at the two or five position of the illustrated thiophene ring. The thiophene ring in A1 and A2 can either be a single thiophene ring, an oligomer series of two, three, or more thiophene rings bivalently linked, or a thiophene ring which is part of a larger fused ring structure. For example, A1 and/or A2 can be represented by -TT- or -TTT- or -TTTT- or -TTTTT- wherein T is a thiophene ring linked at the 2 and 5 position of the thiophene ring. The thiophene rings can be part of a larger structure which includes spacer moieties.

Thiophene rings can be optionally substituted at the 3- and/or 4-positions to facilitate solubility as known in the art including use of optionally substituted alkyl, oligoether, polyether, ester, ketone, or alkyleneoxy substituents including n-alkyl, such as C6-C8 or branched alkyl (e.g., hexyl, ethylhexyl, or methoxyethoxyethoxy substituents).

Intramolecular Non-Covalent Interactions Including Carbonyl Interaction with Thiophene Sulfur A variety of intramolecular non-covalent interactions, such as electrostatic, coulombic, hydrogen bonding or chelates can be used to provide increased rigidity and/or planarity to the polymer chain and its chromophores, although various embodiments described herein are not necessarily limited by theory. Increased rigidity can be used to increase the likelihood for a well behaved excited state and lead to good excitonic diffusion distances and minimization of energy loss pathways from excited state (e.g., charge trapping, polaronic quenching, excited state deactivation, or even localization). Absorption profiling can be used to examine such features.

In particular, while various embodiments described herein are not necessarily limited by theory, it is believed that for at least some embodiments, when a thiophene ring is covalently linked to (I), as shown in IIA or IIB, for example, the carbonyl groups can interact with thiophene sulfur. The carbonyl oxygen is negatively charged compared to the thiophene sulfur which is relatively positively charged. This can provide planarization and/or increase rigidity in the backbone and improve performance. The interactions can be measured by methods known in the art including, for example, x-ray or NOE (Nuclear Overhauser Effect). See, for example, Pomerantz et al., *Synthetic Metals,* 2003, 135-136, 257-258; Pomerantz et al., *Tetrahedron Letters,* 2003, 44(8), 1563-1565; and Pomerantz et al., *Tetrahedron Letters,* 40, 1999, 3317-3320. Also, for sulfur-oxygen interactions, see, for example, Turbiez et al., *Chem.-Eur. J.* 2005, 11, 3742-3752.; and Apperloo et al., J. L. *Chem.-Eur. J.* 2002, 8, 2384-2396.

Donor-Acceptor polymers comprising diketo types of structures, such as dioxypyrrolo-functionality, can provide intramolecular interactions as a "design rule" for the synthesis of new materials for application in organic electronics, such as OPVs, achieving unexpected performances.

The thiophene ring can be part of an isolated thiophene moiety or a fused ring thiophene moiety such as the thiophene found in benzodithiophene.

Vibronic Structure

The polymers described herein can exhibit vibronic structure and/or structured absorption profile as shown in, for example, UV-Vis absorption spectroscopy. Vibronic structure in a p-type chromophore can be an indication of an organized and rigid and/or planarized structure. This can provide a more well-behaved excited state behavior and exciton diffusion length. Vibronic structure can be found in a solid, film state or in a solution state. In particular, for example, the ratio of a first peak (0-0 transition) to second peak (0-1 transition) can be higher than 1.

Vibronic features and vibronic structure can be present. Vibronic structure is described in, for example, *Handbook of Conducting Polymers*, Skotheim, T. A., *Handbook of Conducting Polymers*; Marcel Dekker: New York, 1986, including Chapter 9 (McCullough et al.), Chapter 14 (Scherf), and Chapter 28 (Del Zoppo et al.). See also, Brown et al., *Phys. Rev. B,* 67, 064203 (2003).

Vibronic structure and features can be examined experimentally and theoretically by methods known in the art.

Particular Polymer Structures

Particular polymer structures comprising (I) together with a variety of donors and acceptors are shown in IIIA-K. See also working examples below.

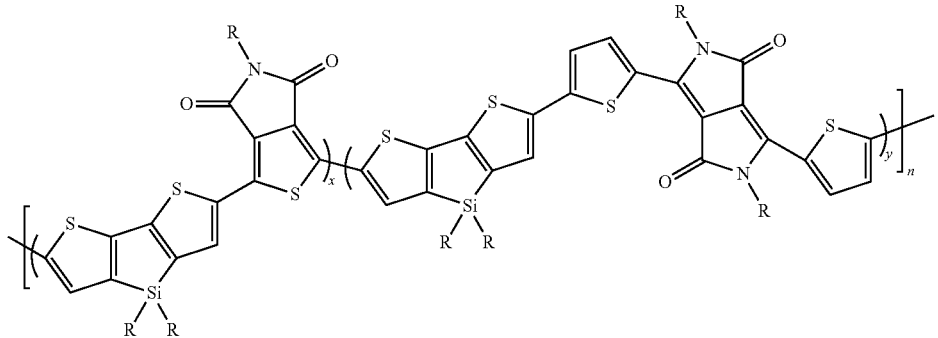

(III-A)

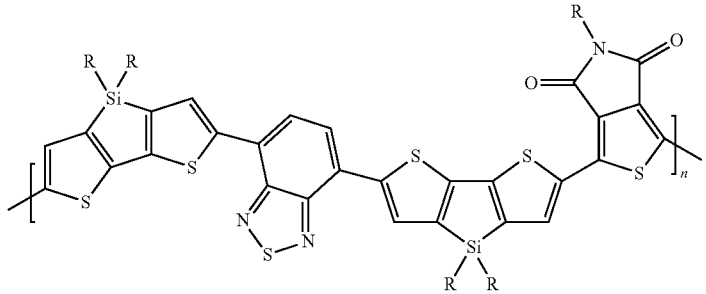

(III-B)

(III-C)
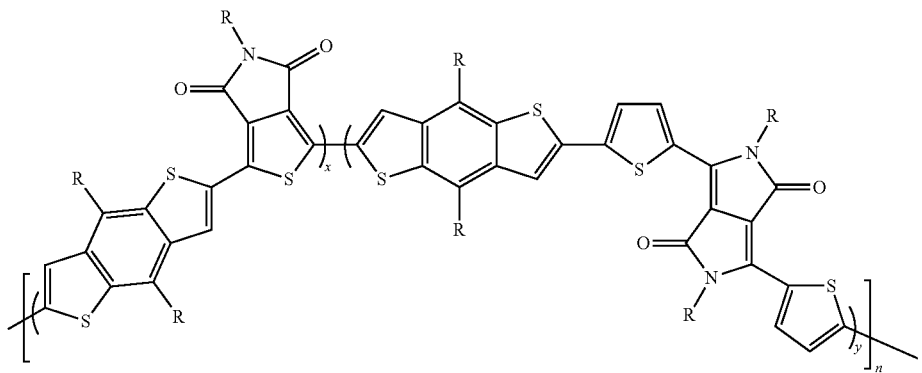
(III-D)
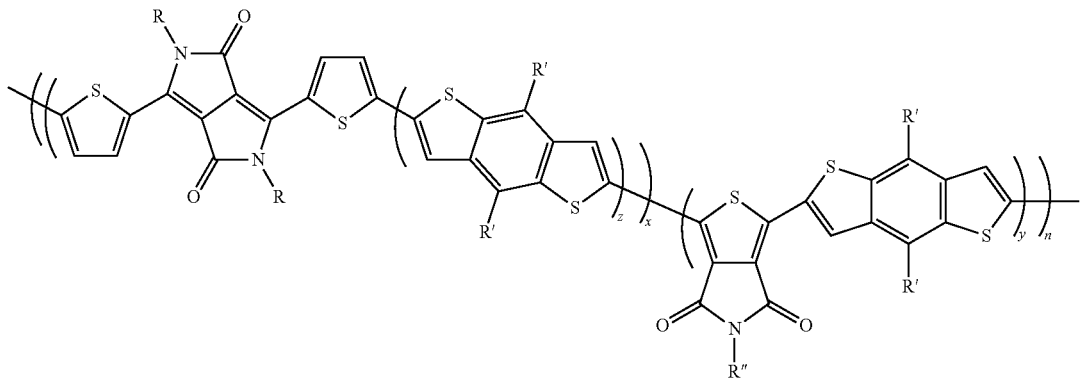
(III-E)
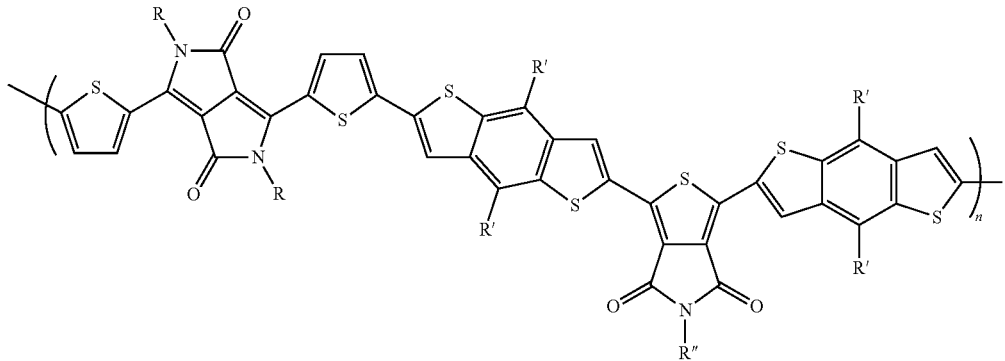
(III-F)
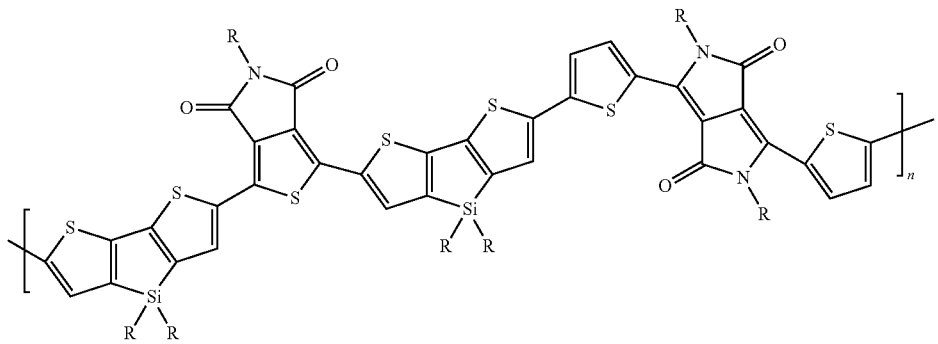

-continued

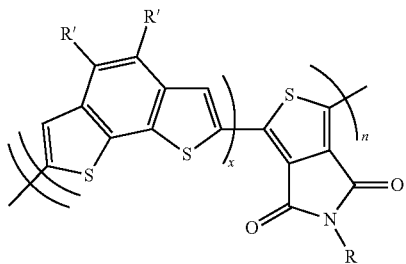
(III-G)

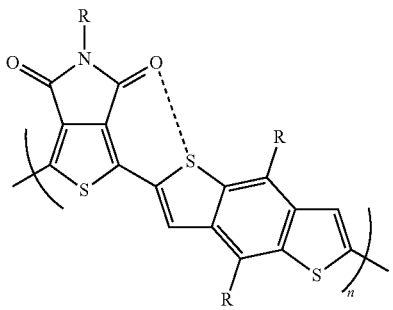
(III-H)

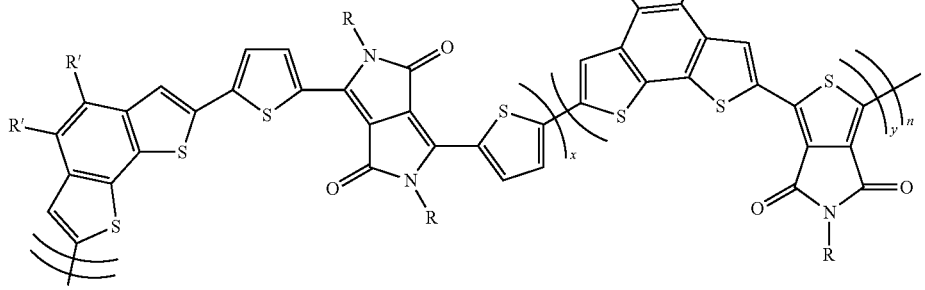
(III-I)

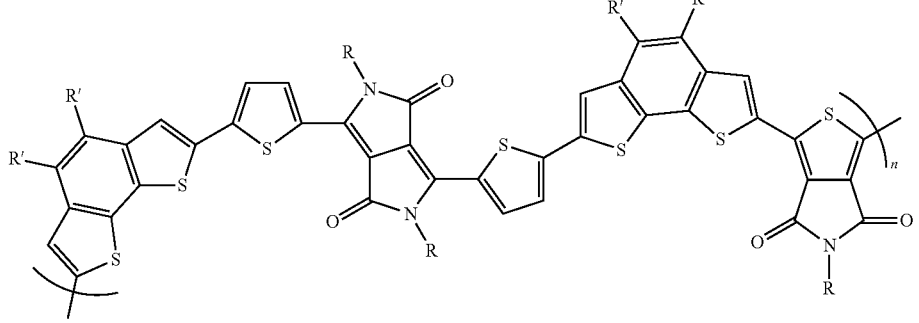
(III-J)

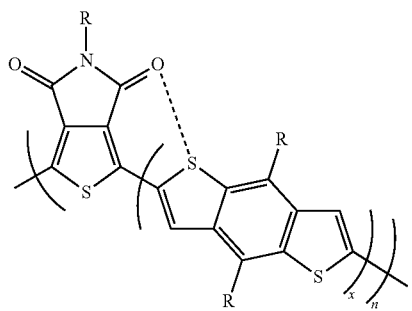
(III-K)

In structures IIIA-K, the variables such as n, x, and y can be greater than one; and these variables can be less than an integer; and these variables can be adapted for coupling to form dimers, trimers, oligomers, and polymers, as known in the art and as described in the specification, figures, claims, and working examples herein. Molecular weight, as well as reaction stoichiometry and order of mixing, can be used to determine these variables n, x, and y. In some structures, the structures may represent statistical representations of polymer materials as known to those skilled in the art.

Donors and Other Acceptors

A variety of donors, or donor moieties, are known in the art. FIG. 1 illustrates an exemplary listing of donor structures which can be used. The structures shown in FIG. 1 can be used in monomers, dimers, trimers, oligomers, and polymers. The side group can be varied and is not limited by side groups shown structure in FIG. 1. See, for example, description of R above for types of side groups which can be used in the structures of (I) which can be also used for donor side groups. In FIG. 1, the representation of —R or R— means a linkage site for a reactive group, or a linkage site for linking into another moiety like a dimer, trimer, oligomer, or polymer. Illustration of two of these sites means the moiety can be bivalently linked to another moiety including a polymer chain.

Symmetrical donor structures can be used. Benzodithiophene units can be used as donor. A particularly useful donor is that shown in Example 9 below. See, for example, Liang et al., *J. Am. Chem. Soc.,* 2009, 131, 56-57; see also *J. Am. Chem. Soc.,* 131, 7792, 2009, ("Highly Efficient Solar Cell Polymers Developed via Fine-Tuning of Structural and Electronic Properties"). See also, Hou et al., *Macromolecules,* 2008, 41, 6012-6018. In addition, the dithienosilole or dithienopyrrole moiety can be used. See, for example, Example 2. Tricyclo units can be used including those that comprise a central ring fused to two other thiophene rings.

Figure 2:
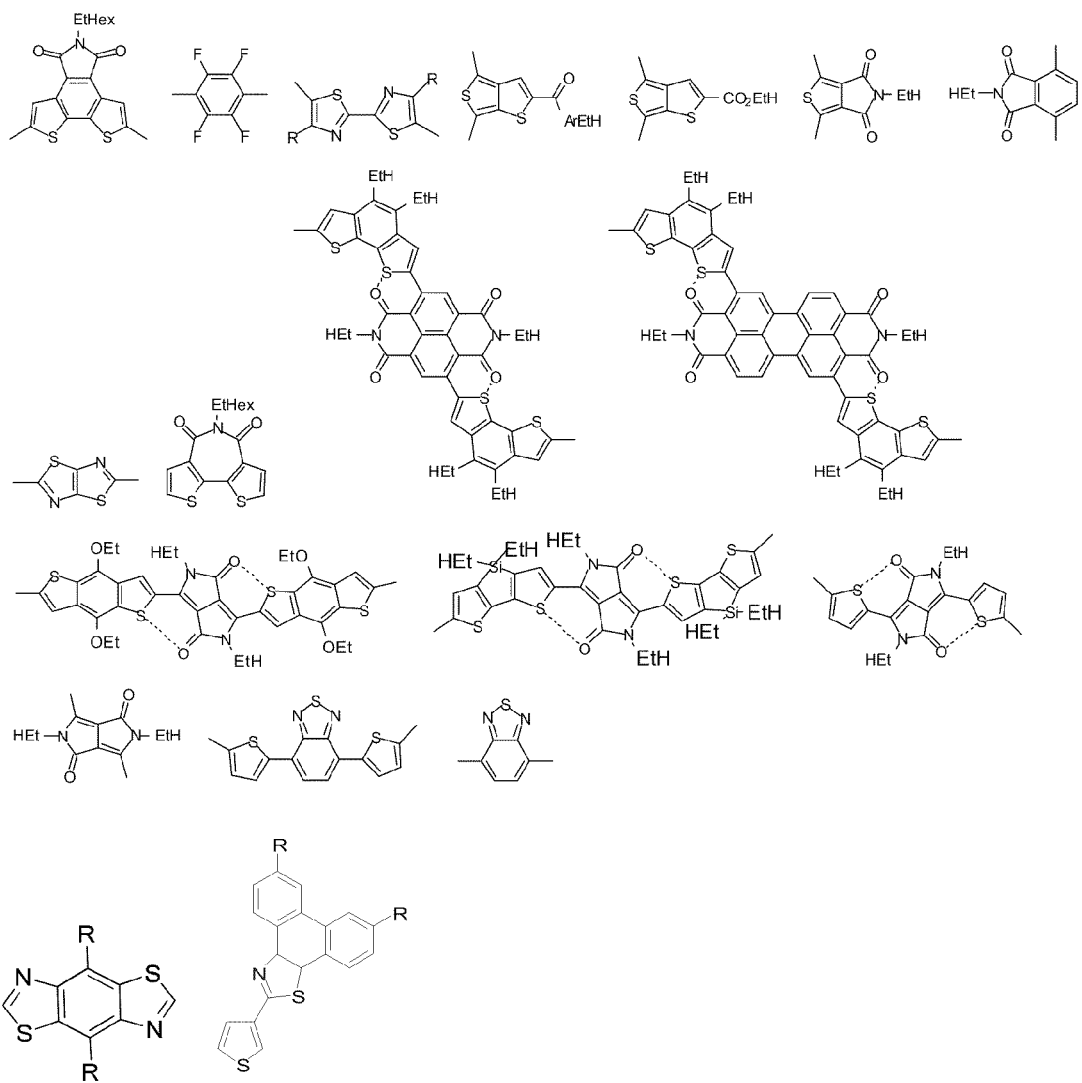
FIG. 2 provides a listing of exemplary acceptor moieties, useful for monomers and polymers. The side groups illustrated are representative and can be adjusted to provide, for example, desired electronic, steric, and reactivity effects. The side groups can also function as solubilizing groups. The side groups also can be optionally substituted.

In addition, other acceptors, or acceptor moieties, can be used with the acceptor of structure (I). Examples include but are not limited to those shown in FIG. 2. The structures shown in FIG. 2 can be used in monomers, dimers, trimers, oligomers, and polymers. The side group can be varied and is not limited by shown structure in FIG. 2. See, for example, description of R above for types of side groups which can be used in the structures of (I) as well as acceptors in FIG. 2. In FIG. 2, the representation of —R or R— means a linkage site for a reactive group, or a linkage site for, after reaction, linking into another moiety like a dimer, trimer, oligomer, or polymer. Two of these sites means the moiety can be bivalently linked to another moiety including a polymer chain.

An example of an acceptor is the diketopyrroleopyrrole-based acceptor moiety. See, for example, Zhou et al., *Chemistry of Materials,* 2009, "Synthesis and Photovoltaic Properties of Diketopyrrolopyrrole-Based Donor-Acceptor Complexes." See, for example, working example 9.

For a single polymer, more than one donor can be used: e.g., D1, D2, D3, and the like. In addition, for a single polymer, more than one acceptor can be used: e.g., A1, A2, A3, and the like.

Polymers can comprise D1-A1 moieties, D2-A2 moieties, D3-A3 moieties, and the like, as well as their intermixed moieties, such as, for example, D1-A2, and the like.

Use of more than one donor or acceptor can provide broader and/or stronger absorption bands and/or vibronic structures.

In particular, examples of donor structures can found in U.S. provisional application No. 61/222,053 filed Jun. 30, 2009.

Spacer moieties can be used as desired.

For purposes of describing additional embodiments, any of the moieties shown in FIGS. 1 and 2 can be called a structure (IV).

Embodiments for Copolymer Architecture Based on D1, D2, A1, and A2

The following chart shows different, exemplary embodiments for copolymer architecture with different donors, D1 and D2 donors, and different acceptors, A1 and A2 acceptors. The Chart I shows examples which are different from the -[D-A]- alternating formula seen in the prior art.

CHART I

-[D1-D2-A1]$_n$-    -[D1-D1-A1]$_n$-
-[(D1-A1)$_x$-(D2-A2)$_y$]$_n$-    -[(D1-A1)$_x$-(D2-A2)$_y$]$_n$-
-[D1-A1-D1-A2]$_n$-
-[(D1-A1)$_x$-(D1-A2)$_y$]$_n$-
-[(D1-D1-A1)$_x$-(D1-D1-A2)$_y$]$_n$-
-[(D1-D2-A1)$_x$-(D1-D2-A2)$_y$]$_n$-

The acceptors, A1, A2, or both can comprise structure I, and can also comprise any of the acceptors listed in FIG. 2.

The donors can be selected from those listed in FIG. 1, for example.

The structures shown in Chart I can be extended to further include additional donors, e.g., D3, D4, D5, and the like, or additional acceptors, e.g., A3, A4, A5, or the like.

In some embodiments, the conjugated backbone can comprise non-thiophene units in the chain of carbons subjected to the conjugation. For example, a benzene ring can form part of the conjugation structure via, for example, benzodithiophene units.

Ratio of Donor and Acceptor

The molar ratio of donor and acceptor can be one, less than one, or more than one. In calculating this ratio, there can be a single donor and/or a single acceptor, or there can be more than one donor and/or more than one acceptor. In other words, the polymer does not need to comprise equal molar amounts of donor and acceptor. The polymer can comprise more donor than acceptor, or more acceptor than donor. Chart I shows examples of this. For example, the ratio can be 2:1. Also, the ratio of different donors and acceptors within the polymer does not need to comprise equal molar amounts, e.g., the total ratio of donor and acceptor moieties in the polymer can be one where donor comprises a sum of different ratios of D1 and D2, and the like, and/or acceptor comprises a sum of different ratios of A1, A2, and the like. In other words, the ratio of the molar amounts of D1 and D2 does not have to be one, and the ratio of the molar amounts of A1 and A2 does not have to be one.

Random or Alternating Copolymers

Different copolymer microstructures can be prepared as known to those skilled in the polymer chemistry arts. For example, random copolymer structures can be produced. Mixed monomer polymerization can be carried out. Non-random copolymer structures can be produced.

For the random copolymer embodiment, one can use an appropriate synthetic sequence to obtain good materials. Synthetic approaches include, for example, Kumada, Suzuki, Negishi or Stille couplings for polymerization. See, for example (a) *Cross-Coupling Reactions: A Practical Guide*, Ed. Miyaura, 2002; (b) *Handbook of Organopalladium Chemistry for Organic Synthesis*, Ed. Negishi, 2002; (c) Kuwano et al., *J. Org. Chem.,* 2002, 67, 6479-6486; (d) Yu et al. *J. Am. Chem. Soc.* 2009, 131, 56; (e) Hou et al., *Macromolecules,* 2008, 41(16), 6012-6018; (f) Blouin et al., *J. Am. Chem. Soc.* 2008 130 (2), 732-742; (g) Swager et al. *Adv. Mater.* 2001, 13, 1775; (h) Koeckelberghs et al. *Macromolecules.* 2007, 40, 4173; (i) *High-Efficient-Low-Cost Photovoltaics*, Springer Verlag Berlin Heidelberg, 2009, Eds: Petrova-Kock, V.; Goetzberger, A., 195-222.

For example, one embodiment provides:

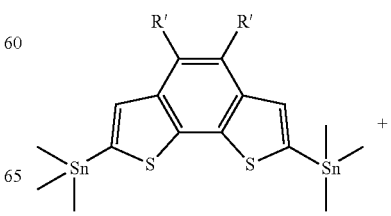

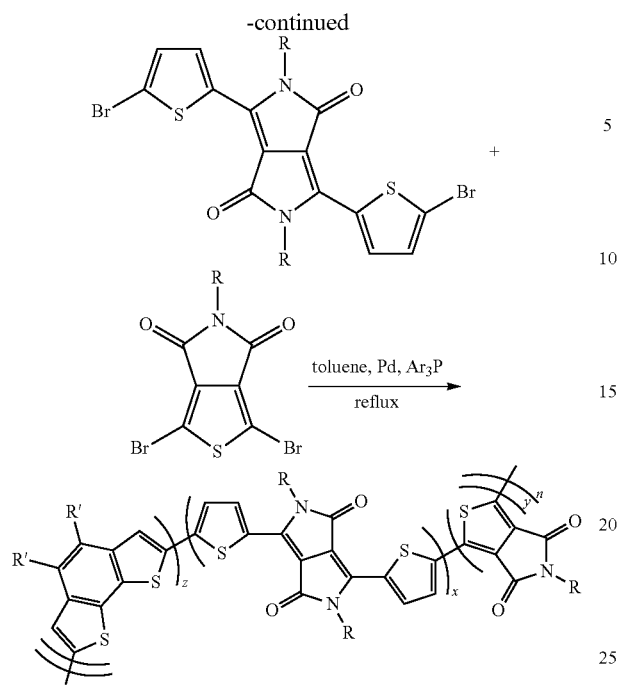
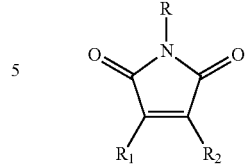

One embodiment provides for preparing high purity intermediates, such as trimers.

Regular alternating copolymer structures can be produced. Chart I shows examples of this.

Polymer Properties/Chromophore/Absorption Spectra

Polymer properties can be adapted to provide the good photovoltaic properties and to follow the design rules noted herein.

Lambda max can be, for example, greater than 600 nm.

Absorption edge can be extended into the red region. The absorption edge can comprise a sharp edge.

Absorption spectra are important parameters for the polymers, particularly for photovoltaic applications. It is known to record absorption spectra, including UV-Vis absorption spectra, for conjugated polymers. See, for example, Brown et al., Phys. Rev. B, 67, 064203 (2003) (describing spectra for different kinds of polythiophenes).

Polymers comprising Structure V

In addition, polymers can be prepared wherein the polymer backbone comprises the moiety (V):

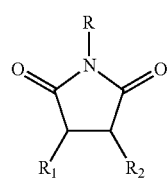

(V)

wherein moiety V is linked bivalently to the polymer backbone via the R1 and R2 groups, which can form a ring. In structure V, the carbon atoms 3 and 4 of the pyrrole ring can be joined by a double bond to form part of an extended conjugated polymer chain, as shown in structure V-A:

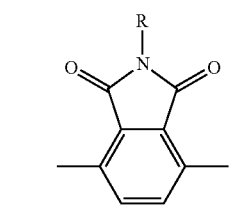

(V-A)

The R1 and R2 groups can link together to form a ring, including, for example, a five- or six-membered ring including an all-carbon ring or a ring comprising a heteroatom, including a heterocyclic ring, including, for example, a thiophene ring or a benzene ring. The ring formed by R1 and R2 can be aromatic or pseudoaromatic. The ring can be bivalently functionalized so it can be incorporated into the polymer backbone.

Structure (I) is an embodiment of structures V and V-A. Another example is structure V-B:

(V-B)

The R groups described herein for (I) can be used in (V) also. For structure (V), as with structure (I), the R group in one or more polymers can be varied, and different R groups can be used such as, for example, R1, R2, R3, or R', R", R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Structure (V) can be used in the analogous manner as Structure (I) is described herein.

Polymers Comprising Structure VI

Polymers can be also prepared which comprise at least one backbone moiety represented by:

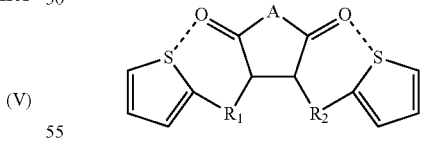

(VI)

wherein A can be an optionally substituted alkylene moiety (e.g., optionally substituted methylene or ethylene, —(CH$_2$)$_x$— or a heteroatom, and wherein the moiety V is bivalently linked to the polymer backbone via the illustrated thiophene rings linked to the R1 and R2 groups. In VI, although a non-covalent interaction is illustrated as a dashed line between the thiophene ring sulfur and the carbonyl oxygen, such interaction is optional and not required. The thiophene rings can be linked to the polymer at their 2- and 5-positions. The thiophene rings can be linked to additional thiophene rings.

As with structure V, in structure VI, the carbon atoms 3 and 4 of the top ring comprising alkylene or heteroatom A can be joined by a double bond to form part of an extended conjugated polymer chain, as shown in structure VI-B:

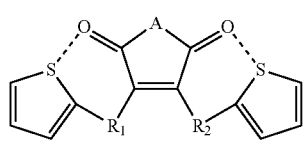

(VI-B)

In the heteroatom embodiment for A, A can be, for example, nitrogen, oxygen, sulfur, or selenium. The nitrogen, if the nitrogen is the heteroatom A, can be functionalized as shown in (I). The R group in structure (I) is adapted for bonding to a nitrogen atom. In other structures, such as VI, described herein, R can bind to other atoms besides nitrogen, and R can be adapted accordingly.

In a manner similar to structure V, $R_1$ and $R_2$ can form five or six-membered rings, including aromatic or pseudoaromatic rings, including heterocyclic rings, including benzene ring or thiophene ring.

Aromatic rings structures including aromatic rings structures, including benzidine ring structures, and biphenyl structures, can be used.

Structures (I), (II), and (V) can be embodiments of structure (VI).

As with Structures (I) and (V), the R groups in structures (VI) (R1 and R2) in one or more polymers can be varied, and different R groups can be used, such as, for example, R1, R2, R3, or R', R'', R''', and the like, wherein all are examples of R. For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Polymers Comprising Structure VII

Polymers can be also prepared wherein the backbone comprises a structure represented by VII:

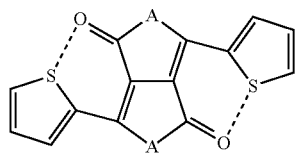

(VII)

Here, A can be an optionally substituted alkylene or heteroatom such as, for example, N, O, S, or Se, as described above for structure (VI). The A group can comprise substituents, such as the R group in structure I. For example, the R group in structure (VII) can be adapted for bonding to a nitrogen atom. In structures such as (VII) described herein, R can bind to other atoms besides nitrogen, and R can be adapted accordingly.

The structure (VII) can be linked into the polymer chain via the illustrated thiophene rings.

As with Structures (I), (V), and (VI), the R groups in structure (VII) in one or more polymers can be varied, and different R groups can be used, such as, for example, R1, R2, R3, or R', R'', R''', and the like, wherein all are examples of R.

For example, a single polymer can be prepared which comprises R1 and R2, wherein each of these are R. For example, a monomer with R1 can be copolymerized with a monomer comprising R2. Alternatively, a polymer comprising R1 can be blended with a polymer comprising R2. The R groups can be the same or different.

Methods of Making Monomers and Oligomers

Monomers, or low molecular weight compounds which can be used for further synthesis and polymerization, can be prepared as known in the art including the arts of organic synthesis and polymer chemistry. See, for example, *March's Advanced Organic Chemistry*, 6th Ed., Wiley, 2007; Nielsen et al., *Org. Lett.*, 2004, V6, 338; Watson et al. *J. Am. Chem. Soc.* 2009 131, 7206-7207.

Examples of monomers include

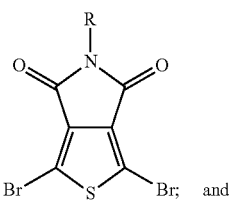

(IA)

and

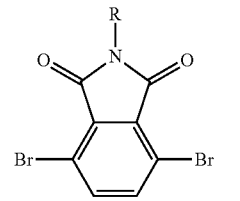

(VB)

For example, thiophene can be brominated at the 3- and 4-positions, and then the bromines converted to acyl chloride at the 3- and 4-positions. The thiophene can then be brominated at the 2- and 5-positions. Then, reaction of both acyl-chlorides with a primary amine like n-butyl amine can result in imide formation and closure of the ring to form a structure shown in I with two bromine sites for polymerization. See Zhang et al. *J. Am. Chem. Soc.*, 120, 22, 1998, 5355-5362.

In general, difunctional monomers can be prepared which show donor or acceptor structures, e.g., X-D-X wherein a donor moiety D is provided with reactive groups X; or Y-A-Y wherein an acceptor A is provided with reactive groups Y; reactive groups X and Y can be adapted to react with each other and covalently couple the donor and acceptor into a dimer.

Dimers can be made and subsequently adapted as needed and polymerized.

Trimers can be made and subsequently adapted as needed and polymerized. For example, a difunctional unit can be reacted with two mono-functional units to prepare a trimer. Oligomers can be made. Oligomers are known in the art. See, for example, Radke et al. *Organic Letters*, 2005, 7, 23, 5253-5256, which describes Stille coupling.

Methods of Making Polymers

Polymerization reactions are known in the art including, for example, electrochemical or oxidative chemical polymerization, or metal promoted cross-coupling polymerizations, e.g., Kumada, Suzuki, Negishi, Horner-Emmons, or Stille coupling ((a) Stille, J. K. *Angew. Chem. Int. Ed. Engl.* 1986, 25, 508; (b) Farina, V. et al. *J. Am. Chem. Soc.* 1991, 113, 9585; (c) Bao, Z. et al. *J. Am. Chem. Soc.* 1995, 117, 12426.), and Yamamoto-type polymerization (Yamamoto, T. et al. *Macromolecules* 1992, 25, 1214.)

Difunctional monomers, dimers, trimers, and/or oligomers can be polymerized as represented by, for example (wherein A and B can couple to provide carbon-carbon bond formation and X and Y are a monomer, dimer, trimer, or the like):
A-X-A+B-Y-B→X-Y (end groups not shown)

Polymers Described in prior Provisional Filings

The following four U.S. provisional applications are incorporated by reference in their entirety, including incorporated by reference for their monomer and polymer structures, including donor and acceptor structures: (i) 61/241,813 filed Sep. 11, 2009 (e.g., disclosing polymers comprising fused ring structures); (ii) 61/248,335 filed Oct. 2, 2009 (e.g., disclosing regular alternating polymers); (iii) 61/289,314 filed Dec. 22, 2009 (e.g., disclosing fluorinated solvents); and (iv) 61/290,844 filed Dec. 29, 2009 (e.g., disclosing polymers comprising arylamine moieties). In particular, the polymers described in these applications can be adapted to comprise the structures described herein including structures I, IIA, IIB, V, VA, VB, VI, VIB, and VII.

Part II

Further Embodiments and Applications Uses of Polymers

The materials, monomers, dimers, trimers, oligomers, polymers, and copolymers described herein in Part I, the working examples, and claims, can be used in organic electronic devices including, for example, OLEDs, OPVs including as OPV active layer, transistors, OFETs, batteries, and printed electronics generally, as well as sensors. The methods described in Part II can be adapted for the particular compounds and polymers being used.

For example, photovoltaic cells (solar cells) are known in the art. See, for example, Sun and Sariciftci, *Organic Photovoltaics, Mechanisms, Materials, and Devices,* 2005. The photovoltaic cell can comprise an active layer comprising a composition comprising at least one p-type material and at least one n-type material. One can engineer HOMO, LUMO, and band gaps for the p- and n-type materials for good performance. The morphology of the active layer can be adapted to provide good performance. For example, a nanoscale morphology can be prepared. An example is a bulk heterojunction. Bilayers can be made as described in, for example, Ayzner et al., *J. Phys. Chem. C.,* 2009, 113, 20050-20060 (e.g., describing all solution-processed bilayers in solar cells).

The photovoltaic device can comprise at least one cathode, at least one anode, and at least one photovoltaic active layer disposed between the cathode and anode. The active layer can comprise a p-type material and an n-type material.

In an OPV active layer, the polymers described herein, which can be a p-type material, can be combined with n-type materials or acceptor moieties, such as, for example, fullerenes and fullerene derivatives. An example of a fullerene derivative is PCBM. Fullerenes can be also derivatized, as described in, for example, PCT Patent Publication WO 2008/018931 filed May 2, 2007 and US Patent Publication 2008/0319207 published Dec. 25, 2008, both to Laird, et al. (Plextronics, Inc.). Other types of n-type materials known in the art can be used. If desired, larger area photovoltaics can be fabricated. See, for example, Bundgaard et al., *Solar Energy Materials and Solar Cells,* 2007, 91, 1019-1025.

Polymer solar cells, including polymer fullerene solar cells, are described in, for example, Hoppe et al., *Adv. Polym. Sci.* (2008), 214: 1-86; Zhu et al., "Design Rules for Efficient Organic Solar Cells," Chapter 13, 195-222 in *High-Efficient Low-Cost Photovoltaics,* Springer, 2009.

OLED devices are known in the art including white OLEDs, or WOLEDs. See, for example, Li and Meng, *Organic Light Emitting Materials and Devices,* CRC Taylor, 2006 and US Patent Publication 2006/0078761 published Apr. 13, 2006. The devices can comprise, for example, multilayer structures including, for example, an anode, including a transparent conductor, such as a transparent conductive oxide (TCO) on glass or PET or PEN; a hole injection layer; an electroluminescent layer, such as a polymer layer; a conditioning layer, such as LiF, and a cathode, such as for example Ca, Al, or Ba.

Methods known in the art can be used to fabricate organic electronic devices including for example OLED devices. Methods known in the art can be used to measure brightness, efficiency, and lifetimes. OLED patents include for example U.S. Pat. Nos. 4,356,429 and 4,539,507 (Kodak). Conducting polymers which emit light are described in for example U.S. Pat. Nos. 5,247,190 and 5,401,827 (Cambridge Display Technologies). See also Kraft et al., "Electroluminescent Conjugated Polymers—Seeing Polymers in a New Light," *Angew. Chem. Int. Ed.,* 1998, 37, 402-428, including device architecture, physical principles, solution processing, multilayering, blends, and materials synthesis and formulation, which is hereby incorporated by reference in its entirety.

In addition, printed electronics are generally known in the art. See, for example, *Printed Organic and Molecular Electronics,* Ed. D. Gamota et al., 2004. For example, Chapters 1 and 2 describe organic semiconductors, Chapter 3 describes manufacturing platforms for printing circuits, Chapter 4 describes electrical behavior of transistors and circuits, Chapter 5 describes applications, and Chapter 6 describes molecular electronics. See also Pope et al., *Electronic Processes in Organic Crystals and Polymers,* 1999.

Solutions and Ink Formulations

The materials, polymers, and copolymers can be put into solution or dispersion form, including ink formulations, for further processing, adapting to the particular application at hand including electronic devices and organic electronic devices, such as, for example, OLED, solar cells and active layers of solar cells.

Lower cost electronic devices can be enabled because polymers, such as those described herein, can be processed into inks which can then be handled in the same manner as inks in conventional printing processes. Ink compositions used for forming, for example, the active layer of an organic photovoltaic device can be made by dissolving p-type and n-type materials in a solvent system, optionally containing other additives.

The solvents and conjugated polymer inks can be formulated or adapted for use in a particular application, such as a solar cell that may include additional additives, such as electron acceptors. The additive(s) and solvents can be adapted to provide good dispersability of the n- and p-type materials, solubility of the n- and p-type materials, and stability of the ink formulation. For example, solvents can be used which provide good solubility or dispersability for fullerenes or fullerene derivative n-type compounds. Solvents can be adapted to be environmentally friendly in view of regulations, and can be, for example, halogen free. In other embodiments additives can be included in the ink that can improve the final film morphology or other properties. For example, solvent additives disclosed in US Patent Publication entitled "Processing Additives for Fabricating Organic Photovoltaic Cells" 2009/0108255 to Bazan et al., published on Apr. 30, 2009 can be included.

Solvent(s) and solvent additive(s) can be removed from the ink compositions, and films can be formed. Solid films can be formed that either comprise solvent(s) and solvent additive(s), are substantially free of solvent(s) and solvent additive(s), or are free of solvent(s) and solvent additive(s). For example, the amount of remaining solvent can be less than about 5% by weight, or less than about 1% by weight, or less than about 0.1% by weight. For example, the amount of remaining solvent additive can be less than about 5% by weight, or less than about 1% by weight, or less than about 0.1% by weight.

Conventional methods can be used to cast polymer materials from the compositions to provide solid forms, including thin film forms and printed forms. For example, the p-type and n-type polymers of the active layer can be dissolved in the solvent to form an ink, and then allowed to dry. Suitable coating methods are known. These include roll-to-roll coating, screen printing, spin casting, spin coating, doctor blading, dip coating, spray coating, or ink jet printing, and other known coating and printing methods.

Ink Components

Ink components known in the art can be used including, for example, solvents and n-type materials. The amounts of the components can be adapted to improve performance.

N-Type Materials

The active layer composition in, for example, a solar cell may include an n-type component or electron acceptor, or an electron acceptor moiety. These can be materials with a strong electron affinity and good electron accepting character. The n-type component should provide fast transfer, good stability, and good processability. The n-type material is desirably soluble in, dispersible in, or otherwise miscible with the solvents in order to provide for solution processing. The n-type component may take the form of particles, including microparticles and nanoparticles, inorganic particles, organic particles, and/or semiconductor particles.

For example, the active layer can comprise an n-type material comprising at least one fullerene structure. Fullerenes are known in the art. Fullerenes can be described as spheroidal carbon compounds. For example, the fullerene surface can present [6,6] bonding and [6,5] bonding as known in the art. The fullerene can have a surface comprising six-membered and five-membered rings. Fullerenes can be for example C60, C70, or C84, and additional carbon atoms can be added via derivative groups. See for example Hirsch, A.; Brettreich, M., *Fullerenes: Chemistry and Reactions*, Wiley-VCH Verlag, Weinheim, 2005, which is hereby incorporated by reference including teachings for fullerene nomenclature and synthesis, derivatization, reduction reactions (Chapter 2), nucleophilic additions (Chapter 3), cycloadditions (Chapter 4), hydrogenation (Chapter 5), radical additions (Chapter 6), transition metal complex formation (Chapter 7), oxidation and reactions with electrophiles (Chapter 8), halogenation (Chapter 9), regiochemistry (Chapter 10), cluster modification (Chapter 11), heterofullerenes (Chapter 12), and higher fullerenes (Chapter 13). Methods described herein can be used to synthesize fullerene derivatives and adducts.

In particular, the active layer can comprise at least one n-type material, wherein the n-type material comprises at least one derivatized fullerene or fullerene derivative. The derivative compound can be, for example, an adduct. The terms "derivatized fullerene," "fullerene derivative" as used herein, can be used interchangeably and can be, for example, fullerenes comprising, from 1 to 84, or 1 to 70, or 1 to 60, from 1 to 20, from 1 to 18, from one to ten, or from one to six, or from one to five, or from one to three substituents each covalently bonded to, for example, one or two carbons in the spheroidal carbon compounds. The derivatized fullerene can comprise a fullerene covalently bonded by [4+2] cycloaddition to at least one derivative moiety, R.

An example of an n-type material is PCBM.

Examples of n-type materials are described in, for example, International Patent Publication No. WO/2008/018931 published on Feb. 14, 2008 and US Patent Publication 2008/0319207 published Dec. 25, 2008, both to Laird, et al. See also, for example, for n-type small molecules and/or polymers for use in OPVs: a) Shin, et al. *Chem. Mater.* 2007, 19, 1892-1894; b) Hoppe, et al. *Adv Polym Sci.* 2008, 214, 1; c) Panagiotis, et al. *Adv. Funct. Mater.* 2008, 18, 1; d) Frechet, J. M. J. et al. *Chem. Mater.* 2009, 21, 1775.

Solvent

The solvents can be halogenated or non-halogenated. The solvents useful for the presently claimed inventions can include, for example, halogenated benzenes, alkyl benzenes, halogenated methane, and thiophenes derivatives, and the like. More specifically, solvent can be for example chlorobenzene, dichlorobenzene, trichlorobenzene, xylenes, toluene, chloroform, 3-methylthiophene, 3-propylthiene, 3-hexylthiophene, and mixtures thereof. At least two solvents can be used.

The solvent system can include at least two solvents, at least one first solvent and at least one second solvent (e.g., a solvent additive), which are different from each other. They can be organic solvents. Particularly useful solvent systems can be used as described in co-pending US patent application entitled "Solvent System for Conjugated Polymers," published as 2008/0299293, to Sheina et al., and co-pending US patent application entitled "Improved Solvent System," Ser. No. 12/541,500 filed Aug. 14, 2009, which are hereby incorporated by reference in their entirety.

Solvent Additives

Solvent additives can be used, wherein a relatively small addition of a component (e.g., 1-6 wt % or 1-3 wt %) can have a large impact on performance. For example, a primary or first solvent can be used in conjunction with a solvent additive. Solvent additives can be volatile and can be removed upon solvent removal. Or solvent additives can be less volatile and stay in the film upon solvent removal.

Different examples exist for solvent additives. For example, a solvent additive can comprise at least one heterocyclic ring. The heterocyclic ring can be, for example, at least one thiophene ring. The second solvent can be for example an alkylthiophene. In some instances the heterocyclic ring is not a nitrogen-containing ring. Or it can be a nitrogen containing ring. Thus, in some embodiments the second solvent is or is not a pyridine, pyrazine, pyrimidine, or a pyrrolidinone. In some embodiments, the heterocyclic ring includes at least one S atom and at least one O atom. Examples of suitable solvent additives include, but are not limited to, thiophene derivatives (i.e., substituted thiophenes). The benzene and/or thiophene ring may be substituted or unsubstituted in different positions on the ring. However, in some instances the thiophene derivatives do not contain halogen atoms. Alkylthiophenes and combinations thereof may be used as the second solvent. The alkyl group can be, for example, C1, C2, C3, C4, and the like up to and including C8, C12, C16, and C20. The alkyl group can be linear or branched. Specific examples of suitable alkylthiophenes include methylthiophene, ethylthiophene, propylthiophene, butylthiophene, pentylthiophene, hexylthiophene, heptylthiophene, octylthiophene, nonylthiophene, and decylthiophene. Fluorinated solvents and additives can be used.

Other examples of solvent systems can be used as described in the aforementioned co-pending US patent applications, in US Patent Publication entitled "Processing Additives for Fabricating Organic Photovoltaic Cells" 2009/0108255 to Bazan et al., published on Apr. 30, 2009 or in Peet, et al., "Efficiency enhancement in low-bandgap polymer solar cells by processing with alkane dithiols," *Nat. Mater.*, 2007, 6, 497-500.

Device Preparation

Devices can be made comprising one or more layers comprising the polymers described herein and one or more electrodes, including anode and cathode. Layers can be built up on a substrate. See, for example, Chen et al., *Advanced Materials*, 2009, 21, 1-16.

Devices using the presently claimed inventions can be made using for example ITO as an anode material on a substrate. Other anode materials can include, for example, metals, such as Au, carbon nanotubes, single or multiwalled, and other transparent conducting oxides. The resistivity of the anode can be maintained below, for example, 15 Ω/sq or less, 25 or less, 50 or less, or 100 or less, or 200 or less, or 250 or less. The substrate can be rigid or flexible and can be, for example, glass, plastics (PTFE, polysiloxanes, thermoplastics, PET, PEN and the like), metals (Al, Au, Ag), metal foils, metal oxides, (TiOx, ZnOx, NiOx, and the like) and semiconductors, such as Si. The ITO on the substrate can be cleaned using techniques known in the art prior to device layer deposition.

A variety of layers can be included between the anode and the active layer of a solar cell or the emissive layer of an OLED. These layers are generally referred to as hole transport layer (HTL), hole injection layers (HIL), hole collection (HCL), electron blocking layers (EBL) and/or interlayers.

Various kinds of hole transport layers, hole injection layers, hole collection layers, and/or hole extraction layers can be used. For example, hole transport layers of various kinds are described in the following references: 1) U.S. Pat. No. 7,569,159, issued Aug. 4, 2009 to Hammond et al.; U.S. Ser. No. 11/826,394, filed Jul. 13, 2007, published Oct. 9, 2008 as 2008/0248313; U.S. Ser. No. 12/422,159, filed Apr. 9, 2009; U.S. Ser. No. 61/108,851, filed Oct. 27, 2008; and U.S. Ser. No. 61/115,877, filed Nov. 18, 2008.

Hole transport layers (HTL) can be added using, for example, spin casting, ink jetting, doctor blading, spray casting, dip coating, vapor depositing, or any other known deposition method.

The HTLs can be formed as films from, for example, PEDOT, PEDOT/PSS or TBD, or NPB, or PLEXCORE® OC inks (Plextronics, Pittsburgh, Pa.).

The thickness of the HTL or HIL layer can be, for example, from about a monolayer to about 10 nm or to about 300 nm thick, or from 30 nm to 60 nm, 60 nm to 100 nm, or 100 nm to 200 nm. The film then can be optionally dried and/or solvent and/or temperature treated and/or annealed at 110 to 200° C. for 1 min to an hour, optionally in an inert atmosphere.

Active layer thickness can be, for example, about 50 nm to about 250 nm, including for an OPV device.

The active layer can be formulated from a mixture of n-type and p-type materials. The n- and p-type materials can be mixed in a ratio of, for example, from about 0.1 to 4.0 (p-type) to about 1 (n-type) based on a weight, or from about 1.1 to about 3.0 (p-type) to about 1 (n-type) or from about 1.1 to about 1.5 (p-type) to about 1 (n-type). The amount of each type of material or the ratio between the two types of components can be varied for the particular application.

The active layer can be then deposited by spin casting, ink jetting, doctor blading, spray casting, dip coating, vapor depositing, or any other known deposition method, on top of the HTL or HIL film. The film is then optionally thermally annealed at, for example, about 40 to about 250° C., or from about 150 to 180° C., for about 10 min to an hour in an inert atmosphere. Solvent annealing can be also carried out as needed. Solvent annealing can be carried out at, for example, ambient temperature (for low boiling solvents). The film can be also optionally dried in solvent saturated and/or inert and/or vacuum atmosphere. The active layer can be also annealed with use of an electric field ("electric field annealing"). For example, a device can be cycled in an electric field which can in some instances improve performance. Internal heating may also contribute to electric field annealing.

A cathode layer can be added to the device, generally using, for example, thermal evaporation of one or more metals. Also, solution processing can be used. For example, a 1 to 15 nm Ca layer is thermally evaporated onto the active layer through a shadow mask, followed by deposition of a 10 to 300 nm Al layer.

A variety of layers can be included between the cathode and the active layer of a solar cell or the emissive layer of an OLED. These layers are generally referred to as electron transport layers (ETL), electron injection layers (EIL), hole blocking layers (HBL) and/or interlayers.

In some embodiments, an optional interlayer may be included between the active layer and the cathode, and/or between the HTL or HIL and the active layer. This interlayer can be, for example, from 0.5 nm to about 100 nm, or from about 1 to 3 nm, thick. The interlayer can comprise an electron conditioning, a hole blocking, or an extraction material, such as LiF, BCP, metal oxides, bathocuprine, fullerenes or fullerene derivatives, such as C60, C70, C84 and other fullerenes and fullerene derivatives discussed herein.

Electron transport layers can be used in, for example, solar cell devices. See, for example, U.S. patent application No. 61/116,963 filed Nov. 21, 2008.

Interfacial modification layers can be used as described in, for example, PCT/US2009/006236 filed Nov. 20, 2009 (Plextronics, Inc.). The interfacial modification layer can comprise, for example, an organic semiconductor which is doped by, for example, a metal (e.g., BPhen:Yb). The interfacial modification layer can be prepared by vacuum deposition methods. It can have a thickness of, for example, 3 nm to 25 nm, or 5 nm to 15 nm. An Al layer can be disposed on top.

The devices can be then encapsulated using a glass cover slip sealed with a curable glue, or in other epoxy or plastic coatings. Cavity glass with a getter/desiccant may also be used.

In addition, the active layer can comprise additional ingredients including, for example, surfactants, dispersants, oxygen and water scavengers.

The active layer can comprise multiple layers or be multi-layered.

The active layer composition can be formed from an ink comprising a mixture as a film. Films and devices can be annealed before use and testing. Thermal/electrical annealing and solvent annealing can be carried out.

Inverted solar cells can be made. See, for example, Chen et al. *Advanced Materials*, 2009, 21, 1-16. Tandem solar cells can be made.

Device Testing

Known solar cell parameters can be measured including for example $J_{SC}$ (mA/cm$^2$) and Voc (V) and fill factor (FF) and power conversion efficiency (%, PCE) by methods known in the art. See for example Hoppe article cited above and references cited therein.

Oriel Solar Simulators can be used to determine PV properties including, for example, FF, Jsc, Voc, and efficiencies. The simulator can be calibrated by methods known in the art including, for example, calibration with a KG5-Si reference cell. External quantum efficiency (EQE) can be measured.

Other properties for the inks, films, and devices can be measured by methods known in the art.

Power conversion efficiency (PCE) can be, for example, at least about 1%, or at least about 2%, or at least about 3%, or at least about 4%, or at least about 5%, or at least about 6%, or at least about 7%, or at least about 8%, or higher.

Fill factor, which can be expressed as a number between 0 and 1, or a percentage between 0 and 100%, can be, for example, at least about 0.4 (40%), or at least about 0.5 (50%), or at least about 0.6, or at least about 0.7, or at least about 0.8, or at least about 0.9 or higher.

Open circuit voltage ($V_{OC}$) in V can be, for example, at least about 0.3, or at least about 0.4, or at least about 0.5, or at least about 0.6 V, or at least about 0.7 V, or at least about 0.8 V, or at least about 0.9 V, or at least about 1.0 V, or at least about 1.1 V, or at least about 1.2 V, or at least about 1.3 V, or higher.

Short circuit current ($J_{SC}$) can be, for example, at least about 0.5, or at least about 0.6, or at least about 0.7, or at least about 0.8, or at least about 0.9, or at least about 1.0, or at least about 2.0, or at least about 3.0, or at least about 4.0, or at least about 5.0, or at least about 10.0, or higher (mA/cm$^2$).

Additional Embodiments Including High Performance Embodiments

Some embodiments provide particularly high performance in, for example, photovoltaic and/or solar cell testing including efficiency and open circuit voltage. See, for example, working examples 14-22 and working example 20 below and devices prepared therefrom and polymers used in the devices. The embodiments comprise, for example, monomers, oligomers, polymers, inks, devices, and methods of making and using same.

For example, one embodiment provides a device comprising: at least one cathode; at least one anode; at least one photovoltaic active layer disposed between the cathode and anode and comprising at least one p-type material and at least one n-type material, wherein the p-type material comprises at least one polymer comprising a donor-acceptor structure, comprising a first acceptor backbone moiety:

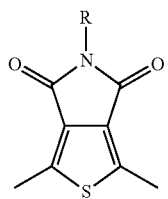

(I)

and wherein the donor comprises at least one benzodithiophene structure, and the polymer comprises at least one second acceptor other than (I). Alternatively, the device can comprise a polymer comprising at least one second acceptor other than (I) which comprises a benzothiadiazole structure and optionally comprises the benzodithiophene structure. In one embodiment, the second acceptor other than (I) comprises a benzothiadiazole structure. In one embodiment, for example, the second acceptor other than (I) comprises a benzothiadiazole structure, and the molar amount of the first acceptor is greater than the molar amount of the second acceptor. In one embodiment, the second acceptor other than (I) comprises a benzothiadiazole structure, and the molar amount of the first acceptor is 55% to 75%, and the molar amount of the second acceptor is 25% to 45%, relative to the total molar amount of the combined first and second acceptor structure. In one embodiment, the second acceptor other than (I) comprises a benzothiadiazole structure, and the molar amount of the first acceptor is about 65%, and the molar amount of the second acceptor is about 35%, relative to the total molar amount of the combined first and second acceptor structure. In one embodiment, the benzodithiophene structure comprises at least one alkyl substituent. In one embodiment, the benzodithiophene structure comprises at least one C6-C12 branched alkyl structure. In one embodiment, the R group is a C6-C12 branched alkyl structure. In another embodiment, the benzodithiophene can be unsubstituted or bis-methyl substituted. One can as appropriate adjust side chain density. In one embodiment, the polymer is a random polymer. In one embodiment, the polymer has a number average molecular weight of at least 10,000, or at least 20,000. In one embodiment, the polymer is soluble in chloroform. In one embodiment, the device has a power conversion efficiency of at least 6%. In one embodiment, the device has an open circuit voltage of at least 0.9 V. In one embodiment, the device has a power conversion efficiency of at least 6%, and an open circuit voltage of at least 0.9 V. In one embodiment, the device has at least one hole transport layer disposed next to the active layer. In one embodiment, the device has at least one hole transport layer disposed next to the active layer, wherein the hole transport layer comprises at least one sulfonated regioregular polythiophene. In one embodiment, the device has at least one interfacial modification layer comprising at least one organic semiconductor doped with at least one metal. In one embodiment, the active layer is annealed. In one embodiment, the active layer is thermally annealed. In one embodiment, the active layer is solvent annealed. In one embodiment, the weight ratio of p-material and n-material is about 1:1.5 to about 1:3, or about 1:1.8 to about 1:2.2. In another embodiment, it is about 1:1. In one embodiment, the active layer has a thickness of about 60 nm to about 200 nm, or about 75 nm to about 80 nm. In one embodiment, the active layer is formed by deposition of an ink comprising at least one fluorinated solvent.

One can adapt the ratio of monomer content to provide the best balance of higher molecular weight, solubility, film formation, and/or performance.

One can adapt the side groups of the monomer, such as branching for example, to provide solubility and/or electronic influence on the polymer backbone as needed.

High performance polymers can be prepared by reaction of at least three monomers including (i) benzodithiophene monomer comprising at least two tin groups (or more generally, groups which will react with halogen in a polymerization reaction, (ii) a monomer comprising the structure (I) comprising at least two halogeno (e.g., two bromo) groups, and (iii) a benzothiadiazole monomer comprising at least two halogeno (e.g., two bromo) groups. See, for example, Example 20 below. The side groups and ratio of monomers can be adapted to achieve best photovoltaic performance, solubility, and film formation. The ratio of donor and acceptor can be about 1:1. Polymerization conditions can be adapted to provide sufficient molecular weight. Polymerization can be carried out to produce random structures.

In another embodiment, the multiple monomer units can be made to be alternating regular structures. For example, the three repeat units in a polymer such as used in Example 20 can be made into a regular alternating structure.

After polymerization, the polymers providing high performance can be formulated with at least one solvent and at least one n-type material to provide an ink.

High performance polymers can be also prepared comprising structures (V), (VI), and/or (VII). For example, polymers comprising these structures (V), (VI), and/or (VII) can be prepared also comprising benzodithiophene as donor and benzothiadiazole as second acceptor structures.

The second acceptor other than (I) can be a structure comprising at least two fused ring structures, or at least three fused ring structures. Benzothiadiazole (BTD) is an example of two fused ring structures. The benzo group of BTD could be further fused into a third ring if desired. One ring structure can be a benzene ring of the second acceptor other than (I), and the benzene ring optionally can be substituted with R groups, and the R groups can form another ring structure. In the second acceptor other than (I), two carbon atoms of the benzene ring can be fused into a second ring structure, as found in, for example, benzothiadiazole (where —N—S—N— forms the second ring). The second ring structure can comprise —N—X(R)—N— wherein X is a heteroatom like sulfur, selenium, oxygen, or nitrogen. R can be present if the heteroatom is nitrogen. Other examples of the second ring include fusing the —N—X(R)—N— or the —N—N—N— ring structure into a benzene ring. The second acceptor other than (I) can comprise at least one heterocyclic ring structure in addition to the benzene ring as in benzothiadiazole. Heteroatoms include, for example, sulfur and/or nitrogen. Examples of such ring structures, including BTD, can be found in, for example, Hou et al., *Macromolecules,* 2008, 41, 6012-6018. See, for example, structures H1, H7, H9, and H11 at page 6013.

Polymers can be prepared which comprise three backbone moieties: a donor, and first and second acceptor moieties. Polymers can be prepared, in one embodiment, which comprise only the three backbone repeat units in Example 20. All other types of repeat units can be excluded in one embodiment.

Examples of high performance polymers include TV-1 and TV-2 below:

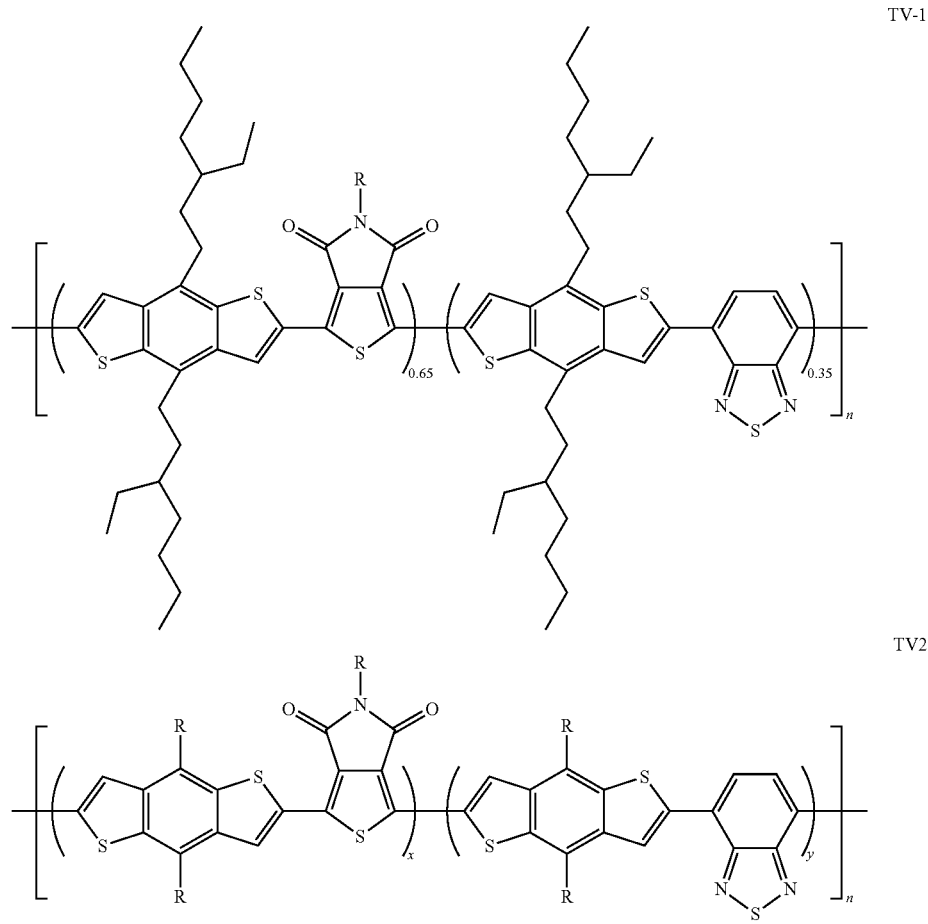

wherein R groups in TV-1 and TV-2, independently of each other, can be adapted to provide branching, solubility, and electronic tuning as described herein. An example of R group in TV-1 and TV-2 is a branched alkyl group like ethylhexyl. Values for x and y and n can be adapted for a particular application.

Part III

Working and Prophetic Examples

Additional embodiments are provided by way of non-limiting working and prophetic examples.

I. Synthesis: Monomers and Polymers

The following synthetic examples are illustrative and not intended to be limiting. Unless specified, reactions were conducted under prepurified nitrogen or argon, using oven-dried and/or flame-dried glassware. Ice/water, dry ice/acetone were used for 0° and −78° C. baths, respectively. Commercial chemicals were purchased from Aldrich Chemical Co., Inc. and used without further purification. Titration of the Grignard/organolithium reagents was performed following the procedure described by Love, et al. *J. Org. Chem.* 1999, 64, 3755.

Materials.

Syntheses of the following materials were adapted from the published procedures:
4,4'-bis(2-ethylhexyl)dithieno[3,2-b:2',3'-d]silole [Lit. Ref.: Hou et al., *J. Am. Chem. Soc.* 2008, 130, 16144];
4,8-dioctyloxybenzo[1,2-b;3,4-b]dithiophene [Lit. Ref.: Hou et al., *Macromolecules* 2008, 41, 6012];
2,5-diethylhexyl-3,6-bis(5-bromothiophen-2-yl)pyrrolo[3,4-c]-pyrrole-1,4-dione [Lit. Ref.: Tamayo et al., *J. Phys. Chem. C* 2008, 112, 15543];
4,7-dibromo-benzo[1,2,5]thiadiazole [Lit. Ref.; Hou et al., *Mater. Chem.* 2002, 10, 2887];
1,3-Dibromo-5-(2-ethylhexyl)thieno[3,4-c]pyrrole-4,6-dione; was received from Acoris, Inc. (synthesis was adapted from Zhang et al., J. M. *J. Am. Chem. Soc.* 1997, 119, 5065).
General synthesis of alkynes from aldehydes was adapted from Roth, et al., *Synthesis, Journal of Synthetic Organic Chemistry*, 2004, 1, 59

Example 1

2,6-bis(trimethyltin)-4,8-diethylhexyloxybenzo[1,2-b;3,4-b]dithiophene

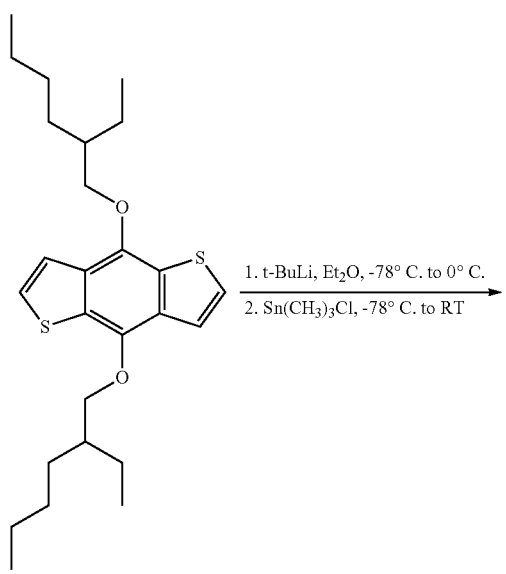

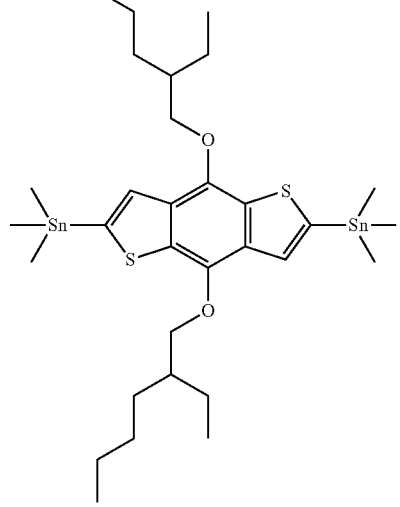

A dry 500-mL three-neck flask was flushed with $N_2$ and was charged with 4,8-diethylhexyloxybenzo[1,2-b;3,4-b] dithiophene (6.9 g, 0.015 mol) and diethyl ether ($Et_2O$) (150 mL, 0.1 M) via deoxygenated syringe. The reaction flask was cooled to −78° C. and a 1.7 M solution of tert-butyllithium in hexanes (23 mL, 0.038 mol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (39 mL, 0.038 mol) was added to the reaction flask dropwise and stirring continued for 1 hour at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with hexanes (150 mL) three times. The combined organic layer was washed with water two times and dried over anhydrous magnesium sulfate ($MgSO_4$). After the product was filtered, the solvent was removed by rotary evaporation. The crude product was purified by recrystallization three times from THF/methanol to yield white crystalline solid (7.3 g, 61%).

Spectral data: $^1$H NMR (300 MHz, $CDCl_3$): $\delta_H$ 7.15 (s, 2H), 4.18 (d, 4H), 1.81 (m, 4H), 1.60 (m, 14H), 1.08 (t, 6H), 0.95 (t, 6H), 0.45 (s, 18H).

Example 2

4,4'-bis(2-ethylhexyl)-5,5'-bis(trimethyltin)dithieno[3,2-b:2',3'-d]silole

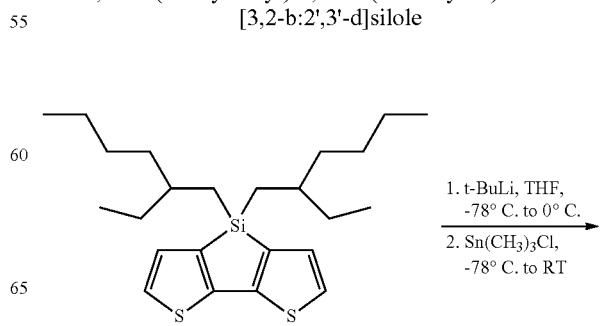

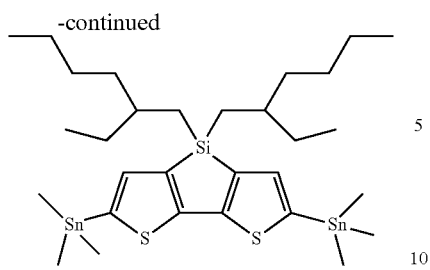

A dry 500-mL three-neck flask was flushed with $N_2$ and was charged with 4,4'-bis(2-ethylhexyl)dithieno[3,2-b:2',3'-d]silole (10.4 g, 0.025 mol) and THF (250 mL, 0.1 M) via deoxygenated syringe. The reaction flask was cooled to −78° C. and a 1.6 M solution of tert-butyllithium in hexanes (37 mL, 0.062 mol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (62 mL, 0.062 mol) was added to the reaction flask dropwise and stirring continued for 1 hour at −78° C. The cooling bath was removed and the reaction mixture was allowed to warm up to ambient temperature. As the reaction was completed, cool DI water (50 mL) was slowly added to the reaction flask. Then, the reaction mixture was poured into 200 mL of cool water and extracted with hexanes (200 mL) three times. The combined organic layer was washed with water two times and dried over anhydrous magnesium sulfate ($MgSO_4$). After the product was filtered, the solvent was removed by rotary evaporation. The product was obtained as yellow-greenish oil (17.5 g, 96%).

Spectral data: $^1$H NMR (300 MHz, $CDCl_3$): $\delta_H$ 7.09 (s, 2H), 1.25 (m, 18H), 0.80 (m, 16H), 0.45 (s, 18H).

Example 3

2-trimethyltin-4,8-diethylhexyloxybenzo[1,2-b;3,4-b]dithiophene

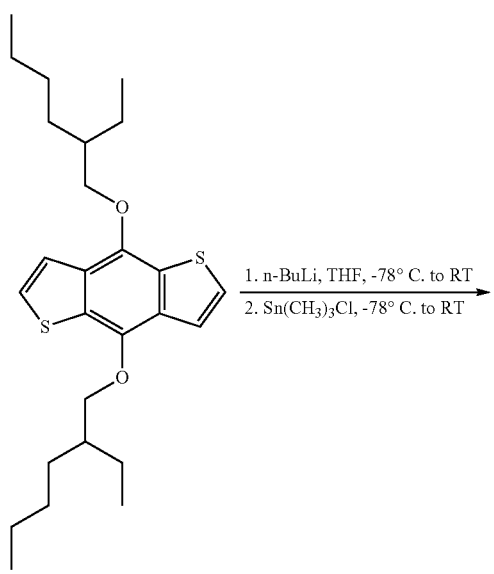

A dry 250-mL three-neck flask was flushed with $N_2$ and was charged with 4,8-diethylhexyloxybenzo[1,2-b;3,4-b]dithiophene (4.0 g, 9.0 mmol) and THF (100 mL, 0.10 M) via deoxygenated syringe. The reaction flask was cooled to −78° C. and a 2.17 M solution of n-butyllithium in hexanes (4.1 mL, 9.0 mmol) was added dropwise via deoxygenated syringe. After 30 minutes of stirring at −78° C., the solution was chilled to 0° C. and stirring was continued for 5 minutes, at which point the reaction mixture was chilled back to −78° C. A 1 M solution of thrimethyltin chloride in THF (13.5 mL, 13.5 mmol) was added to the reaction flask dropwise and stirring continued for 1 hour at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with hexanes (150 mL) three times. The combined organic layer was washed with water two times and dried over anhydrous magnesium sulfate ($MgSO_4$). After the product was filtered, the solvent was removed by rotary evaporation. The product was obtained as yellow oil (5.3 g, 96%).

Spectral data: $^1$H NMR (300 MHz, $CDCl_3$): $\delta_H$ 7.50 (d, 2H), 7.35 (s, 1H), 4.20 (s, 4H), 1.28-1.92 (bm, 20H), 0.98 (d, 12H), 0.46 (t, 9H).

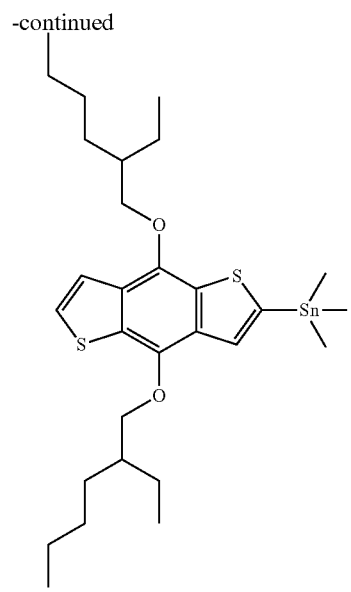

Example 4

1,3-bis(4,8-diethylhexyloxybenzo[1,2-b;3,4-b]dithiophene)-5-(2-ethylhexyl)thieno[3,4-c]pyrrole-4,6-dione

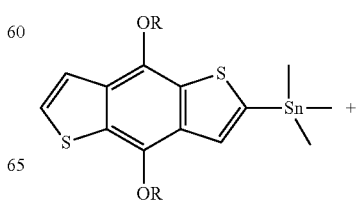

-continued

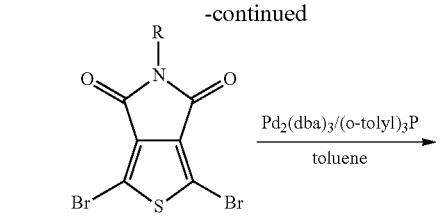

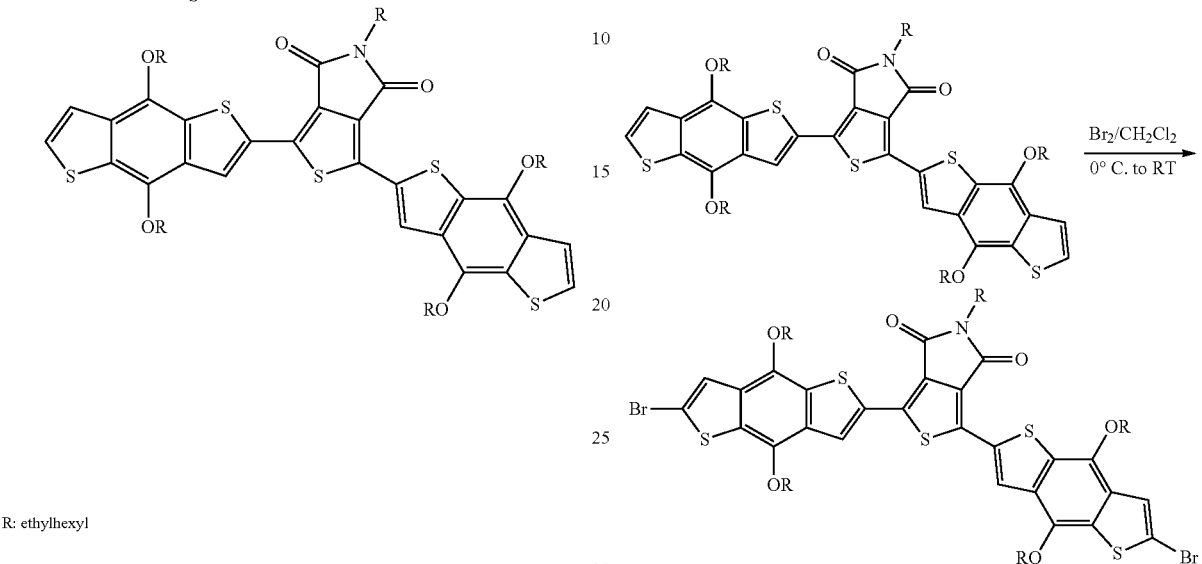

R: ethylhexyl

In a glove box, 2-trimethyltin-4,8-diethylhexyloxybenzo[1,2-b;3,4-b]dithiophene (1.0 g, 1.64 mmol), 1,3-dibromo-5-(2-ethylhexyl)thieno[3,4-c]pyrrole-4,6-dione (0.33 g, 0.78 mmol), tris(dibenzylideneacetone)dipalladium(0) (0.018 g, 0.020 mmol) and tris(o-tolyl)phosphine (0.024 g, 0.080 mmol) were weighted out into a flame dried 50 mL Schlenk flask. Reaction flask was removed from the glove box and 10 mL of deoxygenated toluene were added via syringe. The mixture was evacuated and refilled with argon five times. The reaction flask was immersed into a preheated to 110° C. oil bath and was left stirring under an argon stream for 2 hours. The oil bath was removed and after cooling to room temperature, the final mixture was poured into 40 mL of methyl tert-butyl ether (MTBE) and extracted with it (3×50 mL). The combined organic layer was washed with water two times and dried over anhydrous magnesium sulfate ($MgSO_4$). After the product was filtered, the solvent was removed by rotary evaporation. The product was first passed thru a flash silica gel chromatography column with hexanes/chloroform (gradient), and then thru a biobeads SX-1 column with chloroform. It was obtained as an orange waxy in appearance solid paste (0.40 g, 60%).

Spectral data: $^1H$ NMR (300 MHz, $CDCl_3$): $\delta_H$ 8.76 (s, 2H), 7.47 (d, 2H), 7.42 (d, 2H), 4.32 (d, 4H), 4.20 (d, 4H), 3.63 (d, 2H), 1.25-1.94 (bm, 55H), 0.86-1.08 (bm, 30H).

Example 5

Bromination of 1,3-bis(4,8-diethylhexyloxybenzo[1,2-b;3,4-b]dithiophene)-5-(2-ethylhexyl)thieno[3,4-c]pyrrole-4,6-dione A dry 50-mL three-neck flask equipped with a condenser, a stir bar, addition funnel, and a gas (HBr) outlet was charged with 1,3-bis(4,8-diethylhexyloxybenzo[1,2-b;3,4-b]dithiophene)-5-(2-ethylhexyl)thieno[3,4-c]pyrrole-4,6-dione (0.20 g, 0.17 mmol). The flask was charged with anhydrous methylene chloride ($CH_2Cl_2$) (10 mL). The reaction flask was cooled down to 0° C. and bromine (0.06 mL, 0.37 mmol) in 10 mL of methylene chloride was added dropwise to the reaction flask via addition funnel. The solution mixture was stirred at 0° C. for 2 hours, and then at room temperature (RT) for an additional 6 hours. If necessary, a second portion of bromine solution could be added to the reaction flask and the reaction could proceed for additional 2 hours. Upon completion, the reaction was added to a $NaOH/NaHSO_3$ solution (5%). The layers were separated and the aqueous layer/ was extracted three times with MTBE, the organic layers collected, washed with NaOH, water, and dried over anhydrous $MgSO_4$. After the product was filtered, the solvent was removed by rotary evaporation. The crude product was first passed through a flash silica gel chromatography column with hexanes/chloroform (gradient), and then thru a biobeads SX-1 column with chloroform. It was obtained as an orange viscous solid paste with yields ranging between 70 and 80%. The purity was checked by NMR.

Example 6 poly{2,6'-4,8-diethylhexyloxybenzo[1,2-b;3,4-b]dithiophene-alt-(5-(2-ethylhexypthieno[3,4-c]pyrrole-4,6-dione}

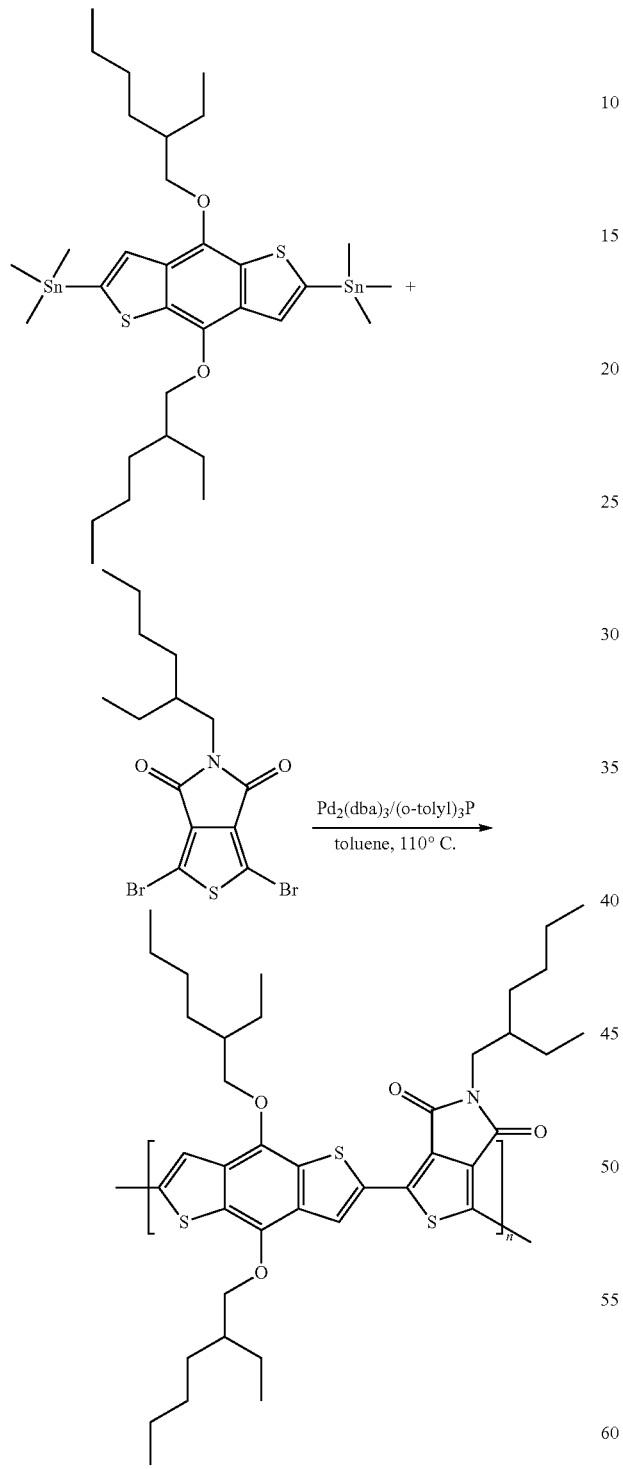

In a glove box, 2,6-bis(trimethyltin)-4,8-diethylhexyloxybenzo[1,2-b;3,4-b]dithiophene (0.4 g, 0.52 mmol), 1,3-dibromo-5-(2-ethylhexyl)thieno[3,4-c]pyrrole-4,6-dione (0.22 g, 0.52 mmol), tris(dibenzylideneacetone)dipalladium(0) (0.012 g, 0.013 mmol) and tris(o-tolyl)phosphine (0.016 g, 0.052 mmol) were weighted out into a flame dried 50 mL Schlenk flask. Reaction flask was removed from the glove box and 6 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.18 g, 50%). Molecular weight was determined by GPC in 1,3,5-trichlorobenzene (1 mL/min at 150° C.) vs. polystyrene standards: $M_n$=24,700, $M_w$=49,100, PDI=2.0.

Example 7 poly{4,4'-bis(2-ethylhexyl)dithieno[3,2-b:2',3'-d]silole-alt-5-(2-ethylhexyl)thieno[3,4-c]pyrrole-4,6-dione}

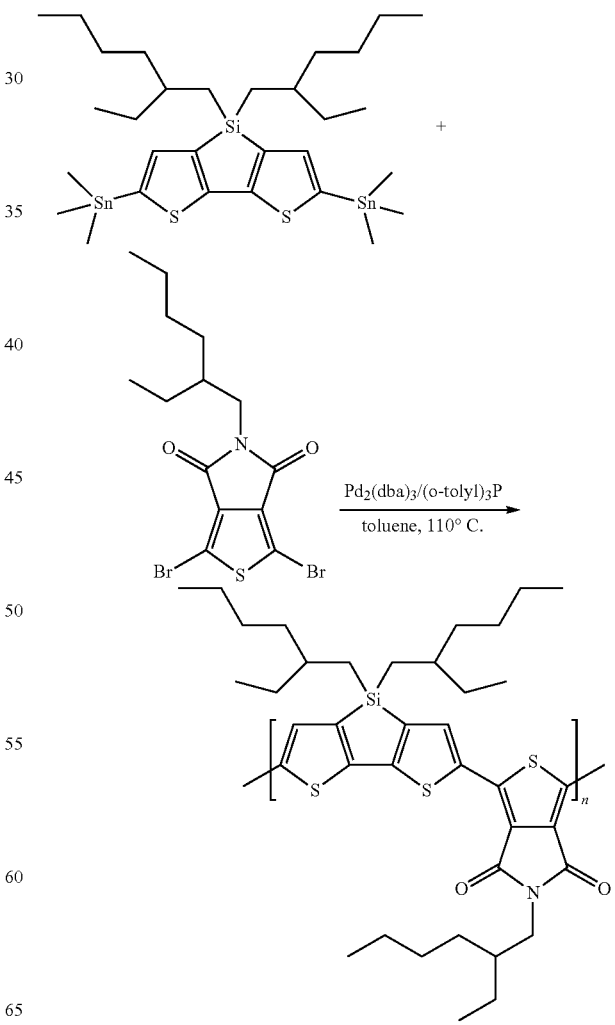

In a glove box, 4,4'-bis(2-ethylhexyl)-5,5'-bis(trimethyltin)dithieno[3,2-b:2',3'-d]silole (0.98 g, 1.3 mmol), 1,3-dibromo-5-(2-ethylhexyl)thieno[3,4-c]pyrrole-4,6-dione (0.50 g, 1.2 mmol), tris(dibenzylideneacetone)dipalladium(0) (0.030 g, 0.033 mmol) and tris(o-tolyl)phosphine (0.040 g, 0.13 mmol) were weighted out into a flame dried 100 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 36 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 500 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.18 g, 20% of chloroform soluble fraction). Molecular weight was determined by GPC in chloroform (1 mL/min at 35° C.) vs. polystyrene standards: $M_n$=9,900, $M_w$=16,000, PDI=1.6.

Example 8 poly{(4,4'-bis(2-ethylhexyl)dithieno[3,2-b:2',3'-d]silole-alt-5-(2-ethylhexyl)thieno[3,4-c]pyrrole-4,6-dione)-alt-(4,4'-bis(2-ethylhexyl)dithieno[3,2-b:2',3'-d]silole-alt-5-diethylhexyl-3,6-dithiophen-2-ylpyrrolo[3,4-c]pyrrole-1,4-dione)}

In a glove box, 4,4'-bis(2-ethylhexyl)-5,5'-bis(trimethyltin)dithieno[3,2-b:2',3'-d]silole (0.44 g, 0.60 mmol), 1,3-dibromo-5-(2-ethylhexyl)thieno[3,4-c]pyrrole-4,6-dione (0.12 g, 0.28 mmol), 2,5-diethylhexyl-3,6-bis(5-bromothiophen-2-yl)pyrrolo[3,4-c]-pyrrole-1,4-dione (0.19 g, 0.28 mmol), tris(dibenzylideneacetone)dipalladium(0) (0.014 g, 0.015 mmol) and tris(o-tolyl)phosphine (0.018 g, 0.059 mmol) were weighted out into a flame dried 50 mL Schlenk flask. Reaction flask was removed from the glove box and 8 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.38 g, 81%). Molecular weight was determined by GPC in chloroform (1 mL/min at 35° C.) vs. polystyrene standards: $M_n$=12,900, $M_w$=95,700, PDI=7.4.

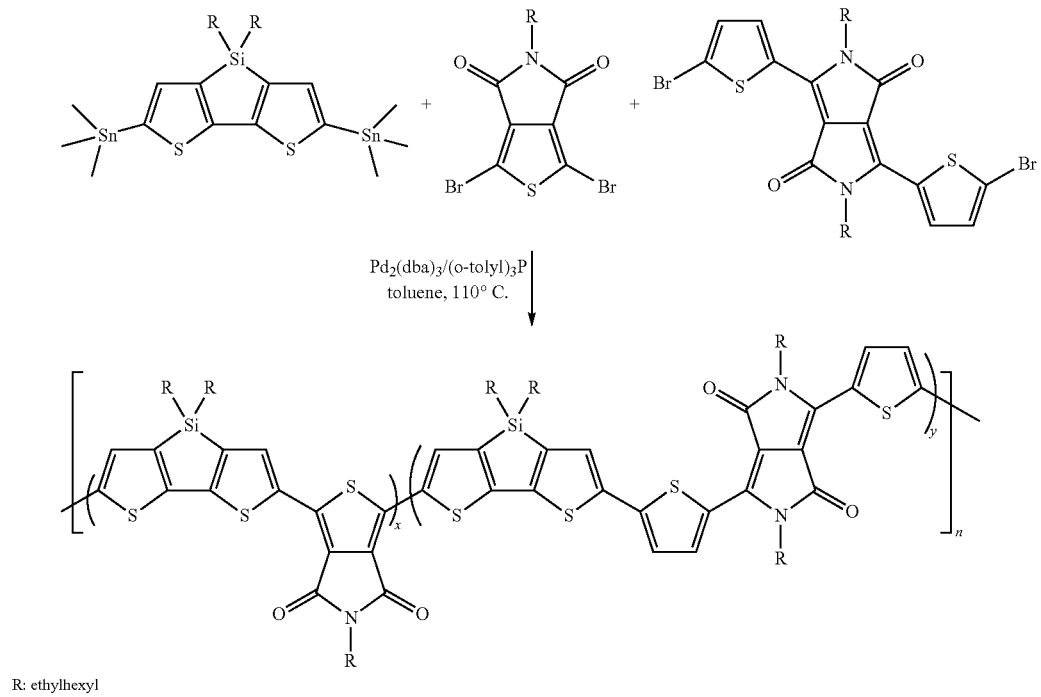

R: ethylhexyl

Example 9 poly{(2,6'-4,8-diethylhexyloxybenzo[1,2-b;3,4-b]dithiophene-alt-(5-(2-ethylhexyl)thieno[3,4-c]pyrrole-4,6-dione)-alt-(2,6'-4,8-diethylhexyloxybenzo[1,2-b;3,4-b]dithiophene-alt-5-diethylhexyl-3,6-dithiophen-2-ylpyrrolo[3,4-c]pyrrole-1,4-dione)}

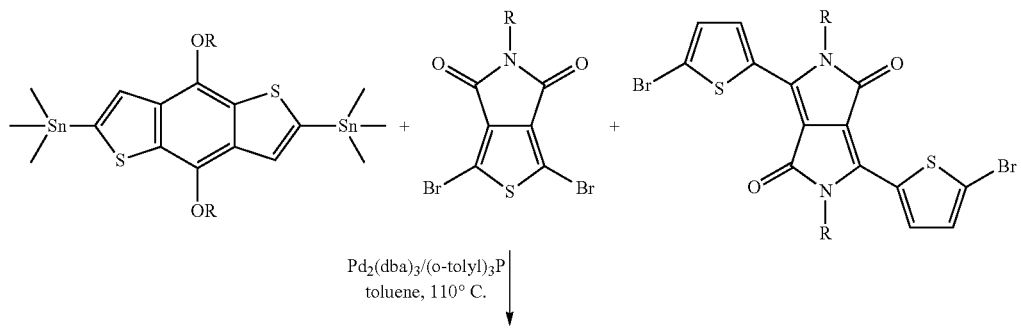

Pd$_2$(dba)$_3$/(o-tolyl)$_3$P
toluene, 110° C.

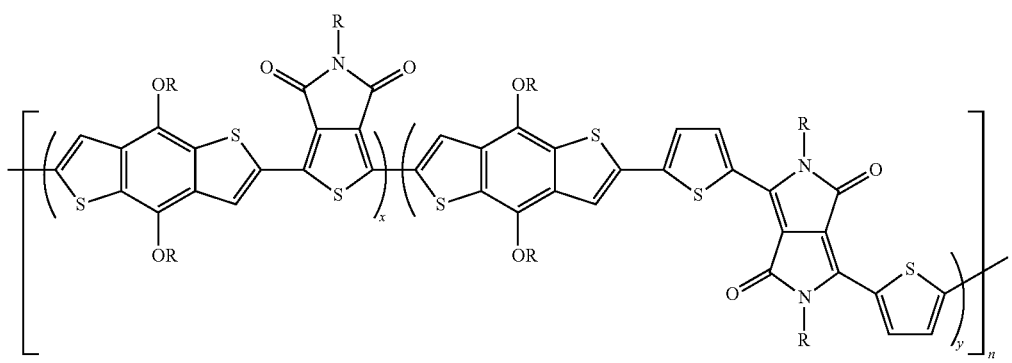

R: ethylhexyl

In a glove box, 2,6-bis(trimethyltin)-4,8-diethylhexyloxybenzo[1,2-b;3,4-b]dithiophene (0.4 g, 0.52 mmol), 1,3-dibromo-5-(2-ethylhexyl)thieno[3,4-c]pyrrole-4,6-dione (0.11 g, 0.26 mmol), 2,5-diethylhexyl-3,6-bis(5-bromothiophen-2-yl)pyrrolo[3,4-c]-pyrrole-1,4-dione (0.18 g, 0.26 mmol), tris(dibenzylideneacetone)dipalladium(0) (0.012 g, 0.013 mmol) and tris(o-tolyl)phosphine (0.016 g, 0.052 mmol) were weighted out into a flame dried 50 mL Schlenk flask. Reaction flask was removed from the glove box and 6 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (0.29 g, 67%). Molecular weight was determined by GPC in 1,3,5-trichlorobenzene (1 mL/min at 150° C.) vs. polystyrene standards: $M_n$=26,100, $M_w$=74,100, PDI=2.8.

Example 10

Structure IIIG. poly{(4,4'-bis(2-ethylhexyl)dithieno[3,2-b:2',3'-d]silole-alt-5-(2-ethylhexyl)thieno[3,4-c]pyrrole-4,6-dione)-alt-(4,4'-bis(2-ethylhexyl)dithieno[3,2-b:2',3'-d]silole-alt-2-benzo[1,2,5]thiadiazole)}

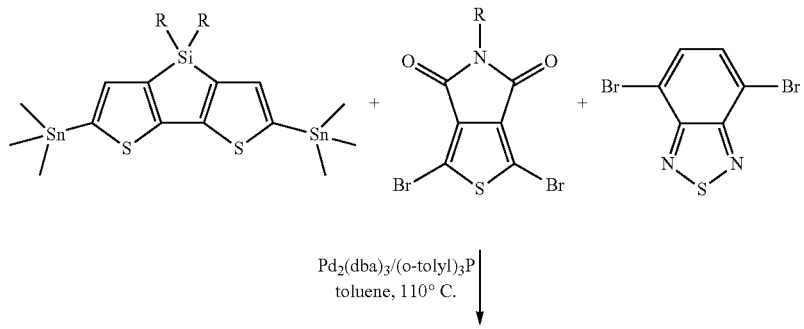

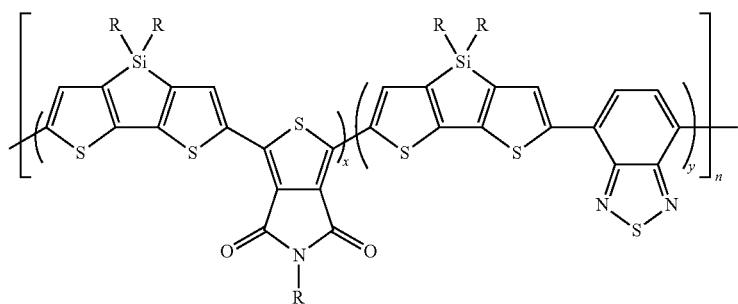

R: ethylhexyl

In a glove box, 4,4'-bis(2-ethylhexyl)-5,5'-bis(trimethyltin)dithieno[3,2-b:2',3'-d]silole (0.40 g, 0.54 mmol), 1,3-dibromo-5-(2-ethylhexyl)thieno[3,4-c]pyrrole-4,6-dione (0.11 g, 0.26 mmol), 4,7-dibromo-benzo[1,2,5]thiadiazole (0.075 g, 0.26 mmol), tris(dibenzylideneacetone)dipalladium(0) (0.012 g, 0.013 mmol) and tris(o-tolyl)phosphine (0.016 g, 0.053 mmol) were weighed out into a flame dried 50 mL Schlenk flask. Reaction flask was removed from the glove box and 7 mL of deoxygenated toluene were added via syringe. The mixture was evacuated and refilled with argon five times. The reaction flask was immersed into a preheated to 110° C. oil bath and was left stirring under an argon stream for 12 hours. The polymerization was quenched with 0.3 mL of 2-iodothiophene and stirred at 110° C. for additional two hours. The oil bath was removed and after cooling to room temperature, 40 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, and hexane. The hexanes fraction was passed through celite, to remove catalyst residuals, and solvent was removed under vacuum to yield a brown-copper colored polymer (0.15 g, 45%). Molecular weight was determined by GPC in chloroform (1 mL/min at 35° C.) vs. polystyrene standards: $M_n$=4,910, $M_w$=10,700, PDI=2.2.

Prophetic Examples

Example 11

(Prophetic) General Procedure for the Synthesis of 4,8-diethylhexyloxybenzo[1,2-b;3,4-b]dithiophene-enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} Via Stille Cross-Coupling Polymerization

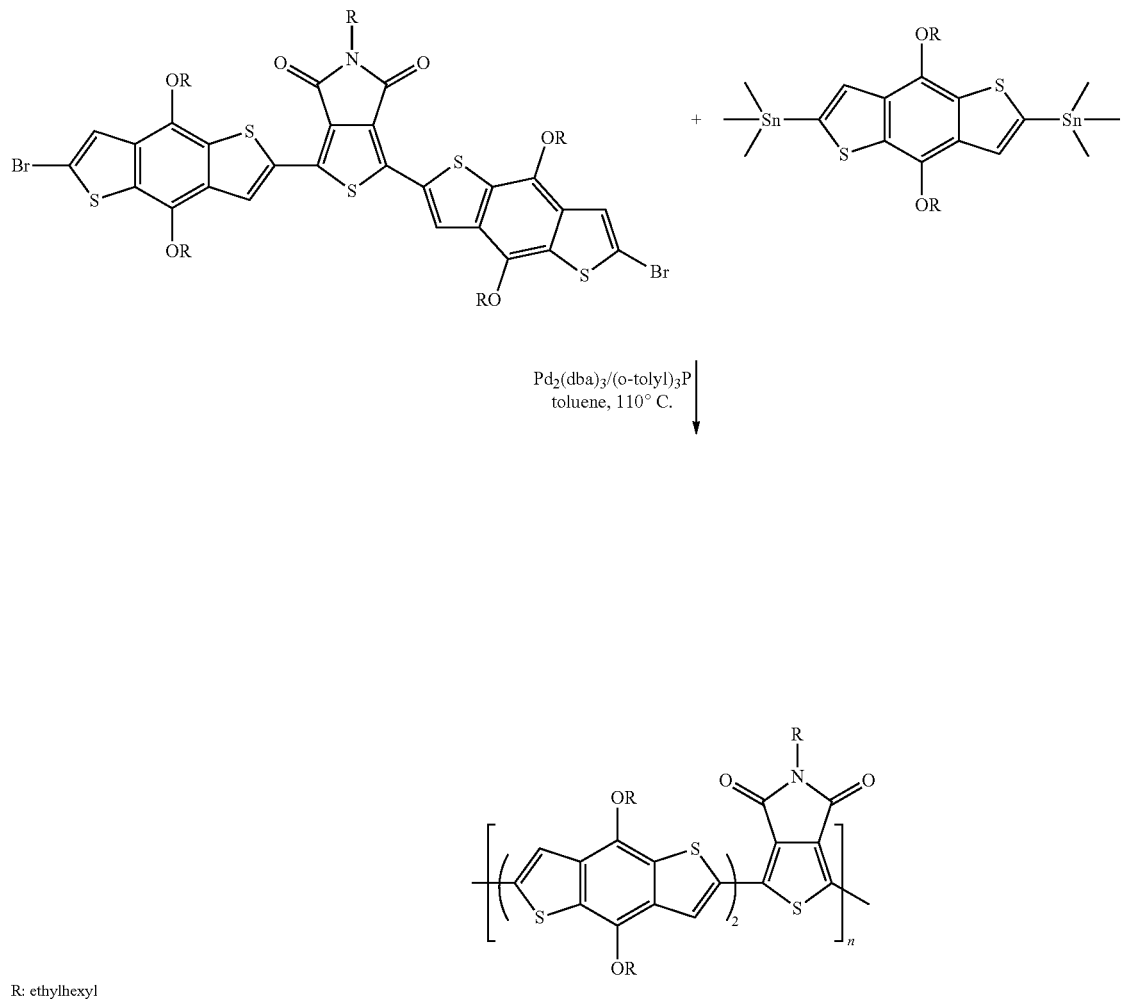

R: ethylhexyl

In a glove box, dibromo-(1,3-bis(4,8-diethylhexyloxybenzo[1,2-b;3,4-b]dithiophene)-5-(2-ethylhexyl)thieno[3,4-c]pyrrole-4,6-dione) (0.50 mmol), 2,6-bis(trimethyltin)-4,8-diethylhexyloxybenzo[1,2-b;3,4-b]dithiophene (0.50 mmol), tris(dibenzylideneacetone)dipalladium(0) (2.5 mol %) and tris(o-tolyl)phosphine (0.050 mmol) are charged into a flame dried 50 mL Schlenk flask. The reaction flask is removed from the glove box and 6 mL of deoxygenated toluene are added via syringe. The mixture is evacuated and refilled with argon five times. The reaction flask is immersed into a preheated to 110° C. oil bath and left stirring under an argon stream for 12 hours. The polymerization is quenched with 0.3 mL of 2-iodothiophene and stirred at 110° C. for additional two hours. The oil bath is removed and after cooling to room temperature, 40 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Hexanes and chloroform fractions are concentrated, re-precipitated in methanol, isolated via filtration, and analyzed by gel permeation chromatography (GPC) and NMR.

Furthermore, in addition to Example 11, a number of other complementary procedures based on transition metal-assisted/catalyzed cross-coupling reactions for the synthesis of alternating dioxopyrrolo-based donor-acceptor polymers that would preserve regular alternation of a monomer sequence in the polymer backbone can be extended to many other organometallic species. Several exemplary synthetic schemes are presented below that involve the use of Grignard (Kumada cross-coupling; lit. ref.: Yamamoto et al., *Macromolecules* 1992, 25, 1214.; Scheme A) and/or organozinc (Negishi cross-coupling; lit. ref: Knochel, et al., Scheme B) reagents, and/or organitin intermediates (Woo, et al., *J. Am. Chem. Soc.* 2008, 130, 16324.; Scheme C).

Scheme A

General Synthetic Scheme for the Synthesis of 4,8-diethylhexyloxybenzo[1,2-b;3,4-b]dithiophene Enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} Via Kumada Cross-Coupling Polymerization

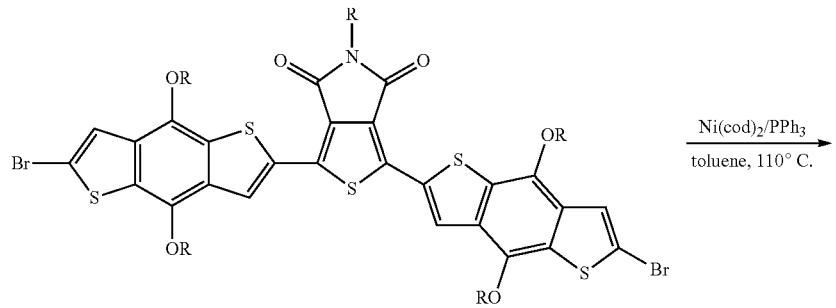

R: ethylhexyl

Scheme B

General Procedure for the Synthesis of 1,3-bis(4,8-diethylhexyloxybenzo[1,2-b;3,4-b]dithiophene)-5-(2-ethylhexyl)thieno[3,4-c]pyrrole-4,6-dione (Top) and 4,8-diethylhexyloxybenzo[1,2-b;3,4-b]dithiophene Enriched poly{bis(2,6'-4,8-diethylhexyloxybenzo[1,2-b;3,4-b]dithiophene)-alt-(5-(2-ethylhexyl)thieno[3,4-c]pyrrole-4,6-dione} Via Negishi Cross-Coupling Reaction

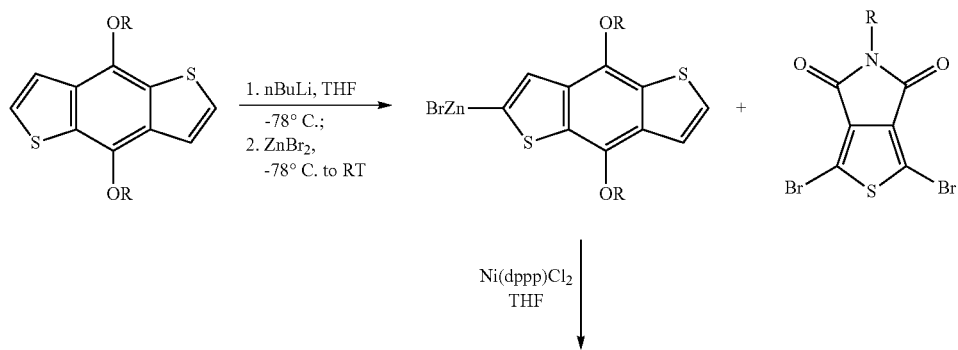

-continued
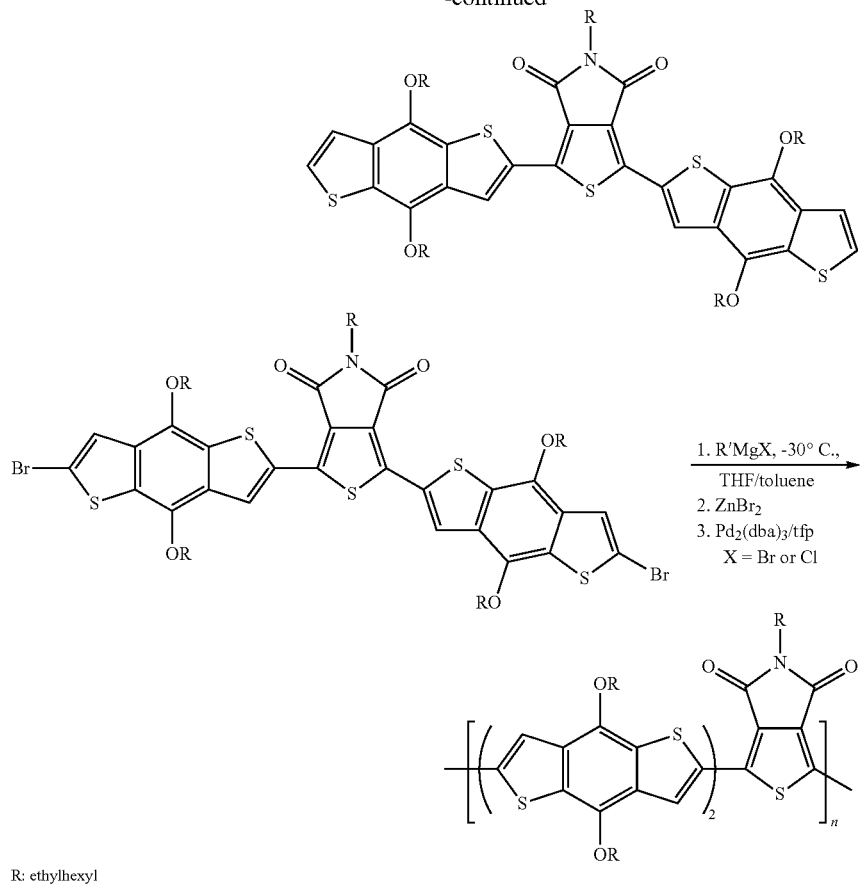
R: ethylhexyl
Scheme C
General Procedure for the Synthesis of 1,3-bis(4,8-diethylhexyloxybenzo[1,2-b;3,4-b]dithiophene)-5-(2-ethylhexyl)thieno[3,4-c]pyrrole-4,6-dione Via Stille Cross-Coupling Reaction
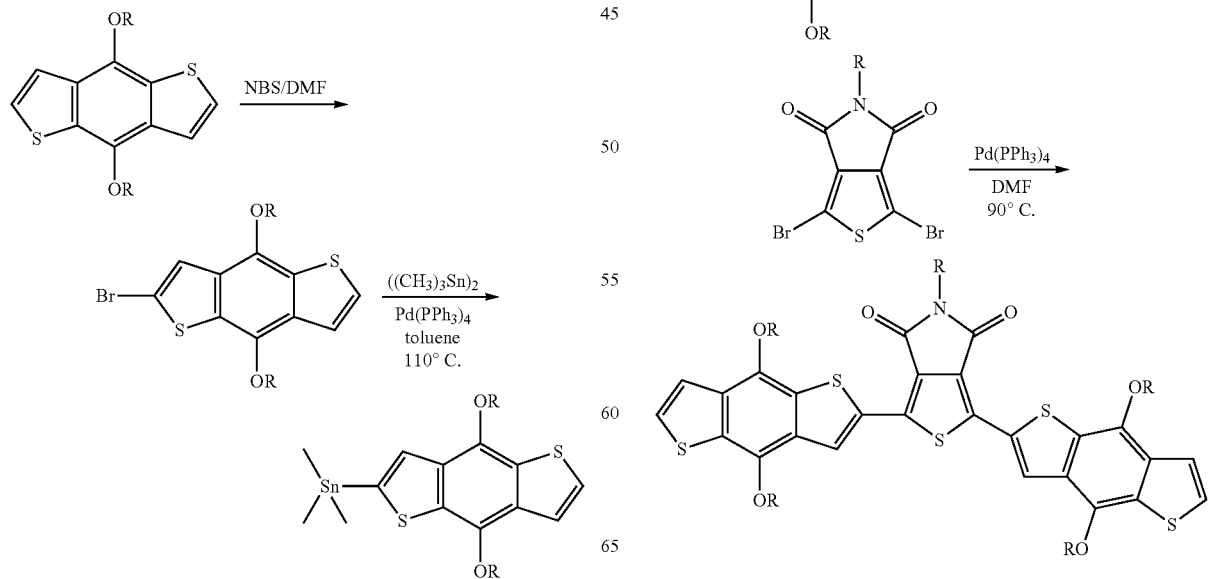

All polymer samples are precipitated in methanol, filtered, and purified by Soxhlet extractions utilizing successively methanol, acetone, hexanes, and chloroform and/or passing thru a bed of celite. Hexanes and chloroform fractions are concentrated, re-precipitated in methanol, isolated via filtration, and analyzed by gel permeation chromatography (GPC) and NMR.

II. Testing of Polymers Including Device Fabrication and Testing

Figure 3:
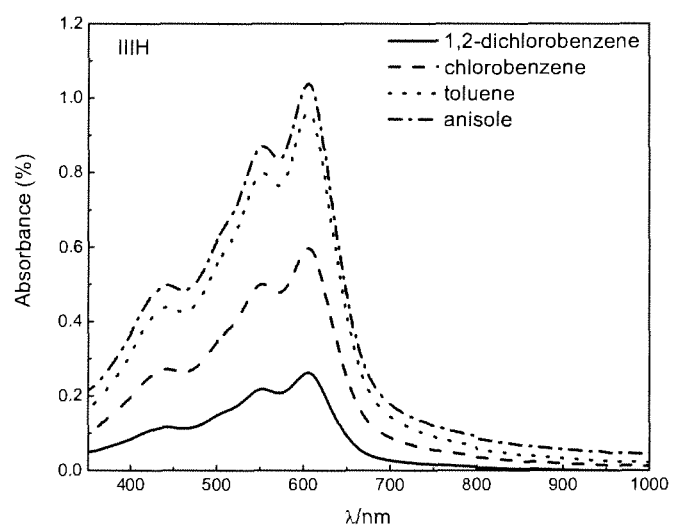
FIG. 3 shows absorption spectra for four films of donor-acceptor polymer prepared from four solutions with four different solvents (no n-type material).

FIG. 3. UV-Vis absorption profile of Polymer III-H (Example 6) Donor-Acceptor polymer containing dioxypyrrolo-functionality in thin films spin cast from different solvents.

FIG. 3 shows the absorption spectrum for a series of films of Polymer III-H/C60-PCBM (Example 6). An important observation in all of these films is the presence of vibronic structure which is indicative of a well-defined chromophore. While not limited by theory, this can result from the presence of strong oxygen-sulfur interactions that can help to rigidify and/or significantly planarize the donor-acceptor units thus reducing dihedral angles between the adjacent thiophene rings. This planarizing non-covalent binding interaction can serve to rigidify the chromophore which presumably helps to increase extinction due to increased packing density, charge transport and yield well-behaved photophysics (e.g., long exciton diffusion lengths and excited state lifetimes). Dihedral twisting is often a consequence of excited state relaxation. Elimination of such effect can yield the aforementioned improved chemico-physical properties. This vibronic structure effect can be seen in rigid chromophores like porphyrin and less so in semi-crystalline conjugated polymers like P3HT. The effect is believed to be non-existent or almost non-existent in most of amorphous D-A conjugated polymers synthesized in the prior art.

Fabrication of Solar Cell Devices Using Polymers and Fullerene Acceptors

Inks were formulated with a fullerene derivative acceptor and solvent.

Indium tin oxide ("ITO") coated glass substrates were purchased from Thin Film Devices ("TFD", Anaheim, Calif.). These substrates were cleaned in a Class 10,000 clean room by sonicating for 20 min in a soap solution, followed by 20 min of sonication in water, 20 min of sonication in acetone and 20 min of sonication in IPA. Finally the substrates were exposed to UV ozone (300 W) for 10 min. After cleaning, each substrate was then coated with a ~30 nm thick layer of Baytron AI4083 (H.C Stark) by spin coating for 5 seconds at 400 rpm in air, followed by a 1 minute at 6000 rpm. The devices were then transferred to a $N_2$ atmosphere glovebox and annealed on a hot plate at 175° C. for 30 min.

The active layer was then spin-coated on top of the PEDOT:PSS layer on a Headway spinner at spin speeds ranging from 300-1000 rpm to obtain the required active layer thickness. The active layer films were either allowed to dry in the glovebox or were annealing on the hot plate to dry. Finally, after annealing, the cathode was vapor deposited from a base pressure of ~7×10⁻⁷. In all of the following working examples, the cathode for the devices was a bilayer of Ca (25 nm) and Al (200 nm). The Ca and Al were deposited at rates of 0.3 Å/s and 4 Å/s respectively. The devices were then encapsulated via a glass cover slip (blanket) encapsulation sealed with EPO-TEK OG112-4 UV curable glue. The encapsulated device was cured under UV irradiation (80 mW/cm²) for 4 minutes and tested as follows.

The photovoltaic characteristics of devices under white light exposure (Air Mass 1.5 Global Filter) were measured using a system equipped with a Keithley 2400 source meter and an Oriel 300 W Solar Simulator based on a Xe lamp with output intensity of 100 mW/cm² (AM1.5G). The light intensity was set using an NREL-certified S1-KG5 silicon photodiode.

Power Conversion Efficiency Determinations

Devices were prepared as described above were tested using an Oriel Solar Simulator and the voltage was swept from reverse to forward bias. From the resulting current that was measured, the power conversion efficiency of each device was determined. Data for each device are summarized in Table 1 as well as relevant processing parameters for each device.

TABLE 1

Photovoltaic Performance of single layer OPVs based on Donor-Acceptor polymers comprising dioxypyrrolo-functionality.

| Polymer | N-type | P:N ratio | Solvent (volume solids) | Drying Conditions | Jsc (mA/cm²) | Voc (V) | FF | PCE (%) |
|---|---|---|---|---|---|---|---|---|
| Ex. 6 | C70-PCBM | 1:1 | dichlorobenzene (0.0157) | No anneal | 8.11 | 0.78 | 0.57 | 3.6 |
| Ex. 9 | C70-PCBM | 1:4 | trichlorobenzene (0.011) | Anneal at 60° C. for 18 minutes | 10.12 | 0.69 | 0.53 | 3.6 |

TABLE 2

Comparison in Absorption coefficients, Alpha, for poly(3-hexylthiophene) and Donor-Acceptor polymers comprising dioxypyrrolo-functionality

| Polymer | Abs | b (cm) | b (nm) | Alpha* (cm⁻¹) |
|---|---|---|---|---|
| P3HT | 0.270 | 6.40 × 10⁻⁶ | 64 | 0.97 × 10⁵ |
| Ex. 9 | 0.196 | 2.25 × 10⁻⁶ | 22 | 2.01 × 10⁵ |
| Ex. 6 | 0.409 | 5.70 × 10⁻⁶ | 57 | 1.65 × 10⁵ |

*$\alpha = 2.3 \times Abs_{(at\,\lambda max)}/b_{(film\,thickness\,in\,cm)}$ [in thin films]

The new polymers exhibit approximately 2× increase in absorptivity (based on alpha) vs. P3HT suggesting more planar structure, dense/small interchain distance that could result in increase in $J_{SC}$ and, thus, superior OPV performance (P3HT is poly(3-hexylthiophene)).

Figure 4:
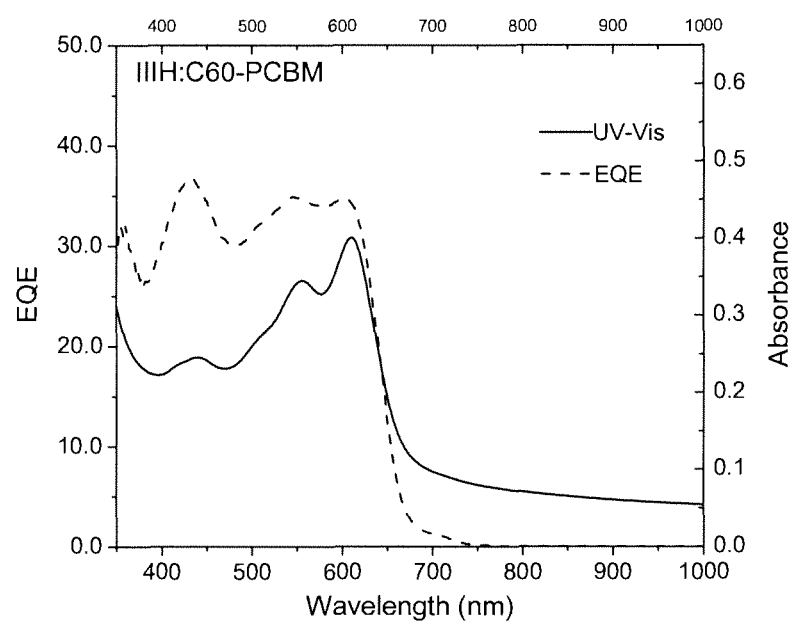
FIG. 4 shows EQE and absorption spectra for donor-acceptor polymer (Example 6) mixed with n-type material (C60 derivative) in a photovoltaic device active layer.

FIG. 4: Comparison of absorption and EQE spectra of device with III-H:C60-PCBM blend. It is evident from the data that the devices based on III-H (Ex. 6) exhibit a relatively broad response range covering from about 400 nm to about 650 nm. The absorption is relatively flat without substantial gaps.

FIG. 5: Comparison of absorption and EQE spectra of device with III-C:C60-PCBM blend (Ex. 9 is Structure III-C). The absorption is broader into the red region compared to FIG. 4.

Additional Embodiments

Example 12

4,8-bis(3-ethylhept-1-ynyl)thieno[2,3-f]benzothiophene

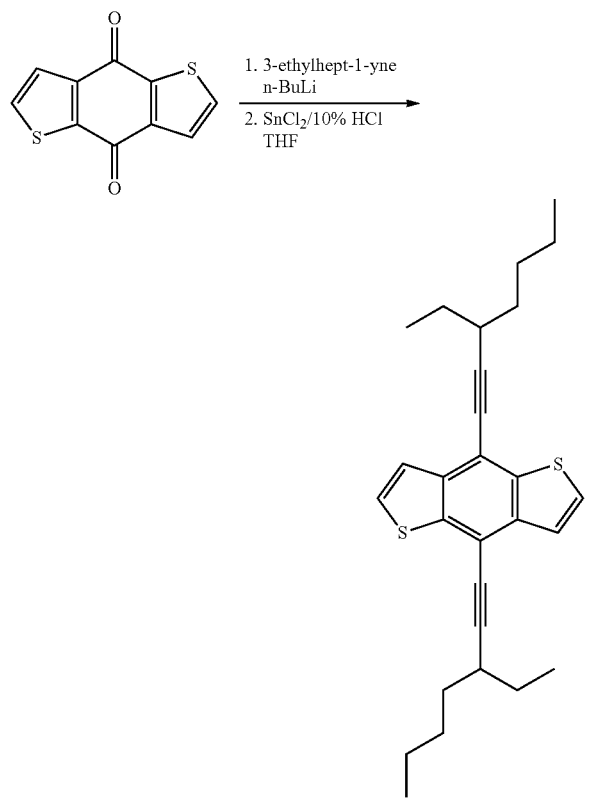 [SMILES: O=C1c2ccsc2C(=O)c2ccsc21 ; CCCCC(C#Cc1c2ccsc2c(C#CC(CC)CCCC)c2ccsc12)CC]

A dry 100-mL three-neck flask with an attached reflux condenser and addition funnel was charged with 3-ethylhept-1-yne (7.96 g, 0.0641 mol) and flushed with N₂. A 2 M solution of iso-propylmagnesium chloride in THF (21.1 mL, 0.0583 mol) was added dropwise via deoxygenated syringe. The reaction mixture was stirred for 30 minutes at ambient temperature and a 0.2 M solution of benzo[1,2-b:4,5-b']dithiophene-4,8-dione (5.7 g, 0.0256 mol) in anhydrous THF (130 mL) was added portion-wise via addition funnel. The reaction was heated to reflux for 1 hour. As the reaction was completed, it was cooled down to room temperature. A solution of SnCl₂ (12 g) dissolved in 10% HCl (114 mL) was added to the reaction flask and stirred, increasing temperature to reflux for 1 hour and then cooling the reaction to ambient temperature. The reaction was poured into 100 mL of cool water with 10 mL of 10% HCl and extracted with MTBE (200 mL) three times. The combined organic layer was dried over anhydrous magnesium sulfate (MgSO₄). After the product was filtered, the solvent was removed by rotary evaporation. The product was purified using column chromatography on silica gel with hexanes to yield colorless oil (7.8 g, 70%).

Example 13

4,8-bis(3-ethylheptyl)thieno[2,3-f]benzothiophene

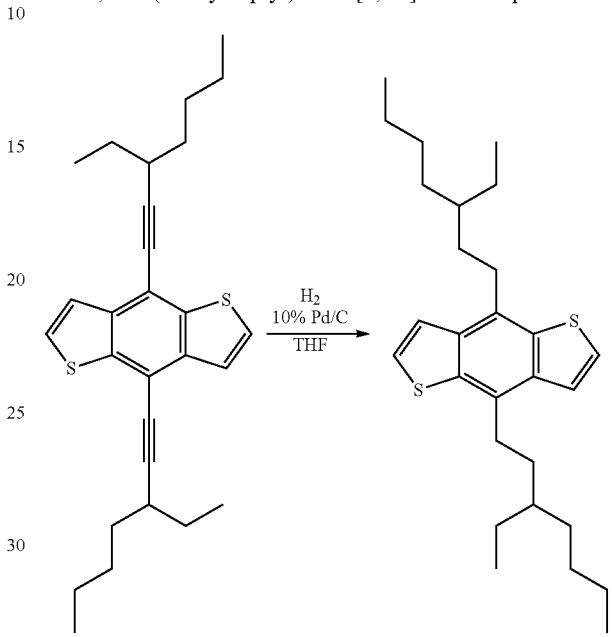

A dry 250 mL 1-neck flask was flushed with N₂ and was charged with 4,8-bis(3-ethylhept-1-ynyl)thieno[2,3-f]benzothiophene (3.04 g, 0.007 mol), Pd/C wet support (0.82 g, 10%) and THF (15 mL, 0.5 M). The flask was evacuated and backfilled with hydrogen. The flask was kept under a hydrogen atmosphere and was monitored by TLC. After the reaction was completed, the mixture was filtered through Celite and solvent was removed by rotary evaporation. The solid was dissolved in hexanes and purified by column chromatography to yield oil (1.66 g, 54%).

Example 14 poly{(2,6'-4,8-diethylhexyloxybenzo[1,2-b;3,4-b]dithiophene-alt-(5-(2-ethylhexyl)thieno[3,4-c]pyrrole-4,6-dione)-ran-(2,6'-4,8-diethylhexyloxybenzo[1,2-b;3,4-b]dithiophene-alt-4,7-[2,1,3-benzothiadiazole])}

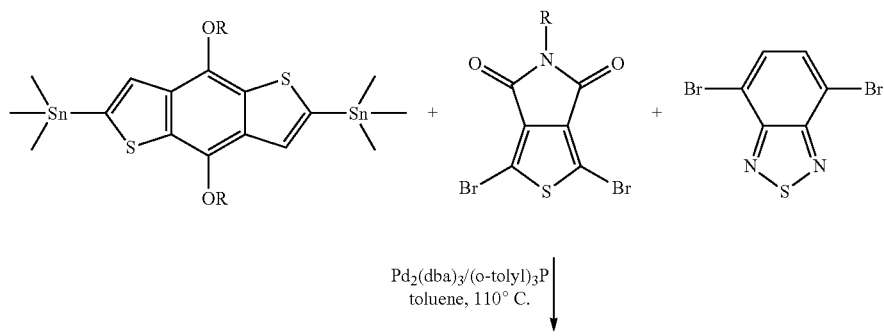

Pd₂(dba)₃/(o-tolyl)₃P
toluene, 110° C.

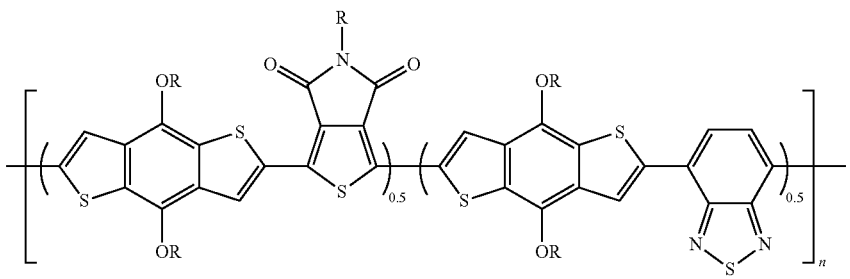

R: ethylhexyl

In a glove box, 2,6-bis(trimethyltin)-4,8-diethylhexyloxybenzo[1,2-b;3,4-b]dithiophene (0.30 g, 0.39 mmol), 1,3-dibromo-5-(2-ethylhexyl)thieno[3,4-c]pyrrole-4,6-dione (0.082 g, 0.19 mmol), 4,7-dibromo-2,1,3-benzothiadiazole (0.057 g, 0.19 mmol), tris(dibenzylideneacetone)dipalladium (0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 10 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.3 mL of 2-iodothiophene and stirred at 110° C. for additional two hours. The oil bath was removed and after cooling to room temperature, 30 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform insoluble fraction was redissolved in oDCB, precipitated in methanol:IPA:water mixture, and the polymer was collected via filtration (0.20 g, 80%). Molecular weight was determined by GPC in 1,3,5-trichlorobenzene (1 mL/min at 150° C.) vs. polystyrene standards: $M_n$=40,100, $M_w$=151,850, PDI=3.8.

Example 15 poly{(2,6'-4,8-diethylhexyloxybenzo[1,2-b;3,4-b]dithiophene-alt-(5-(2-ethylhexyl)thieno[3,4-c]pyrrole-4,6-dione)-ran-(2,6'-4,8-diethylhexyloxybenzo[1,2-b;3,4-b]dithiophene-alt-4,7-[2,1,3-benzothiadiazole])-ran-(2,6'-4,8-diethylhexyloxybenzo[1,2-b;3,4-b]dithiophene-alt-4-(2-ethylhexyl)-N,N-diphenyl-aniline)}

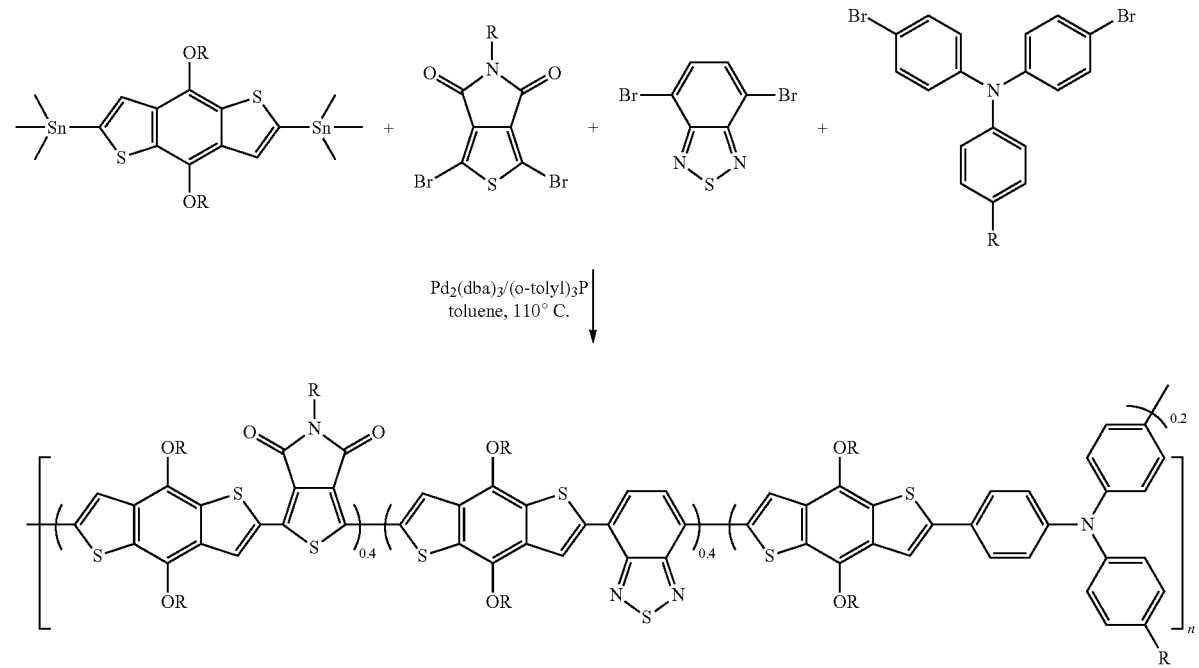

R: ethylhexyl

In a glove box, 2,6-bis(trimethyltin)-4,8-diethylhexyloxybenzo[1,2-b;3,4-b]dithiophene (0.50 g, 0.65 mmol), 1,3-dibromo-5-(2-ethylhexyl)thieno[3,4-c]pyrrole-4,6-dione (0.11 g, 0.26 mmol), 4,7-dibromo-2,1,3-benzothiadiazole (0.76 g, 0.26 mmol), 4-bromo-N-(4-bromophenyl)-N-[4-(2-ethylhexyl)phenyl]aniline (0.067 g, 0.13 mmol), tris(dibenzylideneacetone)dipalladium(0) (15 mg, 0.016 mmol) and tris(o-tolyl)phosphine (0.020 g, 0.065 mmol) were weighted out into a flame dried 100 mL Schlenk flask. Reaction flask was removed from the glove box and 51 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.3 mL of 2-iodothiophene and stirred at 110° C. for additional two hours. The oil bath was removed and after cooling to room temperature, 30 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (40%). Molecular weight was determined by GPC in 1,3,5-trichlorobenzene (1 mL/min at 150° C.) vs. polystyrene standards: $M_n$=15,300, $M_w$=33,100, PDI=2.2.

Example 16 poly{(2,6'-4,8-diethylhexyloxybenzo[1,2-b;3,4-b]dithiophene-alt-(5-(2-ethylhexyl)thieno[3,4-c]pyrrole-4,6-dione)-ran-(2,6'-4,8-diethylhexyloxybenzo[1,2-b;3,4-b]dithiophene-alt-4,7-[2,1,3-benzothiadiazole])-ran-(2,6'-4,8-diethylhexyloxybenzo[1,2-b;3,4-b]dithiophene-alt-9-(2-ethylhexyl)carbazole)}

In a glove box, 2,6-bis(trimethyltin)-4,8-diethylhexyloxybenzo[1,2-b;3,4-b]dithiophene (0.50 g, 0.65 mmol), 1,3-dibromo-5-(2-ethylhexyl)thieno[3,4-c]pyrrole-4,6-dione (0.096 g, 0.23 mmol), 4,7-dibromo-2,1,3-benzothiadiazole (0.066 g, 0.23 mmol), 2,7-dibromo-9-(2-ethylhexyl)carbazole (0.085 g, 0.19 mmol), tris(dibenzylideneacetone)dipalladium(0) (15 mg, 0.016 mmol) and tris(o-tolyl)phosphine (0.020 g, 0.065 mmol) were weighted out into a flame dried 100 mL Schlenk flask. Reaction flask was removed from the glove box and 13 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.2 mL of 2-iodothiophene and stirred at 110° C. for additional two hours. The oil bath was removed and after cooling to room temperature, 30 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (40%). Molecular weight was determined by GPC in 1,3,5-trichlorobenzene (1 mL/min at 150° C.) vs. polystyrene standards: $M_n$=24,220, $M_w$=68,700, PDI=2.8.

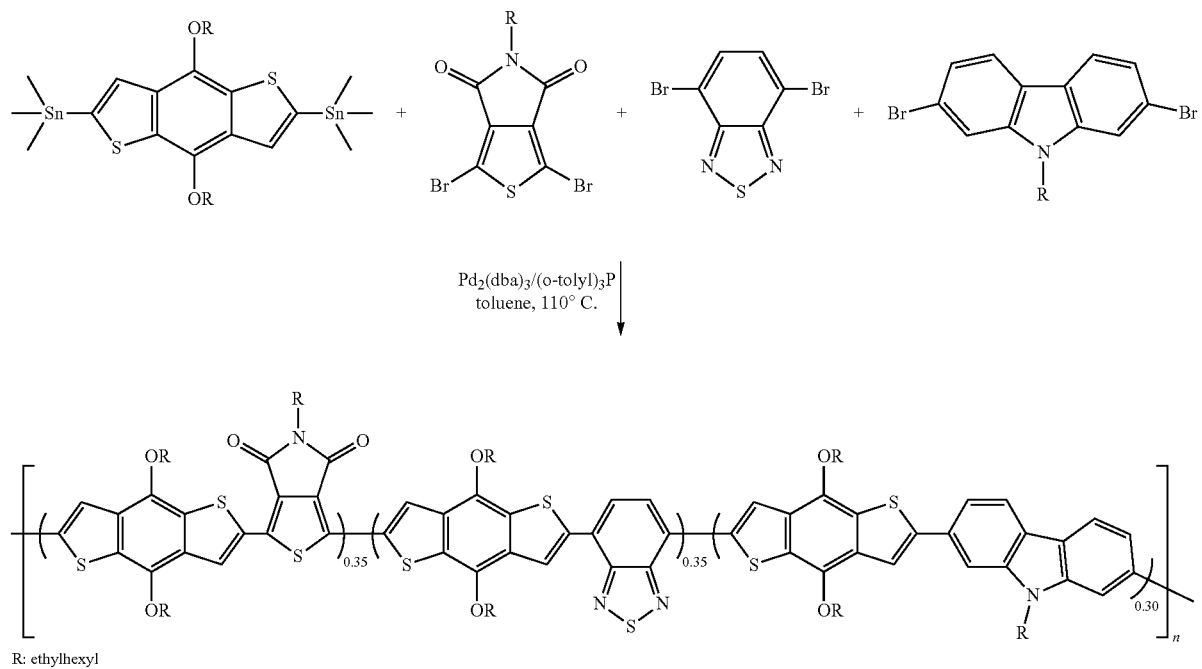

Example 17 poly{(2,6'-4,8-diethylhexyloxybenzo[1,2-b;3,4-b]dithiophene-alt-(5-(3,7-dimethyloctyl)thieno[3,4-c]pyrrole-4,6-dione)-ran-(2,6'-4,8-diethylhexyloxybenzo[1,2-b;3,4-b]dithiophene-alt-4,7-[2,1,3-benzothiadiazole])}

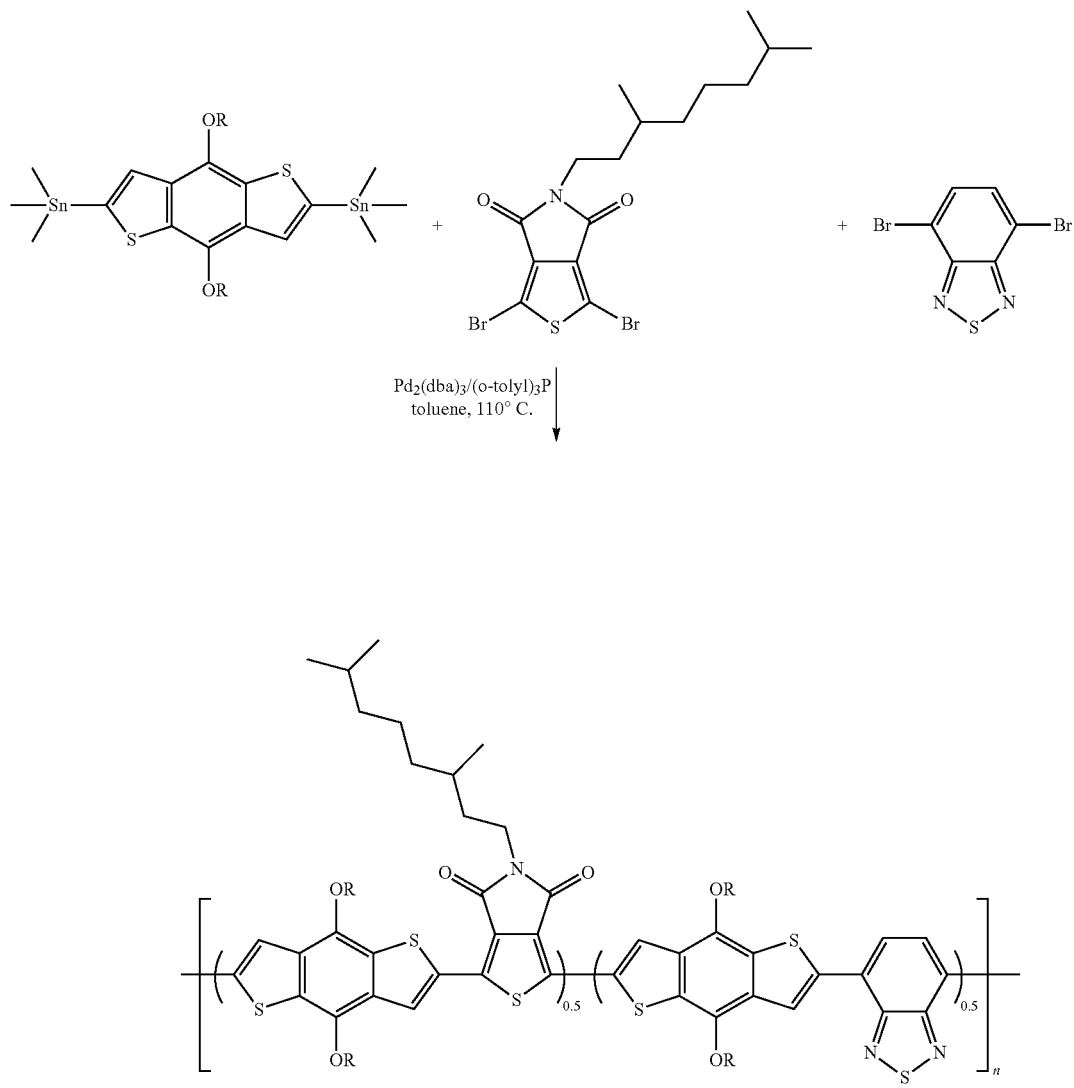

R: ethylhexyl

In a glove box, 2,6-bis(trimethyltin)-4,8-diethylhexyloxybenzo[1,2-b;3,4-b]dithiophene (0.3 g, 0.39 mmol), 1,3-dibromo-5-(3,7-dimethyloctyl)thieno[3,4-c]pyrrole-4,6-dione (0.088 g, 0.19 mmol), 4,7-dibromo-2,1,3-benzothiadiazole (0.057 g, 0.19 mmol), tris(dibenzylideneacetone)dipalladium (0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.2 mL of 2-iodothiophene and stirred at 110° C. for additional two hours. The oil bath was removed and after cooling to room temperature, 30 mL of acidified (1 mL of 5 N HCl) methanol were added to the reaction mixture under vigorous stirring to induce precipitation. The final mixture was poured into 200 mL of methanol and the polymer was collected via filtration. The polymer was purified by consecutive Soxhlet extractions in sequence with MTBE, hexane, and chloroform. The chloroform insoluble fraction was redissolved in oDCB, precipitated in methanol:IPA:water mixture, and the polymer was collected via filtration (0.20 g, 77%). Molecular weight was determined by GPC in 1,3,5-trichlorobenzene (1 mL/min at 150° C.) vs. polystyrene standards: $M_n$=33,800, $M_w$=109,400, PDI=3.8.

Example 18 poly{(2,6'-4,8-diethylhexyloxybenzo[1,2-b;3,4-b]dithiophene-alt-(5-(2-ethylhexyl)thieno[3,4-c]pyrrole-4,6-dione)-ran-(2,6'-4,8-diethylhexyloxybenzo[1,2-b;3,4-b]dithiophene-alt-4,7-[2,1,3-benzothiadiazole])}

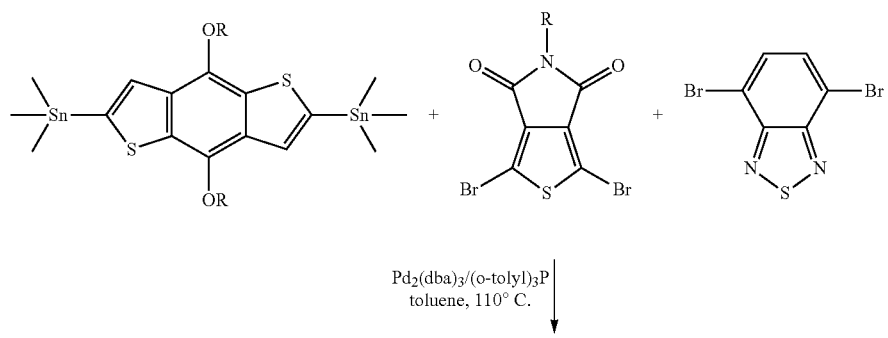

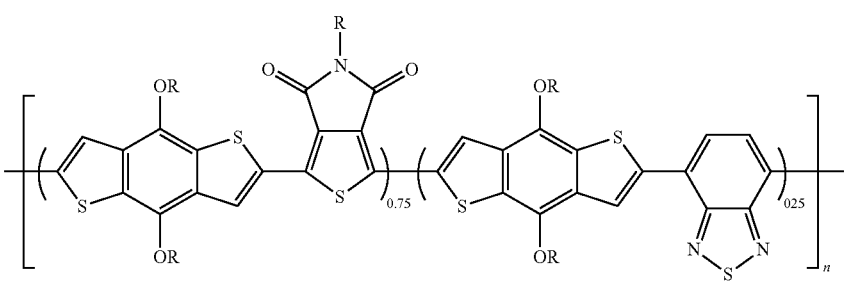

R: ethylhexyl

In a glove box, 2,6-bis(trimethyltin)-4,8-diethylhexyloxybenzo[1,2-b;3,4-b]dithiophene (0.30 g, 0.39 mmol), 1,3-dibromo-5-(2-ethylhexyl)thieno[3,4-c]pyrrole-4,6-dione (0.12 g, 0.29 mmol), 4,7-dibromo-2,1,3-benzothiadiazole (0.028 g, 0.097 mmol), tris(dibenzylideneacetone)dipalladium(0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.2 mL of 2-iodothiophene and stirred at 110° C. for additional two hours. The oil bath was removed and after cooling to room temperature, 30 mL of acidified methanol (2 mL of acetic acid) were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform fraction was passed through celite, to remove catalyst residuals, and solvent was removed under vacuum to yield a brown-copper colored polymer (40%). Molecular weight was determined by GPC in 1,3,5-trichlorobenzene (1 mL/min at 150° C.) vs. polystyrene standards: $M_n$=37,160, $M_w$=103,400, PDI=2.8.

Example 19 poly{(4,8-bis(3-ethylheptyl)thieno[2,3-f]benzothiophene-alt-(5-(2-ethylhexyl)thieno[3,4-c]pyrrole-4,6-dione)-ran-(4,8-bis(3-ethylheptyl)thieno[2,3-f]benzothiophene-alt-4,7-[2,1,3-benzothiadiazole])}

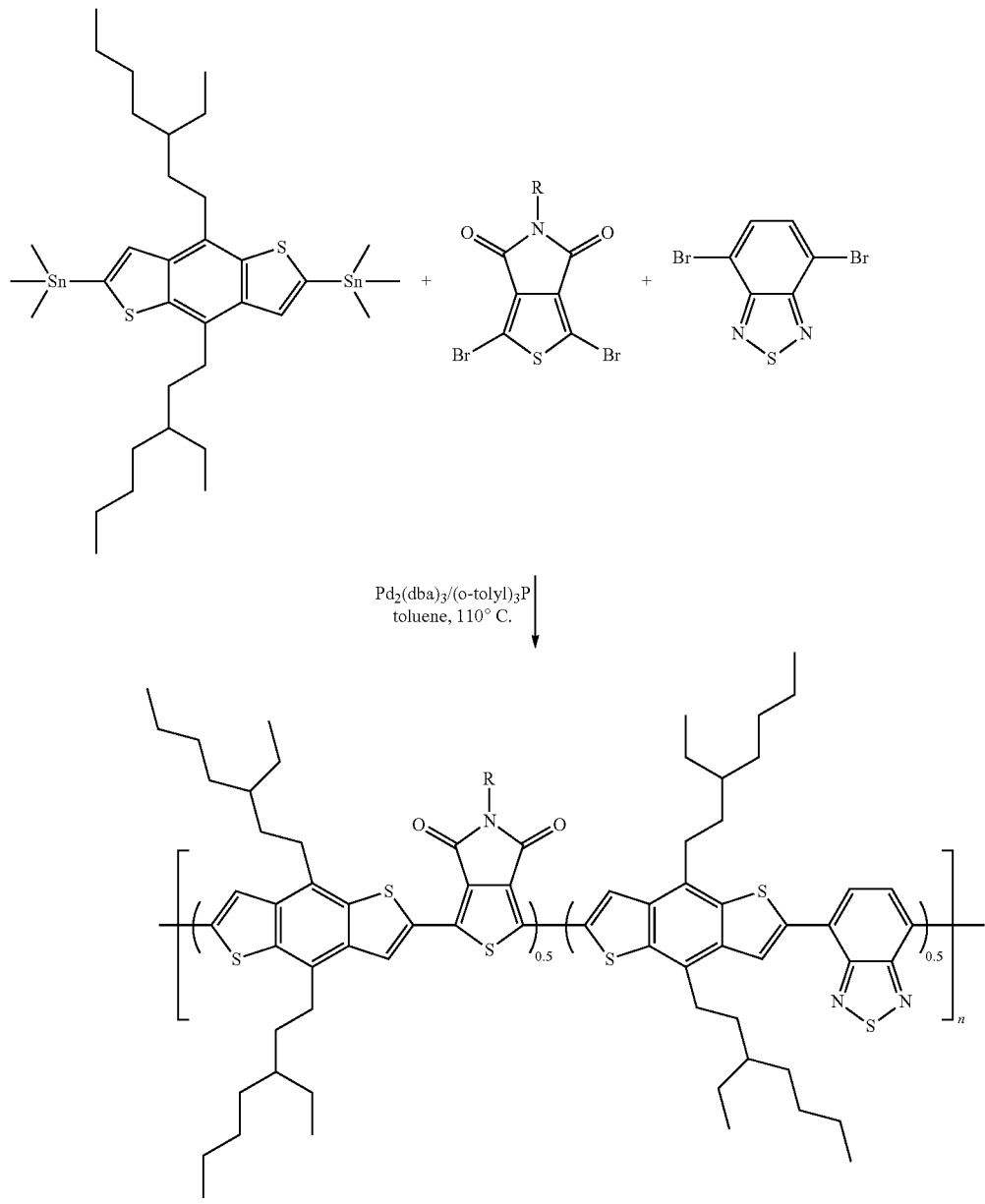

R: ethylhexyl

In a glove box, [4,8-bis(3-ethylheptyl)-6-trimethylstannyl-thieno[2,3-f]benzothiophen-2-yl]-trimethyl-stannane (0.30 g, 0.39 mmol), 1,3-dibromo-5-(2-ethylhexyl)thieno[3,4-c]pyrrole-4,6-dione (0.082 g, 0.19 mmol), 4,7-dibromo-2,1,3-benzothiadiazole (0.057 g, 0.19 mmol), tris(dibenzylideneacetone)dipalladium(0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 14 hours. The polymerization was quenched with 0.2 mL of 2-iodothiophene and stirred at 110° C. for additional two hours. The oil bath was removed and after cooling to room temperature, 30 mL of acidified methanol (2 mL of acetic acid) were added to the reaction mixture under vigorous stirring to induce precipitation. The final mixture was poured into 200 mL of methanol and the polymer was collected via filtration. The polymer was purified by consecutive Soxhlet extractions in sequence with methanol, acetone, hexane, and chloroform. The chloroform insoluble fraction was redissolved in oDCB, precipitated in methanol:IPA:water mixture, and the polymer was collected via filtration (0.20 g, 80%). Molecular weight was determined by GPC in 1,3,5-trichlorobenzene (1 mL/min at 150° C.) vs. polystyrene standards: $M_n$=23,150, $M_w$=88,200, PDI=3.8.

Example 20 poly{(4,8-bis(3-ethylheptyl)thieno[2,3-f]benzothiophene-alt-(5-(2-ethylhexyl)thieno[3,4-c]pyrrole-4,6-dione)-ran-(4,8-bis(3-ethylheptyl)thieno[2,3-f]benzothiophene-alt-4,7-[2,1,3-benzothiadiazole])} benzothiadiazole (0.040 g, 0.14 mmol), tris(dibenzylideneacetone)dipalladium(0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.2 mL of 2-iodothiophene and stirred at 110° C. for additional two hours. The oil bath was removed and after cooling to room temperature, 30 mL of

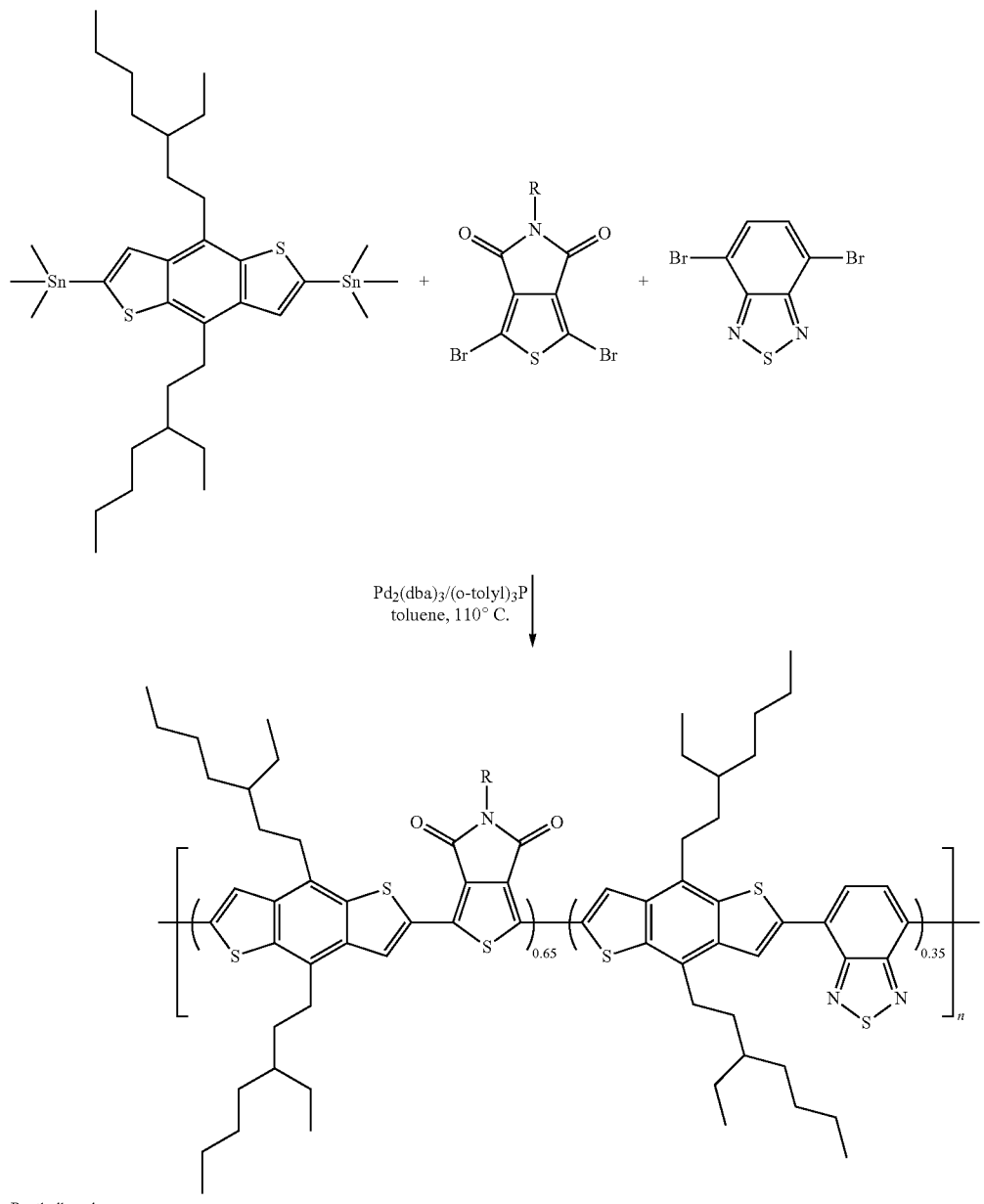

R: ethylhexyl

In a glove box, [4,8-bis(3-ethylheptyl)-6-trimethylstannyl-thieno[2,3-f]benzothiophen-2-yl]-trimethyl-stannane (0.30 g, 0.39 mmol), 1,3-dibromo-5-(2-ethylhexyl)thieno[3,4-c]pyrrole-4,6-dione (0.11 g, 0.25 mmol), 4,7-dibromo-2,1,3-

MTBE were added to the reaction mixture under vigorous stirring to induce precipitation. The final mixture was poured into 200 mL of MTBE and the polymer was collected via filtration. The polymer was purified by consecutive Soxhlet extractions in sequence with MTBE, hexane, and chloroform. The chloroform fraction was passed through celite, to remove catalyst residuals, solvent was removed under vacuum to yield a brown-copper colored polymer that was redissolved in chloroform, precipitated in methanol:IPA:water mixture, and collected via filtration (80%). Molecular weight was determined by GPC in 1,3,5-trichlorobenzene (1 mL/min at 150° C.) vs. polystyrene standards: $M_n$=21,100, $M_w$=77,400, PDI=3.6.

This polymer was converted to ink formulations. Ink formulations were made with and without additives. The polymer and devices performed well when processed from solvents like orthodichlorobenzene without additives. For use of some solvent blends, such as 50:50 mixture of chloroform and orthodichlorobenzene, there was a modest improvement with use of solvent addititives, such as a fluorinated additive, or with use of external treatment like solvent annealing.

Example 21 poly{(4,8-bis(3-ethylheptyl)thieno[2,3-f]benzothiophene-alt-(5-(3,7-dimethyloctyl)thieno[3,4-c]pyrrole-4,6-dione)-ran-(4,8-bis(3-ethylheptyl)thieno[2,3-f]benzothiophene-alt-4,7-[2,1,3-benzothiadiazole])}

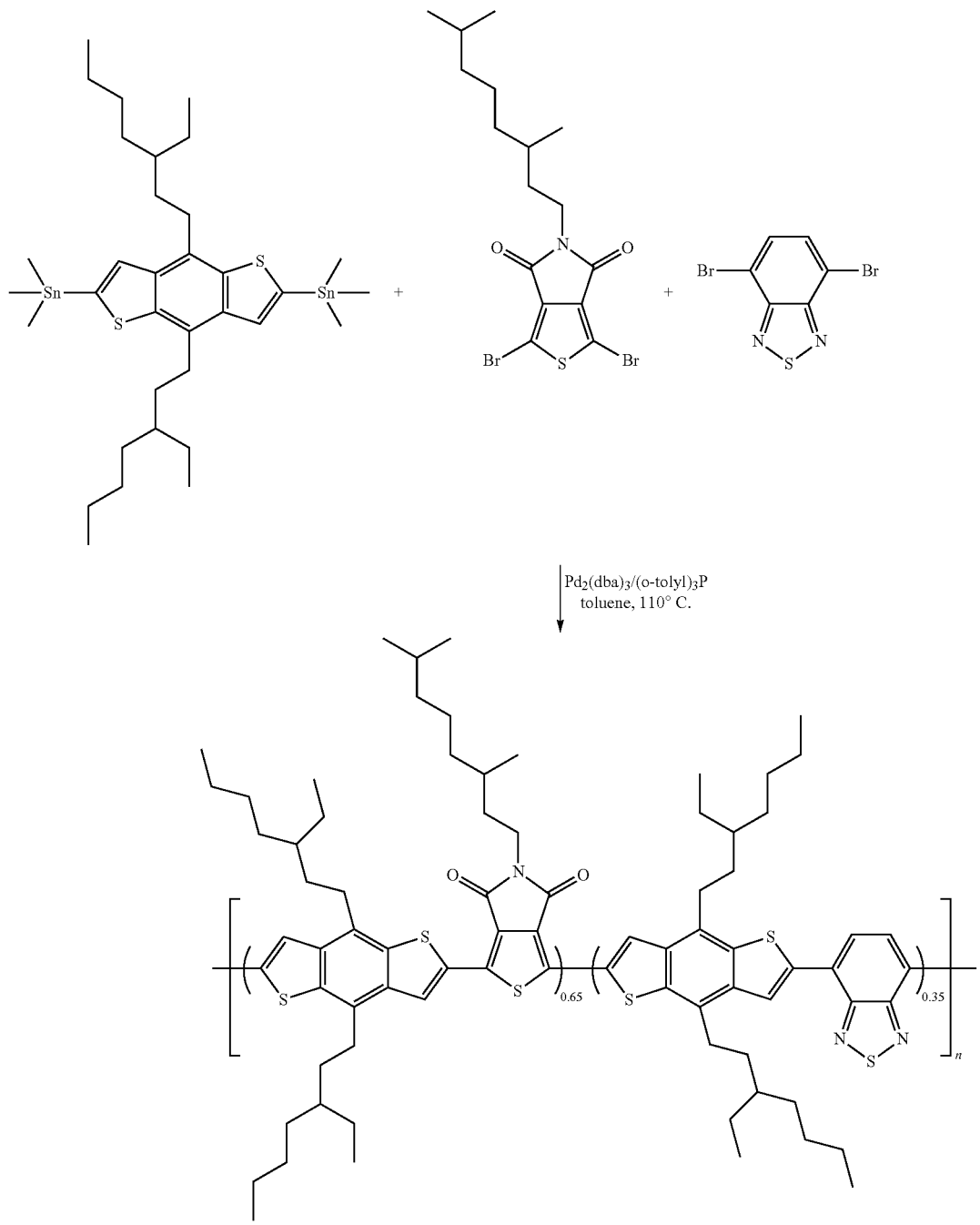

In a glove box, [4,8-bis(3-ethylheptyl)-6-trimethylstannyl-thieno[2,3-f]benzothiophen-2-yl]-trimethyl-stannane (0.30 g, 0.39 mmol), 1,3-dibromo-5-(3,7-dimethyloctyl)thieno[3,4-c]pyrrole-4,6-dione (0.11 g, 0.25 mmol), 4,7-dibromo-2,1,3-benzothiadiazole (0.040 g, 0.14 mmol), tris(dibenzylideneacetone)dipalladium(0) (8.9 mg, 0.010 mmol) and tris(o-tolyl)phosphine (0.012 g, 0.039 mmol) were weighted out into a flame dried 50 mL Schlenk flask. Reaction flask was removed from the glove box and 20 mL of deoxygenated toluene were added via syringe. The mixture was evacuated and refilled with argon five times. The reaction flask was immersed into a preheated to 110° C. oil bath and was left stirring under an argon stream for 48 hours. The polymerization was quenched with 0.2 mL of 2-iodothiophene and stirred at 110° C. for additional two hours. The oil bath was removed and after cooling to room temperature, 30 mL of methanol were added to the reaction mixture under vigorous stirring to induce precipitation. The final mixture was poured into 200 mL of methanol and the polymer was collected via filtration. The polymer was purified by consecutive Soxhlet extractions in sequence with methanol, MTBE, hexane, and chloroform. The chloroform fraction was passed through celite, to remove catalyst residuals, and solvent was removed under vacuum to yield a brown-copper colored polymer that was redissolved in chloroform, precipitated in methanol:IPA:water mixture, and collected via filtration 80%). Molecular weight was determined by GPC in 1,3,5-trichlorobenzene (1 mL/min at 150° C.) vs. polystyrene standards: $M_n$=19,900, $M_w$=65,000, PDI=3.3.

Example 22 poly{(2,6'-4,8-diethylhexyloxybenzo[1,2-b;3,4-b]dithiophene-alt-(5-(2-ethylhexyl)thieno[3,4-c]pyrrole-4,6-dione)-alt-(2,6'-4,8-diethylhexyloxybenzo[1,2-b;3,4-b]dithiophene-alt-4,7-[2,1,3-benzothiadiazole])}

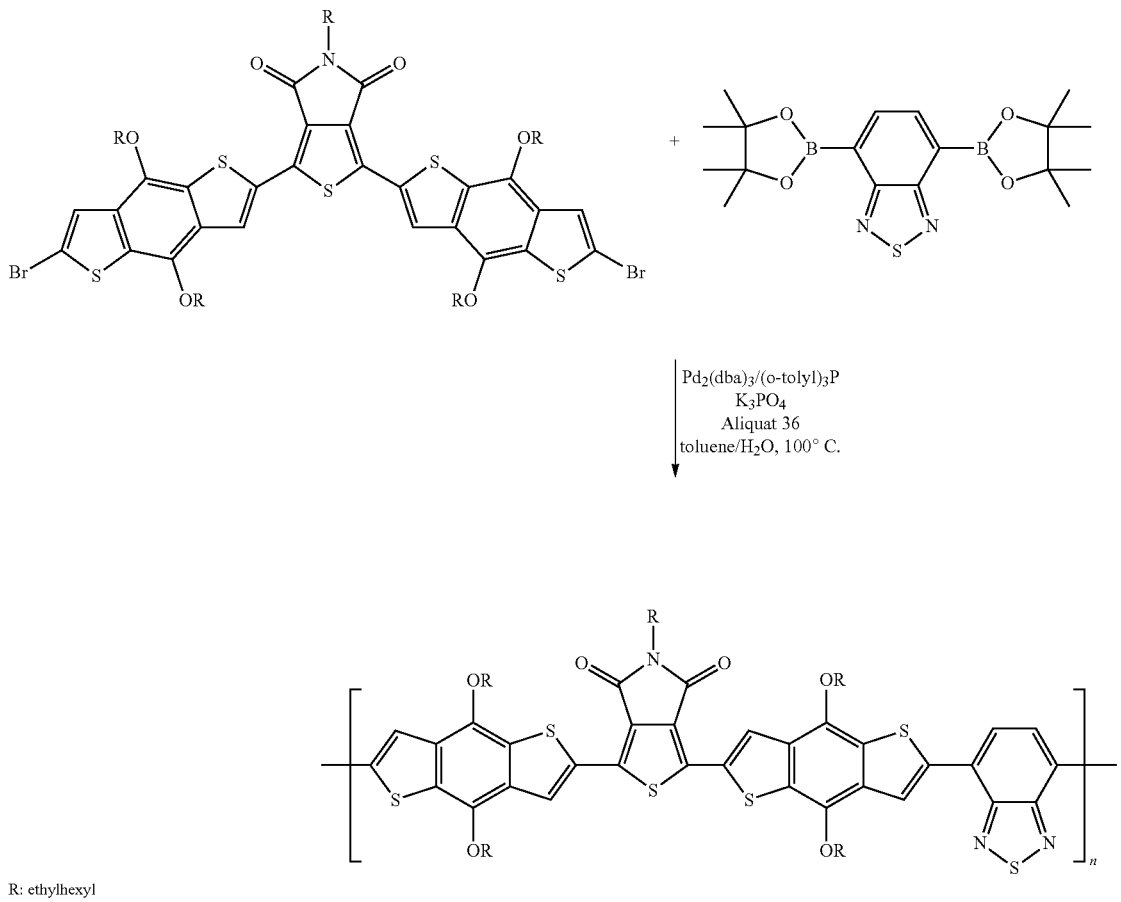

In a glove box, dibromo-1,3-bis(4,8-diethylhexyloxy-benzo[1,2-b;3,4-b]dithiophene)-5-(2-ethylhexyl)thieno[3,4-c]pyrrole-4,6-dione (13.8 mg, 0.105 mmol), 2,1,3-benzothiadiazole-4,7-bis(boronic acid pinacol ester) (40.8 mg, 0.105 mmol), tris(dibenzylideneacetone)dipalladium (0) (2.40 mg, 2.5 mol %), tris(o-tolyl)phosphine (3.20 mg, 0.0105 mmol), and $K_3PO_4$ (0.112 g, 0.525 mmol) were charged into a flame dried 50 mL Schlenk flask. The reaction flask was removed from the glove box and 5 mL of deoxygenated toluene, 0.5 mL water, and catalytic amount of Aliquat 36 were added via syringe. The mixture was evacuated and refilled with argon five times. The reaction flask was immersed into a preheated to 100° C. oil bath and left stirring under an argon stream for 72 hours. The polymerization was quenched with 0.3 mL of 2-iodothiophene and stirred at 100° C. for additional two hours. The oil bath was removed and after cooling to room temperature, 50 mL of methanol were added to the reaction mixture under vigorous stirring to induce precipitation. The final mixture was poured into 200 mL of methanol, and polymer was collected via filtration. The polymer was purified by consecutive Soxhlet extractions in sequence with methanol, acetone, hexane, and chloroform. The chloroform soluble fraction and chloroform insoluble fraction (that was redissolved in oDCB) were passed through celite, to remove catalyst residuals. Solvent was removed under vacuum to yield a brown-copper colored polymer that was redissolved in oDCB, precipitated in methanol:IPA:water mixture, and collected via filtration (~30% per each fraction). Molecular weight was determined by GPC in 1,3,5-trichlorobenzene (1 mL/min at 150° C.) vs. polystyrene standards: $M_n$=26,100, $M_w$=60,300, PDI=2.3 [CHCl$_3$ insoluble fraction]; $M_n$= 20,000, PDI=2.0 [CHCl$_3$ soluble fraction].

Additional Prophetic Embodiments

Example 23

General Procedure for Synthesis of Random Alternating Copolymers Via Stille Cross-Coupling Polymerization In a glove box, 2,6-bis(trimethyltin)-4,8-diethylhexyloxybenzo[1,2-b;3,4-b]dithiophene (0.39 mmol), 1,3-dibromo-5-(2-ethylhexyl)thieno[3,4-c]pyrrole-4,6-dione (0.26 mmol), 4,7-dibromo-2,1,3-benzothiadiazole (0.26 mmol), 4-trimethyltin-N-(4-trimethyltin phenyl)-N-[4-(2-ethylhexyl)phenyl]aniline (0.13 mmol), tris(dibenzylideneacetone)dipalladium (0) (15 mg, 0.016 mmol) and tris(o-tolyl)phosphine (0.020 g, 0.065 mmol) are weighted out into a flame dried 100 mL Schlenk flask. Reaction flask is removed from the glove box and 50 mL of deoxygenated toluene are added via syringe. The mixture is evacuated and refilled with argon five times. The reaction flask is immersed into a preheated to 110° C. oil bath and is left stirring under an argon stream for 48 hours. The polymerization is quenched with 0.3 mL of 2-iodothiophene and stirred at 110° C. for additional two hours. The oil bath is removed and after cooling to room temperature, 30 mL of methanol are added to the reaction mixture under vigorous stirring to induce precipitation. The final mixture is poured into 200 mL of methanol and the polymer is collected via filtration. The polymer is purified by consecutive Soxhlet extractions in sequence with methanol, acetone, hexane, and

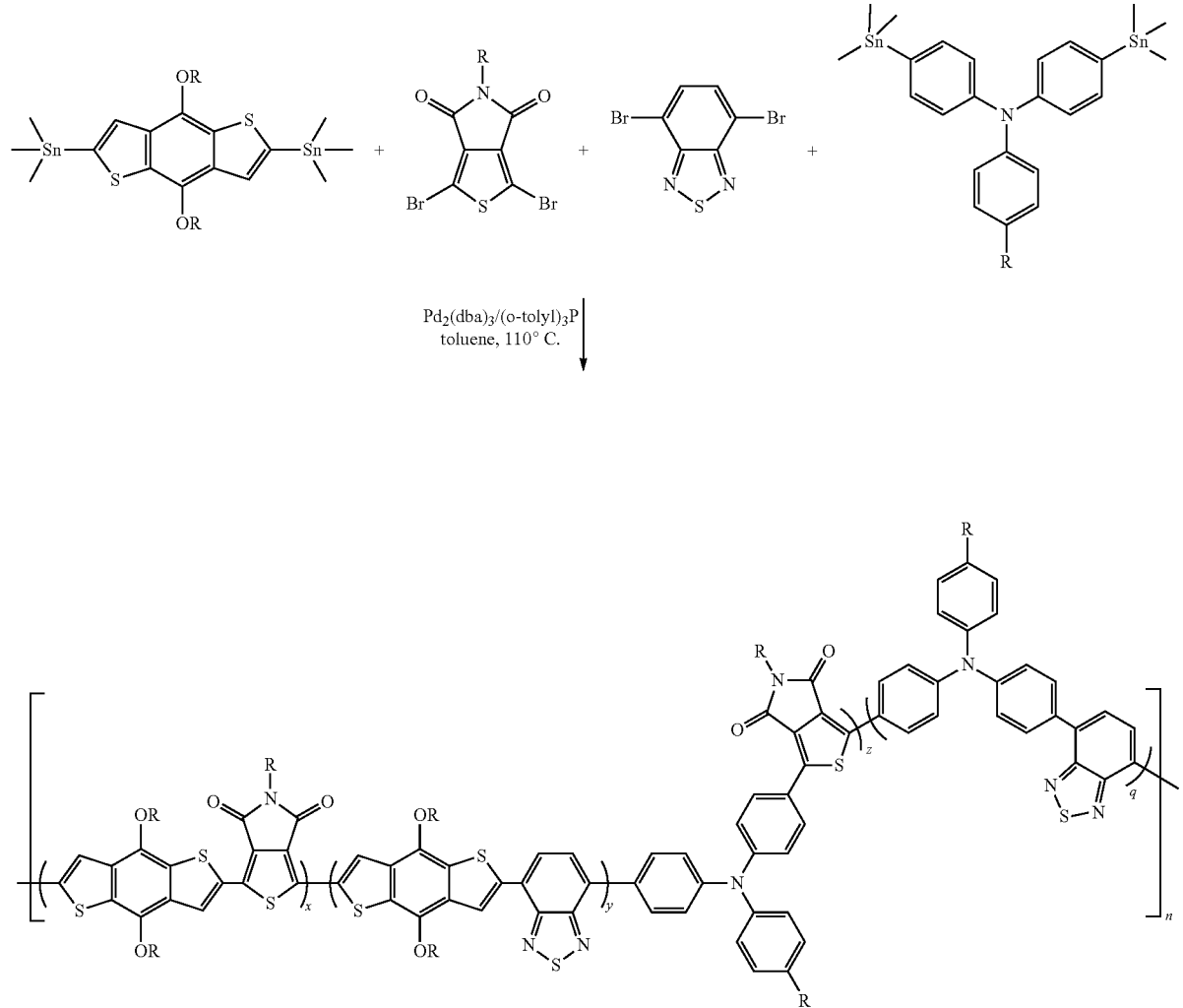

R: ethylhexyl chloroform. Chloroform fraction is concentrated, passed through celite, to remove catalyst residuals, re-precipitated in methanol, isolated via filtration, and analyzed by gel permeation chromatography (GPC) and NMR.

Example 24

General Procedure for the Synthesis of Alternating Copolymers Via Suzuki Cross-Coupling Polymerization The reaction flask is removed from the glove box and 15 mL of deoxygenated toluene, water, and catalytic amount of Aliquat 36 are added via syringe. The mixture is evacuated and refilled with argon five times. The reaction flask is immersed into a preheated to 100° C. oil bath and left stirring under an argon stream for 24 hours. The polymerization is quenched with 0.3 mL of 2-iodothiophene and stirred at 100° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified

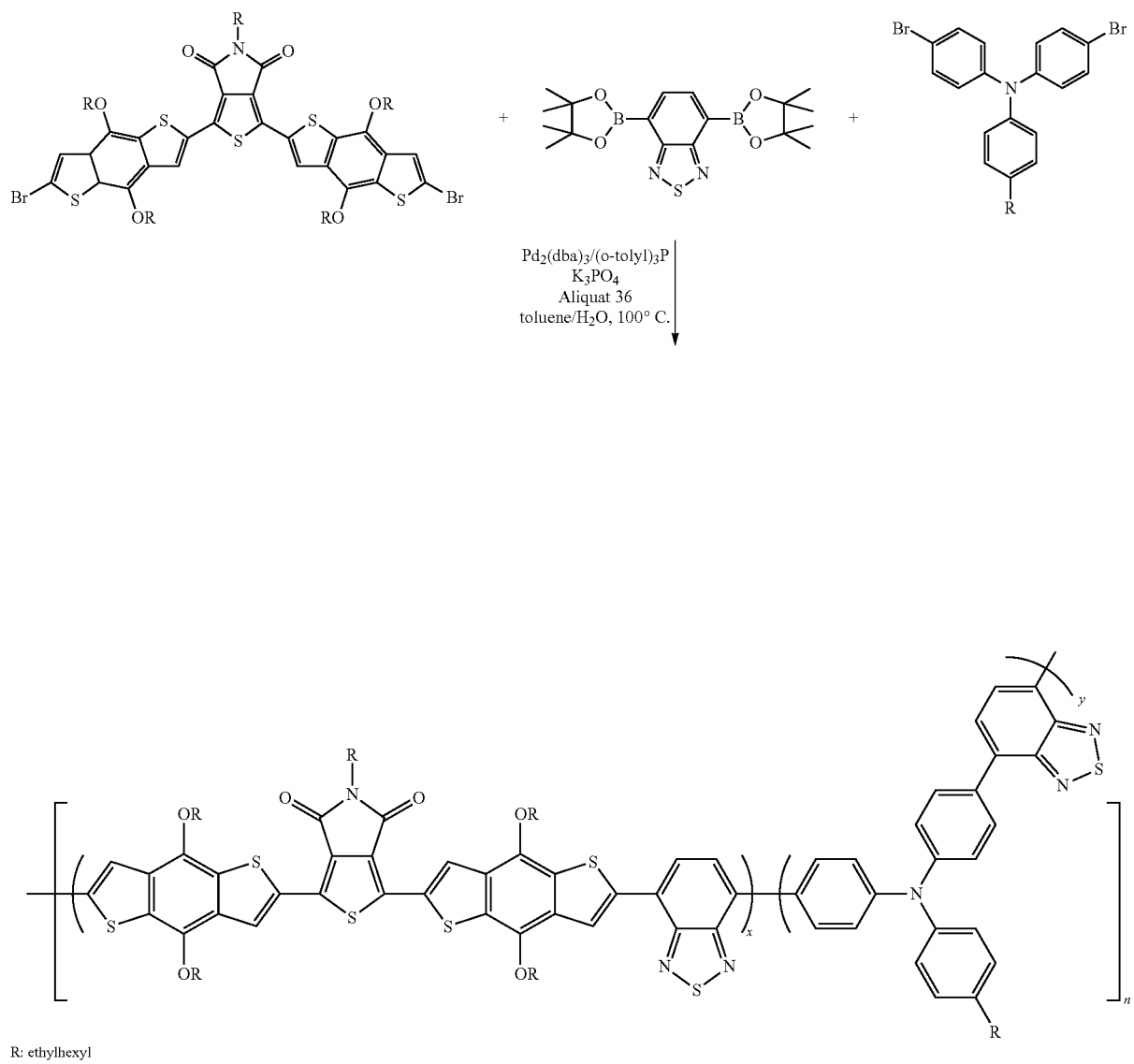

R: ethylhexyl

In a glove box, dibromo-1,3-bis(4,8-diethylhexyloxybenzo[1,2-b;3,4-b]dithiophene)-5-(2-ethylhexyl)thieno[3,4-c]pyrrole-4,6-dione (0.40 mmol), 2,1,3-benzothiadiazole-4,7-bis(boronic acid pinacol ester) (0.50 mmol), 4-bromo-N-(4-bromophenyl)-N-[4-(2-ethylhexyl)phenyl]aniline (0.10 mmol), tris(dibenzylideneacetone)dipalladium (0) (2.5 mol %) and tris(o-tolyl)phosphine (0.050 mmol), $K_3PO_4$ (2.5 mmol) are charged into a flame dried 50 mL Schlenk flask.

by consecutive Soxhlet extractions in sequence with methanol, acetone, hexane, and chloroform. The chloroform fraction is passed through celite, to remove catalyst residuals, and solvent is removed under vacuum to yield polymer. Chloroform fraction is concentrated, re-precipitated in methanol, isolated via filtration, and analyzed by gel permeation chromatography (GPC) and NMR.

Example 25

General Procedure for the Synthesis of Alternating Copolymers Via Suzuki Cross-Coupling Polymerization

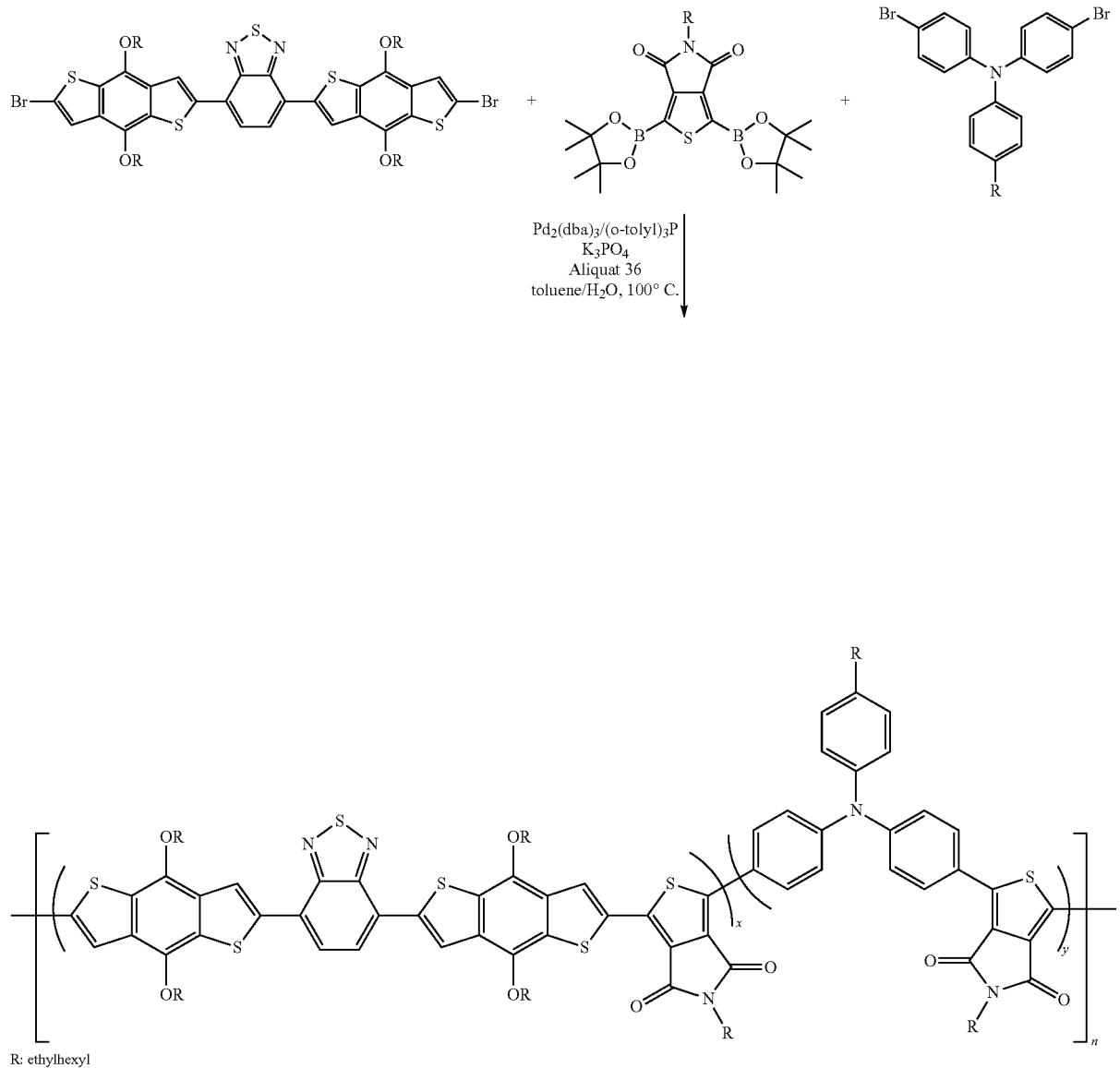

R: ethylhexyl

In a glove box, 4,7-bis[2-bromo-4,8-bis(2-ethylhexoxy) thieno[2,3-f]benzothiophen-6-yl]-2,1,3-benzothiadiazole (0.40 mmol), 5-(2-ethylhexyl)-1,3-bis(4,4,5,5-tetramethyl-1,3,2-dioxaborolan-2-yl)thieno[3,4-c]pyrrole-4,6-dione (0.50 mmol), 4-bromo-N-(4-bromophenyl)-N-[4-(2-ethylhexyl) phenyl]aniline (0.10 mmol), tris(dibenzylideneacetone)dipalladium (0) (2.5 mol %) and tris(o-tolyl)phosphine (0.050 mmol), $K_3PO_4$ (2.5 mmol) are charged into a flame dried 50 mL Schlenk flask. The reaction flask is removed from the glove box and 15 mL of deoxygenated toluene, water, and catalytic amount of Aliquat 36 are added via syringe. The mixture is evacuated and refilled with argon five times. The reaction flask is immersed into a preheated to 100° C. oil bath and left stirring under an argon stream for 24 hours. The polymerization is quenched with 0.3 mL of 2-iodothiophene and stirred at 100° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Chloroform fraction is concentrated, re-precipitated in methanol, isolated via filtration, and analyzed by gel permeation chromatography (GPC) and NMR.

Example 26

General Procedure for the Synthesis of Alternating Copolymers Via Suzuki Cross-Coupling Polymerization

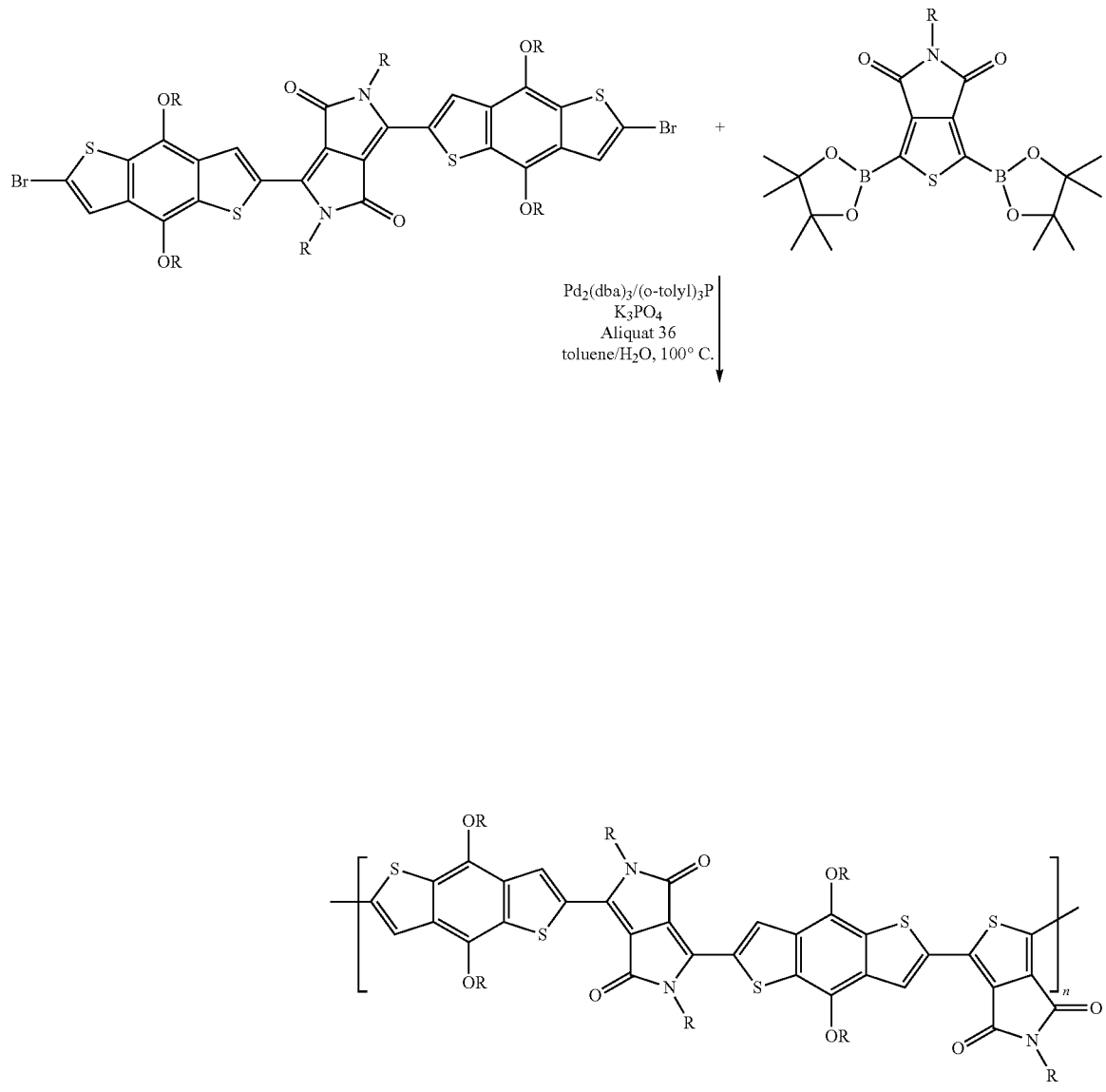

R: ethylhexyl

In a glove box, dibromo-4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione (0.50 mmol), 5-(2-ethylhexyl)-1,3-bis(4,4,5,5-tetramethyl-1,3,2-dioxaborolan-2-yl)thieno[3,4-c]pyrrole-4,6-dione (0.50 mmol), tris(dibenzylideneacetone)dipalladium (0) (2.5 mol %) and tris(o-tolyl)phosphine (0.050 mmol), $K_3PO_4$ (2.5 mmol) are charged into a flame dried 50 mL Schlenk flask. The reaction flask is removed from the glove box and 15 mL of deoxygenated toluene, water, and catalytic amount of Aliquat 36 are added via syringe. The mixture is evacuated and refilled with argon five times. The reaction flask is immersed into a preheated to 100° C. oil bath and left stirring under an argon stream for 24 hours. The polymerization is quenched with 0.3 mL of 2-iodothiophene and stirred at 100° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Chloroform fraction is concentrated, re-precipitated in methanol, isolated via filtration, and analyzed by gel permeation chromatography (GPC) and NMR.

Example 27

General Procedure for the Synthesis of Alternating Copolymers Via Suzuki Cross-Coupling Polymerization

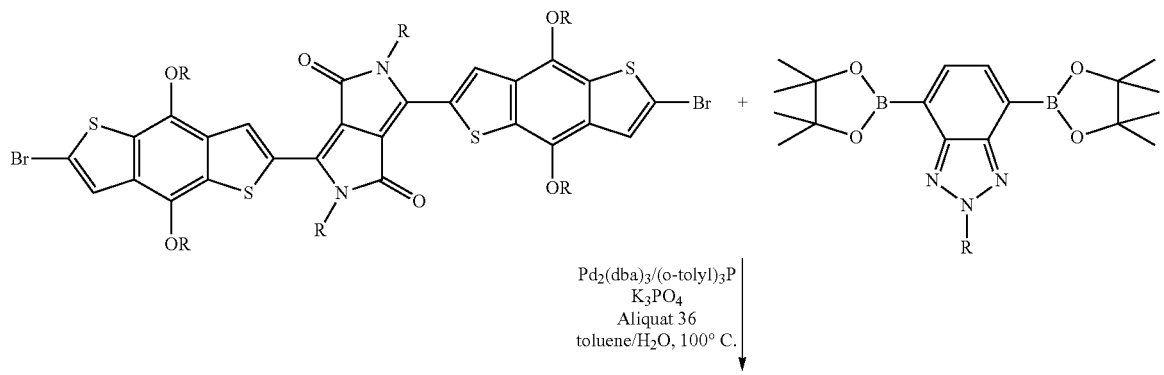

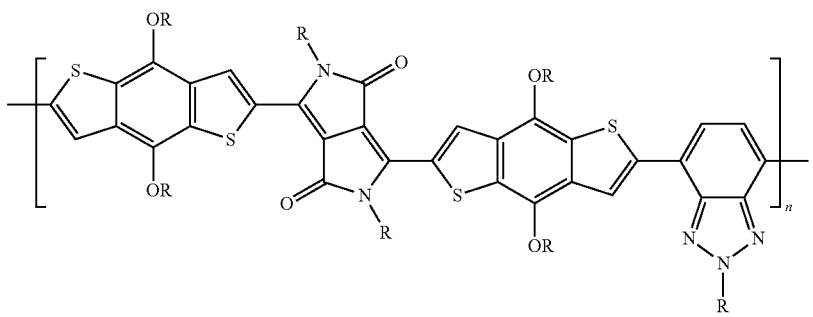

R: ethylhexyl

In a glove box, dibromo-4-[4-(2-ethylhexoxy)-8-(2-ethylhexyl)thieno[2,3-f]benzothiophen-6-yl]-1-[8-(2-ethylhexoxy)-4-(2-ethylhexyl)thieno[2,3-f]benzothiophen-6-yl]-2,5-dihydropyrrolo[3,4-c]pyrrole-3,6-dione (0.50 mmol), 2-(2-ethylhexyl)-4,7-bis(4,4,5,5-tetramethyl-1,3,2-dioxaborolan-2-yl)benzotriazole (0.50 mmol), tris(dibenzylideneacetone)dipalladium (0) (2.5 mol %) and tris(o-tolyl)phosphine (0.050 mmol), $K_3PO_4$ (2.5 mmol) are charged into a flame dried 50 mL Schlenk flask. The reaction flask is removed from the glove box and 15 mL of deoxygenated toluene, water, and catalytic amount of Aliquat 36 are added via syringe. The mixture is evacuated and refilled with argon five times. The reaction flask is immersed into a preheated to 100° C. oil bath and left stirring under an argon stream for 24 hours. The polymerization is quenched with 0.3 mL of 2-iodothiophene and stirred at 100° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Chloroform fraction is concentrated, re-precipitated in methanol, isolated via filtration, and analyzed by gel permeation chromatography (GPC) and NMR.

Example 28

General Procedure for the Synthesis of Alternating Copolymers Via Suzuki Cross-Coupling Polymerization

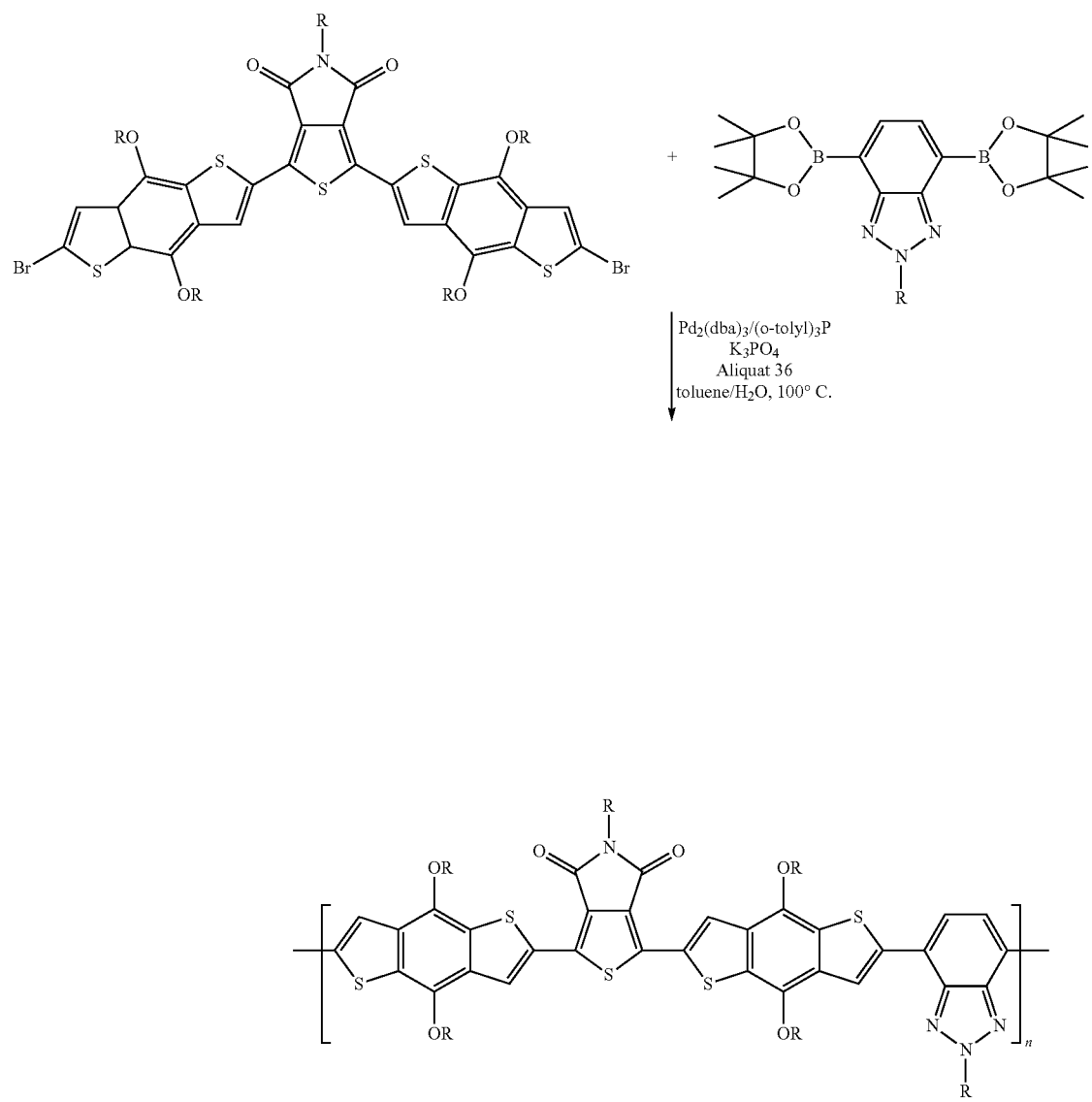

R: ethylhexyl

In a glove box, dibromo-1,3-bis(4,8-diethylhexyloxy-benzo[1,2-b;3,4-b]dithiophene)-5-(2-ethylhexyl)thieno[3,4-c]pyrrole-4,6-dione (0.50 mmol), 2-(2-ethylhexyl)-4,7-bis(4,4,5,5-tetramethyl-1,3,2-dioxaborolan-2-yl)benzotriazole (0.50 mmol), tris(dibenzylideneacetone)dipalladium (0) (2.5 mol %) and tris(o-tolyl)phosphine (0.050 mmol), $K_3PO_4$ (2.5 mmol) are charged into a flame dried 50 mL Schlenk flask. The reaction flask is removed from the glove box and 15 mL of deoxygenated toluene, water, and catalytic amount of Aliquat 36 are added via syringe. The mixture is evacuated and refilled with argon five times. The reaction flask is immersed into a preheated to 100° C. oil bath and left stirring under an argon stream for 24 hours. The polymerization is quenched with 0.3 mL of 2-iodothiophene and stirred at 100° C. for additional two hours. The oil bath is removed and after cooling to room temperature, 15 mL of methanol are added to the reaction mixture under vigorous stirring to induce precipitation. The final mixture is poured into 200 mL of methanol, and polymer is collected via filtration. The polymer is purified by consecutive Soxhlet extractions in sequence with methanol, acetone, hexane, and chloroform. The chloroform fraction is passed through celite, to remove catalyst residuals, and solvent is removed under vacuum to yield polymer. Chloroform fraction is concentrated, re-precipitated in methanol, isolated via filtration, and analyzed by gel permeation chromatography (GPC) and NMR.

Other prophetic embodiments include:

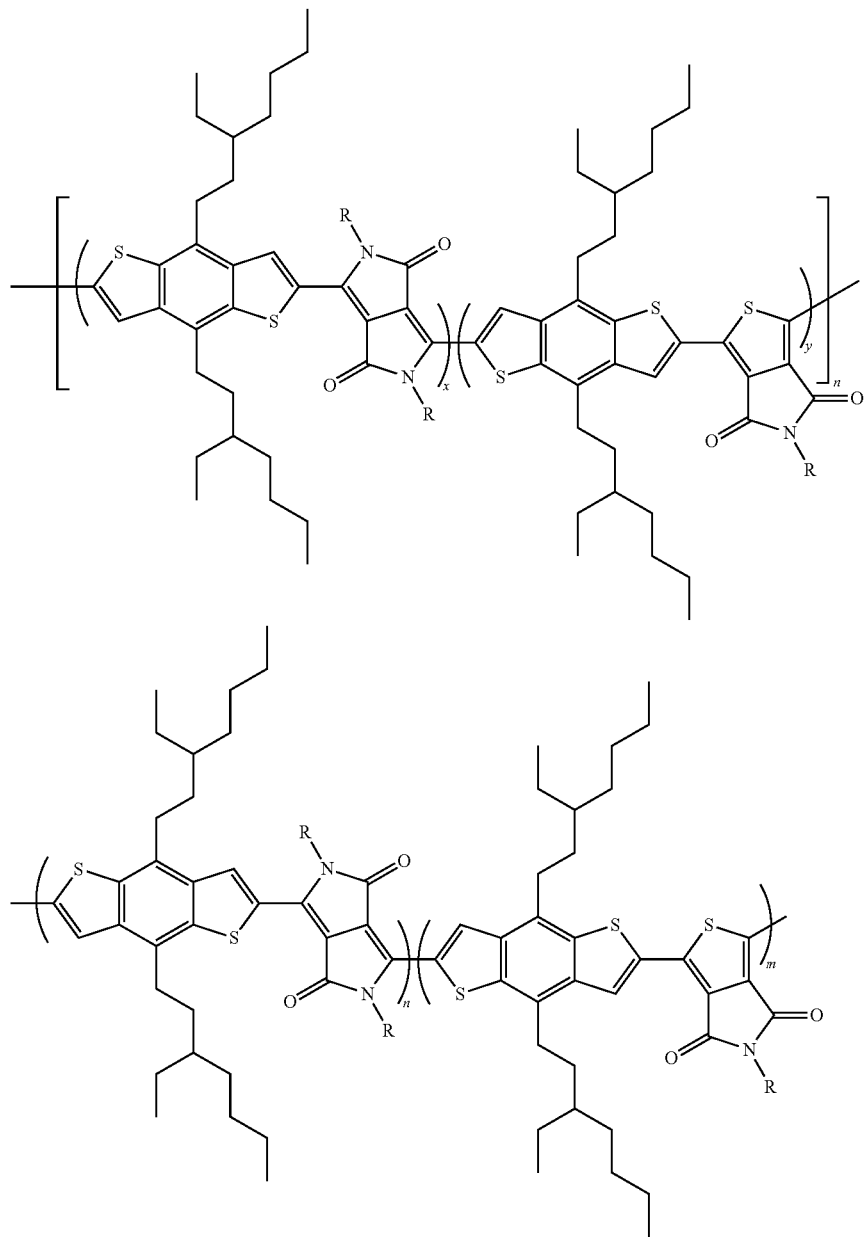

TABLE 3

Photovoltaic Performance of single layer OPVs based on Donor-Acceptor polymers comprising dioxypyrrolo-functionality

| Polymer Exp. # | n-type | p/n ratio | Conc/Solvent/additive[1] | HIL | Cathode | Anneal T °C./t/atm² | $J_{SC}$ mA/cm2 | $V_{OC}$ (V) | FF | $\eta$(%) |
|---|---|---|---|---|---|---|---|---|---|---|
| Exp 6 | C70PCBM | 1:1 | 0.0157/oDCB | PEDOT:PSS | Ca/Al | NA | 8.11 | 0.78 | 0.57 | 3.6 |
| Exp 9 | C70PCBM | 1:4 | 0.0110/TCB | PEDOT:PSS | Ca/Al | 60/18/GB | 10.12 | 0.69 | 0.53 | 3.7 |
| Exp 14 | C70PCBM | 1:2 | 0.0157/oDCB | PEDOT:PSS | Ca/Al | NA | 11.24 | 0.81 | 0.52 | 4.73 |
|  | C70PCBM | 1:2 | 0.0157/oDCB | PEDOT:PSS | Ca/Al | 120/15/Sol | 11.38 | 0.84 | 0.57 | 5.42 |

TABLE 3-continued

Photovoltaic Performance of single layer OPVs based on Donor-Acceptor polymers comprising dioxypyrrolo-functionality

| Polymer Exp. # | n-type | p/n ratio | Conc/Solvent/additive[1] | HIL | Cathode | Anneal T° C./t/atm[2] | $J_{SC}$ mA/cm2 | $V_{OC}$ (V) | FF | η(%) |
|---|---|---|---|---|---|---|---|---|---|---|
| Exp 16 | C70PCBM | 1:2 | 0.0157/TCB | PEDOT:PSS | Ca/Al | NA | 9.67 | 0.83 | 0.50 | 3.98 |
| Exp 17 | C70PCBM | 1:2 | 0.0157/oDCB | PEDOT:PSS | Ca/Al | NA | 9.26 | 0.83 | 0.39 | 2.99 |
| | C70PCBM | 1:2.3 | 0.0157/oDCB/DIO | PEDOT:PSS | Ca/Al | NA | 11.17 | 0.79 | 0.45 | 3.94 |
| | C70PCBM | 1:2.3 | 0.0157/oDCB | PEDOT:PSS | Ca/Al | NA | 10.75 | 0.77 | 0.52 | 4.32 |
| Exp 18 | C70PCBM | 1:3 | 0.0157/oDCB | PEDOT:PSS | Ca/Al | NA | 8.50 | 0.85 | 0.62 | 4.45 |
| Exp 19 | C70PCBM | 1:2 | 0.0157/oDCB | PEDOT:PSS | Ca/Al | NA | 9.43 | 0.83 | 0.45 | 3.51 |
| | C70PCBM | 1:2.3 | 0.0157/oDCB | PEDOT:PSS | Ca/Al | NA | 10.00 | 0.85 | 0.49 | 4.16 |
| | C70PCBM | 1:2 | 0.0157/oDCB | PEDOT:PSS | Ca/Al | 120/15/Sol | 9.93 | 0.93 | 0.52 | 4.80 |
| Exp 20 | C70PCBM | 1:2 | 0.0157/TCB | PEDOT:PSS | Ca/Al | NA | 9.52 | 0.91 | 0.62 | 5.39 |
| | C70PCBM | 1:2 | 0.0157/TCB | HIL A | Ca/Al | NA | 9.68 | 0.98 | 0.66 | 6.30 |
| | C70PCBM | 1:2 | 0.0157/TCB | HIL A | Bphen:Yb | NA | 10.58 | 0.99 | 0.62 | 6.51 |
| Exp 21 | C70PCBM | 1:2.3 | 0.0157/TCB | PEDOT:PSS | Ca/Al | NA | 9.27 | 0.88 | 0.58 | 4.76 |
| | C70PCBM | 1:2.3 | 0.0157/TCB | HIL A | Ca/Al | 120/15/Sol | 8.47 | 0.96 | 0.60 | 4.84 |
| | C70PCBM | 1:2 | 0.0157/TCB | HIL A | Bphen:Yb | NA | 9.56 | 0.98 | 0.55 | 5.13 |

[1]oDCB:DIO-dichlorobenzene:diiodooctane (97:3%); TCB-trichlorobenzene
[2]GB-glove box (N[2]); Sol-solvent atmosphere (CHCl3) for 15 minutes
Note:
HIL A is an HIL ink formulation comprising 96.860 parts water; 2.826 parts Nafion (sulfonated perfluorinated copolymer); and 0.314 parts sulfonated polythiophene as described in PCT publication WO 2008/073149.

TABLE 4

Comparison in Absorption coefficients, Alpha, for poly(3-hexylthiophene) and Donor-Acceptor polymers comprising dioxypyrrolo-functionality

| Polymer | Abs | b (cm) | b (nm) | Alpha* (cm$^{-1}$) |
|---|---|---|---|---|
| P3HT | 0.270 | 6.40 × 10$^{-6}$ | 64 | 0.97 × 10$^5$ |
| Ex. 9 | 0.196 | 2.25 × 10$^{-6}$ | 22 | 2.01 × 10$^5$ |
| Ex. 6 | 0.409 | 5.70 × 10$^{-6}$ | 57 | 1.65 × 10$^5$ |
| Ex. 14 | 0.621 | 8.40 × 10$^{-6}$ | 84 | 1.70 × 10$^5$ |

*$\alpha = 2.3 \times Abs_{(at\ \lambda max)}/b_{(film\ thickness\ in\ cm)[in\ thin\ films]}$ The new polymers exhibit approximately 2× increase in absorptivity (based on alpha) vs. P3HT suggesting more planar structure, dense/small interchain distance that could result in increase in $J_{SC}$ and, thus, superior OPV performance (P3HT is poly(3-hexylthiophene)).

FIG. 6A shows the J-V curve of D-A polymer and $C_{70}$-PCBM (device fabrication/formulation details and OPV characteristics are listed in Table 3, third entry for Ex. 20 with OPV efficiency of 6.51%).

FIG. 6B shows voltage dependence of photocurrent for the same device as 6A under AM1.5G simulated illumination (100 mW/cm$^2$). Photocurrent was defined as a difference between a current density under illumination and in dark. Effective voltage was defined as a difference between a compensation voltage (voltage where photocurrent is equal to zero) and the applied voltage.

FIG. 6B also shows that photocurrent is relatively low at low bias (about 10 mA/cm$^2$) and increases significantly at large negative bias. At large negative bias, all or substantially all photogenerated electron-hole pairs are believed to be dissociated and collected at the electrodes. In this particular device, photocurrent reaches 11.9 mA/cm$^2$ at a bias voltage of −5 V and does not reach the saturation limit, which suggests that maximum photocurrent in this material is even higher than this value and that the morphology requires further optimization.

Figure 7:
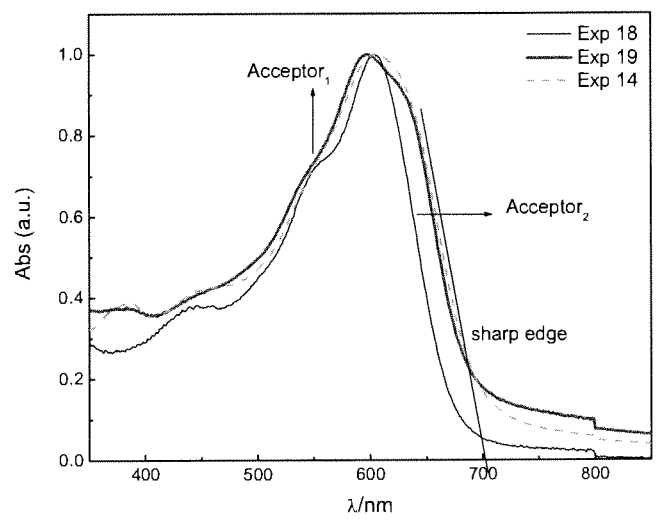
FIG. 7 shows UV-Vis spectral testing.

FIG. 7. Normalized UV-Vis absorption profile of regiorandom Donor-Acceptor polymers comprising dioxypyrrolo-functionality in solid state. Materials properties (e.g., processability, solubility, planarity/order and/or band gap) of D-A polymers disclosed in this invention can be tuned by varying molar composition and/or functionality of starting materials (FIG. 7 shows appearance of spectral features and/or red shift in the absorption profile with increasing dioxypyrrolo-containing acceptor or benzothiadiazole moiety, respectively).

Figure 8:
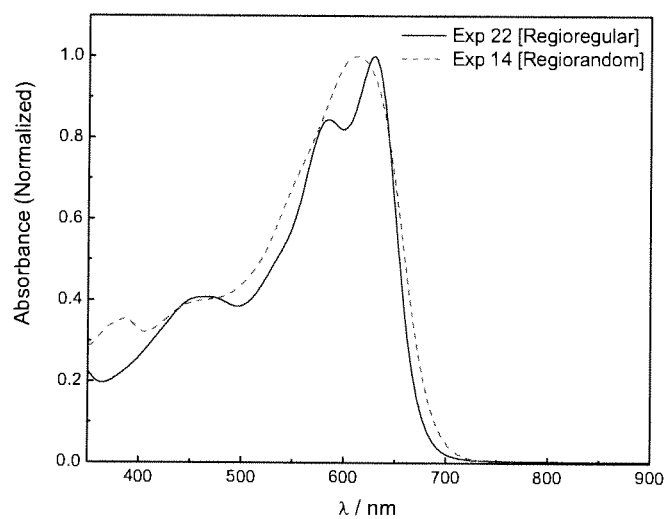
FIG. 8 shows UV-Vis spectral testing.

FIG. 8. Normalized UV-Vis absorption profile of regioregular vs. regiorandom Donor-Acceptor polymers (Exp 22 and 14, respectively) in TCB solvent. Spectral features and/or vibronic structure present in the absorption profile are indicative of improved planarity/order of the regioregular polymer vs. regiorandom one that can result in improved OPV performance.

Part IV

Additional Embodiments

Part IVa:
Another example of a moiety which can be included in the polymer is represented by Z-1, below:

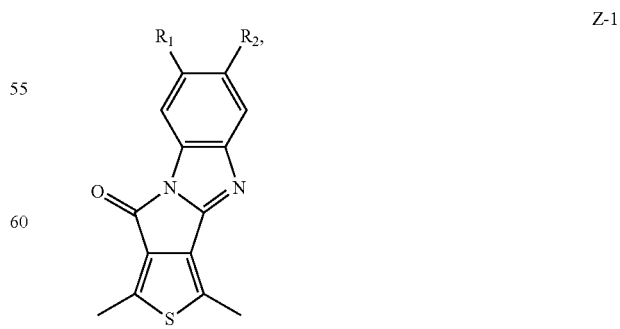

Z-1 wherein R1 and R2 can be, independently, the same or different, such as an optionally substituted hydrocarbon group such as, for example, hydrogen, or linear or branched groups, such as an alkyl, aryl, arylalkyl, or alkylaryl group. For example, R1 and R2 can be, independently, a C1 to C25 group. An optional substitution on R1 and/or R2 can introduce heteroatoms such as nitrogen or oxygen as in amine, carbonyl, alkoxy, or carboxyl structures. An example is a branched alkyl group such as ethylhexyl for both R1 and R2.

Other examples of Z-1 structure is shown below as Z-2 and Z-3, wherein R, R1, and/or R2 can be a wide variety of groups including, for example, optionally substituted C1-C25 alkyl or aryl:

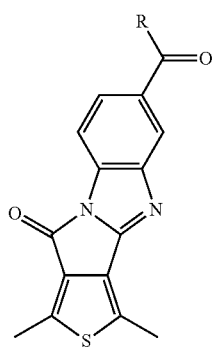

Z-2

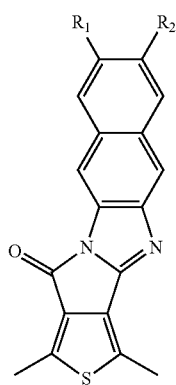

Z-3

Other embodiments which can be included in monomers, oligomers, and polymers can comprise, for example:

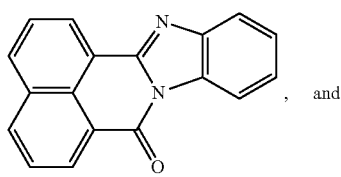

, and

Z-4

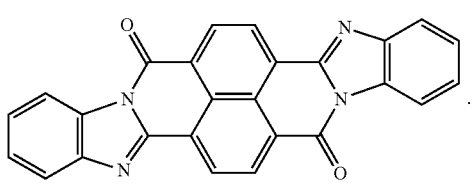

Z-5

In this Part, describing units such as Z-1, Z-2, and Z-3, the synthesis can be adapted from WO 2005/123,737 A2. The bromination can be adapted from *Org. Lett.* 2004, 6, 3381.

Example

Synthesis of
1,2-bis((2-ethylhexyl)oxy)-4,5-dinitrobenzene

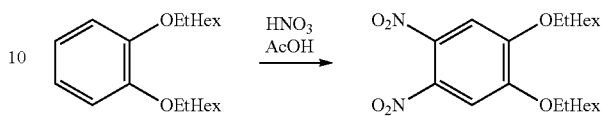

A 1 L round bottom flask, equipped with an addition funnel, was charged with 1,2-bis(2-ethylhexyl)oxy-benzene (10 g, 0.03 mol). After the flask was cooled to 0° C. on an ice bath, methylene chloride [$CH_2Cl_2$] (160 mL) and glacial acetic acid (160 mL) were added. Concentrated nitric acid (100 mL) was added dropwise via an addition funnel. The solution was stirred at 0° C. for 10 min then warmed to room temperature and stirred for another 30 min. The reaction was cooled again to 0° C. and 200 mL of nitric acid were added dropwise. The reaction was stirred at 0° C. for 10 min and warmed to room temperature overnight. Completion of the reaction was monitored by TLC. The reaction was poured onto ice water and extracted with $CH_2Cl_2$. The organic fraction was dried over anhydrous $MgSO_4$, and the solvent was evaporated to yield the product (8.9 g, 70%).

Prophetic Example

Synthesis of
4,5-bis((2-ethylhexyl)oxy)benzene-1,2-diamine

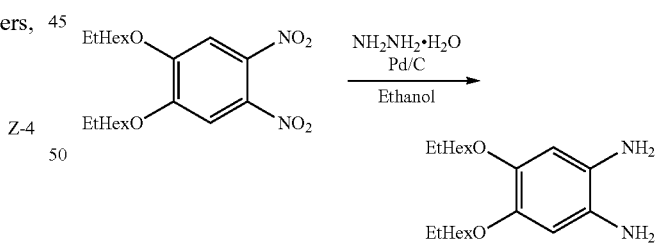

A 250 mL 3-neck round bottom flask fitted with a condenser is charged with 1,2-bis((2-ethylhexyl)oxy)-4,5-dinitrobenzene (8.9 g, 0.021 mol), hydrazine monohydrate (11.6 g, 0.231 mol), Pd/C (0.27 g), and ethanol (100 mL). The mixture is warmed to reflux under nitrogen overnight. The mixture is filtered while hot under a nitrogen blanket. A solid is precipitated out upon cooling, washed with methanol and dried overnight under vacuum to yield the product as a white solid.

Prophetic Example

Synthesis of 6,7-bis((2-ethylhexyl)oxy)-10H-benzo[d]thieno[3',4':3,4]pyrrolo[1,2-a]imidazol-10-one

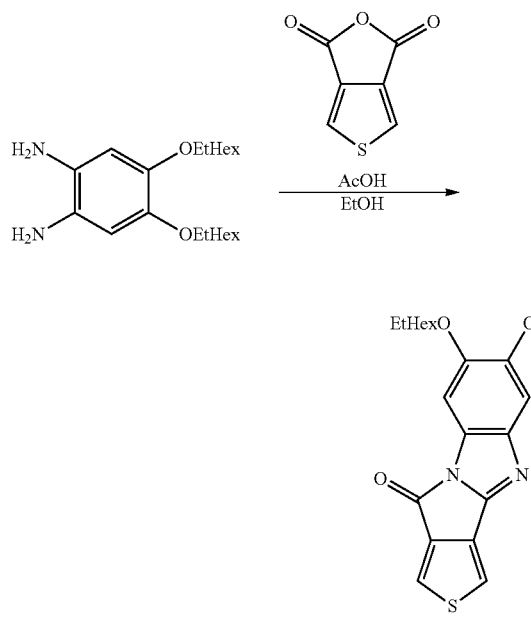

A mixture of 4,5-bis((2-ethylhexyl)oxy)benzene-1,2-diamine (5.8 g, 0.016 mol) and thieno[3,4-c]furan-1,3-dione (2.5 g, 0.016 mol) is refluxed in a 100 mL acetic acid:ethanol (1:1) solvent blend for 24 hours. The solvent is distilled off and the crude product is purified by column chromatography (CHCl$_3$) to yield the final product.

Prophetic Example

Synthesis of 1,3-dibromo-6,7-bis((2-ethylhexyl)oxy)-10H-benzo[d]thieno[3',4':3,4]pyrrolo[1,2-a]imidazol-10-one

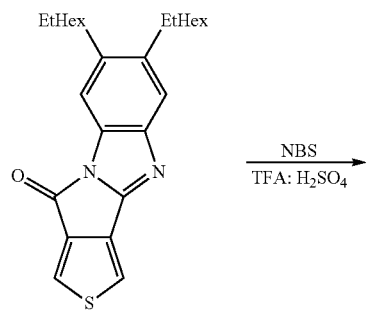

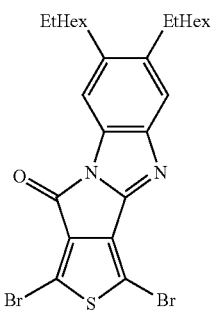

6,7-bis((2-ethylhexyl)oxy)-10H-benzo[d]thieno[3',':3,4]pyrrolo[1,2-a]imidazol-10-one (5.4 g, 0.011 mol) is dissolved in 12 mL of concentrated sulfuric acid and 40 mL of trifluoroacetic acid. N-bromosuccinimide (NBS) (7.8 g, 0.044 mol) is added, and the mixture is stirred at 55° C. overnight. The solution is poured into ice water and is extracted with MTBE. The organic fractions are collected, dried over anhydrous MgSO$_4$, filtered, and concentrated down. The crude product is purified by column chromatography.

Polymers (including donor acceptor copolymers), inks, and devices can be made and tested from the monomer, including photovoltaic devices.

Part IVb:

Patent applications U.S. Ser. No. 12/828,121 and PCT/US2010/040664, each filed Jun. 30, 2010 describe a series of polymers which can be adapted as described herein, including adapted to include the structure I. For example, four polymers are represented below:

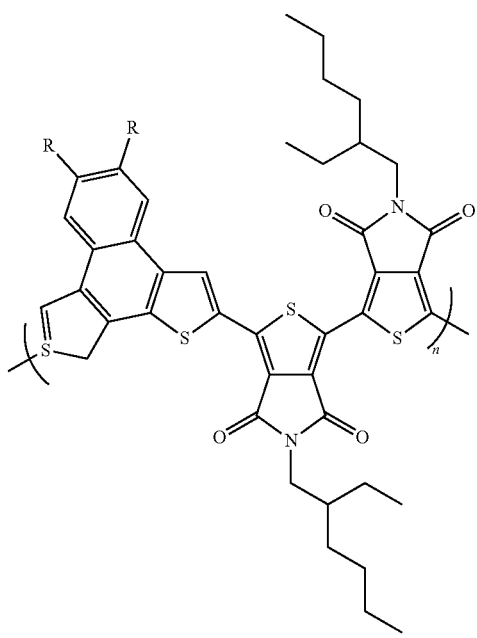

-continued

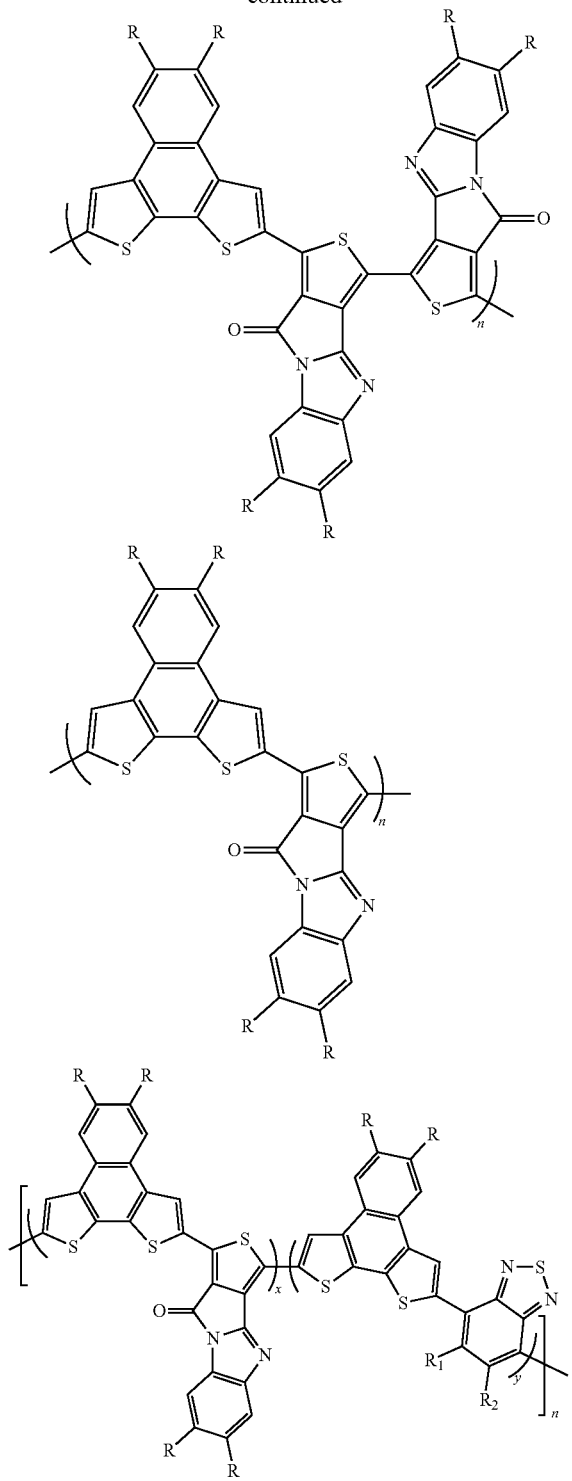

In these structures, the R groups, independently of each other, and the molecular weight can be adapted to provide soluble polymers as described herein. The R group can be, independently, hydrogen, halogen (including fluoro, chloro, bromo, or iodo), or another group which tailors the band gap and HOMO/LUMO electronic energy levels.

Example

Synthesis of (5,6-bis(2-ethylhexyl)naphtho[2,1-b:3,4-b']dithiophene-2,9-diyl)bis(trimethylstannane)

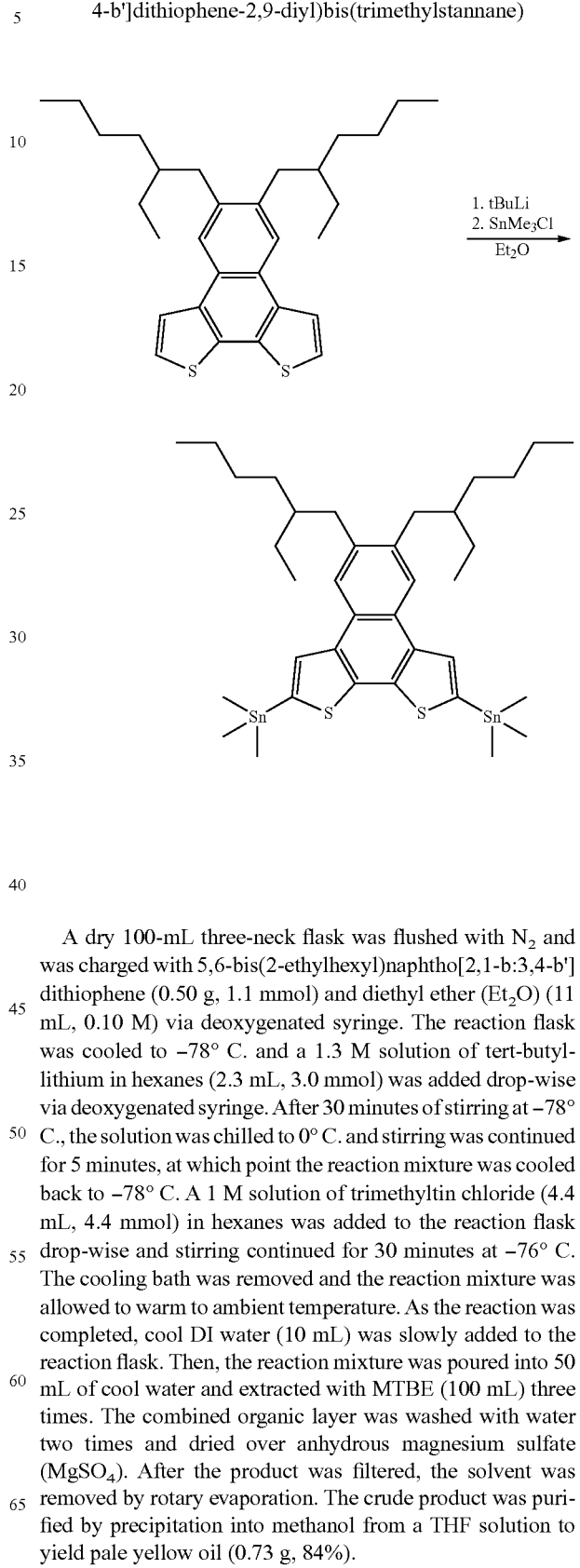

A dry 100-mL three-neck flask was flushed with $N_2$ and was charged with 5,6-bis(2-ethylhexyl)naphtho[2,1-b:3,4-b'] dithiophene (0.50 g, 1.1 mmol) and diethyl ether ($Et_2O$) (11 mL, 0.10 M) via deoxygenated syringe. The reaction flask was cooled to −78° C. and a 1.3 M solution of tert-butyllithium in hexanes (2.3 mL, 3.0 mmol) was added drop-wise via deoxygenated syringe. After 30 minutes of stirring at −78° C., the solution was chilled to 0° C. and stirring was continued for 5 minutes, at which point the reaction mixture was cooled back to −78° C. A 1 M solution of trimethyltin chloride (4.4 mL, 4.4 mmol) in hexanes was added to the reaction flask drop-wise and stirring continued for 30 minutes at −76° C. The cooling bath was removed and the reaction mixture was allowed to warm to ambient temperature. As the reaction was completed, cool DI water (10 mL) was slowly added to the reaction flask. Then, the reaction mixture was poured into 50 mL of cool water and extracted with MTBE (100 mL) three times. The combined organic layer was washed with water two times and dried over anhydrous magnesium sulfate ($MgSO_4$). After the product was filtered, the solvent was removed by rotary evaporation. The crude product was purified by precipitation into methanol from a THF solution to yield pale yellow oil (0.73 g, 84%).

Example

Synthesis of poly(3-(5,6-bis(2-ethylhexyl)naphtho[2,1-b:3,4-b']dithiophen-2-yl)-alt-5,5'-bis(2-ethylhexyl)-4H,4'H-[1,1'-bithieno[3,4-c]pyrrole]-4,4',6,6'(5H,5'H)-tetraone)

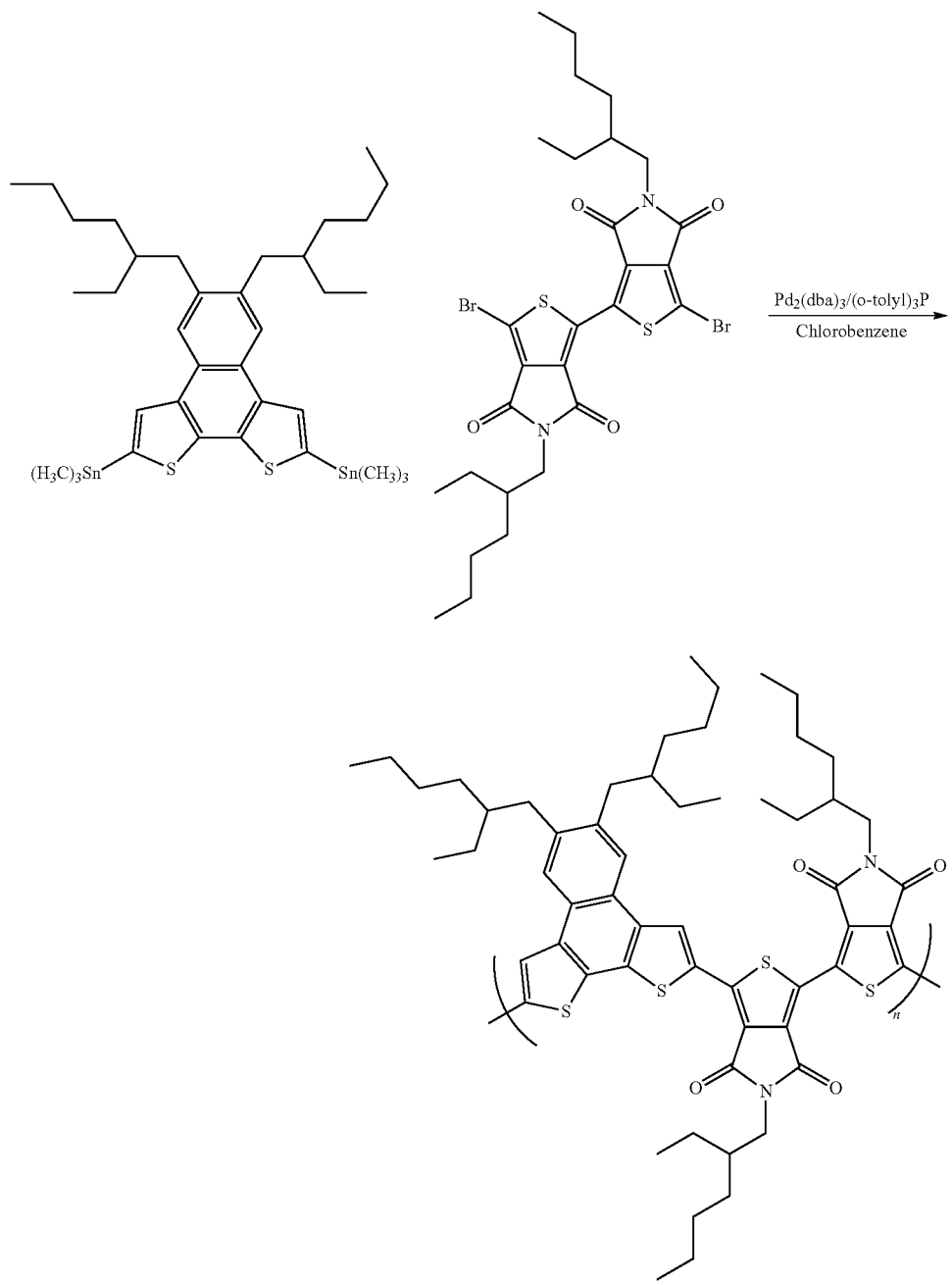

In a glove box, 3,3'-dibromo-5,5'-bis(2-ethylhexyl)-4H,4'H-[1,1'-bithieno[3,4-c]pyrrole]-4,4',6,6'(5H,5'H)-tetraone (304 mg, 0.44 mmol), (5,6-bis(2-ethylhexyl)naphtho[2,1-b:3,4-b']dithiophene-2,9-diyl)bis(trimethylstannane) (350 mg, 0.44 mmol), $Pd_2$ $dba_3$ (10 mg, 0.011 mmol), P(o-tolyl)$_3$ (13 mg, 0.044 mmol) were charged in a 100 mL schlenk flask. The flask was removed from a glove box, connected to a vac/argon line, and the side arm was flushed with five vacuum-argon cycles, after which the flask was open to argon. Anhydrous toluene (20 mL), degassed with argon overnight, was added via a deoxygenated syringe. The flask was purged five times with argon, and immersed into a preheated to 110° C. flask for 48 hours. After cooling, methanol was added to precipitate the polymer. The polymer was filtered through Soxhlet thimble and Soxhlet extraction was performed in sequence with methanol, MTBE, hexane and chloroform. The final polymer was isolated as a chloroform insoluble fraction (270 mg, 65%). Molecular weight was determined by GPC in chlorobenzene (1 mL/min at 80° C.) vs. polystyrene standards: $M_n$=23,700, $M_w$=168,300, PDI=7.1. The polymer was labeled APP-1, and solar cell preparation and testing performance is shown in Table 5.

TABLE 5

Photovoltaic Performance of single layer OPVs based on Donor-Acceptor polymers comprising dioxypyrrolo-functionality (see Table 3 above for abbreviations)

| Polymer Exp. # | n-type | p/n ratio | Conc/Solvent/additive[1] | HIL | Cathode | Anneal T °C./t/atm[2] | $J_{SC}$ mA/cm[2] | $V_{OC}$ (V) | FF | $\eta$(%) |
|---|---|---|---|---|---|---|---|---|---|---|
| APP-1 | C70PCBM | 1:2 | 0.011/CHCl$_3$:oDCB (66:34) | HIL A | Ca/Al | NA | 6.41 | 1.05 | 0.50 | 3.49 |
|  | C70PCBM | 1:2 | 0.011/CHCl$_3$:oDCB (66:34) | HIL A | Ca/Al | NA | 6.45 | 1.05 | 0.50 | 3.56 |
| BPP-I | C70PCBM | 1:2 | 0.0157/CB:TCB:DBT (90:10 + 3) | HIL A | Ca/Al | NA | 7.06 | 0.87 | 0.45 | 2.83 |
|  | C70PCBM | 1:2 | 0.0157/CB:TCB:DBT (90:10 + 3) | HIL A | Ca/Al | NA | 6.45 | 0.87 | 0.45 | 2.78 |
| LRB-1 | C70PCBM | 1:2 | 0.0157/oDCB:DIO (100 + 3) | HIL A | Ca/Al | NA | 5.93 | 0.94 | 0.39 | 2.17 |

DBT-dibromotoluene

Part IVc:

A synthetic scheme is provided for preparing a moiety to build into a polymer backbone.

Example

Synthesis of 2,6-dibromo-4,8-bis(3-ethylheptyl)benzo[1,2-b:4,5-b']dithiophene

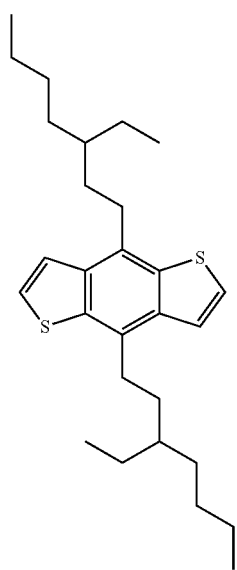

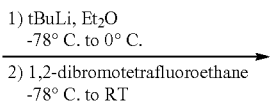
1) tBuLi, Et$_2$O
-78° C. to 0° C.
2) 1,2-dibromotetrafluoroethane
-78° C. to RT -continued

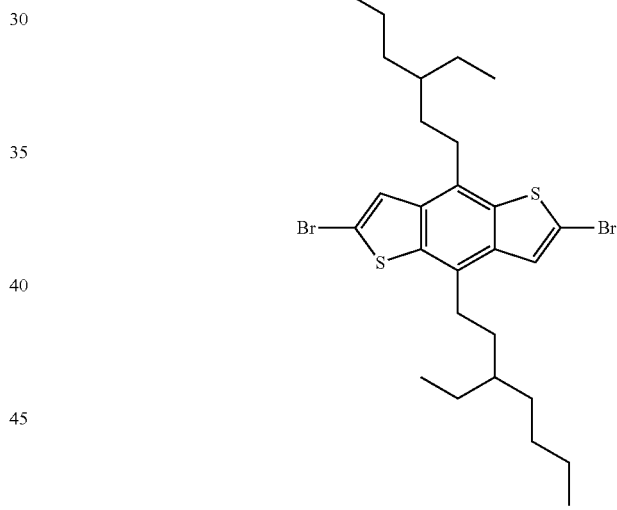

A dry 500-mL three-neck flask was flushed with N$_2$ and was charged with 4,8-bis(3-ethylheptyl)benzo[1,2-b:4,5-b']dithiophene (5.9 g, 0.013 mol) and diethyl ether (Et$_2$O) (133 mL, 0.1 M) via deoxygenated syringe. The reaction flask was cooled to −78° C. and a 1.3 M solution of tert-butyllithium in hexanes (28 mL, 0.036 mol) was added dropwise via deoxygenated syringe. After 30 minutes of stirring at −78° C., the solution was chilled to 0° C. and stirring was continued for 5 minutes, at which point the reaction mixture was chilled back to −78° C. 1,2-Dibromotetrafluoroethane (6.3 mL, 0.053 mol) was added to the reaction flask dropwise and stirring continued for 30 minutes at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with MTBE (150 mL) three times. The combined organic layer was washed with water two times and dried over anhydrous magnesium sulfate (MgSO$_4$). After the product was filtered, the solvent was removed by rotary evaporation. The crude product was purified by Silica column chromatography using hexanes to yield a yellow solid (7.0 g, 88%).

Spectral data: $^1$H NMR (300 MHz, CDCl$_3$): $\delta_H$ 7.39 (s, 2H), 3.0-2.9 (m, 4H), 1.7-1.6 (m, 4H), 1.5-1.3 (m, 18H), 1.0-0.9 (t, 12H).

Example

Synthesis of 6-bromo-4,8-bis(3-ethylheptyl)benzo[1,2-b:4,5-b]dithiophene-2-carbonitrile

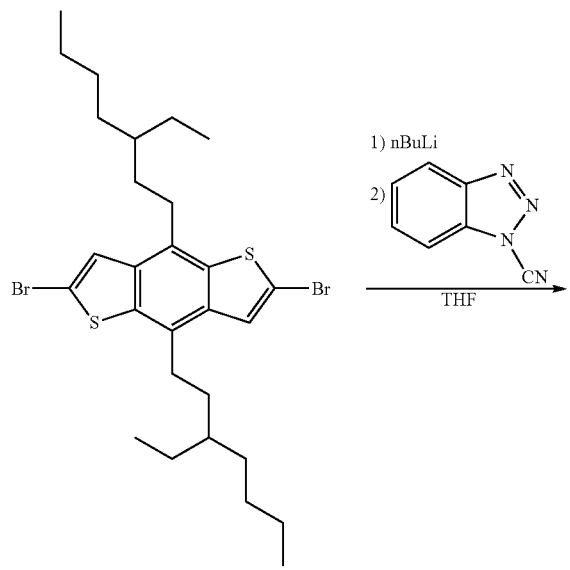

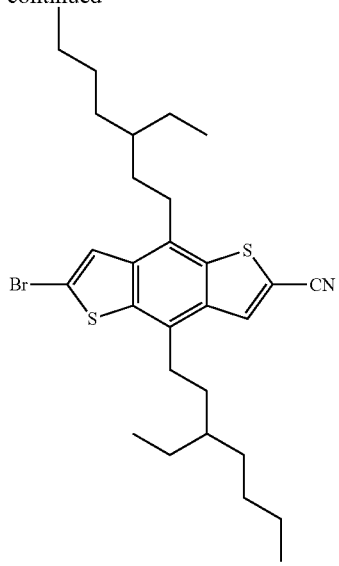

2,6-Dibromo-4,8-bis(3-ethylheptyl)benzo[1,2-b:4,5-b]dithiophene (6.7 g, 0.011 mol) was dissolved in 56 mL dry THF and cooled to −78° C. A 2.1 M solution of n-BuLi (5.2 mL) in hexanes was added drop-wise and the reaction was monitored for completion. The suspension was then transferred into another flask containing 1-cyanoimidazole (2.07 g, 0.022 mol) dissolved in THF and pre-cooled to −78° C. The reaction was monitored by TLC and when complete, the reaction mixture was poured into a saturated ammonium chloride solution and stirred for 30 min. The mixture was extracted with MTBE and the organic layers dried over MgSO$_4$. The solvent was evaporated and the crude product was purified by column chromatography (75%).

Prophetic Example

Synthesis of 3,6-bis(6-bromo-4,8-bis(3-ethylheptyl)benzo[1,2-b:4,5-b']dithiophen-2-yl)pyrrolo[3,4-c]pyrrole-1,4(2H,5H)-dione

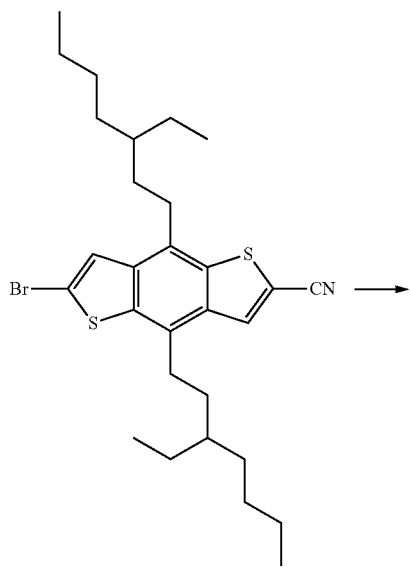

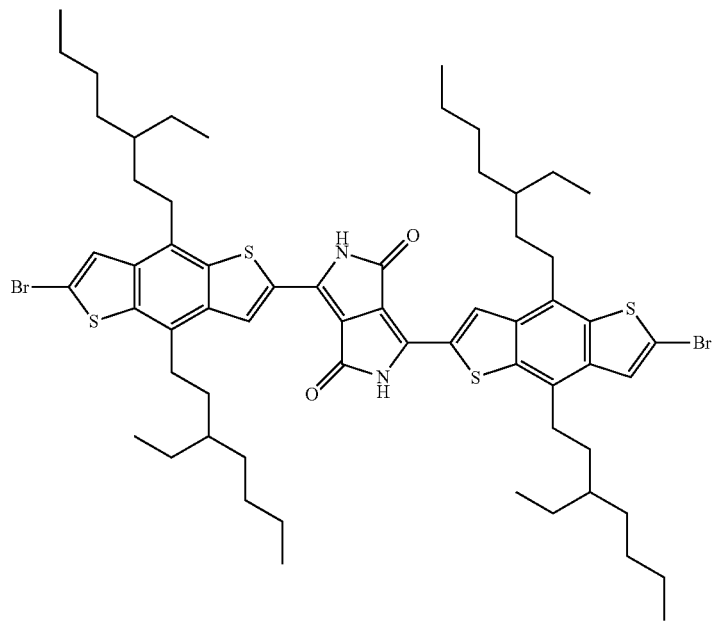

Sodium metal (0.71 g, 0.031 mol) and amyl alcohol (20 mL) are added to a 100 mL 3 neck flask with an attached thermometer and reflux condenser. A catalytic amount of $FeCl_3$ is added and the mixture is set to 90° C. until the sodium is completely melted. The mixture is cooled to 50° C. and the nitrile is added portion-wise (0.015 mol). The mixture is again warmed to 90° C. and a solution of amyl alcohol (5 mL) and isopropyl succinate (1.17 mL) are added over 30 min by a syringe pump. The reaction is stirred at 90° C. overnight and then cooled to 50° C. Glacial acetic acid (20 mL) is added to the flask and the mixture is set back to reflux for 30 min. After cooling to RT, the reaction is diluted with water and the product is extracted with MTBE. Combined organic fractions are dried over anhydrous $MgSO_4$, filtered, and solvent is removed by rotary evaporation. The product is purified by column chromatography.

Prophetic Example

Synthesis of 3,6-bis(6-bromo-4,8-bis(3-ethylheptyl)benzo[1,2-b:4,5-b']dithiophen-2-yl)-2,5-bis(2-ethylhexyl)pyrrolo[3,4-c]pyrrole-1,4(2H,5H)-dione

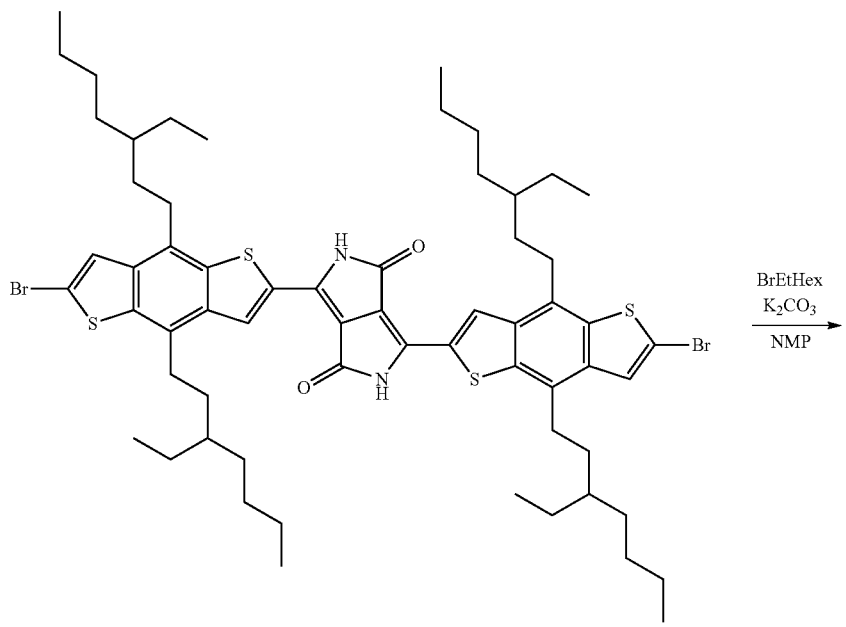

-continued

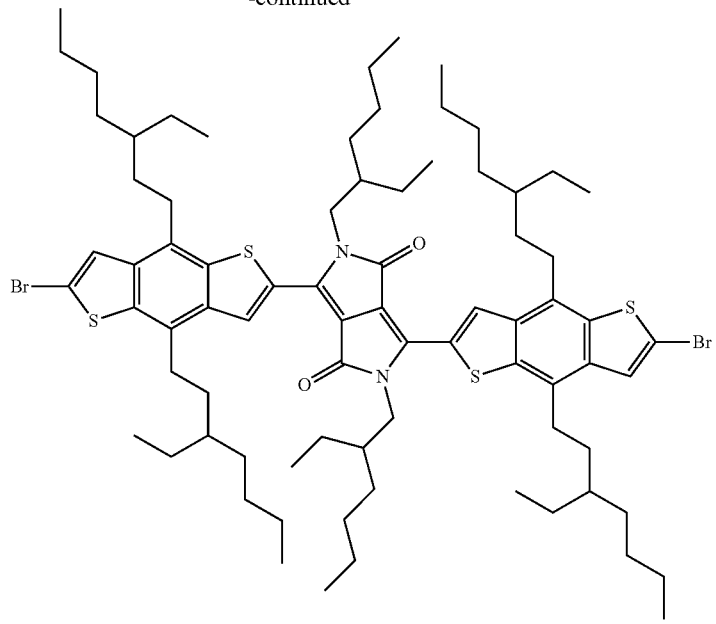

An oven dried 100 mL flask is charged with 3,6-bis(6-bromo-4,8-bis(3-ethylheptyl)benzo[1,2-b:4,5-b]dithiophen-2-yl)pyrrolo[3,4-c]pyrrole-1,4(2H,5H)-dione (0.0017 mol), $K_2CO_3$ (0.005 mol), and 20 mL of NMP. The mixture is warmed to 120° C. for 1 hour. 2-Ethylhexylbromide is added drop-wise to the reaction flask and stirred at 120° C. for 12 hours. The mixture is cooled to room temperature, poured into water, and followed by extraction with $CHCl_3$. The combined organic layers are dried over $MgSO_4$, filtered, and solvent removed by rotary evaporation. The product is purified by column chromatography with a hexanes:$CHCl_3$ (1:1) mixture.

The monomer can be incorporated into polymer structures including structures comprising structure I.

Part IVd:

Additional embodiments for monomers, oligomers, and polymers include the structures:

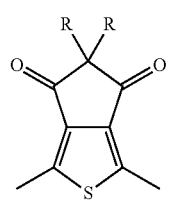
SNP-1

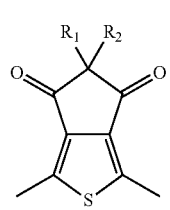
SNP-2

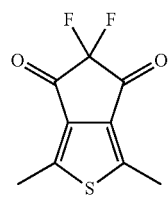
SNP-3 wherein the R groups, R, R1, and R2 can be hydrogen or a solubilizing group.

Prophetic Examples

Note: the synthesis of intermediate 4H-cyclopenta[c]thiophene-4,6(5H)-dione can be carried out according to procedures outlined by Dallemagne and co-workers. See, for example, Dallemagne et al., *Heterocycles*, 36, 2, 1993 287-294; Dallemagne et al., *Tetrahedron Letters*, 27, 23, 2607-2610. However, the prophetic synthesis outlined below can be more straightforward and easier to scale up.

Prophetic Example

Synthesis of diethyl thiophene-3,4-dicarboxylate

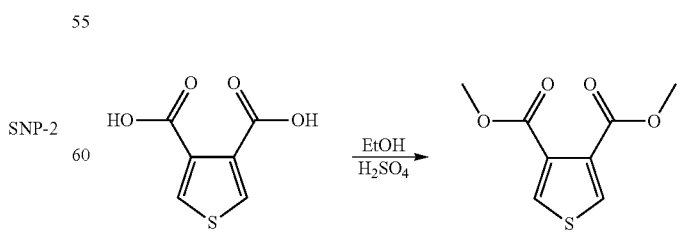

Thiophene-3,4-dicarboxylic acid (10 g, 58 mmol) is placed in a 3 dry 3-neck round bottom flask equipped with an argon inlet and a water condenser. Dry ethanol (100 mL) is added to the flask along with a catalytic amount of cc. sulfuric acid (1 mL). The reaction completion is determined by taking aliquot for NMR analysis. When complete, the reaction is cooled to room temperature. The ethanol is evaporated and the resulting product is purified via column chromatography, using a 100% hexane to 60% hexane/40% ethyl acetate gradient.

Prophetic Example

Synthesis of 4H-cyclopenta[c]thiophene-4,6(5H)-dione

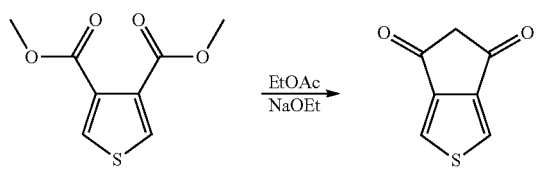

In a dry 3-neck flask with an argon inlet and a water condenser, diethyl thiophene-3,4-dicarboxylate (3.7 g, 16.2 mmol) is mixed with sodium ethoxide (1.1 g, 16.2 mmol). After heating to 100° C. ethyl acetate (1.4 g, 16.2 mmol) is added through syringe pump over one hour. The mixture was further heated for a few hours. The residue was redissolved in water at 70° C. and concentrated sulfuric acid is added (1 mL). The mixture is heated at this temperature for one hour to ensure complete decarboxylation.

Prophetic Example

Synthesis of 5,5-dioctyl-4H-cyclopenta[c]thiophene-4,6(5H)-dione

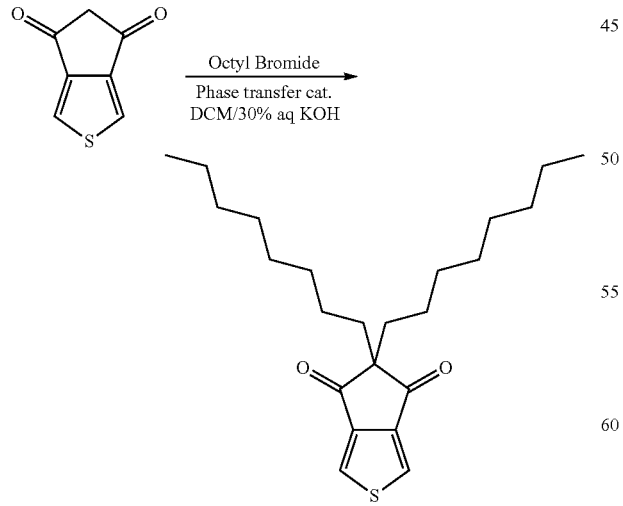

In a round bottom flask, 4H-cyclopenta[c]thiophene-4,6(5H)-dione (0.3 g, 2 mmol) and dioctyl bromide (1.53 g, 7.9 mmol) are dissolved in dichloromethane (10 mL). A 30% potassium hydroxide aqueous solution (10 mL) is added as well as benzyltriethylammonium chloride (120 mg, 0.5 mmol). The mixture is stirred at room temperature overnight. The organic phase is separated and the aqueous phase is further extracted with dichloromethane. The combined organic layer is washed with water, dried with anhydrous MgSO$_4$. After filtering, the solvent is removed under vacuum and the mixture is purified by flash chromatography using hexane/chloroform gradient.

Prophetic Example

Synthesis of 1,3-dibromo-5,5-dioctyl-4H-cyclopenta[c]thiophene-4,6(5H)-dione

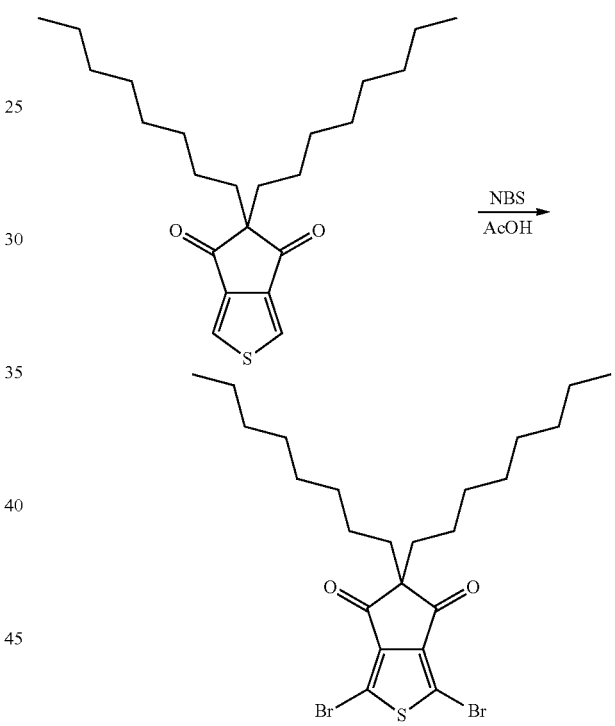

In a three neck round-bottom flask equipped with an argon inlet and protected from light with aluminum foil, 5,5-dioctyl-4H-cyclopenta[c]thiophene-4,6(5H)-dione (1 g, 1.87 mmol) is dissolved in acetic acid. NBS (830 mg, 4.7 mmol) is added in one portion to the solution. The mixture is stirred overnight and completion is determined by TLC. After completion the mixture is poured in water, and then extracted with MTBE. The combined organic layers are washed with water, and then dried with magnesium sulfate. After filtration the solvent is evaporated. The resulting product is purified by silica column chromatography using hexane/chloroform gradient.

Prophetic Example

Synthesis of poly(1-(4,8-bis((2-ethylhexyl)oxy)-4-a,7a-dihydrobenzo[1,2-b:4,5-b']dithiophen-2-yl)-alt-5,5-dioctyl-4H-cyclopenta[c]thiophene-4,6(5H)-dione)

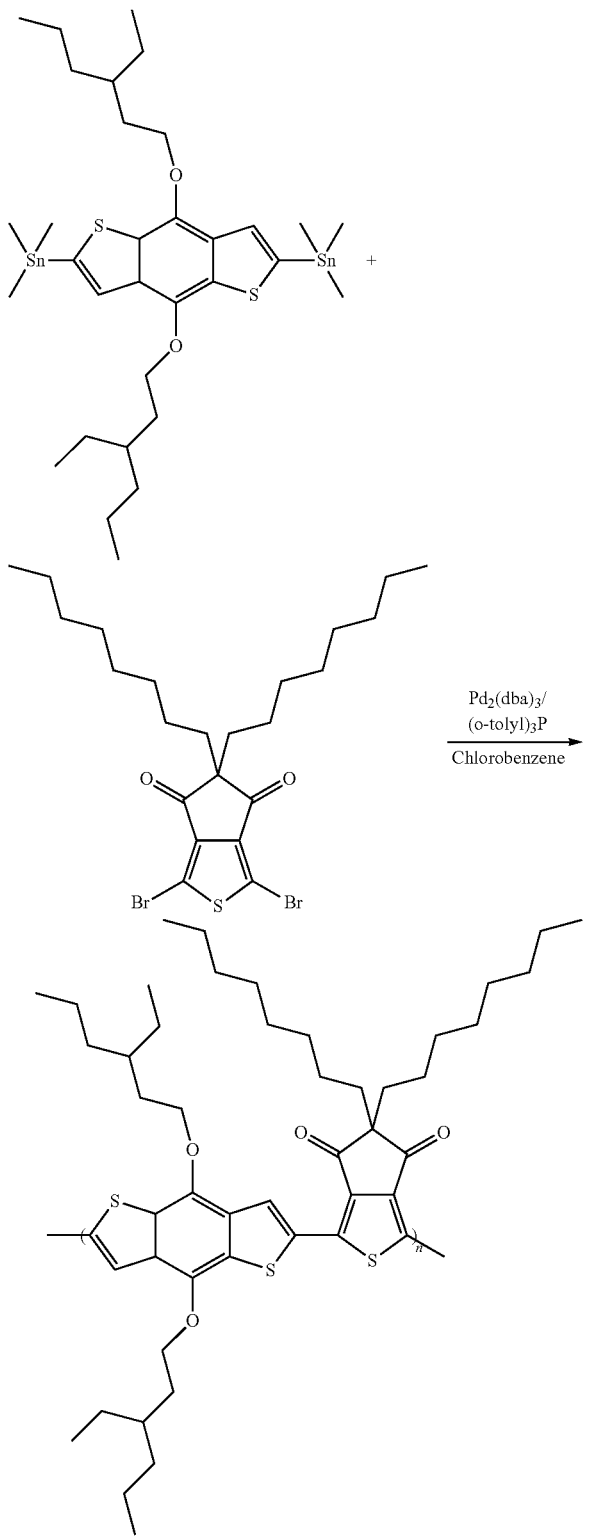

In a glove box, 1,3-dibromo-5,5-dioctyl-4H-cyclopenta[c]thiophene-4,6(5H)-dione (1 eq), 4,8-bis(2-ethylhexyloxy) benzo[1,2-b:4,5-b']dithiophene-2,6-diyl)bis(trimethylstannane) (1 eq), $Pd_2$ $dba_3$ (0.025 eq), P(o-tolyl)$_3$ (0.1 eq) are charged in a 100 mL schlenk flask. After connecting the flask to vac/argon line, the side arm is flushed with 5 vacuum-argon cycles and the flask is open to argon. Toluene, degassed with argon overnight is added. The flask is purged five times through vacuum-argon cycles, and then placed in a preheated flask at 110° C. for 48 hours. After cooling, methanol is added to precipitate the polymer. The polymer is filtered through Soxhlet thimble and Soxhlet extraction is performed in sequence with methanol, MTBE, hexane and chloroform.

The synthesis and polymerization can be adapted so that the side groups are different than what is exemplified, as described elsewhere herein.

Part IVe:

The structure described herein as (I) can be linked to itself to form larger structures such as (I)-(I) or (I)-(I) or (I)-(I)-(I). The side group R can be the same or different as (I) is linked to itself.

For example, other groups which can be included in monomers, oligomers, and polymers include:

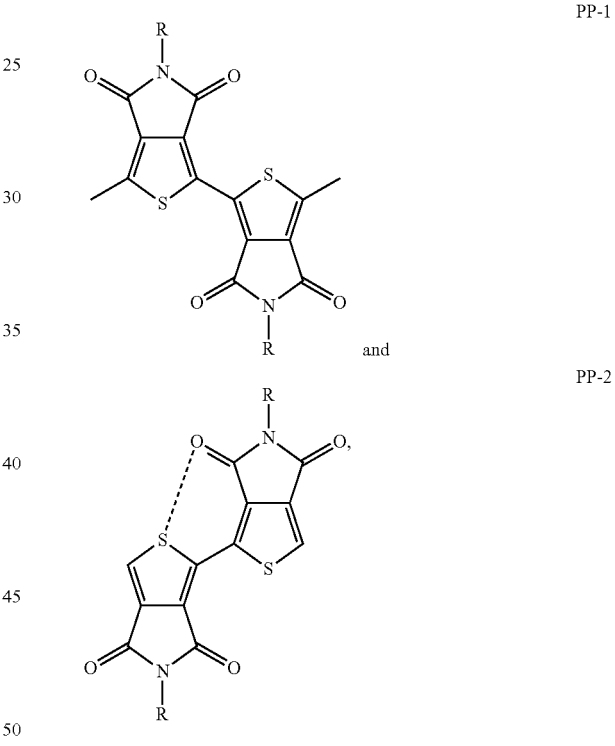

showing an interaction between oxygen and sulfur, wherein R can be a solubilizing group as described herein, wherein X can be, for example, nitrogen, a bivalent carbon, or two carbons of an optionally substituted phenyl ring linking the two carbonyls and forming the optionally substituted phenyl ring.

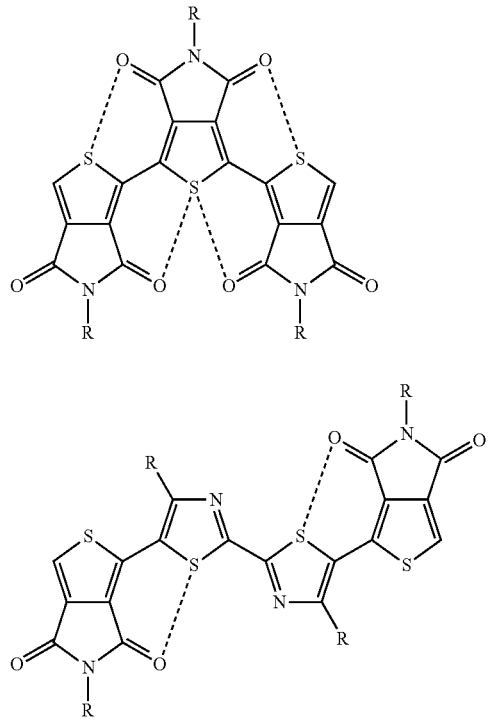

PP-4

PP-5

Example

Synthesis of 1-bromo-5-(2-ethylhexyl)-4H-thieno[3,4-c]pyrrole-4,6(5H)-dione

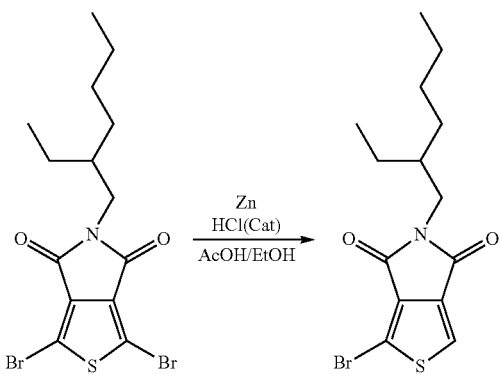 [SMILES: CCCCC(CC)CN1C(=O)c2c(Br)sc(Br)c2C1=O ; CCCCC(CC)CN1C(=O)c2csc(Br)c2C1=O]

1,3-Dibromo-5-(2-ethylhexyl)-4H-thieno[3,4-c]pyrrole-4,6(5H)-dione (2.6 g, 5 mmol) was placed in a three neck round-bottom flask equipped with a water condenser with ethanol (35 mL), acetic acid (10 mL) and three drops of 1 M HCl. The mixture was heated until the starting material was fully dissolved. At this point, zinc (310 mg, 5 mmol) was added in one portion. Mixture was refluxed for one hour after which an aliquot was taken for GC analysis and NMR, indicating reaction completion. After cooling, the solution was filtered through fritted glass to eliminate remaining Zn particles and solvent was evaporated under vacuum. Product was obtained by silica chromatography (1.1 g, 52%), using a 100% hexane to 100% $CHCl_3$ gradient.

Spectral data: $^1$H NMR (300 MHz, $CDCl_3$): δ0.88 (t, 3H, 6.8 Hz), 0.9 (t, 3H, 7.4 Hz), 1.2-1.4 (m, 8H), 1.72-1.84 (m, 1H), 3.5 (d, 2H, 7.2 Hz), 7.72 (s, 1H).

Example

Synthesis of 5,5'-bis(2-ethylhexyl)-4H,4'H-[1,1'-bithieno[3,4-c]pyrrole]-4,4',6,6'(5H,5'H)-tetraone

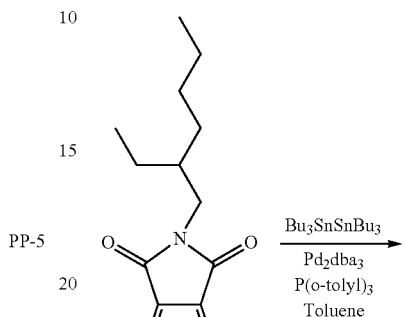

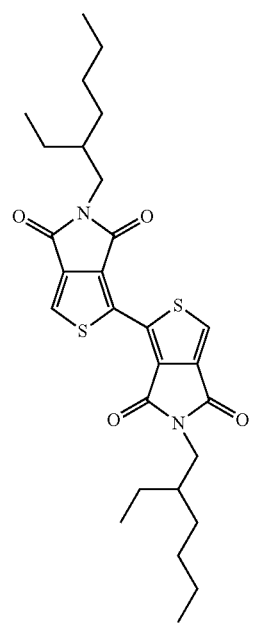

1-Bromo-5-(2-ethylhexyl)-4H-thieno[3,4-c]pyrrole-4,6 (5H)-dione (2.2 g, 6 mmol), $Pd_2 dba_3$ (137 mgs, 0.15 mmol), P(o-tolyl)$_3$ (182 mg, 0.6 mmol) and bis(tributyltin) (1.7 g, 3 mmol) were charged in a schlenk flask. Outside of the glove box, the flask was connected to argon line and toluene (40 ml, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with MgSO4 and the solvent was evaporated after filtration. The final product is obtained as a yellow solid by Silica chromatography using a 100% hexane/100% chloroform gradient.

Spectral data: $^1$H NMR (300 MHz, $CDCl_3$): $δ_H$ 0.82-0.96 (m, 12H), 1.16-1.46 (m, 16H), 1.72-1.87 (m, 2H), 3.54 (d, 4H), 7.88 (s, 2H).

Example

Synthesis of 3,3'-dibromo-5,5'-bis(2-ethylhexyl)-4H,4'H-[1,1'-bithieno[3,4-c]pyrrole]-4,4',6,6'(5H,5'H)-tetraone

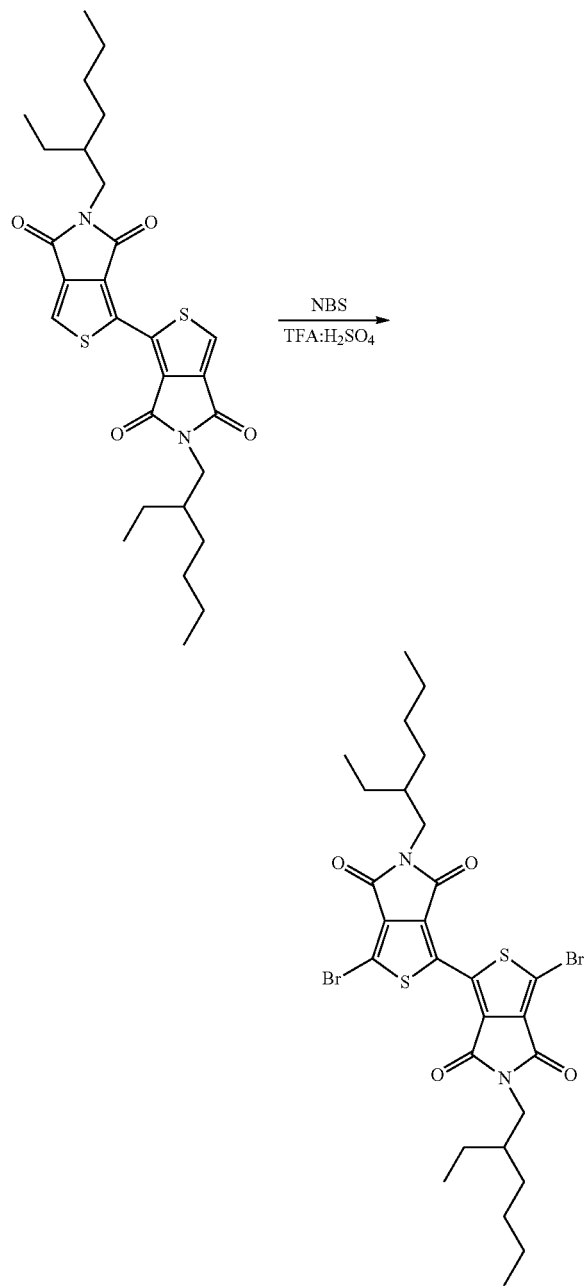

5,5'-Bis(2-ethylhexyl)-4H,4'H-[1,1'-bithieno[3,4-c]pyrrole]-4,4',6,6'(5H,5'H)-tetraone (1.7 g, 3.21 mmol) was dissolved in a 3:1 mixture of trifluoracetic acid (53 ml) and sulfuric acid (12 mL) in a 3-neck round bottom flask under nitrogen atmosphere, wrapped with aluminum foil and equipped with internal thermometer. N-bromosuccinimide (NBS) (1.26 g, 7.1 mmol, recrystallized before use) was added in one portion. An exotherm was observed immediately after addition, and the reaction was allowed to stir until the temperature was returned to room temperature. An aliquot was taken for NMR, which confirmed reaction was complete. The mixture was poured in ice-cold water and the aqueous solution was then extracted with CHCl$_3$. The organic phase was washed with water, dried with anhydrous MgSO$_4$ and the solvent was removed under vacuum. The mixture was purified by Silica column chromatography using a 100% hexane to 100% CHCl$_3$ gradient to yield a yellow solid (1.5 g, 70%).

Spectral data: $^1$H NMR (300 MHz, CDCl$_3$): δ$_H$ 0.82-0.96 (m, 12H), 1.2-1.4 (m, 16H), 1.72-1.86 (m, 2H), 3.54 (d, 4H).

Example

Synthesis of 1-bromo-5-(heptadecan-9-yl)-4H-thieno[3,4-c]pyrrole-4,6(5H)-dione

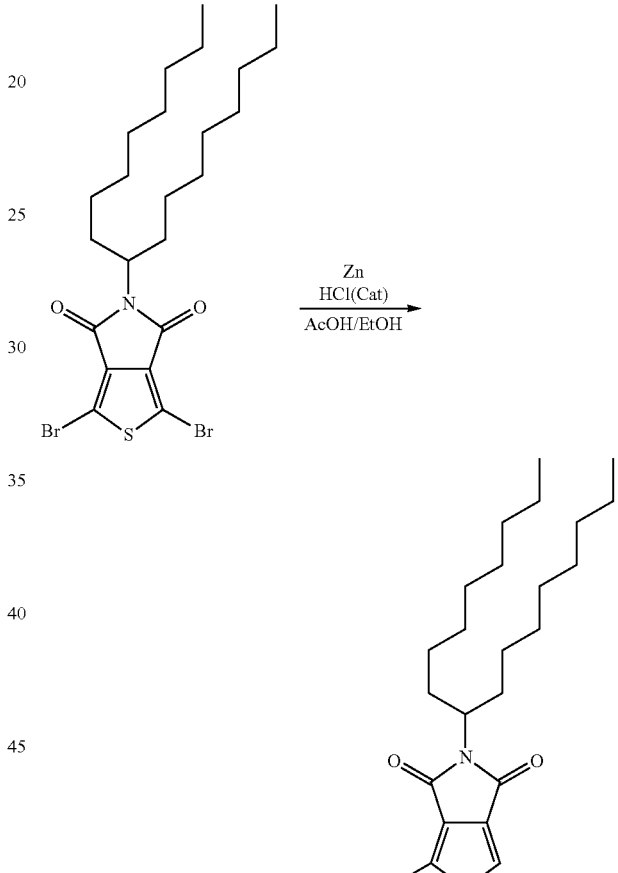

1,3-Dibromo-5-(heptadecan-9-yl)-4H-thieno[3,4-c]pyrrole-4,6(5H)-dione (9.43 g, 20.04 mmol) and zinc (1.31 g, 20.04 mmol) were placed in a 3 neck round-bottom flask equipped with a water condenser with ethanol (130 mL), acetic acid (40 mL) and 1 M HCl (2.5 mL). Mixture was refluxed for one hour after which an aliquot was taken for NMR analysis, which indicated reaction was complete. After cooling, the solution was filtered through fritted glass to eliminate remaining Zn particles and solvent was evaporated under vacuum. Product was obtained by silica chromatography, using a 100% hexane to 100% CHCl$_3$ gradient.

Spectral data: $^1$H NMR (300 MHz, CDCl$_3$): δ$_H$ 0.8-0.9 (t, 6H), 1.13-1.34 (m, 24H), 1.56-1.72 (m, 2H), 1.92-2.08 (m, 2H), 4.02-4.16 (m, 1H), 7.7 (s, 1H).

Example

Synthesis of 5,5'-di(heptadecan-9-yl)-4H,4'H-[1,1'-bithieno[3,4-c]pyrrole]-4,4',6,6'(5H,5'H)-tetraone

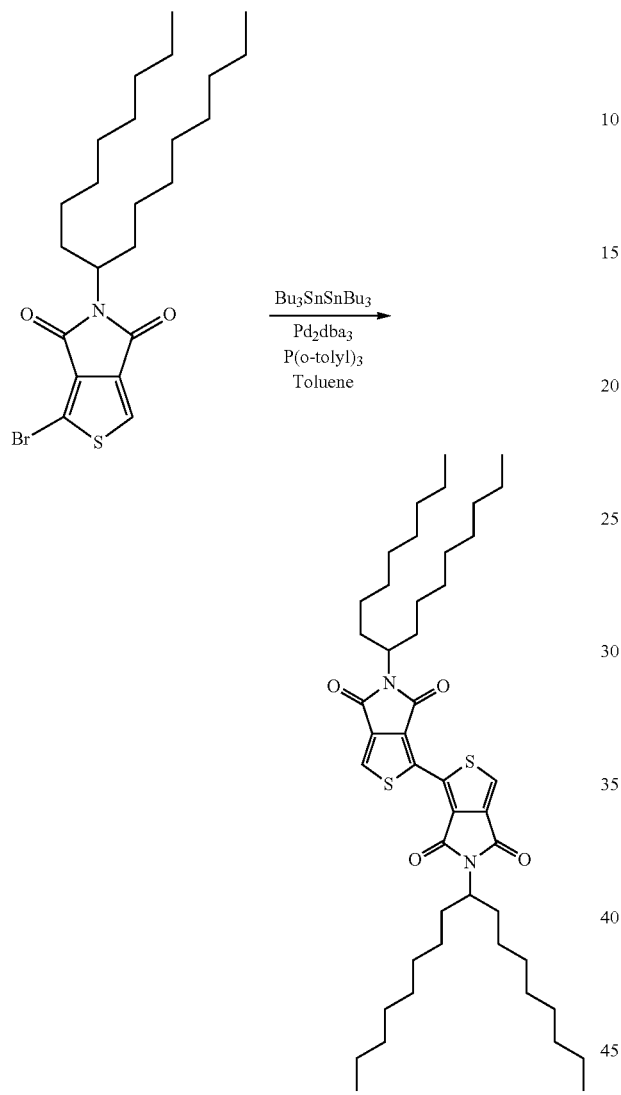

1-bromo-5-(heptadecan-9-yl)-4H-thieno[3,4-c]pyrrole-4,6(5H)-dione (575 mg, 1.22 mmol), Pd$_2$dba$_3$ (28 mg, 0.03 mmol), (o-tolyl)$_3$P (37.2 mg, 0.122 mmol) and bis(tributyltin) (0.31 mL, 0.61 mmol) were charged in a schlenk flask. Outside of the glove box, the flask was connected to argon line and toluene (10 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with anhydrous MgSO$_4$ and the solvent was evaporated after filtration. The final product is obtained as a yellow solid by Silica chromatography using a 100% hexane/100% chloroform gradient (347 mg, 36% yield).

Spectral data: $^1$H NMR (300 MHz, CDCl$_3$): $\delta_H$ 0.85 (broad t, 12H, 6.92 Hz), 1.12-1.36 (m, 48H), 1.58-1.76 (m, 4H), 1.95-2.13 (m, 4H), 4.07-4.2 (m, 2H), 7.86 (s, 2H). $^{13}$C NMR (CDCl$_3$, 75 MHz): $\delta$ 14.31, 22.86, 26.92, 29.43, 29.5, 29.66, 32.04, 32.49, 53.26, 126.43, 132.55, 136.84.

Example

Synthesis of 3,3'-dibromo-5,5'-di(heptadecan-9-yl)-4H,4'H-[1,1'-bithieno[3,4-c]pyrrole]-4,4',6,6'(5H,5'H)-tetraone

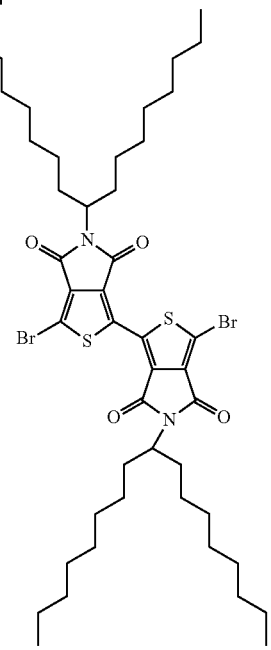

5,5'-Di(heptadecan-9-yl)-4H,4'H-[1,1'-bithieno[3,4-c]pyrrole]-4,4',6,6'(5H,5'H)-tetraone (347 mg, 0.444 mmol) was dissolved in a 4:1 mixture of trifluoracetic acid (16 mL) and sulfuric acid (4 mL) in a 3-neck round bottom flask under nitrogen atmosphere, wrapped with aluminum foil and equipped with internal thermometer. N-bromosuccinimide (178 mg, 1 mmol, recrystallized before use) was added in one portion. An exotherm was observed immediately after addition, and the reaction was allowed to stir until the temperature was returned to room temperature. An aliquot was taken for NMR, which confirmed reaction was complete. The mixture was poured in ice-cold water and the aqueous solution was then extracted with CHCl$_3$. The organic phase was washed with water, dried with anhydrous MgSO$_4$ and the solvent was removed under vacuum. The mixture was purified by Silica column chromatography using a 100% hexane to 100% CHCl$_3$ gradient (406 mg, 97%).

Spectral data: $^1$H NMR (300 MHz, CDCl$_3$): $\delta_H$ 0.83 (t, 12H, 6.94); 1.1-1.32 (m, 48H), 1.57-1.73 (m, 4H), 1.9-2.08 (m, 4H), 4.02-4.17 (m, 2H).

$^{13}$C NMR (CDCl$_3$, 75 MHz): $\delta$ 14.06, 22.6, 26.66, 29.16, 29.21, 29.37, 31.77, 32.16, 53.67, 115.98, 132.57, 133.75, 134.04.

Example

Synthesis of 5-(heptadecan-9-yl)-1,3-di(thiophen-2-yl)-4H-thieno[3,4-c]pyrrole-4,6(5H)-dione and toluene (70 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with MgSO$_4$ and the solvent was evaporated after filtration. The product was first purified by silica chromatography using a 100% hexane/100% chloroform gradient. The final product, a yellow solid was further purified by dissolution in chloroform followed by precipitation with methanol (1.2 g, 56%).

Spectral data: $^1$H NMR (300 MHz, CDCl$_3$): $\delta_H$ 0.8 (t, 6H, 7.22 Hz), 1.13-1.35 (m, 24H), 1.62-1.77 (m, 2H), 1.97-2.17 (m, 2H), 4.1-4.24 (m, 1H), 7.13 (dd, 2H, 3.7 Hz, 5.1 Hz), 7.44 (dd, 5.1 Hz, 1.1 Hz).

Example

Synthesis of 1,3-bis(5-bromothiophen-2-yl)-5-(heptadecan-9-yl)-4H-thieno[3,4-c]pyrrole-4,6(5H)-dione

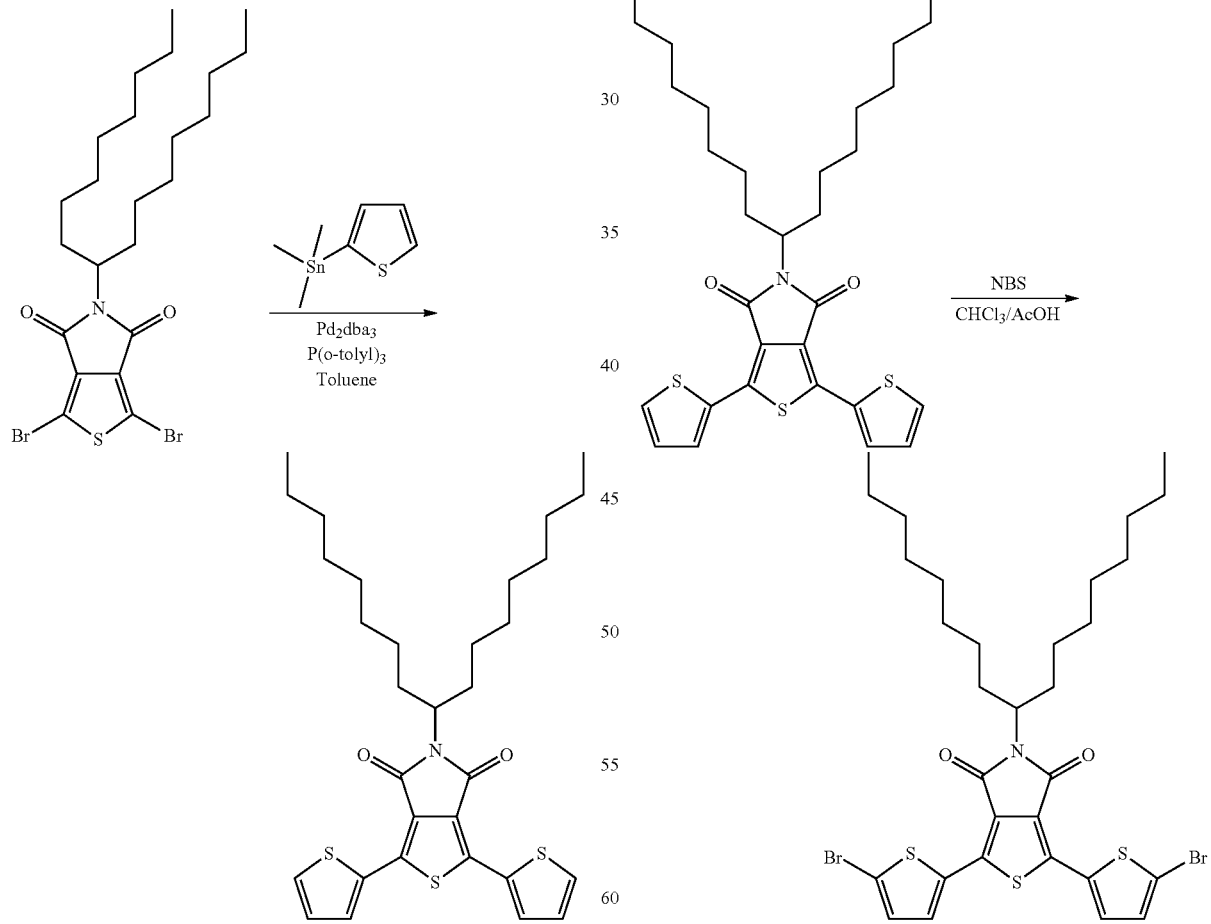

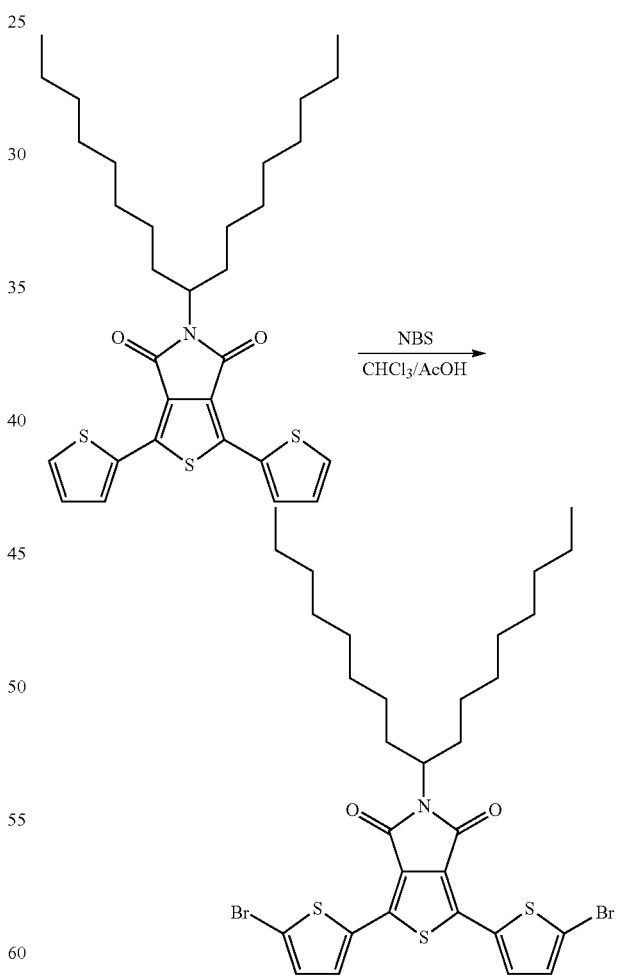

1,3-Dibromo-5-(heptadecan-9-yl)-4H-thieno[3,4-c]pyrrole-4,6(5H)-dione (2 g, 3.64 mmol), Pd$_2$dba$_3$ (167 mg, 0.18 mmol), (o-tolyl)$_3$P (221 mg, 0.72 mmol) and 2-trimethyltinthiophene (3.4 g, 9.1 mmol) were charged in a schlenk flask. Outside of the glove box, the flask was connected to argon line 5-(Heptadecan-9-yl)-1,3-di(thiophen-2-yl)-4H-thieno[3,4-c]pyrrole-4,6(5H)-dione (0.62 g, 1.115 mmol) was dissolved in a 1:1 mixture of acetic acid (20 mL) and chloroform (20 mL) in a 3-neck round bottom flask under nitrogen atmosphere, wrapped with aluminum foil and equipped with internal thermometer. N-bromosuccinimide (0.4 g, 2.23 mmol, recrystallized before use) was added in one portion. An exotherm was observed immediately after addition, and the reaction was allowed to stir until the solution returned to room temperature. An aliquot was taken for NMR, which confirmed reaction was complete. The mixture was poured in ice-cold water and the aqueous solution was then extracted with $CHCl_3$. The organic phase was washed with water, dried with anhydrous $MgSO_4$ and the solvent was removed under vacuum. The mixture was purified by Silica column chromatography using a 100% hexane to 100% $CHCl_3$ gradient. The product is then further purified by first dissolving in the minimum amount of chloroform followed by a large amount of methanol to precipitate the pure product, obtained as a yellow solid after filtration (0.5 g, 63%).

Spectral data: $^1$H NMR (300 MHz, $CDCl_3$): $\delta_H$ 0.85 (t, 6H, 7 Hz), 1.17-1.31 Hz (m, 24H), 1.6-1.78 (m, 2H), 1.95-2.15 (m, 2H), 4.07-4.21 (m, 1H), 7.08 (d, 2H, 4.25 Hz), 7.64 (d, 2H, 4.25 Hz).

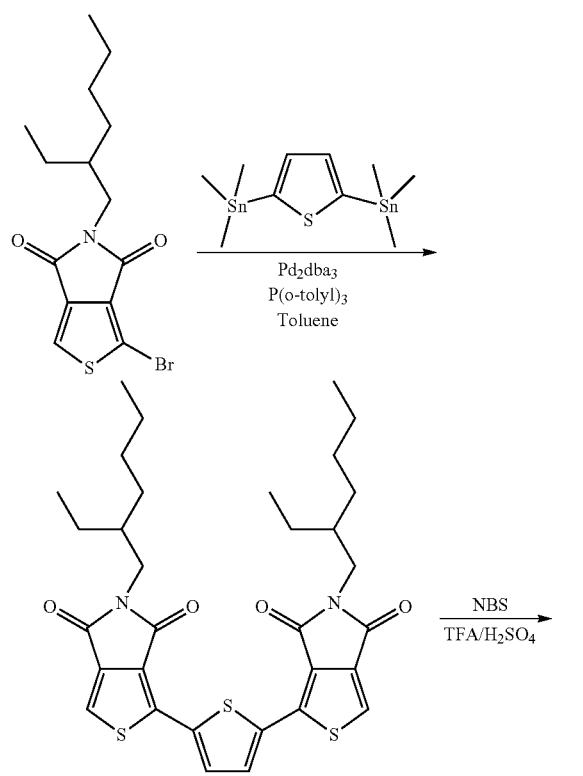


Example

Synthesis of 1,1'-(thiophene-2,5-diyl)bis(5-(2-ethylhexyl)-4H-thieno[3,4-c]pyrrole-4,6(5H)-dione)

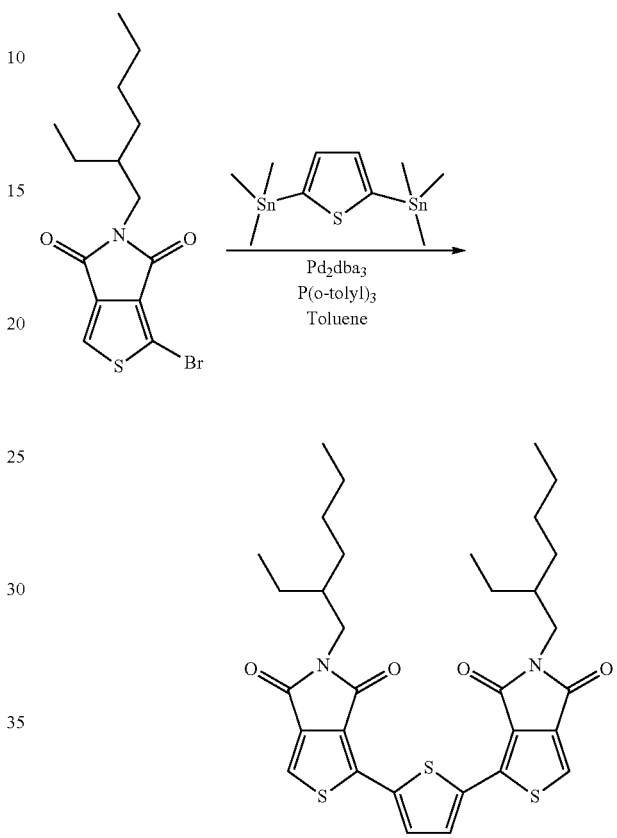

In a glove box, 1-bromo-5-(2-ethylhexyl)-4H-thieno[3,4-c]pyrrole-4,6(5H)-dione (1.55 g, 4.5 mmol), 2,5-bis(trimethyltin)-thiophene (0.74 g, 1.8 mmol), $Pd_2$ $dba_3$ (41 mg, 0.045 mmol) and tris(o-tolyl)phosphine (55 mg, 0.18 mmol) were charged in a schlenk flask. Outside of the glove box, the flask was connected to argon line and toluene (11 mL, bubbled with argon overnight) was added. The flask was purged with vacuum argon cycles, and then was placed in a preheated oil bath at 110° C. The mixture was stirred at that temperature for 12 hours, after which it was cooled and a KF solution in water was added. The solution was stirred for one hour. After separation, the aqueous phase was further extracted with toluene. The organic phase was washed with water, dried with anhydrous $MgSO_4$ and the solvent was evaporated after filtration. The product was first purified by silica chromatography using a 100% hexane/100% chloroform gradient. The final product, a yellow solid was further purified by dissolution in chloroform followed by precipitation with methanol.

Spectral data: $^1$H NMR (300 MHz, $CDCl_3$): $\delta_H$ 0.92 (t, 12H, 7.33 Hz), 1.22-1.42 (m, 16H), 1.76-1.92 (m, 2H), 3.56 (d, 4H, 7.51 Hz), 7.67 (s, 2H), 8.02 (s, 2H).

Example

Synthesis of poly(3-(4,8-bis(heptan-3-yloxy)benzo[1,2-b:4,5-b']dithiophen-2-yl)-alt-5,5'-bis(2-ethylhexyl)-4H,4'H-[1,1'-bithieno[3,4-c]pyrrole]-4,4',6,6'(5H,5'H)-tetraone)

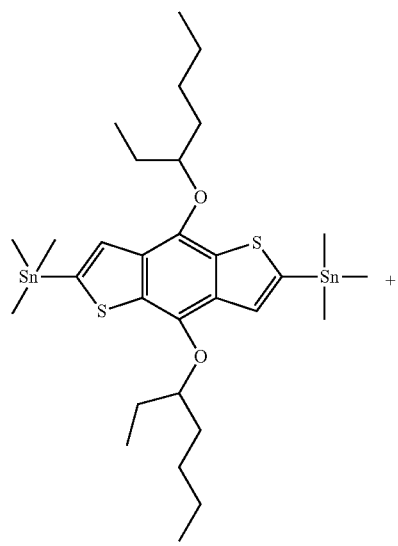

+

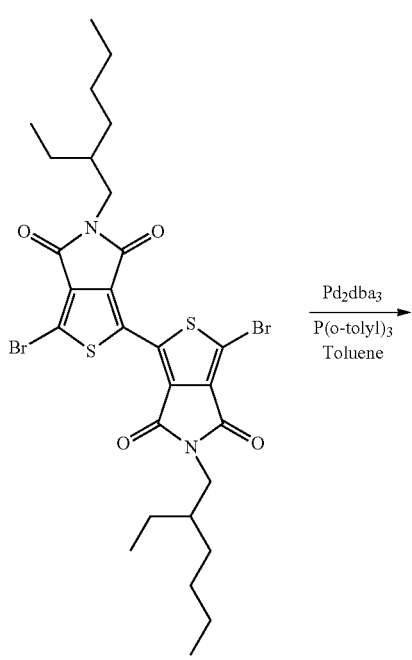

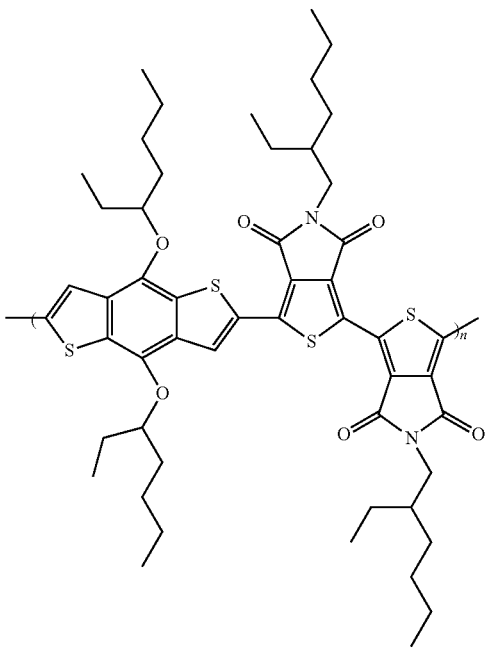

In a glove box, 3,3'-dibromo-5,5'-bis(2-ethylhexyl)-4H,4'H-[1,1'-bithieno[3,4-c]pyrrole]-4,4',6,6'(5H,5H)-tetraone (267 mg, 0.388 mmol), (4,8-bis(2-ethylhexyl)benzo[1,2-b:4,5-b']dithiophene-2,6-diyl)bis(trimethylstannane) (300 mg, 0.39 mmol), $Pd_2 dba_3$ (9 mg, 0.01 mmol), P(o-tolyl)$_3$ (12 mg, 0.04 mmol) were charged in a 100 mL schlenk flask. After connecting the flask to vac/argon line, the side arm was flushed with 5 vacuum-argon cycles and the flask was open to argon. Toluene (20 mL), degassed with argon overnight was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform (340 mg). Molecular weight was determined by GPC in chlorobenzene (1 mL/min at 80° C.) vs. polystyrene standards: $M_n$=25,000, $M_w$=137,500, PDI=5.5.

Example

Synthesis of poly(3-(4,8-bis(2-ethylhexyl)benzo[1,2-b:4,5-b]dithiophen-2-yl)-alt-5,5'-di(heptadecan-9-yl)-4H,4'H-[1,1'-bithieno[3,4-c]pyrrole]-4,4',6,6'(5H,5H)-tetraone)

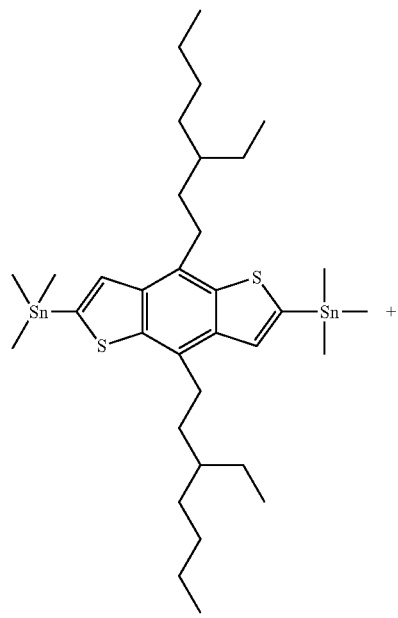

+

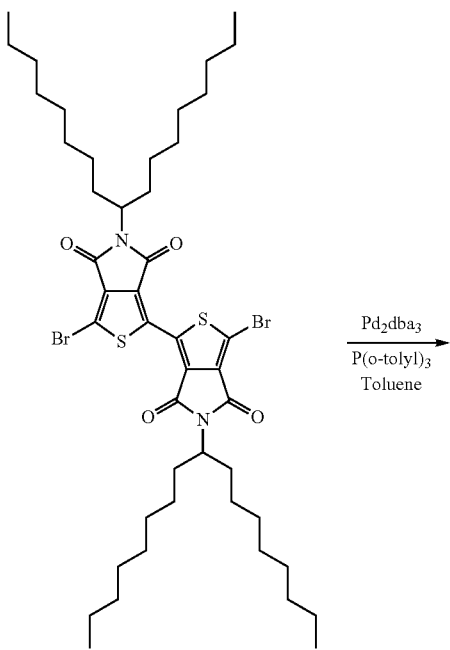

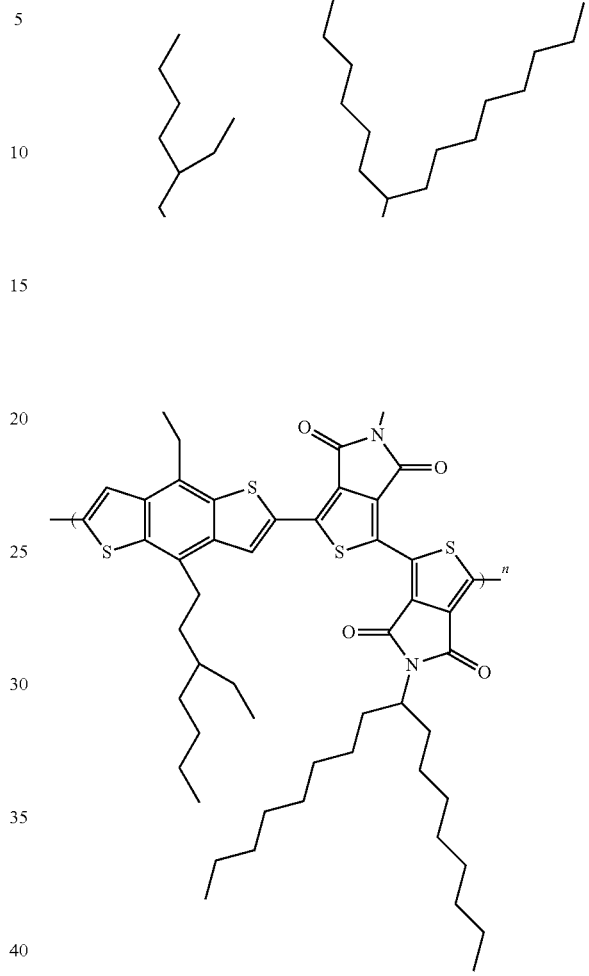

In a glove box, 3,3'-dibromo-5,5'-di(heptadecan-9-yl)-4H,4H,4'H-[1,1'-bithieno[3,4-c]pyrrole]-4,4',6,6'(5H,5'H)-tetraone (0.454 mmol), (4,8-bis(2-ethylhexyl)benzo[1,2-b:4,5-b]dithiophene-2,6-diyl)bis(trimethylstannane) (0.454 mmol), $Pd_2 dba_3$ (10.4 mg, 0.011 mmol), P(o-tolyl)$_3$ (13.8 mg, 0.044 mmol) were charged in a 100 mL schlenk flask. After connecting the flask to vac/argon line, the side arm was flushed with 5 vacuum-argon cycles and the flask was open to argon. Toluene (20 mL), degassed with argon overnight was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform (200 mg). Molecular weight was determined by GPC in chlorobenzene (1 mL/min at 80° C.) vs. polystyrene standards: $M_n$=27,300, $M_w$=62,800, PDI=2.3.

Example 5
Synthesis of poly(3-(4,8-bis(2-ethylhexyl)benzo[1,2-b:4,5-b]dithiophen-2-yl)-ran-5,5'-bis(2-ethylhexyl)-4H,4'H-[1,1'-bithieno[3,4-c]pyrrole]-4,4',6,6'(5H,5'H)-tetraone)
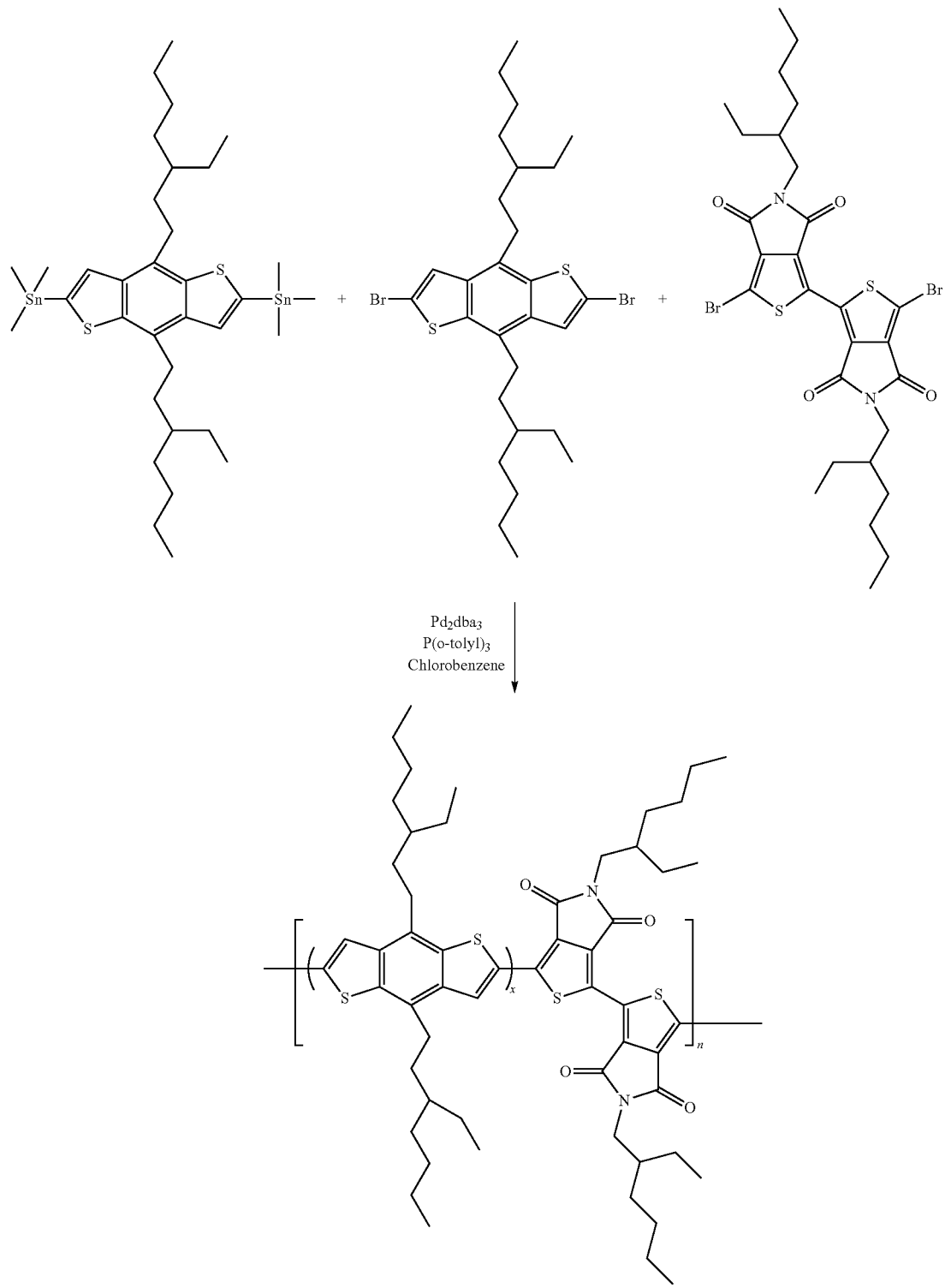

In a glove box, 3,3'-dibromo-5,5'-bis(2-ethylhexyl)-4H,4H',4'H-[1,1'-bithieno[3,4-c]pyrrole]-4,4',6,6'(5H,5'H)-tetraone (180 mg, 0.262 mmol), 2,6-dibromo-4,8-bis(3-ethylheptyl)benzo[1,2-b:4,5-b']dithiophene (77.4 mg, 0.129 mmol), (4,8-bis(2-ethylhexyl)benzo[1,2-b:4,5-b']dithiophene-2,6-diyl)bis(trimethylstannane) (300 mg, 0.390 mmol), Pd$_2$dba$_3$ (9.00 mg, 0.010 mmol), P(o-tolyl)$_3$ (12.0 mg, 0.040 mmol) were charged in a 50 mL Schlenk flask. After connecting the flask to vac/argon line, the side arm was flushed with 5 vacuum-argon cycles and the flask was open to argon. Chlorobenzene (10 mL), degassed with argon overnight, was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, (335 mg). Molecular weight was determined by GPC in chlorobenzene (1 mL/min at 80° C.) vs. polystyrene standards: $M_n$=7,000, $M_w$=12,600, PDI=1.8.

Example

Synthesis of poly{(3-4-(5,9-diethyltridecan-7-yl)-4H-dithieno[3,2-b:2',3'-d]pyrrol-2-yl)-alt-(5,5'-bis(2-ethylhexyl)-4H,4'H-[1,1'-bithieno[3,4-c]pyrrole]-4,4',6,6'(5H,5'H)-tetraone)}

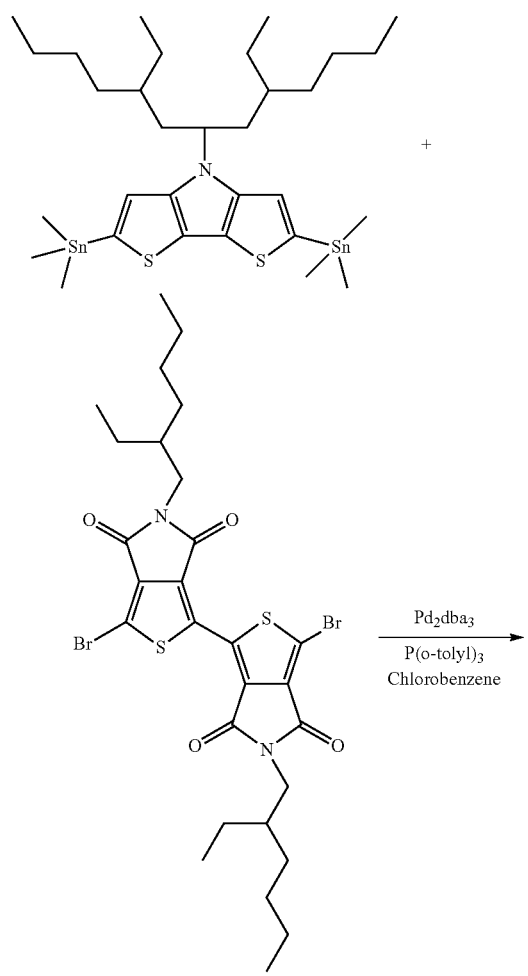

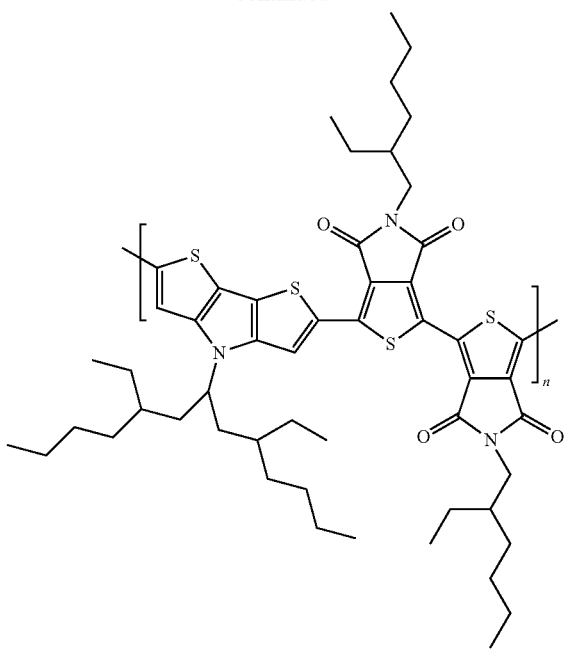

In a glove box, 4-(5,9-diethyltridecan-7-yl)-2,6-bis(trimethylstannyl)4H-dithieno[3,2-b:2',3'-d]pyrrole (0.30 g, 0.40 mmol), 1-bromo-3-[3-bromo-5-(2-ethylhexyl)-4,6-dioxothieno[3,4-c]pyrrol-1-yl]-5-(2-ethylhexyl)thieno[3,4-c]pyrrole-4,6-dione (0.28 g, 0.40 mmol), tris(dibenzylideneacetone)dipalladium(0) (9.2 mg, 0.010 mmol) and tris(o-tolyl)phosphine (12 mg, 0.040 mmol) were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a 110° C. oil bath and left stirring under an argon stream for 2 days. After cooling to room temperature, 40 mL of methanol were added to the reaction mixture. The polymer was collected via filtration and purified by consecutive Soxhlet extractions in sequence with methanol, MTBE, hexane, and chloroform. The chloroform solution was passed through celite to remove catalyst residuals, and solvent was removed under vacuum to yield polymer. The polymer was re-dissolved in a small amount of chloroform, re-precipitated in the mixture of IPA, water and methanol, isolated via centrifuge and dried to yield 64% of polymer. Molecular weight was determined by GPC in chlorobenzene (1 mL/min at 80° C.) vs. polystyrene standards: $M_n$=24,400, $M_w$=47,300, PDI=1.9.

Example

Synthesis of 4,8-dimethylbenzo[1,2-b:4,5-b']dithiophene

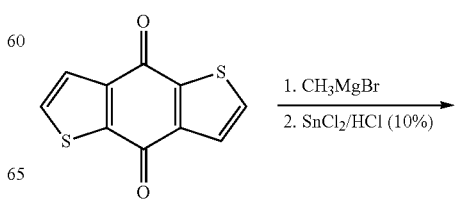

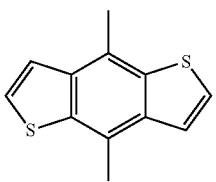

A dry 250-mL three-neck flask equipped with a reflux condenser and an addition funnel was flushed with N$_2$ and was charged with a 1 M solution of methylmagnesium bromide (11 mL) in THF via deoxygenated syringe. A 0.1 M solution of benzo[1,2-b:4,5-b']dithiophene-4,8-dione (1.0 g, 4.5 mmol) in THF (40 mL) was added portion-wise. The reaction was heated to reflux for 1 hour. As the reaction was completed, the flask was cooled to ambient temperature and a solution of SnCl$_2$ (2.1 g) dissolved in 10% HCl (20 mL) was added to the reaction flask. The stirring continued with increasing temperature to reflux for 1 hour and then cooling the reaction to ambient temperature. The reaction was poured into 100 mL of cool water with 10 mL of 10% HCl and extracted with CHCl$_3$ (100 mL) three times. The combined organic layer was dried over anhydrous magnesium sulfate (MgSO$_4$). After the product was filtered, the solvent was removed by rotary evaporation. The product was purified using column chromatography on silica gel with hexanes/chloroform (gradient) to yield white solid (0.46 g, 40%).

Spectral data: $^1$H NMR (300 MHz, CDCl$_3$): $\delta_H$ 7.42 (dd, 4H), 2.8 (s, 6H).

Example

Synthesis of (4,8-dimethylbenzo[1,2-b:4,5-b']dithiophene-2,6-diyl)bis(trimethylstannane)

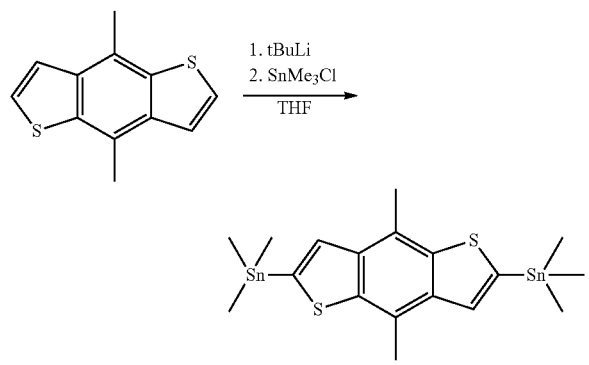

A dry 250-mL three-neck round bottom flask was flushed with N$_2$ and was charged with 4,8-dimethylbenzo[1,2-b:4,5-b']dithiophene (1.02 g, 4.70 mmol) and anhydrous tetrahydrofuran (THF) (75.0 mL, 0.01 M) via deoxygenated syringe. The reaction flask was cooled to −78° C. and a 1.3 M solution of tert-butyllithium in hexanes (9.00 mL, 23.0 mmol) was added drop-wise via deoxygenated syringe. After 30 minutes of stirring at −78° C., the solution was chilled to 0° C. and stirring was continued for 5 minutes, at which point the reaction mixture was cooled back to −78° C. A 1 M solution of trimethyltin chloride (19.0 mL, 37.0 mmol) in hexanes was added to the reaction flask dropwise and stirring continued for 30 minutes at −76° C. The cooling bath was removed and the reaction mixture was allowed to warm to ambient temperature. As the reaction was completed, cool DI water (10 mL) was slowly added to the reaction flask. Then, the reaction mixture was poured into 50 mL of cool water and extracted with MTBE (100 mL) three times. The combined organic layer was washed with water two times and dried over anhydrous magnesium sulfate (MgSO$_4$). After the product was filtered, the solvent was removed by rotary evaporation. The crude product was purified by precipitation into methanol from a THF solution to yield white solid (1.90 g, 74%).

Spectral data: $^1$H NMR (300 MHz, CDCl$_3$): $\delta_H$ 7.59 (s, 2H), 2.8 (s, 6H), 0.54 (s, 18H).

Example

Synthesis of 2,6-bis(trimethylstannyl)benzo[1,2-b:4,5-b']dithiophene

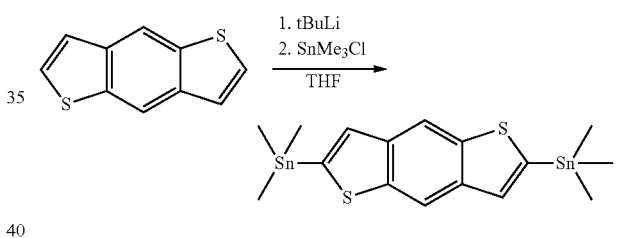

A dry 1 L three-neck round bottom flask was flushed with N$_2$ and was charged with benzo[1,2-b:4,5-b']dithiophene (5.20 g, 26.3 mmol) and anhydrous tetrahydrofuran (THF) (300 mL, 0.01 M) via deoxygenated syringe. The reaction flask was cooled to −78° C. and a 1.3 M solution of tert-butyllithium in hexanes (53.0 mL, 68.8 mmol) was added dropwise via deoxygenated syringe. After 30 minutes of stirring at −78° C., the solution was chilled to 0° C. and stirring was continued for 5 minutes, at which point the reaction mixture was cooled back to −78° C. A 1 M solution of trimethyltin chloride (105 mL, 100 mmol) in hexanes was added to the reaction flask dropwise and stirring continued for 30 minutes at −76° C. The cooling bath was removed and the reaction mixture was allowed to warm to ambient temperature. As the reaction was completed, cool DI water (50 mL) was slowly added to the reaction flask. Then, the reaction mixture was poured into 300 mL of cool water and extracted with MTBE (300 mL) three times. The combined organic layer was washed with water two times and dried over anhydrous magnesium sulfate (MgSO$_4$). After the product was filtered, the solvent was removed by rotary evaporation. The crude product was purified by precipitation into methanol from a THF solution to yield white solid (12.0 g, 88%).

Spectral data: $^1$H NMR (300 MHz, CDCl$_3$): $\delta_H$ 8.24 (s, 2H), 7.42 (s, 2H), 0.42 (s, 18H).

Example

Synthesis of poly(3-(4,8-dimethylbenzo[1,2-b:4,5-b]dithiophen-2-yl)-alt-5,5'-di(heptadecan-9-yl)-4H,4'H-[1,1'-bithieno[3,4-c]pyrrole]-4,4',6,6'(5H,5'H)-tetraone)

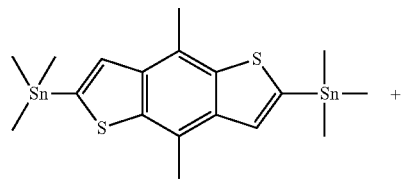

+

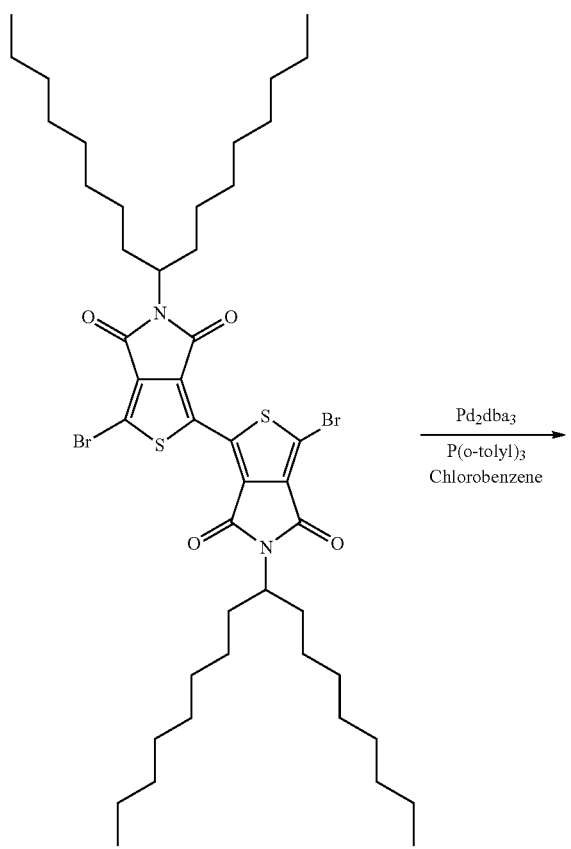

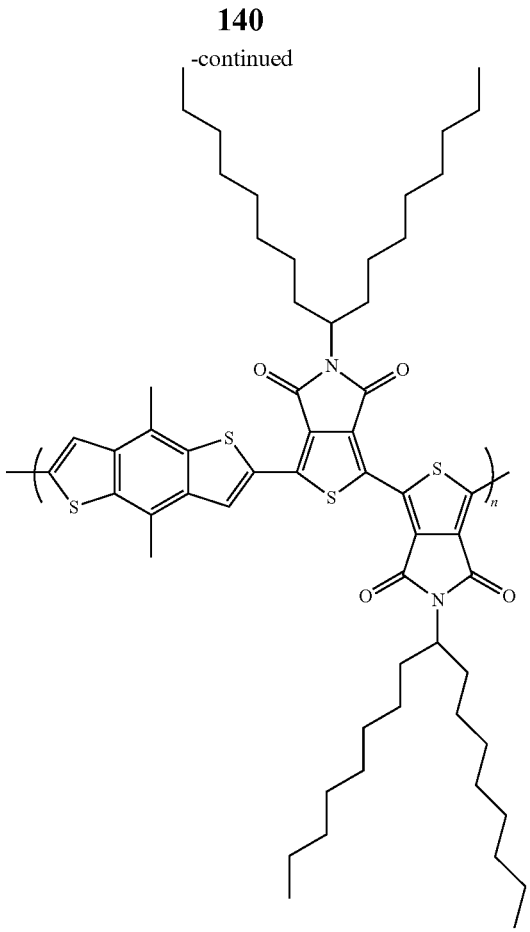

In a glove box, 3,3'-dibromo-5,5'-di(heptadecan-9-yl)-4H,4'H-[1,1'-bithieno[3,4-c]pyrrole]-4,4',6,6'(5H,5'H)-tetraone (345.2 mg, 0.37 mmol), (4,8-dimethylbenzo[1,2-b:4,5-b]dithiophene-2,6-diyl)bis(trimethylstannane) (200 mg, 0.37 mmol), Pd$_2$dba$_3$ (9 mg, 0.0098 mmol), P(o-tolyl)$_3$ (12 mg, 0.039 mmol) were charged in a 100 mL schlenk flask. After connecting the flask to vac/argon line, the side arm was flushed with 5 vacuum-argon cycles and the flask was open to argon. Chlorobenzene (20 mL, degassed with argon overnight) was added. The flask was purged five times through vacuum-argon cycles, then placed in a preheated flask at 110° C. for 48 hours. After cooling, methanol was added to precipitate the polymer. The polymer was filtered through Soxhlet thimble and Soxhlet purification was performed with methanol, MTBE, hexane. The polymer was extracted through CHCl$_3$ Soxhlet, and obtained as a reflective brown solid after solvent evaporation under vacuum (250 mg).

Example

Synthesis of poly(3-(benzo[1,2-b:4,5-b]dithiophen-2-yl)-alt-5,5'-bis(1-octylnonyl)-4H,4'H-[1,1'-bithieno[3,4-c]pyrrole]-4,4',6,6'(5H,5'H)-tetraone)

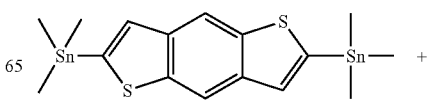

+

-continued

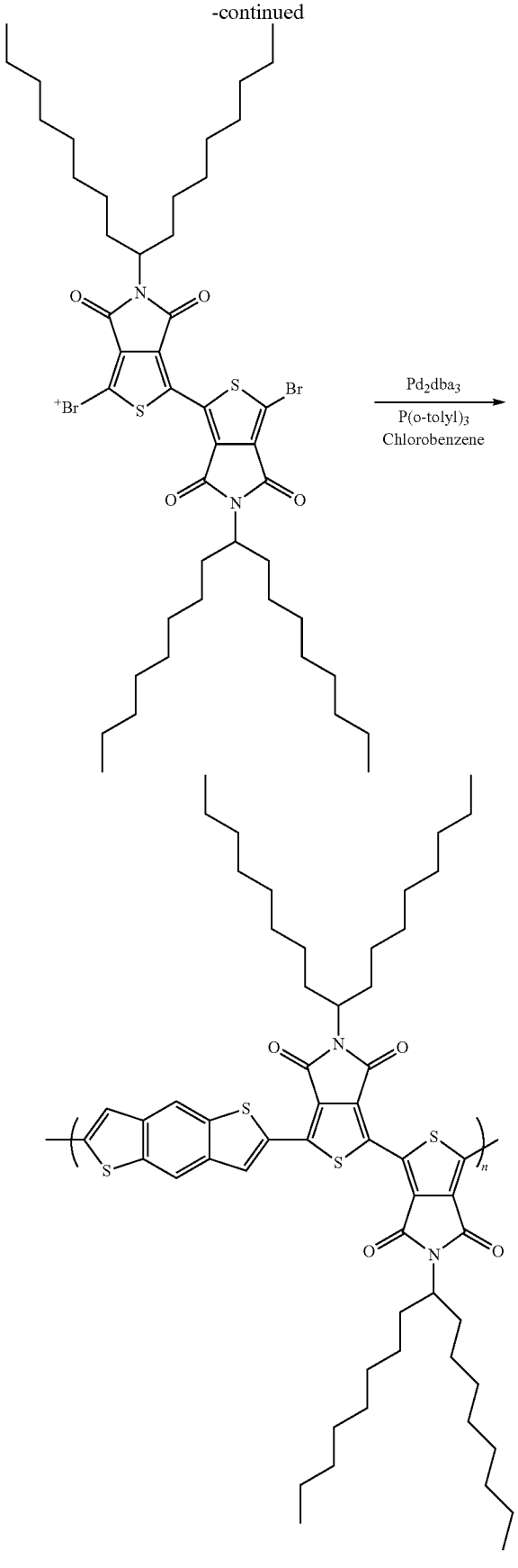

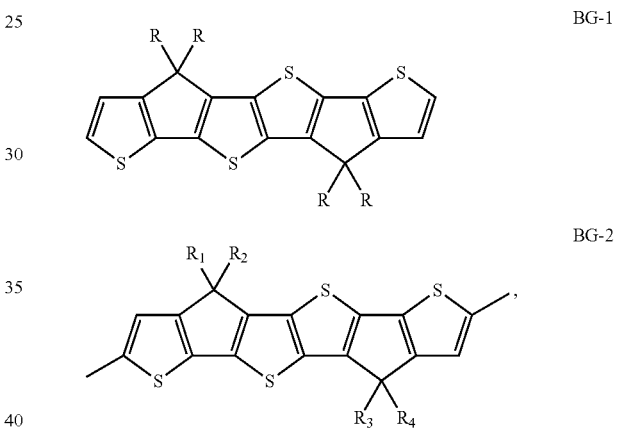

In a glove box, 3,3'-dibromo-5,5'-di(heptadecan-9-yl)-4H,4'H-[1,1'-bithieno[3,4-c]pyrrole]-4,4',6,6'(5H,5'H)-tetraone (364 mg, 0.388 mmol), benzo[1,2-b:4,5-b]dithiophene-2,6-diyl)bis(trimethylstannane) (200 mg, 0.388 mmol), $Pd_2 dba_3$ (9 mg, 0.0098 mmol) and P(o-tolyl)$_3$ (12 mg, 0.039 mmol) were charged in a 100 mL schlenk flask. After connecting the flask to vac/argon line, the side arm was flushed with 5 vacuum-argon cycles and the flask was open to argon. Chlorobenzene (20 mL, degassed with argon overnight) was added. The flask was purged five times through vacuum-argon cycles, and then placed in a preheated flask at 110° C. for 48 hours. After cooling, methanol was added to precipitate the polymer. The polymer was filtered through Soxhlet thimble and Soxhlet extraction was performed in sequence with methanol, MTBE, hexane and chloroform. After drying, polymer was collected from thimble as a reflective brown solid (210 mg).

Part IVf:

Other groups which can be included in donor acceptor polymers are illustrated below as BG-1 and BG-2:

wherein BG-2 shows particular locations for linking the group into a polymer, or bonding to a reactive group. The groups R1, R2, R3, and/or R4 can be, independently, a variety of groups including, for example, hydrogen or solubilizing groups as described herein. They can be, for example, C1-C25 optionally substituted alkyl, aryl, alkylaryl, or arylalkyl. Examples include phenyl, wherein the phenyl is optionally further substituted at the 4 position with, for example, an alkyl group such as, for example, a branched group, such as, for example, ethylhexyl.

Example

Synthesis of 2,5-bis(trimethylstannyl)thieno[3,2-b]thiophene

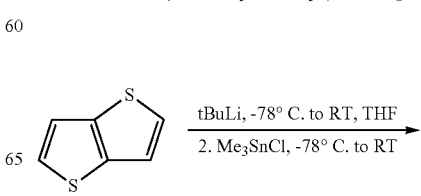

-continued

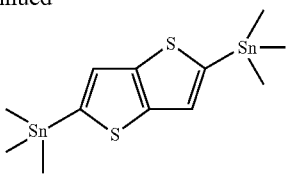

In a 3-neck round bottom flask equipped with an argon inlet and an addition flannel, thieno[3,2-b]thiophene (7.5 g, 54 mmol) was dissolved in tetrahydrofuran (1 L). After the solution was cooled to −78° C. using an isopropanol/dry ice bath, t-BuLi (100 mL, 170 mmol) was transferred by cannula to the addition funnel. The organolithium reagent was then added dropwise. After completion of the addition, the mixture was stirred for 20 min at −78° C. then warmed up with an isopropanol bath at room temperature for 30 minutes during which a yellow precipitate formed. The solution was cooled back at −78° C., and after cannula transfer to the addition funnel, trimethyltin chloride (200 mL of 1 M solution in THF, 200 mmol) was added dropwise. During addition of trimethyltin chloride, the precipitate disappeared and the solution turned light brown. After warming to room temperature the solution was stirred for 30 minutes then was poured into ice-cold water. The aqueous phase was further extracted with hexane. The combined organic phase were washed with cold water then dried with magnesium sulfate. After filtration, the solvent is evaporated under vacuum to yield a grey-brown solid. The product was purified by precipitation of a chloroform solution into methanol followed by filtration (13.2 g, 53%).

Spectral data: $^1$H NMR (CDCl$_3$, 300 MHz): $\delta_H$ 0.41 (s, 18H), 7.26 (s, 2H).

$^{13}$C(CDCl$_3$, 75 MHz): δ 7.99, 126.29, 141.4, 147.62.

Example

Synthesis of methyl 2-bromothiophene-3-carboxylate

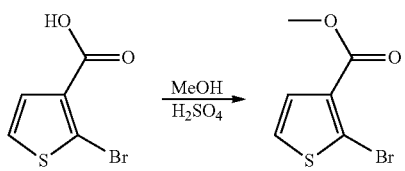

Thiophene-2-bromo-3-carboxylic acid (10 g, 45 mmol) was placed in a 3 dry 3-neck round bottom flask equipped with an argon inlet and a water condenser. Dry methanol (100 mL) was added to the flask along with a catalytic amount of cc. sulfuric acid (1 mL). The reaction completion was determined by taking aliquot for NMR analysis. When complete, the reaction was cooled to room temperature. The methanol was evaporated and the resulting product was purified via column chromatography, using a 100% hexane to 60% hexane/40% ethyl acetate gradient to yield clear slightly yellow oil (9 g, 91%).

Spectral data: $^1$H NMR (CDCl$_3$, 300 MHz): $\delta_H$ 3.89 (s, 3H), 7.23 (d, 5.76), 7.36 (d, 5.78 Hz).

$^{13}$C NMR (CDCl$_3$, 75 MHz): δ 52.13, 120.15, 126.09, 129.48, 131.07, 162.61.

Example

Synthesis of dimethyl 2,2'-(thieno[3,2-b]thiophene-2,5-diyl)bis(thiophene-3-carboxylate)

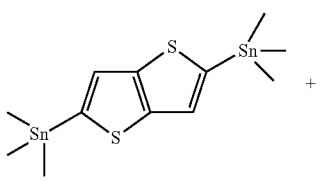

In a glove box, 2,5-bis(trimethylstannyl)thieno[3,2-b]thiophene (2.67 g, 5.7 mmol), methyl 2-bromothiophene-3-carboxylate (2.5 g, 11.31 mmol), Pd$_2$ dba$_3$ (131 mg, 0.14 mmol) and P(o-tolyl)$_3$ (174 mg, 0.57 mmol) were charged in a Schlenk flask. The flask was connected to an argon/vacuum line and side arm was purged 5 times before the flask was open to argon. Toluene (100 mL, purged overnight with argon) was added and the mixture was purged five times with vacuum argon cycles. The flask was placed in a preheated bath at 110° C. and the mixture was stirred overnight. Over time a yellow-green precipitate formed. After cooling, the precipitate was filtered and washed with hexane. NMR analysis indicated product was pure (2 g, 42%) and as a result it was used without further purification.

Spectral data: $^1$H NMR (CDCl$_3$, 300 MHz): $\delta_H$ 3.85 (s, 6H), 7.25 (d, 2H, 5.46 Hz), 7.51 (d, 2H, 5.39 Hz).

$^{13}$C(CDCl$_3$, 75 MHz): δ 52.11, 121.47, 124.77, 128.07, 130.88, 147.69, 163.69.

Example 145

Synthesis of (2,2'-(thieno[3,2-b]thiophene-2,5-diyl)bis(thiophene-3,2-diyl))bis(bis(4-(2-ethylhexyl)phenyl)methanol)

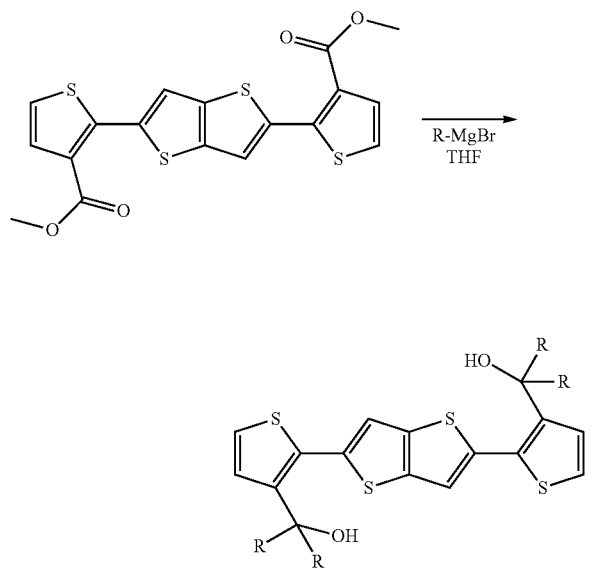

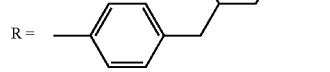

A flame-dried 3-neck round bottom flask equipped with an argon inlet, a water condenser and an addition funnel, was charged with magnesium (0.81 g, 33 mmol) and anhydrous THF (30 mL) that was added via deoxygenated syringe. A few crystals of iodine were added to initiate reaction, and 4-(2-ethylhexyl)-phenylbromide (7.5 g, 27.9 mmol) was added dropwise. The solution was refluxed for a few hours, until GC analysis of an aliquot showed no starting material remained. After cooling, dimethyl 2,2'-(thieno[3,2-b]thiophene-2,5-diyl)bis(thiophene-3-carboxylate) (2.0 g, 4.8 mmol) was added in one portion. And the solution was refluxed and its progress was monitored by TLC. Upon reaction completion, the reaction was cooled and poured in 1 M HCl solution. The aqueous phase was extracted with MTBE. The combined organic phases were washed with water then dried with anhydrous magnesium sulfate. After filtration the solvent was removed under vacuum, and the final product, a dark orange viscous oil, was obtained after silica column chromatography using 100% hexane to 100% $CHCl_3$ gradient (2.6 g, 48%).

Example 146

Synthesis of 5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene

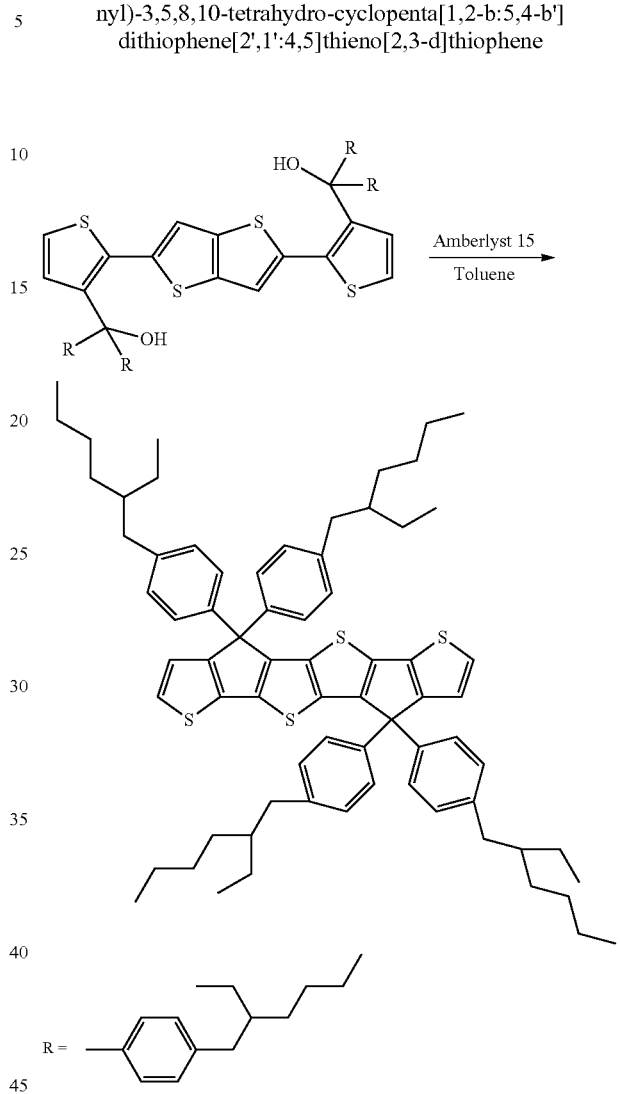

(2,2'-(Thieno[3,2-b]thiophene-2,5-diyl)bis(thiophene-3,2-diyl))bis(bis(4-(2-ethylhexyl)phenyl)methanol) (2.1 g, 1.78 mmol) was charged in a schlenk flask under argon atmosphere. Toluene (200 mL, bubbled overnight with argon) was added along with Amberlyst 15 (1 g). The flask was purged with vacuum-argon cycles 5 times then placed in a preheated bath at 110° C. The reaction was monitored by TLC using hexane as eluent. When the reaction was completed, it was cooled to room temperature, and immediately filtered through silica plug to yield the product as a yellow-orange solid (1.1 g, 57%). Spectral data:

$^1$H NMR ($CDCl_3$, 300 MHz): $\delta_H$ 0.72-0.96 (t, 24H, 7.39 Hz) 1.12-1.35 (m, 32H), 1.43-1.6 (m, 4H), 2.46 (d, 8H, 6.9 Hz), 7.03 (d, 8H, 8.21 Hz), 7.07 (d, 2H, 4.86 Hz), 7.13 (d, 8H, 7.95 Hz), 7.15 (d, 2H, ~3.9 Hz).

$^{13}$C($CDCl_3$, 75 MHz): $\delta$ 10.94, 14.34, 23.2, 25.62, 29.01, 32.49, 39.9, 41.01, 62.11, 123.54, 125.36, 127.83, 129.48, 135.15, 137.31, 140.82, 148.68, 157.24.

Example

Synthesis of (5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene-2,7-diyl)bis(trimethylstannane)

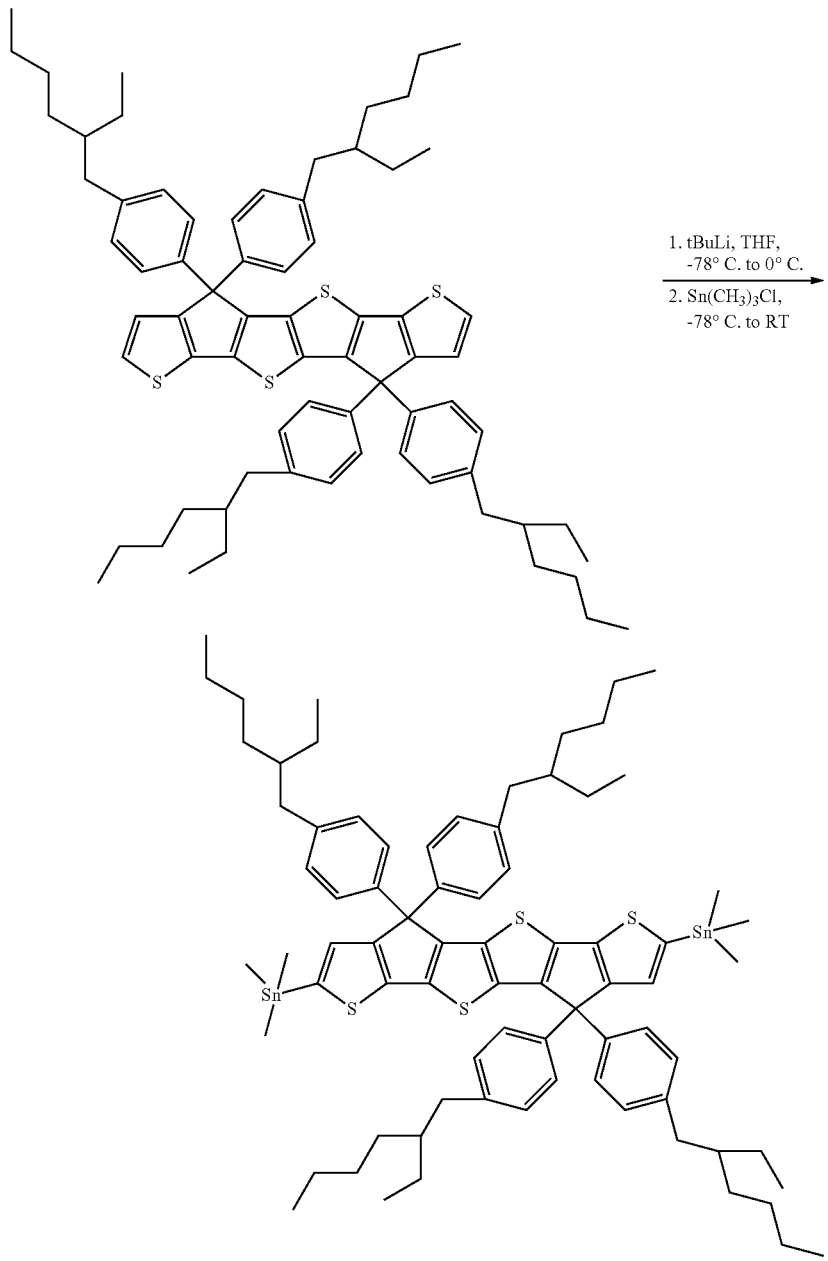

The starting compound (530 mg, 0.49 mmol) was dissolved in THF (150 mL) in a dry schlenk flask. The solution was cooled to −78° C. and ter-butyllithium (0.87 mL of 1.7 M solution, 1.5 mmol) was added dropwise via syringe. After completion of the addition, the mixture was stirred 60 min at −78° C. the 15 minutes at room temperature (using IPA bath at RT) during which the solution turned from orange to dark brown-orange. The solution was cooled back at −78° C., and trimethyltin chloride (2 mL of 1 M solution in THF, 2 mmol) was added dropwise. The mixture is warmed to room temperature following completion of the addition and stirred at that temperature for 30 minutes then was poured into ice-cold water. The aqueous phase was further extracted with hexane. The combined organic phase were combined and washed with cold water then dried with magnesium sulfate. After filtration, the solvent was evaporated under vacuum to yield an orange solid. The product was purified by precipitation of a chloroform solution into methanol followed by filtration (540 mg, 78%).

Spectral data: $^1$H NMR (CDCl$_3$, 300 MHZ) $\delta_H$ 0.36 (s, 18H), 0.83 (t, 12H, 6.04 Hz), 0.84 (t, 12H, 7.21 Hz), 1.13-1.34 (m, 32H), 1.46-1.59 (m, 4H), 2.46 (d, 8H, 6.86 Hz), 7.03 (d, 8H, 8.18 Hz), 7.07 (s, 2H), 7.13 (d, 8H, 8.36 Hz).

Example

Synthesis of Donor-Acceptor Random Copolymer Based on 5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene

In a glove box, 1,3-dibromo-5-(2-ethylhexyl)-4H-thieno[3,4-c]pyrrole-4,6(5H)-dione (43.78 mg, 0.10 mmol), (5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene-2,7-diyl)bis(trimethylstannane) (224 mg, 0.159 mmol), 4,7-dibromobenzo[c][1,2,5]thiadiazole (16.38 mg,

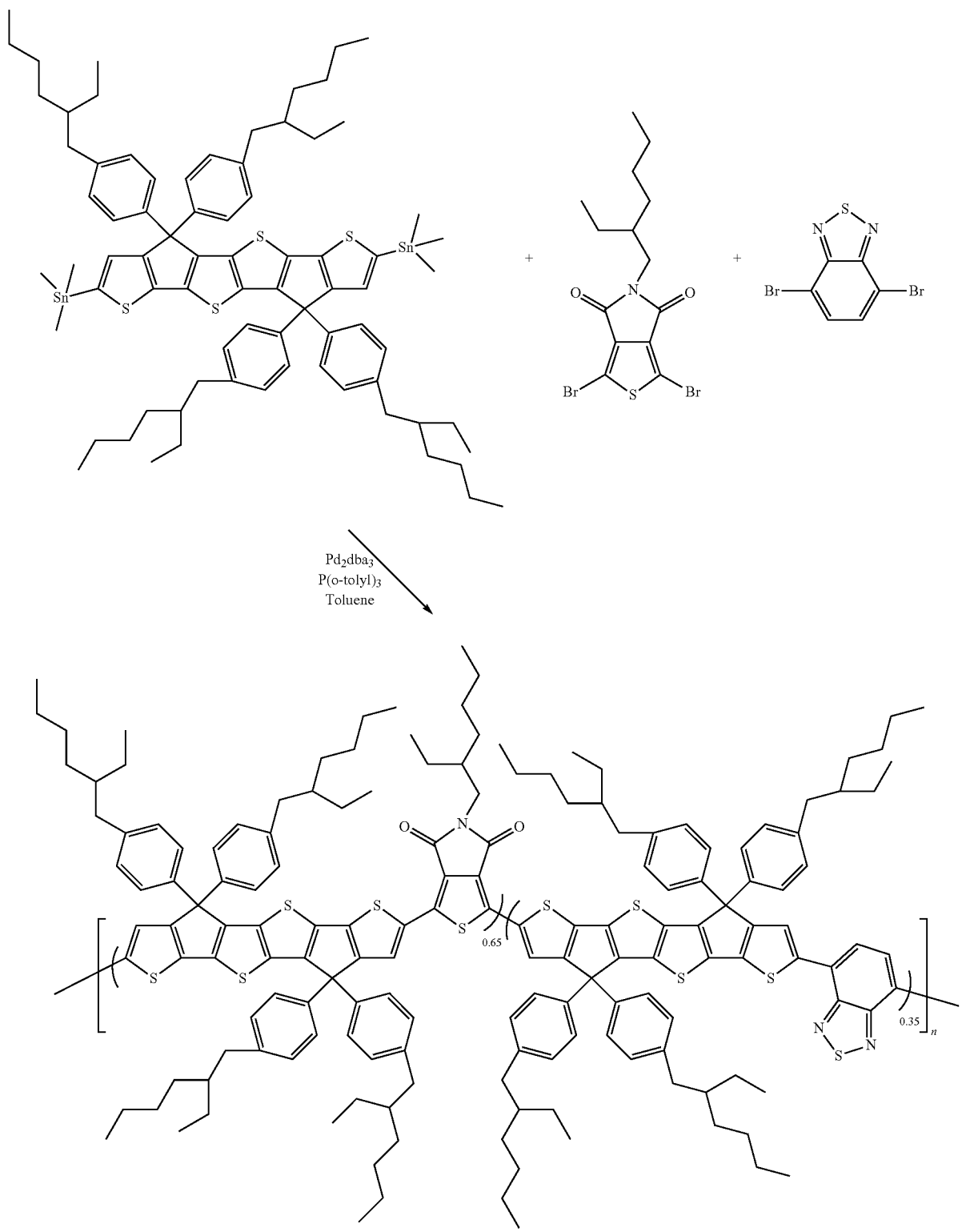

0.056 mmol), Pd$_2$dba$_3$ (3.64 mg, 0.004 mmol), P(o-tolyl)$_3$ (4.84. mg, 0.016 mmol) were charged in a 100 ml Schlenk flask. After connecting the flask to vac/argon line, the side arm was flushed with 5 vacuum-argon cycles and the flask was opened to argon. Toluene (10 mL), degassed with argon overnight, was added. The flask was purged five times through vacuum-argon cycles then placed in a preheated flask at 110° C. for 48 hours. After cooling, methanol was added to precipitate the polymer. The polymer was filtered through Soxhlet thimble and Soxhlet extraction was performed with methanol, MTBE, hexane and chloroform (100 mg). Molecular weight was determined by GPC in chlorobenzene (1 mL/min at 80° C.) vs. polystyrene standards: $M_n$=28,100, $M_w$=47,800, PDI=1.7.

Example

Synthesis of Donor-Acceptor random copolymer based on 5,5,10,10-tetrakis(4-(2-ethylhexyl)phenyl)-3,5,8,10-tetrahydro-cyclopenta[1,2-b:5,4-b']dithiophene[2',1':4,5]thieno[2,3-d]thiophene and 5,5'-bis(2-ethylhexyl)-4H,4'H-[1,1'-bithieno[3,4-c]pyrrole]-4,4',6,6'(5H,5'H)-tetraone

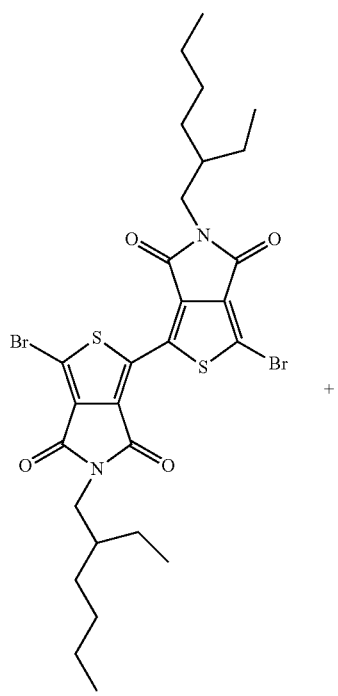

+

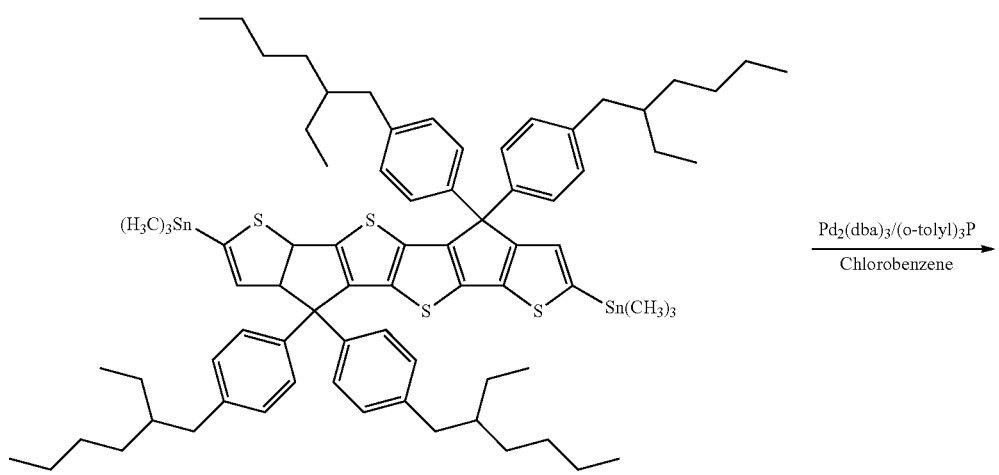

-continued

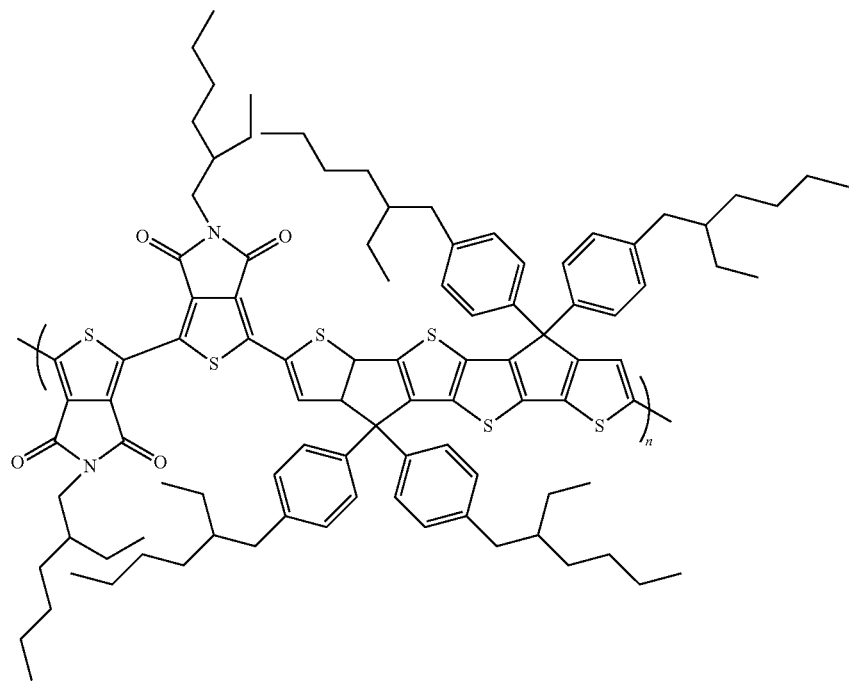

In a glove box, (5,5,10,10-tetrakis(4-(2-ethylhexyl)phenyl)-3,5,8,10-tetrahydro-cyclopenta[1,2-b:5,4-b]dithiophene[2',1':4,5]thieno[2,3-d]thiophene-2,7-diyl)bis(trimethylstannane) (0.40 mmol), 1-bromo-3-[3-bromo-5-(2-ethylhexyl)-4,6-dioxo-thieno[3,4-c]pyrrol-1-yl]-5-(2-ethylhexyl)thieno[3,4-c]pyrrole-4,6-dione (0.40 mmol), tris(dibenzylideneacetone)dipalladium(0) (9.2 mg, 0.010 mmol) and tris(o-tolyl)phosphine (12 mg, 0.040 mmol) were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a 110° C. oil bath and left stirring under an argon stream for 2 days. After cooling to room temperature, 40 mL of methanol were added to the reaction mixture. The polymer was collected via filtration and purified by consecutive Soxhlet extractions in sequence with methanol, MTBE, hexane, and chloroform. The chloroform solution was passed through celite to remove catalyst residuals, and solvent was removed under vacuum to yield polymer. The polymer was re-dissolved in a small amount of chloroform, re-precipitated in the mixture of IPA, water and methanol, isolated via centrifuge and dried (200 mg). Molecular weight was determined by GPC in chlorobenzene (1 mL/min at 80° C.) vs. polystyrene standards: $M_n$=31,500, $M_w$=91,350, PDI=2.9. The polymer was called BPP-1, and solar cell preparation and testing performance is shown in Table V.

Part IVg:

The monomers, oligomers, and polymers can also comprise the following structures:

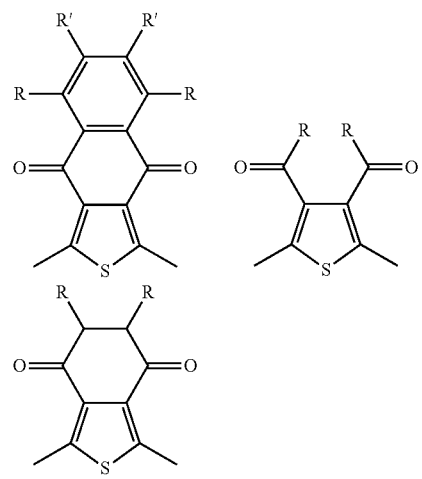

wherein again R and R' can be independently of each other a hydrogen or a solubilizing group.

Example

Synthesis of 1,2-bis(2-ethylhexyl)benzene

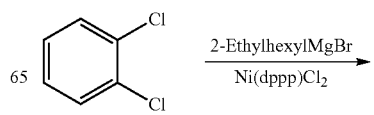

-continued

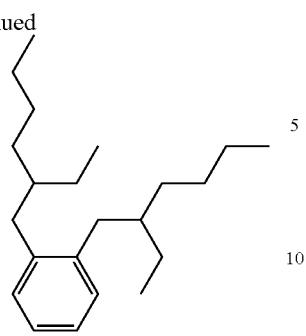

A dry 1 L three-neck round bottom flask, equipped with a condenser and an addition funnel, was charged with Ni(dppp)$_2$Cl$_2$ (0.99 g, 1.83 mmol) and dichlorobenzene (26.7 g, 182 mmol). The reaction solution was cooled down to 0° C. and then (2-ethylhexyl)magnesium bromide solution (400 mmol) was added dropwise via the addition funnel under nitrogen. After addition was complete, the reaction was heated to reflux for 12 hours and then cooled down to room temperature. The reaction solution was poured into 100 mL of DI water. The mixture was extracted with MTBE (3×100 mL). The organic phase was combined, dried over anhydrous MgSO$_4$, filtered and the solvent was removed by rotary evaporation. The mixture was purified by distillation under a reduced pressure to give the product (11.5 g, 21%) as colorless oil.

Spectral data: $^1$H NMR (300 MHz, CDCl$_3$): $\delta_H$ 7.10 (s, 4H), 2.60-2.45 (m, 4H), 1.56 (m, 2H), 1.35-1.20 (m, 16H), 0.89-0.84 (t, 12H).

Example

Synthesis of 2,5-dibromothiophene-3,4-dicarboxylic acid

[Synthesis can be adapted from Lit. Ref Zhang et al. *J. Am. Chem. Soc.* 1997, 119, 5065]

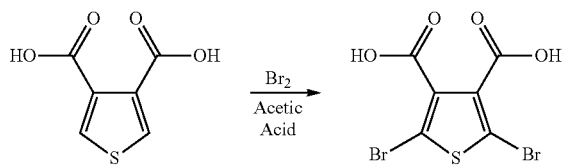

A 500 mL one neck round bottom flask was charged with thiophene-3,4-dicarboxylic acid (29 g, 0.17 mol) and glacial acetic acid (280 mL). Bromine (52 mL, 1.0 mol) was added dropwise to the reaction flask and the mixture was stirred for 12 hours at RT. An aqueous solution of sodium bisulfate was added until the reddish color disappeared. The mixture was basified and filtered. The filtrate was acidified to give a gray solid which was filtered, washed with cold water, and dried to give the product. The crude product was recrystallized twice from water (60%).

Spectral data: $^1$H NMR (300 MHz, CDCl$_3$): $\delta_H$ 13.6 (br s, 2H).

$^{13}$C NMR (300 MHz, DMSO): $\delta$ 162.5, 135.0, 118.

Example

Synthesis of 1,3-dibromo-6,7-bis(2-ethylhexyl)naphtha[2,3-c]thiophene-4,9-dione)

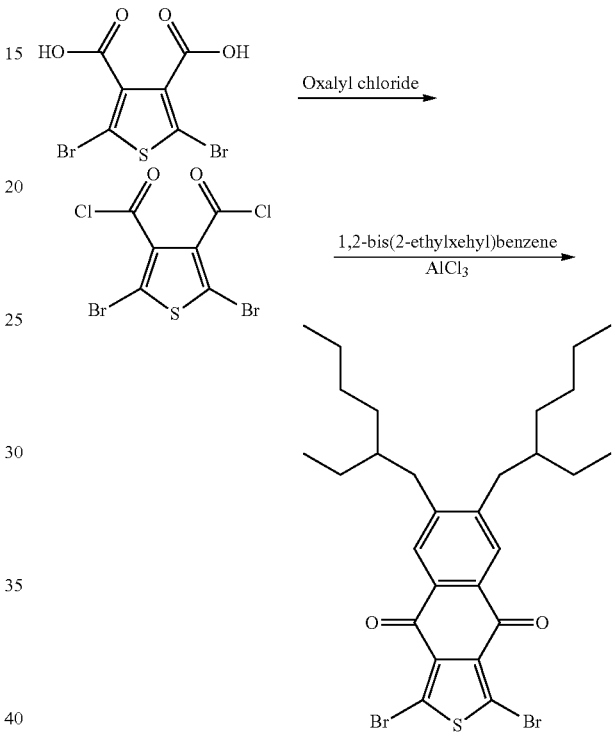

A 100 mL three-neck round bottom flask was charged with a solution of 2,5-dibromothiophene-3,4-dicarboxylic acid (3.0 g, 9.0 mmol) and cooled to 0° C. Oxalyl chloride (4.6 g, 36 mmol) was added in one portion to the reaction flask and a drop of anhydrous DMF was added as the catalyst. The mixture was heated to reflux for 1 hour, and then cooled to room temperature. Rotary evaporator was used to remove oxalyl chloride and solvent. The residual acid chloride was dried, re-dissolved in CH$_2$Cl$_2$ and then added slowly to AlCl$_3$ (5.3 g. 40 mmol) in dichloromethane (CH$_2$Cl$_2$) at 0° C. The mixture was stirred at 0° C. for 10 min. 1,2-bis(2-ethylhexyl)benzene (2.7 g, 9.0 mmol) was added drop-wise. The mixture was stirred for 30 min and then poured into ice. The mixture was extracted with CH$_2$Cl$_2$ (3×100 mL). The combined organic layer was washed with a saturated solution of NaHCO$_3$, water and then dried over anhydrous MgSO$_4$. The residue, which remained after the solvent was evaporated, was purified by flash chromatography with 10% ethyl acetate in hexanes to give the product as a yellow solid (2.0 g, 37%).

Spectral data: $^1$H NMR (300 MHz, CDCl$_3$): $\delta_H$ 8.0 (s, 2H), 2.70-2.62 (d, 4H), 1.70-1.50 (m, 6H), 1.40-1.20 (m, 12H), 0.90-0.80 (t, 12H).

Example

Synthesis of poly{[(3-(4,8-bis(2-ethylhexyl)benzo[1,2-b:4,5-b']dithiophen-2-yl)-alt-(6,7-bis(2-ethylhexyl)naphtha[2,3-c]thiophene-4,9-dione)]-ran-[(3-(4,8-bis(2-ethylhexyl)benzo[1,2-b:4,5-b']dithiophen-2-yl)-alt-(benzo[c][1,2,5]thiadiazole)]}

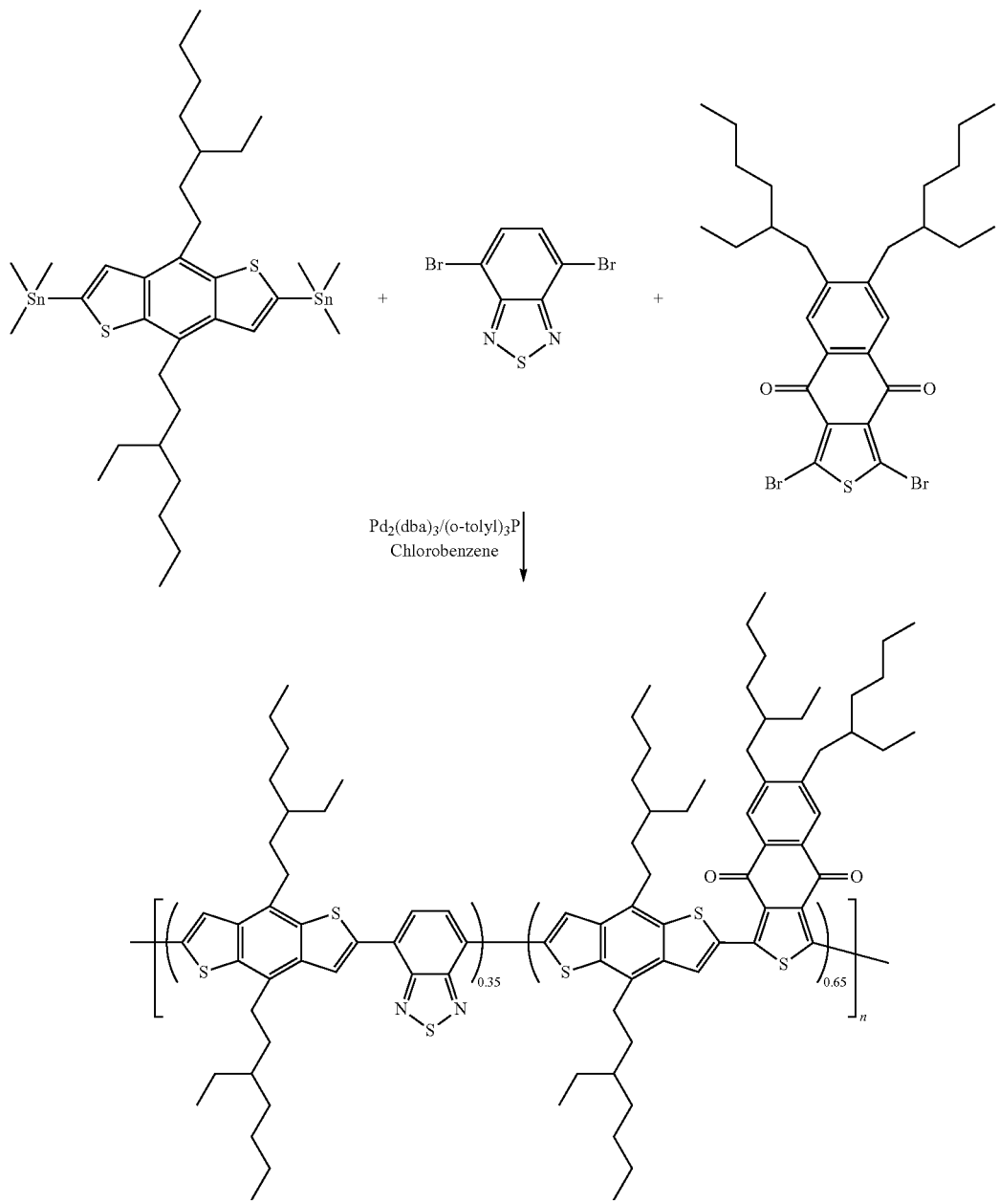

In a glove box, (4,8-bis(3-ethylheptyl)benzo[1,2-b:4,5-b']dithiophene-2,6-diyl)bis(trimethylstannane) (0.30 g, 0.39 mmol), 4,7-dibromo-2,1,3-benzothiadiazole (0.040 g, 0.14 mmol), 1,3-dibromo-6,7-bis(2-ethylhexyl)naphtha[2,3-c]thiophene-4,9-dione) (0.15 g, 0.253 mmol), tris(dibenzylideneacetone)dipalladium(0) (9.0 mg, 0.010 mmol) and tris(o-tolyl)phosphine (12 mg, 0.039 mmol) were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a preheated to 110° C. oil bath and left stirring under an argon stream for 2 days. After cooling to room temperature, 40 mL of methanol were added to the reaction mixture. The polymer was collected via filtration and purified by consecutive Soxhlet extractions in sequence with methanol, MTBE, hexane, and chloroform. The chloroform solution was passed through celite to remove catalyst residuals, and solvent was removed under vacuum to yield polymer. The polymer was re-dissolved in a small amount of chloroform, re-precipitated in the mixture of IPA, water and methanol, isolated via centrifuge and dried to yield 85% of polymer. Molecular weight was determined by GPC in chlorobenzene (1 mL/min at 80° C.) vs. polystyrene standards: $M_n$=41,440, $M_w$=124,500, PDI=3.0. The polymer was called LRB-1, and solar cell preparation and testing is shown in Table 5.

Part IVh:

Example 5

Synthesis of 4-(3-ethylhept-1-yn-1-yl)-8-(3-ethyl-non-1-yn-1-yl)benzo[1,2-b:4,5-b']dithiophene

Example

Synthesis of (4-(3-ethylhept-1-yn-1-yl)-8-(3-ethyl-non-1-yn-1-yl)benzo[1,2-b:4,5-b']dithiophene-2,6-diyl)bis(triisopropylsilane)

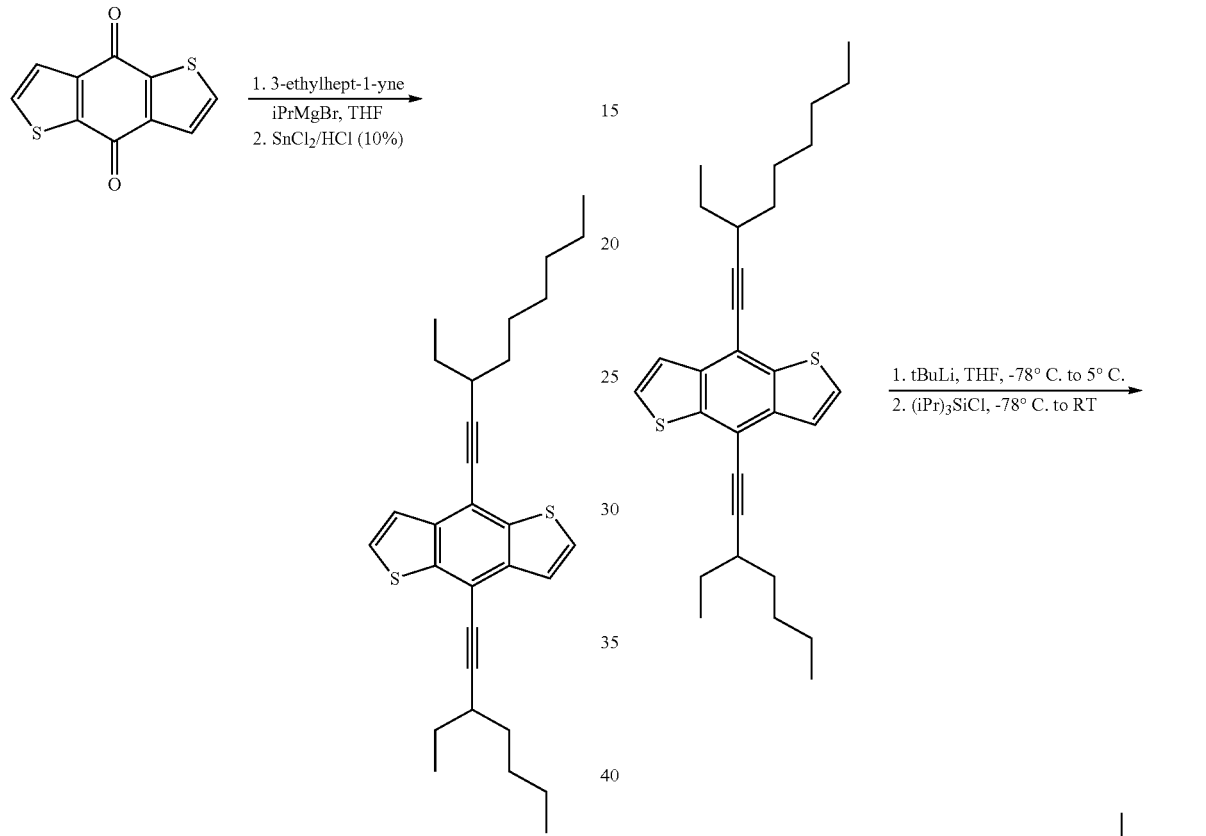

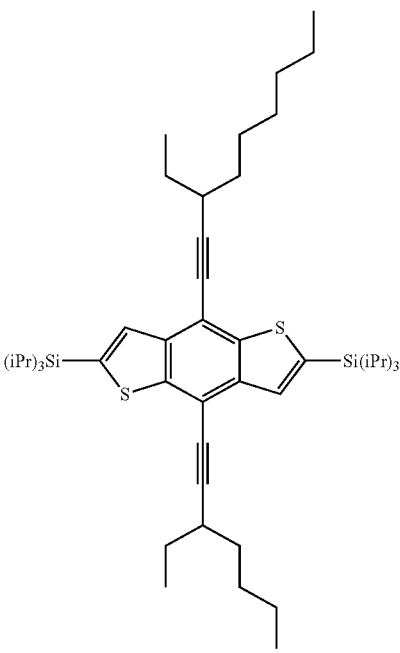

A dry 250-mL three-neck flask equipped with a reflux condenser and an addition funnel was flushed with $N_2$ and was charged with 3-ethylhept-1-yne (2.8 g, 0.022 mol). A 2.0 M solution of iso-propylmagnasium bromide in THF (10.2 mL, 0.022 mol) was added dropwise via deoxygenated syringe. After 15 minutes of stirring at ambient temperature, a 0.2 M solution of benzo[1,2-b:4,5-b']dithiophene-4,8-dione (2.0 g, 9.0 mmol) in THF (44 mL) was added portion-wise. The reaction was heated to reflux for 1 hour. As the reaction was completed, the flask was cooled to ambient temperature and a solution of $SnCl_2$ (4.2 g) dissolved in 10% HCl (40 mL) was added to the reaction flask. The stirring continued with increasing temperature to reflux for 1 hour and then cooling the reaction to ambient temperature. The reaction was poured into 200 mL of cool water with 20 mL of 10% HCl and extracted with MTBE (200 mL) three times. The combined organic layer was dried over anhydrous magnesium sulfate ($MgSO_4$). After the product was filtered, the solvent was removed by rotary evaporation. The product was purified using column chromatography on silica gel with hexanes/chloroform (gradient) to yield colorless oil (3.24 g, 83%).

Spectral data: $^1$H NMR (300 MHz, $CDCl_3$): $\delta_H$ 7.58-7.56 (d, 2H), 7.51-7.49 (d, 2H), 2.7 (m, 2H), 1.76-1.34 (m, 16H), 1.19 (t, 6H), 0.97 (t, 6H).

A dry 250-mL three-neck flask was flushed with $N_2$ and was charged with 4-(3-ethylhept-1-yn-1-yl)-8-(3-ethylnon-1-yn-1-yl)benzo[1,2-b:4,5-b']dithiophene (2.0 g, 4.6 mmol) and THF (100 mL, 0.05 M) via deoxygenated syringe. The reaction flask was cooled to −78° C. and a 1.3 M solution of tert-butyllithium in hexanes (8.8 mL, 0.012 mol) was added drop-wise via deoxygenated syringe. After 30 minutes of stirring at −78° C., the solution was chilled to 0° C. and stirring was continued for 5 minutes, at which point the reaction mixture was cooled back to −78° C. Triisopropylsilyl chloride (4.0 mL, 0.018 mol) was added to the reaction flask drop-wise and stirring continued for 30 minutes at −76° C. The cooling bath was removed and the reaction mixture was allowed to warm to ambient temperature. As the reaction was completed, cool DI water (20 mL) was slowly added to the reaction flask. Then, the reaction mixture was poured into 100 mL of cool water and extracted with MTBE (150 mL) three times. The combined organic layer was washed with water two times and dried over anhydrous magnesium sulfate ($MgSO_4$). After the product was filtered, the solvent was removed by rotary evaporation. The crude product was purified by precipitation into methanol from a chloroform solution to yield white solid (3.13 g, 91%).

Spectral data: $^1H$ NMR (300 MHz, $CDCl_3$): $\delta_H$ 7.73 (5, 2H), 2.72 (m, 2H), 1.75-1.60 (m, 12H), 1.48-1.35 (m, 10H), 1.23-1.16 (m, 42H), 0.97 (t, 6H).

Example

Synthesis of (4,8-bis(3-ethylheptyl)benzo[1,2-b:4,5-b']dithiophene-2,6-diyl)bis(triisopropylsilane)

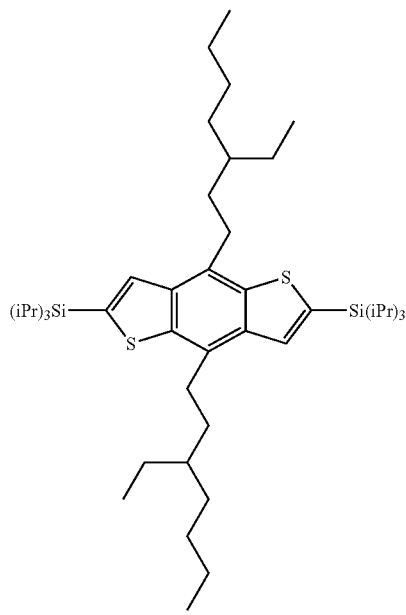

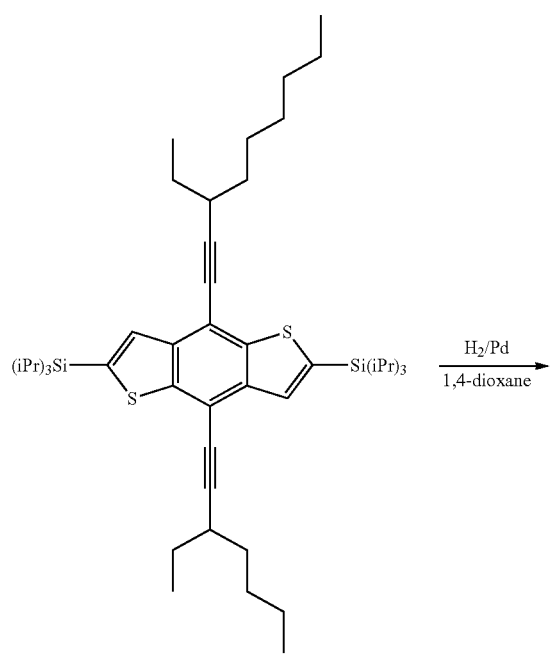

A dry 100 mL three-neck round bottom flask equipped with a condenser was flushed with $N_2$ and was charged with (4-(3-ethylhept-1-yn-1-yl)-8-(3-ethylnon-1-yn-1-yl)benzo[1,2-b:4,5-b']dithiophene-2,6-diyl)bis(triisopropylsilane) (2.5 g, 3.3 mmol), Pd/C dry support (0.70 g, 10%) and anhydrous 1,4-dioxane (30 mL, 0.11 M). The flask was evacuated and backfilled with hydrogen. The reaction was kept under a hydrogen atmosphere and slowly heated to 95° C. Completion of hydrogenation was monitored by TLC. After hydrogenation was complete, the mixture was cooled to ambient temperature, filtered through Celite, and solvent was removed by rotary evaporation. The solid was dissolved in chloroform and precipitated into methanol to yield white solid (2.42 g, 97%).

Spectral data: $^1H$ NMR (300 MHz, $CDCl_3$): $\delta_H$ 7.59 (s, 2H), 3.21-3.15 (m, 4H), 1.80-1.72 (m, 4H), 1.5-1.3 (m, 24H), 1.18-1.16 (d, 36H), 0.95-0.9 (m, 12H).

Example 163

Synthesis of 4,8-bis(3-ethylheptyl)benzo[1,2-b:4,5-b']dithiophene

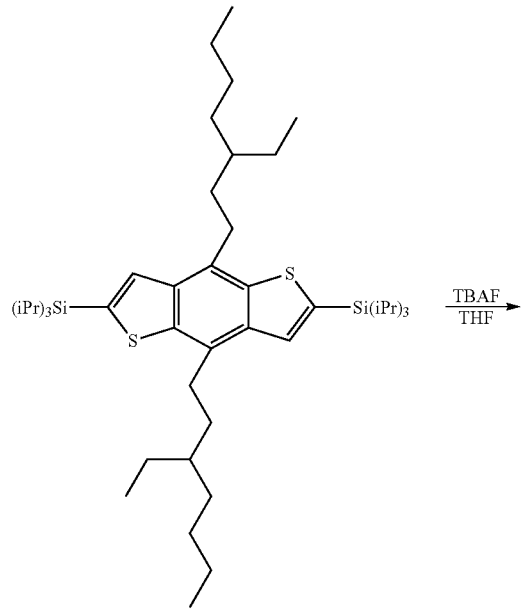

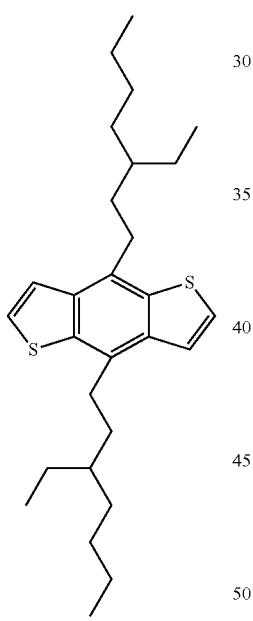

A dry 100 mL three-neck round bottom flask equipped with a nitrogen adapter was flushed with $N_2$ and was charged with (4,8-bis(3-ethylheptyl)benzo[1,2-b:4,5-b']dithiophene-2,6-diyl)bis(thriisopropylsilane) (2.0 g, 2.6 mmol) and anhydrous THF (6.5 mL) via hydrogenated syringe. A 1 M TBAF solution in THF (6.5 mL) was added drop-wise to the reaction flask. Completion of reaction was monitored by TLC. After the reaction was complete (30 minutes at ambient temperature), solvent was removed by rotary evaporation. The target product was purified using column chromatography on silica gel with hexanes to yield slightly yellow oil (0.98 g, 85%) (product can also be purified via vacuum distillation).

Spectral data: $^1$H NMR (300 MHz, CDCl$_3$): $\delta_H$ 7.46 (s, 4H), 3.2-3.1 (m, 4H), 1.8-1.7 (m, 4H), 1.5-1.3 (m, 18H), 0.96-0.92 (m, 12H).

Example 164

Synthesis of (4,8-bis(3-ethylheptyl)benzo[1,2-b:4,5-b]dithiophene-2,6-diyl)bis(trimethylstannane)

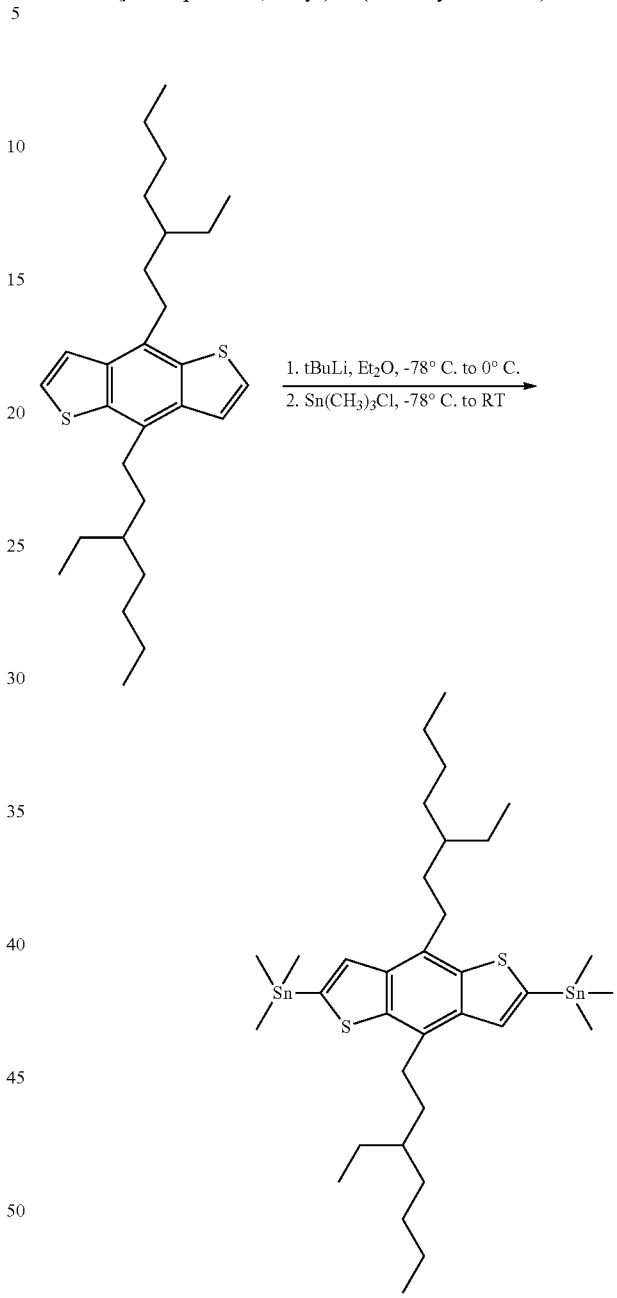

A dry 100-mL three-neck flask was flushed with $N_2$ and was charged with 4,8-bis(3-ethylheptyl)benzo[1,2-b:4,5-b] dithiophene (0.50 g, 1.1 mmol) and diethyl ether (Et$_2$O) (11 mL, 0.10 M) via deoxygenated syringe. The reaction flask was cooled to −78° C. and a 1.3 M solution of tert-butyllithium in hexanes (2.3 mL, 3.0 mmol) was added drop-wise via deoxygenated syringe. After 30 minutes of stirring at −78°

C., the solution was chilled to 0° C. and stirring was continued for 5 minutes, at which point the reaction mixture was cooled back to −78° C. A 1 M solution of trimethyltin chloride (4.4 mL, 4.4 mmol) in hexanes was added to the reaction flask drop-wise and stirring continued for 30 minutes at −76° C. The cooling bath was removed and the reaction mixture was allowed to warm to ambient temperature. As the reaction was completed, cool DI water (10 mL) was slowly added to the reaction flask. Then, the reaction mixture was poured into 50 mL of cool water and extracted with MTBE (100 mL) three times. The combined organic layer was washed with water two times and dried over anhydrous magnesium sulfate (MgSO$_4$). After the product was filtered, the solvent was removed by rotary evaporation. The crude product was purified by precipitation into methanol from a THF solution to yield white solid (0.71 g, 84%).

Spectral data: $^1$H NMR (300 MHz, CDCl$_3$): δ0.49 (s, 2H), 3.2 (m, 4H), 1.75 (m, 4H), 1.6-1.20 (m, 18H), 0.95 (m, 12H), 0.4 (s, 18H).

Example

Synthesis of poly{[(2,6'-4,8-bis(3-ethylheptyl)benzo [1,2-b:4,5-b']dithiophene)-alt-(5-(2-ethylhexyl) thieno[3,4-c]pyrrole-4,6-dione)]-ran-[(2,6'-4,8-bis(3-ethylheptyl)benzo[1,2-b:4,5-b']dithiophene)-alt-(benzo[c][1,2,5]thiadiazole)]}

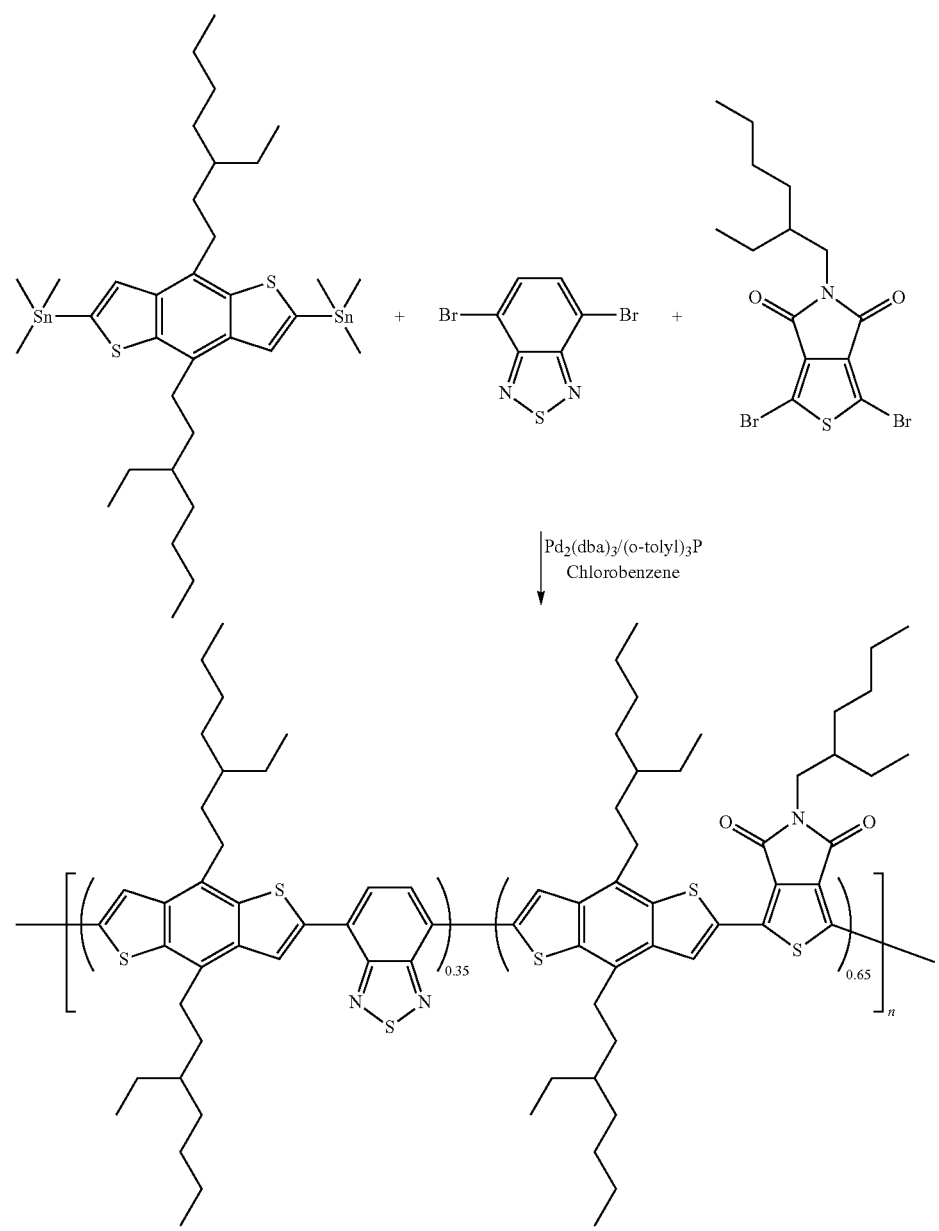

In a glove box, (4,8-bis(3-ethylheptyl)benzo[1,2-b:4,5-b]dithiophene-2,6-diyl)bis(trimethylstannane) (0.30 g, 0.39 mmol), 4,7-dibromo-2,1,3-benzothiadiazole (0.040 g, 0.14 mmol), 1,3-dibromo-5-(2-ethylhexyl)-4H-thieno[2,4-c]pyrrole-4,6(5H)-dione (0.11 g, 0.25 mmol), tris(dibenzylideneacetone)dipalladium(0) [Pd$_2$(dba)$_3$] (9.0 mg, 0.010 mmol) and tris(o-tolyl)phosphine (12 mg, 0.039 mmol) [(o-tolyl)$_3$P] were charged into a flame dried 50 mL Schlenk flask. The reaction flask was removed from the glove box and 10 mL of deoxygenated chlorobenzene were added via syringe. The mixture was evacuated and refilled with argon five times. The reaction flask was immersed into a preheated to 110° C. oil bath and left stirring under an argon stream for 3 hours, cooled down to ambient temperature and another portions of Pd$_2$(dba)$_3$ and (o-tolyl)$_3$P (9.0 mg and 12 mg, respectively) were added. The mixture was evacuated and refilled with argon five times, finally immersed into a preheated to 110° C. oil bath, and left stirring under an argon stream for 2 days. After cooling to room temperature, 40 mL of MTBE/methanol (50:50 mixture) were added to the reaction flask. The polymer was collected via filtration and purified by consecutive Soxhlet extractions in sequence with methanol, MTBE, hexane, and chloroform. The chloroform solution was passed through a bed of silica gel and celite to remove catalyst and/or other small molecules or residuals, and solvent was removed under vacuum to yield polymer. The polymer was re-dissolved in a small amount of chloroform, re-precipitated in the mixture of IPA, water and methanol, isolated via centrifuge, dried to yield a brown-copper colored polymer (0.21 g, 80%). Molecular weight was determined by GPC in chlorobenzene (1 mL/min at 80° C.) vs. polystyrene standards: $M_n$=24,000, $M_w$=90,500, PDI=3.8.

Part IVi:
Synthesis adapted from a) Yao, Y.-H.; Kung, L.-R.; Hsu, C.-S. *J. of Polymer Research* 2006, 13, 277; b) Nielsen, C. B; Bjornholm, T. *Org. Lett.* 2004, 6, 3381.

Example

Synthesis of
4-(3-ethylhept-1-yn)-2,3,5,6-tetrafluoroaniline

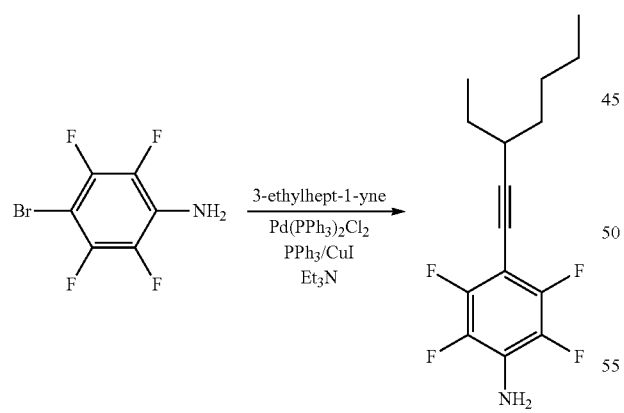

4-Bromo-2,3,5,6-tetrafluoro-aniline (5.0 g, 20 mmol) in 41 mL of triethylamine was purged with nitrogen for 30 min. 3-Ethylhept-1-yne (3.1 g, 25 mmol), bis[triphenylphosphine]palladium (II) chloride (0.72 g, 1 mmol), triphenylphosphine (0.15 eq), and copper (I) iodide (0.39 g, 2.0 mmol) were added into the reaction solution. The reaction mixture was sealed in a flask and heated to 85° C. for 12 hours. After cooling to room temperature, the mixture was diluted with 500 mL hexanes and eluted through a thick pad of silica gel. Removal of solvent by rotary evaporation gave the product.

Prophetic Example

Synthesis of
4-(3-ethylheptyl)-2,3,5,6-tetrafluoroaniline

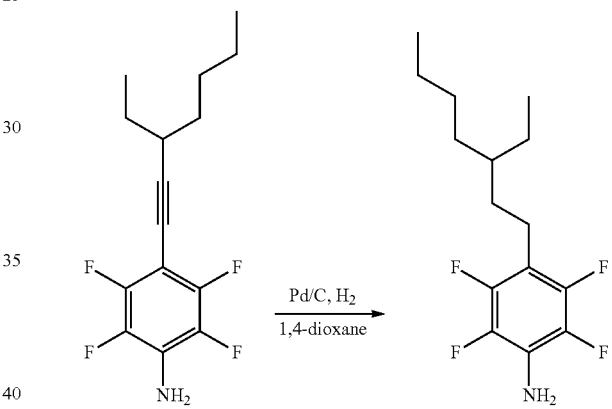

A dry 100 mL three-neck round bottom flask equipped with a condenser is flushed with N$_2$ and is charged with 4-(3-ethylhept-1-yn)-2,3,5,6-tetrafluoroaniline (0.5 mmol), Pd/C [10 wt % dry support] (20%) and anhydrous 1,4-dioxane (0.10 M). The flask was evacuated and backfilled with hydrogen. The reaction was kept under a hydrogen atmosphere and slowly heated to 95° C. Completion of hydrogenation was monitored by TLC. After hydrogenation was complete, the mixture was cooled to ambient temperature, filtered through Celite, and solvent was removed by rotary evaporation. The target molecule is purified via Silica column chromatography.

Prophetic Example

Synthesis of 5-(4-(3-ethylheptyl)-2,3,5,6-tetrafluorophenyl)-4H-thieno[3,4-c]pyrrole-4,6(5H)-dione

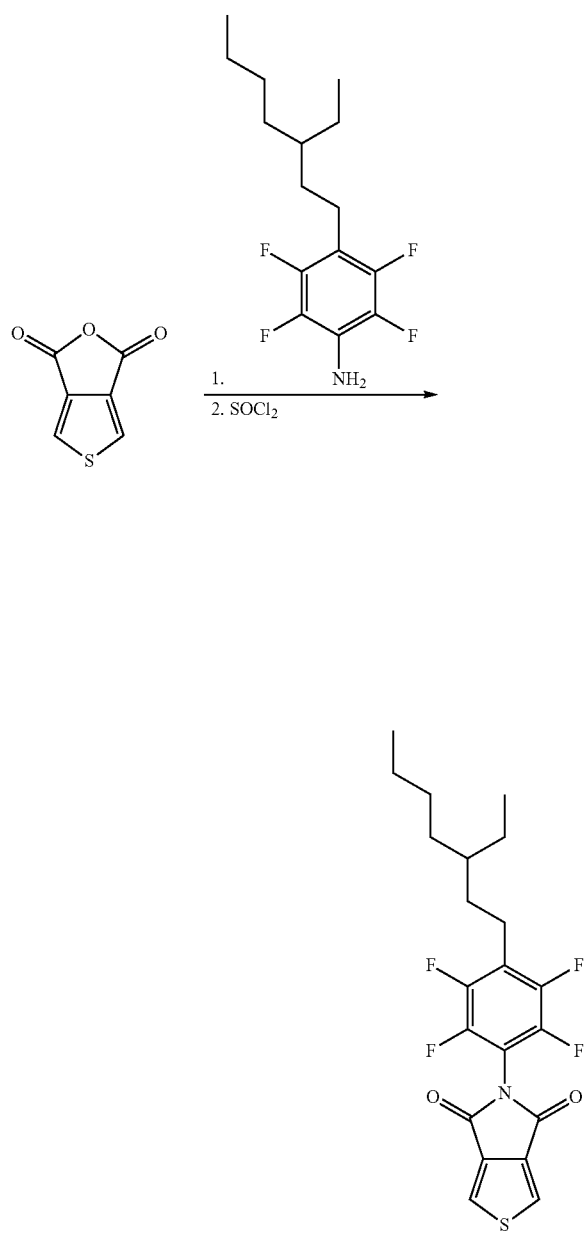

A solution of thiophene-3,4-dicarboxylic anhydride (8.0 mmol) and 4-(3-ethylheptyl)-2,3,5,6-tetrafluoroaniline (8.5 mmol) in 125 ml of toluene is refluxed for 24 h. The crude product is collected by filtration of the cold reaction mixture. Another portion of product can be recovered by washing the filtrate with 5% hydrochloric acid and then evaporating the solvent. The target molecule is purified by recrystallization from toluene, dissolved in 150 ml of thionyl chloride and refluxed for 3 hrs. The reaction mixture is concentrated down, dried, and purified.

Prophetic Example

Synthesis of 1,3-dibromo-5-(4-(3-ethylheptyl)-2,3,5,6-tetrafluorophenyl)-4H-thieno[3,4-c]pyrrole-4,6(5H)-dione

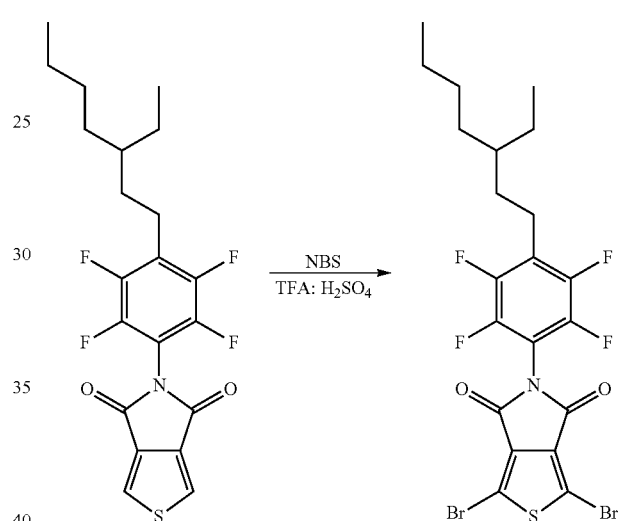

5-(4-(3-Ethylheptyl)-2,3,5,6-tetrafluorophenyl)-4H-thieno[3,4-c]pyrrole-4,6(5H)-dione (0.5 mmol) was dissolved in a 4:1 mixture of trifluoracetic acid (16 mL) and sulfuric acid (4 mL) in a 3-neck round bottom flask under nitrogen atmosphere, wrapped with aluminum foil and equipped with internal thermometer. N-bromosuccinimide (1 mmol, recrystallized before use) was added in one portion. An exotherm was observed immediately after addition, and the reaction was allowed to stir until the temperature was returned to room temperature. An aliquot was taken for NMR, which confirmed reaction was complete. The mixture was poured in ice-cold water and the aqueous solution was then extracted with $CHCl_3$. The organic phase was washed with water, dried with anhydrous $MgSO_4$ and the solvent was removed under vacuum. The mixture was purified by Silica column chromatography using a 100% hexane to 100% $CHCl_3$ gradient.

Prophetic Example

Synthesis of poly{[(2,6'-4,8-bis(3-ethylheptyl)benzo[1,2-b:4,5-b']dithiophene)-alt-(5-(4-(3-ethylheptyl)-2,3,5,6-tetrafluorophenyl)-4H-thieno[3,4-c]pyrrole-4,6(5H)-dione]-ran-[(2,6'-4,8-bis(3-ethylheptyl)benzo[1,2-b:4,5-b']dithiophene)-alt-(benzo[c][1,2,5]thiadiazole)]}

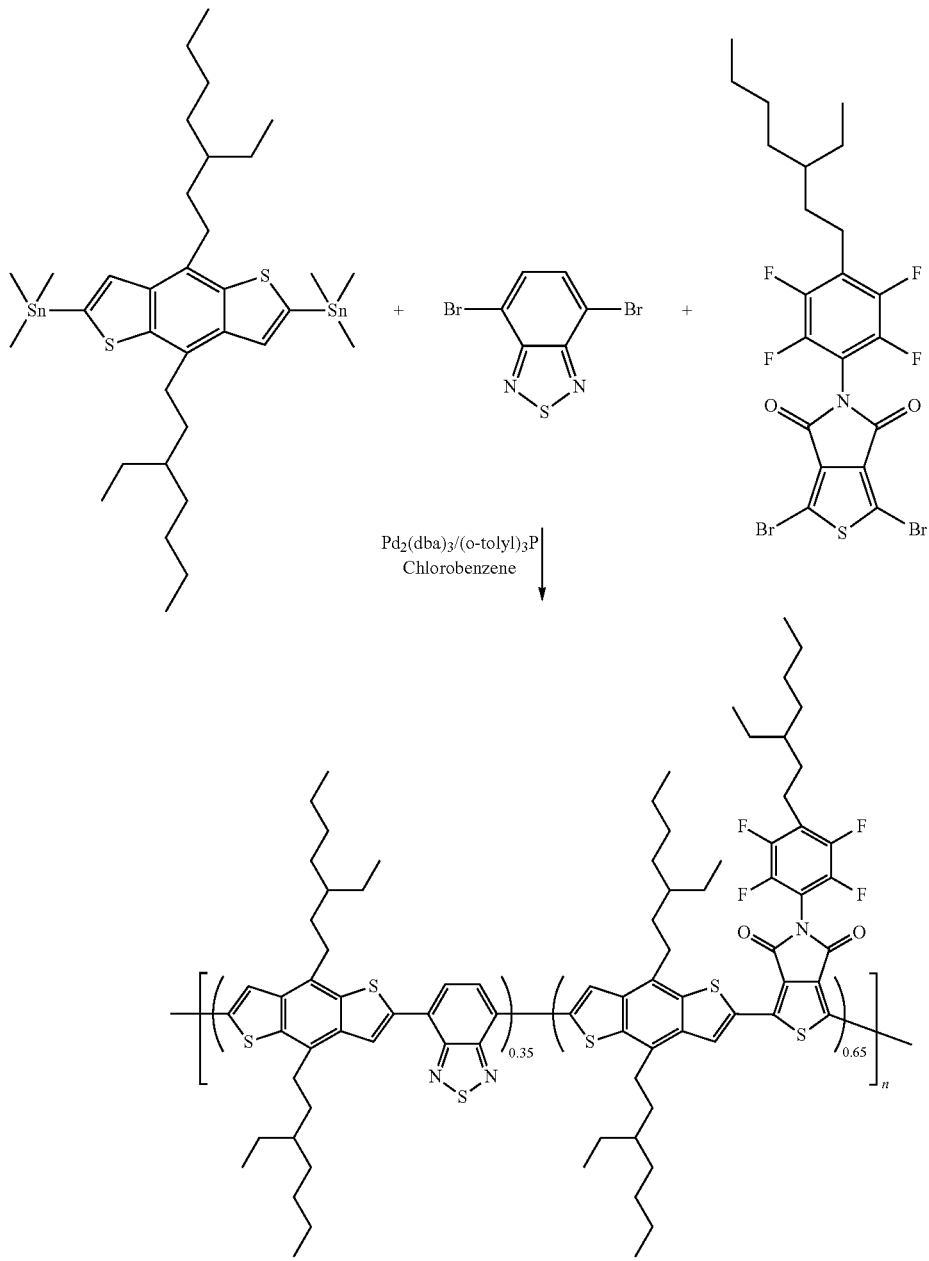

In a glove box, (4,8-bis(3-ethylheptyl)benzo[1,2-b:4,5-b']dithiophene-2,6-diyl)bis(trimethylstannane) (0.39 mmol), 4,7-dibromo-2,1,3-benzothiadiazole (0.14 mmol), 1,3-dibromo-5-(4-(3-ethylheptyl)-2,3,5,6-tetrafluorophenyl)-4H-thieno[3,4-c]pyrrole-4,6(5H)-dione (0.25 mmol), tris(dibenzylideneacetone)dipalladium(0) [$Pd_2(dba)_3$] (0.010 mmol) and tris(o-tolyl)phosphine (0.039 mmol) [$(o\text{-tolyl})_3P$] are charged into a flame dried 50 mL Schlenk flask. The reaction flask is removed from the glove box and 10 mL of deoxygenated chlorobenzene are added via syringe. The mixture is evacuated and refilled with argon five times. The reaction flask is immersed into a preheated to 110° C. oil bath and is left stirring under an argon stream for 3 hours, cooled down to ambient temperature and another portions of $Pd_2(dba)_3$ and $(o\text{-tolyl})_3P$ (0.010 mmol and 0.039 mmol, respectively) are added. The mixture is evacuated and refilled with argon five times, finally immersed into a preheated to 110° C. oil bath, and left stirring under an argon stream for 2 days. After cooling to room temperature, 40 mL of MTBE/methanol (50:50 mixture) are added to the reaction flask. The polymer is collected via filtration and purified by consecutive Soxhlet extractions in sequence with methanol, MTBE, hexane, and chloroform. The chloroform solution is passed through celite to remove catalyst residuals, and solvent is removed under vacuum to yield polymer. The polymer is re-dissolved in a small amount of chloroform, re-precipitated in the mixture of IPA, water and methanol, isolated via centrifuge, dried. Molecular weight is determined by GPC in chlorobenzene (1 mL/min at 80° C.) vs. polystyrene standards.

Part IVj:

U.S. provisional application 61/248,335 filed Oct. 2, 2009 provides additional embodiments. These embodiments can be adapted to include structures described herein including structure I.

Of particular interest are regular alternating copolymers comprising at least three moieties. In some cases, the at least three moieties comprise at least one donor moiety and at least one acceptor moiety. They may comprise two or more donor moieties or two or more acceptor moieties. They may even comprise two or more donor moieties and two or more acceptor moieties. They may further comprise spacer moieties.

Some examples of such copolymers follow, where D1 and D2 denote donor moieties, and A1 and A2 denote acceptor moieties are shown in Chart II below.

CHART II

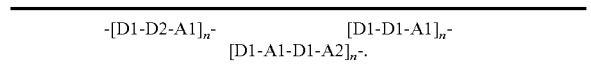

where n is an integer. Other embodiments include, for example, -[A1-A2-D1]$_n$- and -[A1-A1-D1]$_n$-.

Part IVk:

U.S. provisional application 61/290,844 filed Dec. 29, 2009 provides additional embodiments. These embodiments can be adapted to include structures described herein including structure I.

In addition, arylamine embodiments can be provided. For example, the donor acceptor polymers can comprise nitrogen in the backbone conjugation. An example is to have an arylamine group in the backbone. The arylamine can optionally comprise carbazole or can be not a carbazole. Arylamine units can be donor moieties, although the donor or acceptor character can be tuned by the substituents on the arylamine.

Important embodiments include polymers, wherein the polymer comprises an arylamine moiety in the polymer backbone. Arylamine polymer backbones are known in the art. For example, arylamine backbone moieties, also known as arylamine repeat moieties, are described in U.S. provisional Appl. No. 61/108,851, filed Oct. 27, 2008, by Seshadri et al., entitled "Polyarylamine Ketones," and in U.S. provisional Appl. No. 61/115,877, filed Nov. 18, 2008, by Sheshadri et al., entitled "Aminobenzene Compositions," both of which are incorporated by reference in their entirety. Arylamines are also described in, for example, U.S. Pat. No. 7,166,010, patent publication WO 2003/037844, and patent publication WO 2008/032631, all of which are incorporated by reference in their entirety.

Arylamine moieties can comprise, for example, a single nitrogen atom, or can comprise multiple nitrogen atoms, including two, three, or more nitrogen atoms.

The conjugated polymer backbone can comprise nitrogen atoms without breaking the conjugation as known in the art.

The arylamine can be substituted with side groups as known in the art. In one particular embodiment, the arylamine can be substituted with at least one donor, and with at least one acceptor. In another embodiment, the arylamine can be substituted with a dye.

FIG. 16 of 61/290,844 illustrates examples of arylamine backbone moieties, which are incorporated by reference.

FIG. 17 of 61/290,844 illustrates examples of particular arylamine polymers, which are incorporated by reference.

Arylamine backbone moieties are known in the art. See, for example, Lim et al., Organic Letters, 2006, 8(21), 2703-4706; Fusake et al., Polymers for Advanced Technologies, 2002, 13, 601-604; Shirota et al., Chem. Rev., 2007, 107, 953-1010; Z. Li and H. Meng, Eds., Organic Light-Emitting Materials and Devices, CRC Press (Taylor and Francis Group, LLC), Boca Raton (2007) and references therein. Arylamine backbone moieties can each comprise at least one nitrogen atom and at least one benzene ring, so that the polymer backbone can comprise both at least one aryl group and nitrogen atom from the arylamine. The aryl group may also appear in the side group. One or more nitrogens may appear in the side group. As a non-limiting example, an arylamine backbone moiety can comprise one benzene ring bonded to a nitrogen atom; two benzene rings bonded to a nitrogen atom; or three benzene rings bonded to a nitrogen atom.

An arylamine backbone moiety can comprise one or more aromatic groups, such as, for example, benzene, naphthalene, anthracene, and phenanthracene groups. The aromatic groups may be substituted or unsubstituted. As a non-limiting example, they can be substituted with one or more $C_1$-$C_{10}$ alkyl, perfluoroalkyl, thioalkyl, alkoxy, alkylaryl, arylalkyl, arlyoxy, heteroaryl, cyano, halo, and alkylhio groups, or a combination thereof.

In some embodiments, an arylamine backbone moiety may comprise N,N'-diphenyl benzidine. The N,N'-diphenyl benzidine aryl groups can be, for example, unsubstituted, or can be, for example, substituted with, as non-limiting examples, $C_1$-$C_{10}$ alkyl, perfluoroalkyl, thioalkyl, alkoxy, alkylaryl, arylalkyl, aryloxy, heteroaryl, cyano, halo, alkylthio, trialkyl silyl, trialkoxysilyl, and trialkyl silyloxy groups. Commonly, substitution of an aryl group of N,N'-diphenyl benzidine can involve one or more aryl groups that do not become part of the polymer backbone. The arylamine backbone moiety may commonly comprise N,N'-diphenyl-1,4-phenylenediamine. The N,N'-diphenyl-1,4-phenylenediamine aryl groups can be, for example, unsubstituted, or can be, for example, substituted with, as non-limiting examples, $C_1$-$C_{10}$ alkyl, perfluoroalkyl, thioalkyl, alkoxy, alkylaryl, arylalkyl, aryloxy, heteroaryl, cyano, halo, alkylthio, trialkyl silyl, trialkoxysilyl, and trialkyl silyloxy groups. Commonly, substitution of an aryl group of N,N'-diphenyl-1,4-phenylenediamine can involve one or more aryl groups that do not become part of the polymer backbone. In some embodiments, the arylamine backbone moiety can comprise a mixture of arylamine backbone moieties.

Part IVl:

U.S. provisional application 61/289,314 filed Dec. 22, 2009 provides additional embodiments. These embodiments can be adapted to include structures described herein including structure I.

In some embodiments, inks may comprise one or more fluorinated solvents, or inks may comprise solvent blends that comprise one or more fluorinated solvents, or inks may comprise one or more fluorinated solvent additives.

For example, one embodiment provides a composition comprising: (i) at least one donor acceptor conjugated polymer, (ii) at least one n-type material different from the polymer, (iii) at least one solvent for the polymer, (iv) at least one fluorinated solvent additive which is different than the solvent. The donor acceptor conjugated polymer and the n-type material can form a bulk heterojunction. In some embodiments, a fluorous solvent or additive can be used in combination with a non-fluorous solvent.

The amount of the fluorinated solvent in the solvent blend, or additive, can be, for example, about 50 wt. % or less, or about 25 wt. % or less, or about 10 wt. % or less, or about 5 wt. % or less, or about 3 wt. % or less, relative to the total amount of solvent and liquid component. In some embodiments, the lower amount can be, for example, at least about 0.1 wt. %, or at least about 1 wt. % or at least about 2 wt. %. In some embodiments, the only halogenated solvent is a fluorinated solvent. In some embodiments, the solvent system comprises a halogenated solvent and a fluorinated solvent different than the halogenated solvent. In some embodiments, the solvent system can comprise a non-halogenated solvent and a fluorinated solvent. The solvent system can comprise at least two, at least three, or at least four solvents, including at least one fluorinated solvent.

Fluorinated solvents are described in, for example, *Handbook of Fluorous Chemistry*, Ed Gladysz, Curran, Horvath, Wiley, 2004, including chapters 3 and 6 on fluorinated solvents. Fluorinated solvents and materials can be also obtained from, for example, SynQuest Lab., Inc., Alachua, Fla.

Fluorinated solvents or additives can be, for example, ionic or nonionic. They can be volatile and removed from the solid material upon removal of solvent. They can be fully fluorinated, perfluorinated, or partially fluorinated. They can be liquid at room temperature and pressure. Isomeric mixtures can be used.

Fluorinated solvent additive can be, for example, an alkyl or aryl compound. Fluorinated solvent additive can be, for example, fluoroalkane, perfluoroalkane, fluoroalkene, perfluoroalkene, fluoroalkyne, or perfluoroalkyne. The fluorinated solvent additive can be, for example a benzene derivative or an alkane derivative.

Fluorinated aromatic solvents may be used as solvents or in solvent blends, or as additives. Examples of such solvents include chloropentafluorobenzene, pentafluorothiophenol (pentafluorobenzenethiol), 2-chlorobenzotrifluoride, 3-chlorobenzotrifluoride, 4-chlorobenzotrifluoride, o-fluorotoluene, α,α,α-trifluorotoluene (benzotrifluoride), 2,5-dichlorobenzotrifluoride, 3,4-dichlorobenzotrifluoride, 2,4-dichlorobenzotrifluoride, pentafluorobenzene, hexafluorobenzene, octafluorotoluene, 1,3-bis(trifluoromethyl)benzene (BTFMB), 1-chloro-2,4-difluorobenzene, 1-chloro-2,5-difluorobenzene, 1,3-dichloro-2-fluorobenzene, 2,4-dichloro-1-fluorobenzene, and 2,3,4,5,6-pentafluoroaniline. Other examples include hexafluorobenzene (HFB) and octafluorotoluene (OFT). Another example is a difluoroalkane.

Other fluorinated solvents may be used as solvents or in solvent blends, or as additives. Examples of such solvents include perfluorodecalin, perfluor-1,3-dimethylcylclohexane, perfluorononane, hexadecafluoroheptane, 1,6-diiodoperfluorohexane, and methoxynonafluorobutane.

The density of the fluorinated compound can be, for example, about 1.3-1.9 g/cc. The boiling point can be, for example, about 50° C. to about 300° C., or about 50° C. to about 250° C., or about 50° C. to about 200° C. about 100° C. to about 175° C.

The fluorinated solvent, solvent blend, or additive can improve the performance of an organic electronic device. For example, efficiency can be improved when the solar cell active layer is prepared with fluorinated solvent, solvent blend, or additive.

Some examples of advantages and effects of fluorinated or fluorous solvents include:

1. High density fluorous solvent can in at least some embodiments offer orthogonal segregation of species more soluble in it (either through p- or n-type that can be fluorinated to subsequently improve: (i) Miscibility (or lack of miscibility, e.g., selectively fluorinated p-types can limit undesirable intercalation with fullerenes and their non-fluorinated derivatives that can prevent recombination), (ii) Packing density, (iii) Charge transport [Lit. Ref.: a) A. Facchetti et al. *Adv. Mater.* 2003, 15, 33; b) P. H. Wobkenberg et al. *Appl. Phys. Lett.* 2008, 92, 143310 (Fluorine containing $C_{60}$ derivatives for high-performance electron transporting field-effect transistors and integrated circuits); c) Q. Wei et al. *Adv. Mater.* 2008, 20, 2211 (Self-organized buffer layers in organic solar cells], (iv) alter energy levels (HOMO/LUMO), (v) Inter-intra-molecular interactions, (vi) Compatibility with fluoro-containing HTLs or HILs 2. A range of temperature-dependent miscibility with various organic solvents 3. Moisture repellant 4. Ambient, UV, and Environmental stability 5. Increase in OPV device lifetime In particular, a combination is to use fluorinated solvent together with thermal annealing of an OPV active layer.

Fluorinated solvent additives can be used in combination with fluorinated polymers, fluorinated n-type materials, including fluorinated fullerenes, fluorinated interlayers (e.g., HIL), and other fluorinated materials and solvents. Both the p-type material and the n-type material in the active layer can be fluorinated. Fluorinated fullerenes are described in, for example, Wei et al., *Adv. Mater.* 2008, 20, 2211-2216. Fluoropolymers have also been used in solar cells. See Kang et al., *Applied Physics Letters* 93, 133302 (2008). For fluorinated polymers, fluorination can be in the backbone or on a side group.

Another embodiment provides a composition comprising: (i) at least one donor acceptor conjugated polymer, (ii) at least one n-type material different from the polymer, (iii) at least one solvent for the polymer, and (iv) at least one fluorinated solvent additive which is different than the solvent.

In one embodiment, the amount of additive relative to the total amount of solvent and additive is about 10 wt. % or less. In one embodiment, the amount of additive relative to the total amount of solvent and additive is about 5 wt. % or less. In one embodiment, the amount of additive relative to the total amount of solvent and additive is about 1 wt. % to about 5 wt. %.

In one embodiment, the solvent does not comprise halogen. In one embodiment, the solvent is a benzene derivative.

In one embodiment, the additive is a non-ionic compound. In one embodiment, the additive is perfluorinated. In one embodiment, the additive is partially fluorinated.

In one embodiment, the fluorinated additive has a boiling point of about 50° C. to about 300° C. In one embodiment, the fluorinated additive has a boiling point of about 100° C. to about 175° C.

In one embodiment, the fluorinated additive is a benzene derivative. In one embodiment, the fluorinated additive is a fluorinated aromatic solvent. In one embodiment, the fluorinated additive is HFB, OFT, or BTFMB.

In one embodiment, the polymer is a fluorinated polymer. In one embodiment, the polymer comprises a fluorinated backbone. In one embodiment, the polymer comprises a fluorinated side group.

In one embodiment, the n-type material is a fullerene derivative. In one embodiment, the n-type material is a C60 or a C70 fullerene derivative. In one embodiment, the n-type material is fluorinated.

In one embodiment, the polymer is fluorinated and the n-type material is fluorinated.

In one embodiment, the weight ratio of polymer to n-type material is about 1:1 to about 1:6. In one embodiment, the weight ratio of polymer to n-type material is about 1:2 to about 1:5.

In one embodiment, the weight percentage of the combined amount of polymer and n-type material is about 0.001 to about 0.2. In one embodiment, the weight percentage of the combined amount of polymer and n-type material is about 0.003 to about 0.1.

In one embodiment, the polymer comprises at least one nitrogen in the polymer backbone. In one embodiment, the polymer comprises at least one arylamine in the polymer backbone.

In one embodiment, the polymer comprises at least one tricyclic unit comprising three fused rings.

In one embodiment, the polymer comprises at least one donor moiety comprising at least three fused rings, wherein the central ring is a benzene ring which is fused to two thiophene rings.

In one embodiment, the polymer comprises a molecular weight Mn of at least 10,000.

In one embodiment, further provided is a composition comprising: (i) at least one donor acceptor conjugated polymer adapted to function with an n-type material and function in an active layer of a solar cell, (ii) at least one n-type material different from the polymer which is adapted to function with the polymer in an active layer of a solar cell, (iii) at least one solvent for the polymer and n-type material, (iv) at least one fluorinated solvent additive which is different than the solvent and present in amounts less than the solvent, wherein the fluorinated solvent additive increases the power conversion efficiency of a solar cell device comprising an active layer fabricated from the composition, compared to a device comprising an active layer fabricated from a substantially similar composition without the solvent additive.

In one embodiment, the fluorinated solvent also increases the fill factor, the open circuit voltage, and/or the short circuit current. In one embodiment, the power conversion efficiency is increased by at least 50% with use of the fluorinated additive. In one embodiment, the power conversion efficiency is increased by at least 100% with use of the fluorinated additive. In one embodiment, the power conversion efficiency is increased by at least 150% with use of the fluorinated additive. In one embodiment, the power conversion efficiency is at least 4% with use of the fluorinated additive. In one embodiment, the power conversion efficiency is at least 5% with use of the fluorinated additive. In one embodiment, the power conversion efficiency is at least 6% with use of the fluorinated additive. In one embodiment, the open circuit voltage is at least 0.7 V with use of the fluorinated additive. In one embodiment, the open circuit voltage is at least 0.8 V with use of the fluorinated additive. In one embodiment, the short circuit current is at least 10 mA/cm$^2$ with use of the fluorinated additive. In one embodiment, the short circuit current is at least 11 mA/cm$^2$ with use of the fluorinated additive. In one embodiment, the fill factor is at least 40% with use of the fluorinated additive. In one embodiment, the fill factor is at least 50% with use of the fluorinated additive.

In one embodiment, the amount of additive relative to the total amount of solvent and additive is about 5 wt. % or less. In one embodiment, the amount of additive relative to the total amount of solvent and additive is about 1 wt. % to about 5 wt. %.

In one embodiment, the solvent does not comprise halogen.

In one embodiment, the solvent is a benzene derivative.

In one embodiment, the additive is a non-ionic compound. In one embodiment, the additive is perfluorinated. In one embodiment, the additive is partially fluorinated. In one embodiment, the fluorinated additive has a boiling point of about 50° C. to about 300° C. In one embodiment, the fluorinated additive has a boiling point of about 100° C. to about 175° C.

In one embodiment, the fluorinated additive is a benzene derivative or an alkane derivative.

In one embodiment, the fluorinated additive is a fluorinated aromatic solvent.

In one embodiment, the polymer is a fluorinated polymer.

In one embodiment, the n-type material is a fullerene derivative. In one embodiment, the n-type material is fluorinated.

In one embodiment, the weight ratio of polymer to n-type material is about 1:1 to about 1:6. In one embodiment for an ink, the weight percentage of the combined amount of polymer and n-type material is about 0.001 to about 0.2.

Part IVm:

Still other embodiments for monomers, oligomers, and polymers include, for example:

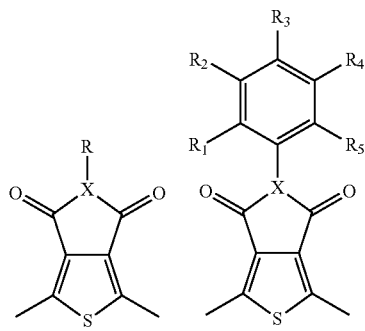

wherein X and the R groups (R, R1, R2, R3, R4, R5) can be as described herein for hydrogen, halogen, or solubilizing groups as described elsewhere herein.

Part IVn:

For purification of polymers described herein, polymers can be passed through celite, silica gel, and/or metal-scavenger-functionalized silica gel (e.g., thiol functionalized silica gel). Also, polymers can be passed through recycling GPC to remove small molecular weight fractions and/or low molecular weight residual impurities carried on through monomer synthesis and/or polymer post-polymerization handling.

Part IVo:

The Polymer Listing, below, provides structures A-NNNN for a series of polymers which comprise structure I. The side groups can be adapted from what is illustrated in the Polymer Listing to provide, for example, solubility or electronic energy level tuning as described elsewhere herein. In addition, the molecular weight and values for n, x, m, and the like, can be adapted as described elsewhere herein to provide oligomers, lower molecular weight polymers, moderate molecular weight polymers, and higher molecular weight polymers. Corresponding oligomers can be also prepared analogous to these polymers.

Polymer Listing:

| Identifier | Polymer Structure |
|---|---|
| A | 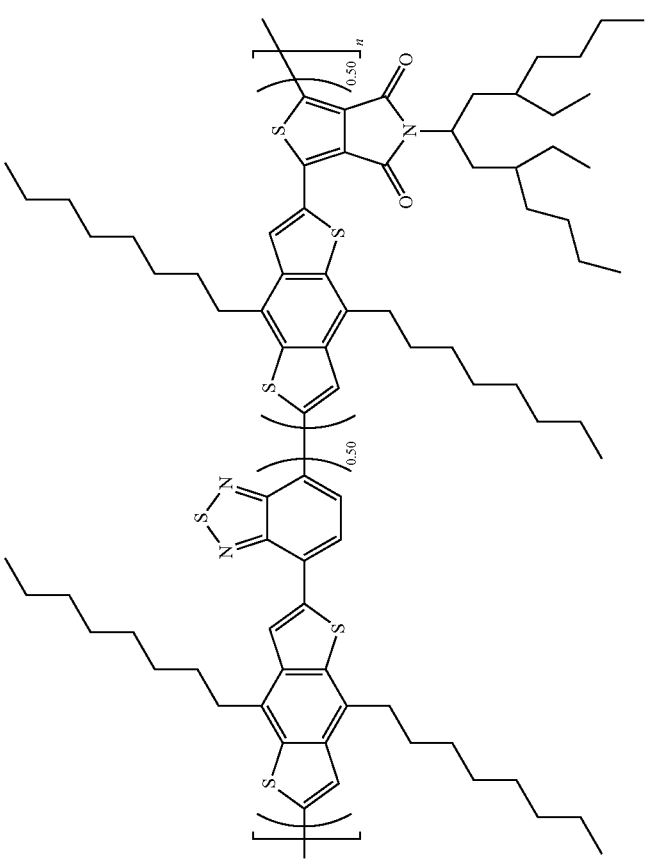 |

| Identifier | Polymer Structure |
|---|---|
| B | -continued (structure) |

| Identifier | Polymer Structure |
|---|---|
| C | 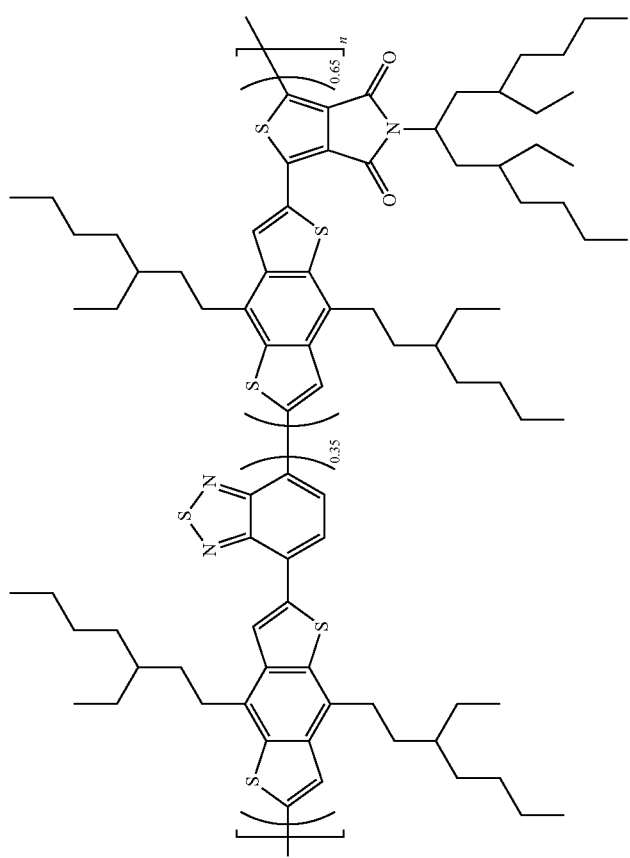 |

| Identifier | Polymer Structure |
|---|---|
| D | 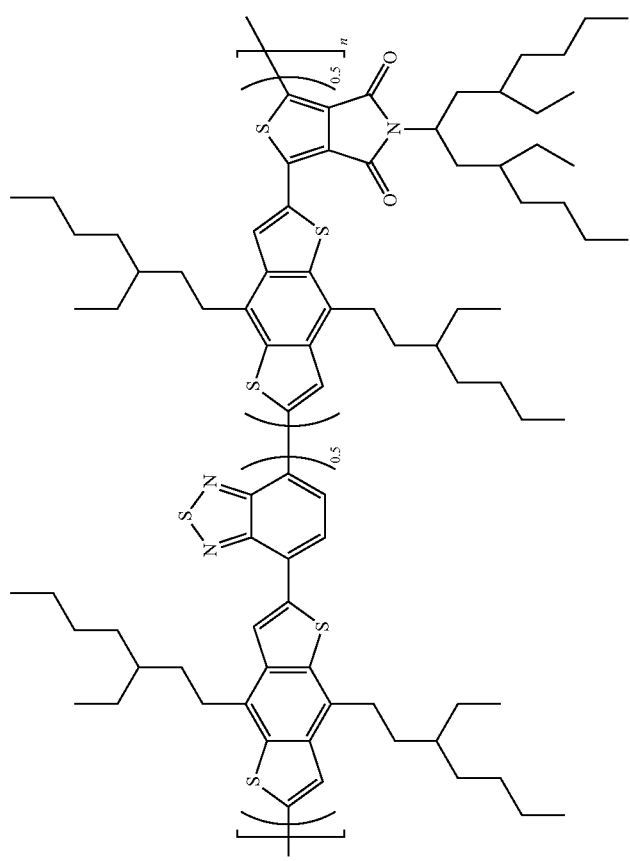 |

| Identifier | Polymer Structure |
|---|---|
| E | 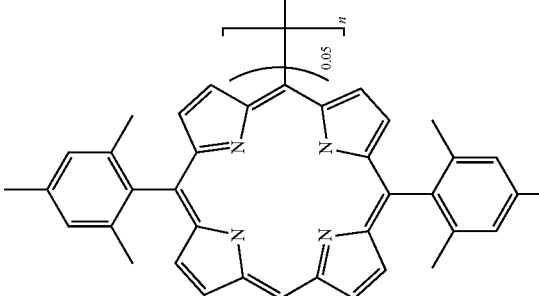 |

| Identifier | Polymer Structure |
|---|---|
| F | 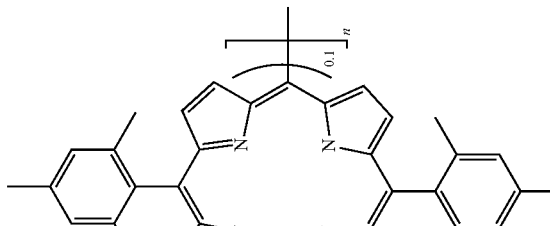 |

| Identifier | Polymer Structure |
|---|---|
| G | 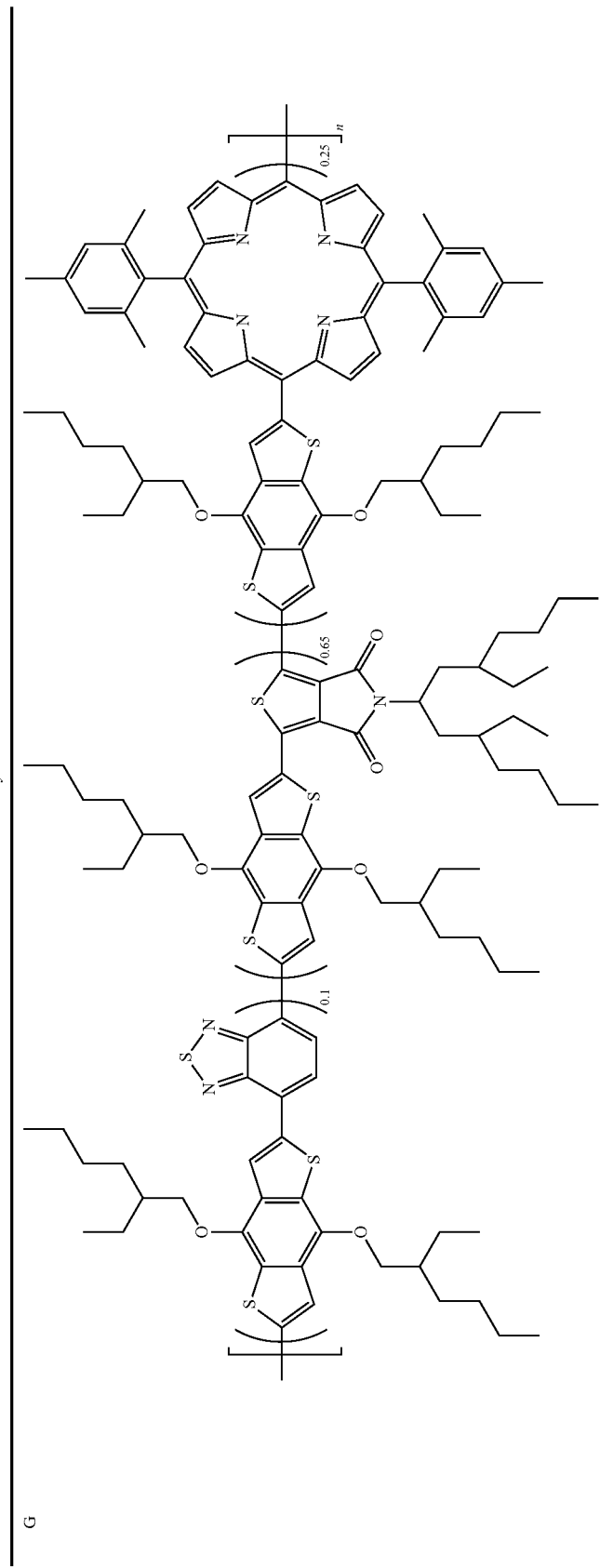 |

| Identifier | Polymer Structure |
|---|---|
| H | 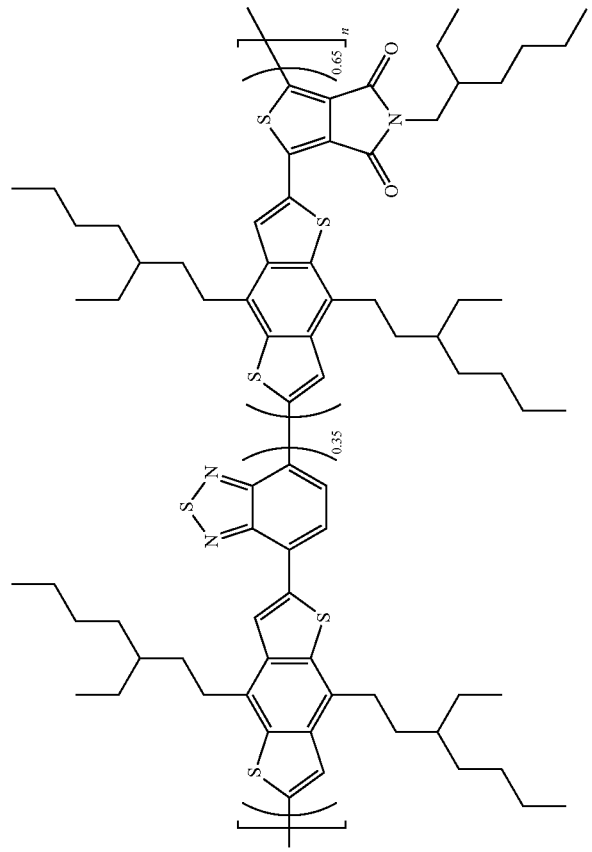 |

| Identifier | Polymer Structure |
|---|---|
| I | 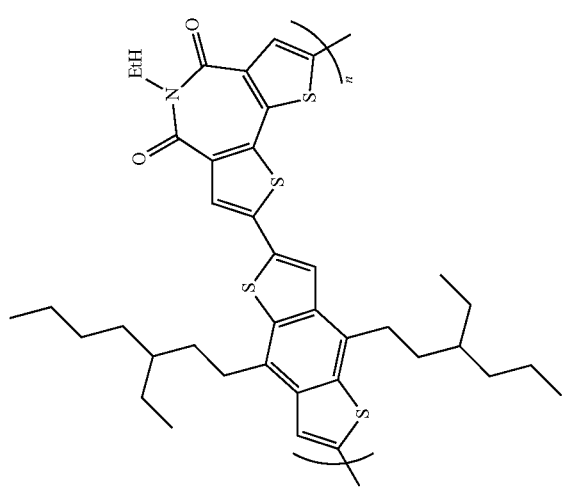 |

| Identifier | Polymer Structure |
|---|---|
| J | 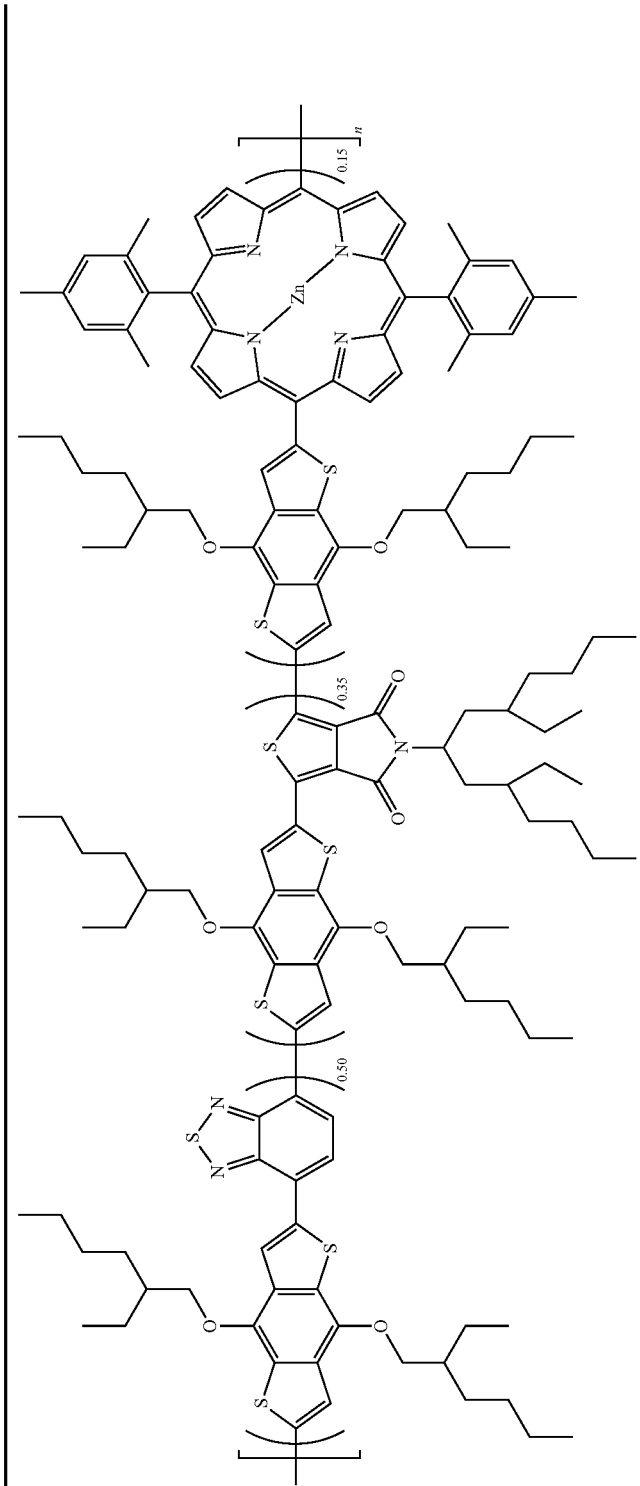 |
-continued

| Identifier | Polymer Structure |
|---|---|
| K | -continued (structure) |

| Identifier | Polymer Structure |
|---|---|
| L | 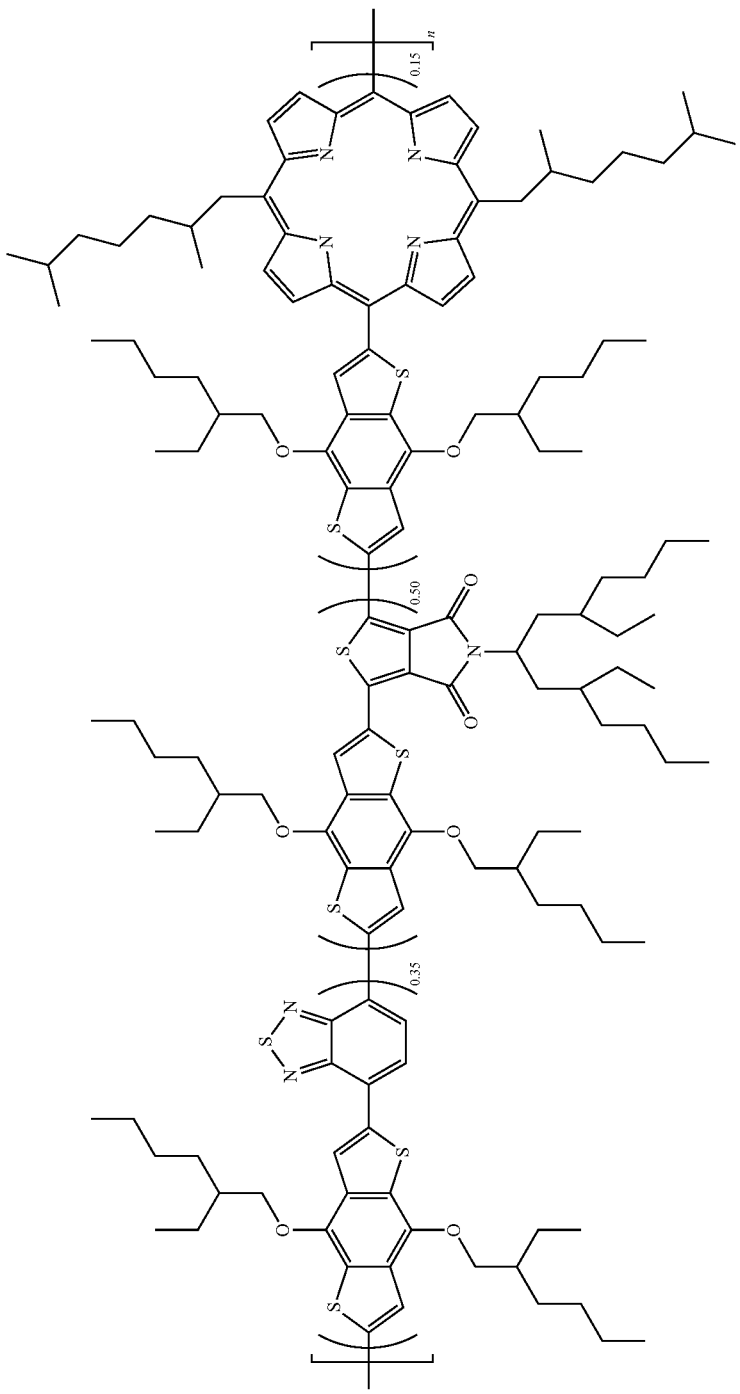 |

-continued
| Identifier | Polymer Structure |
|---|---|
| M | 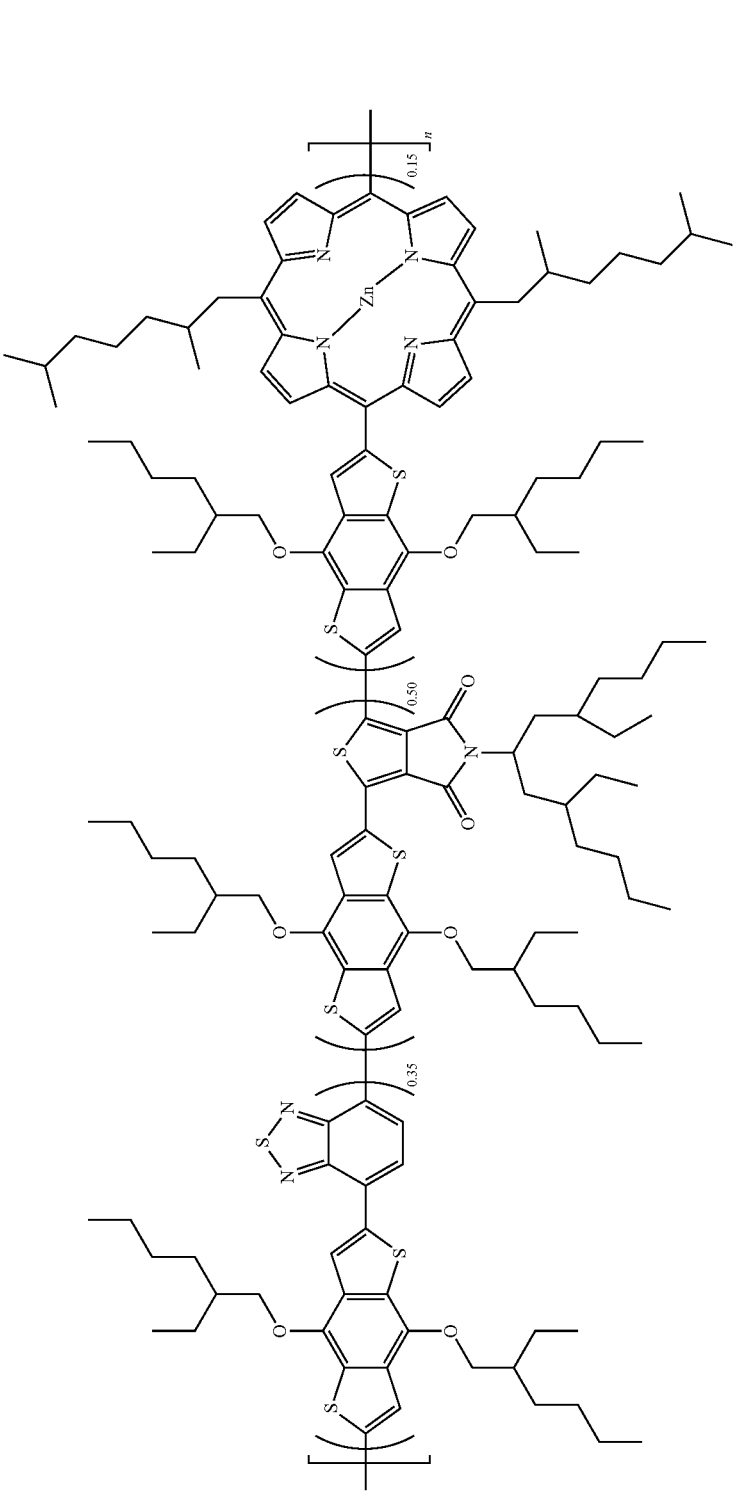 |

| Identifier | Polymer Structure |
|---|---|
| N | 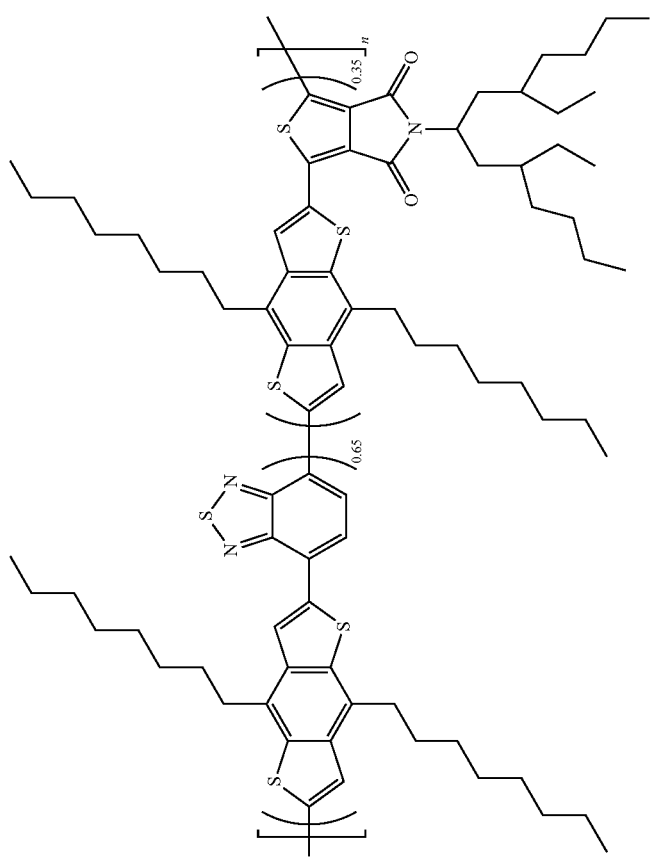 |

| Identifier | Polymer Structure |
|---|---|
| O | 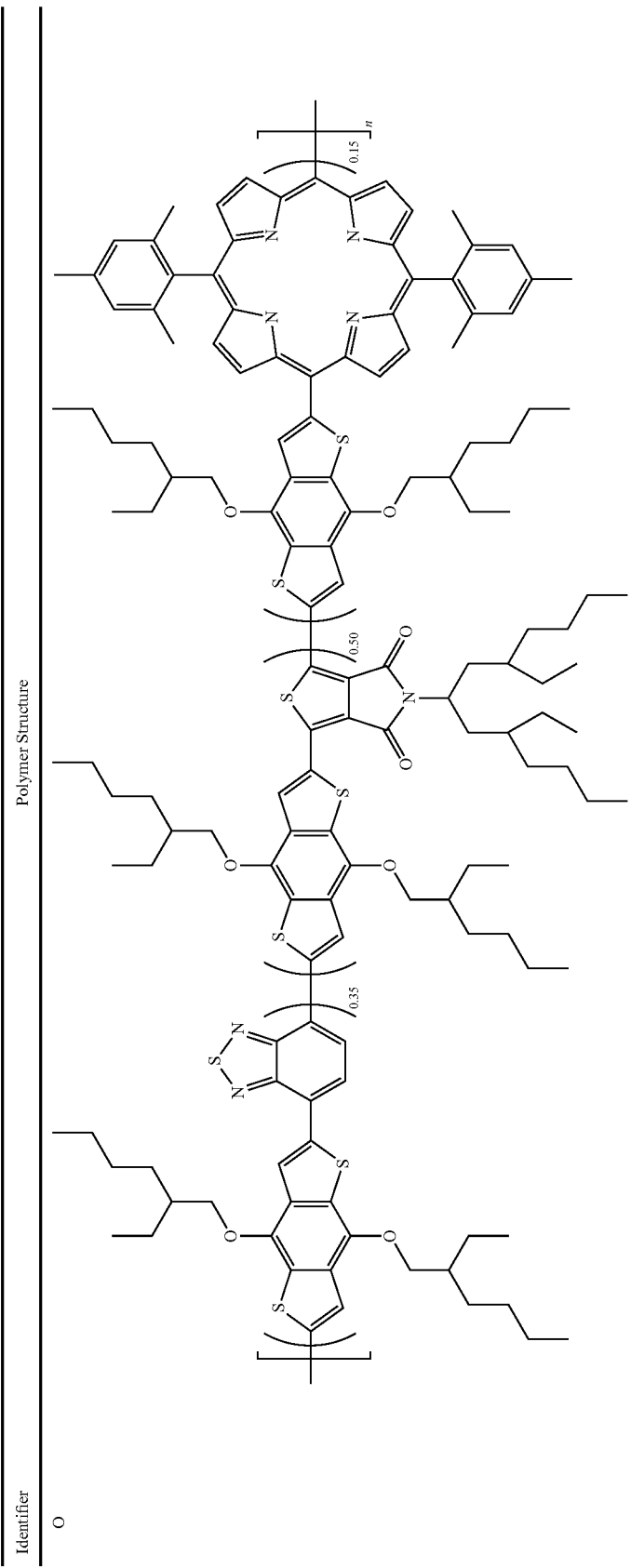 |

| Identifier | Polymer Structure |
|---|---|
| P | 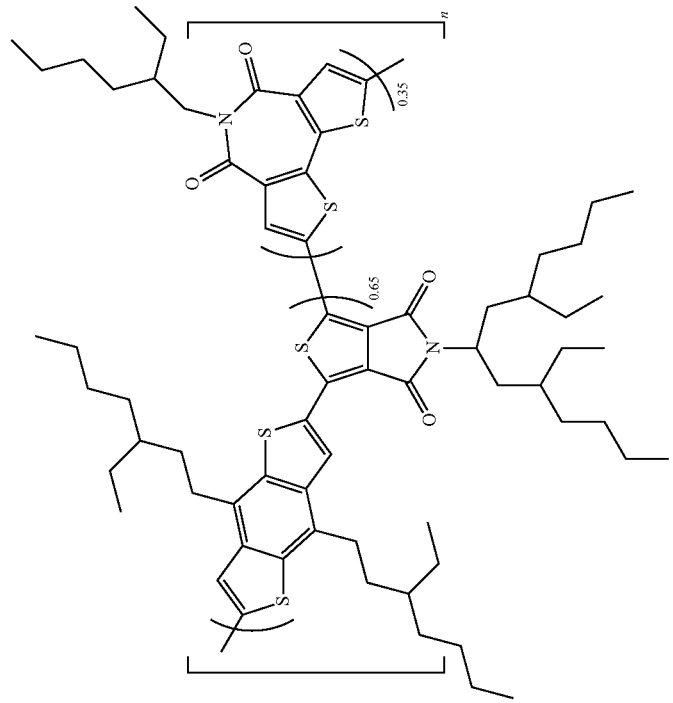 |

| Identifier | Polymer Structure |
|---|---|
| Q | 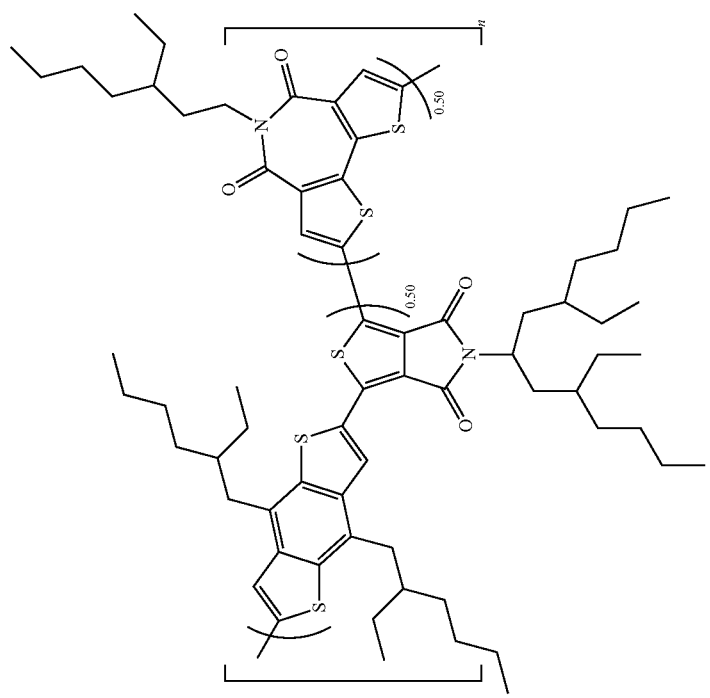 |

| Identifier | Polymer Structure |
|---|---|
| R | 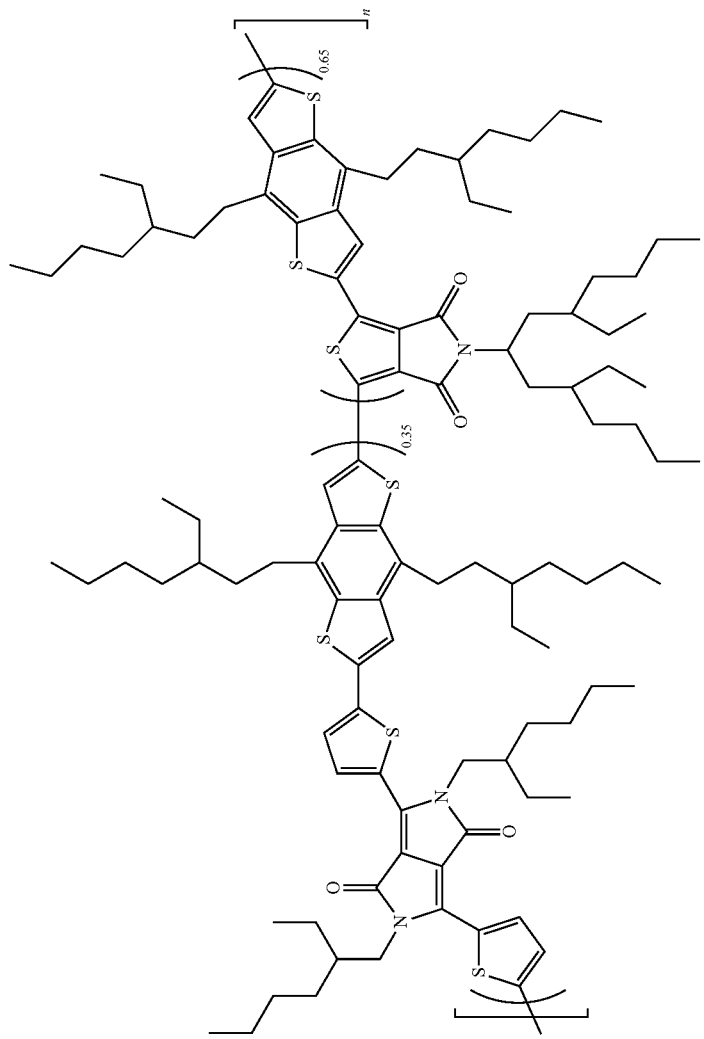 |

| Identifier | Polymer Structure |
|---|---|
| s | 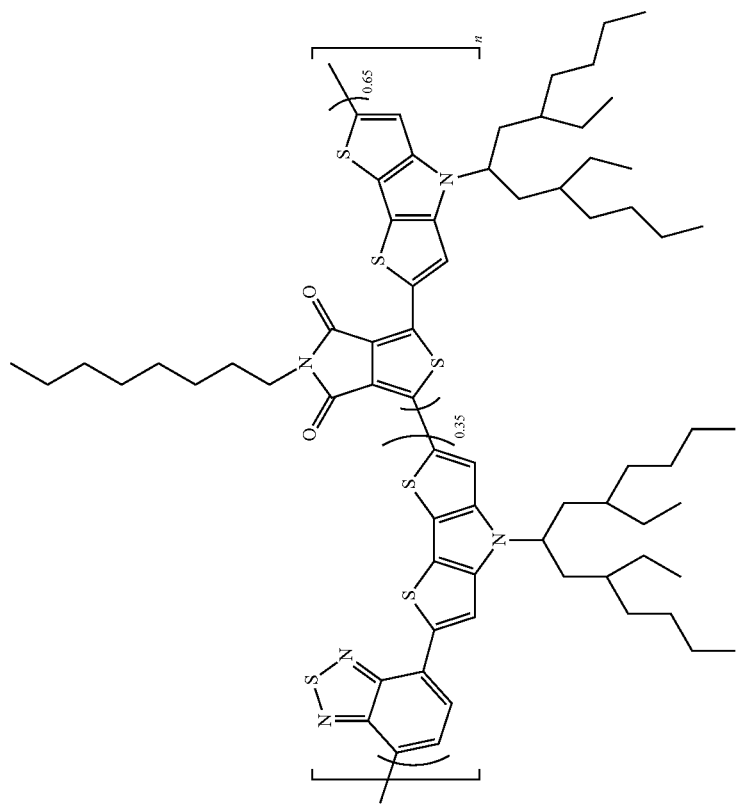 |

| Identifier | Polymer Structure |
|---|---|
| T | 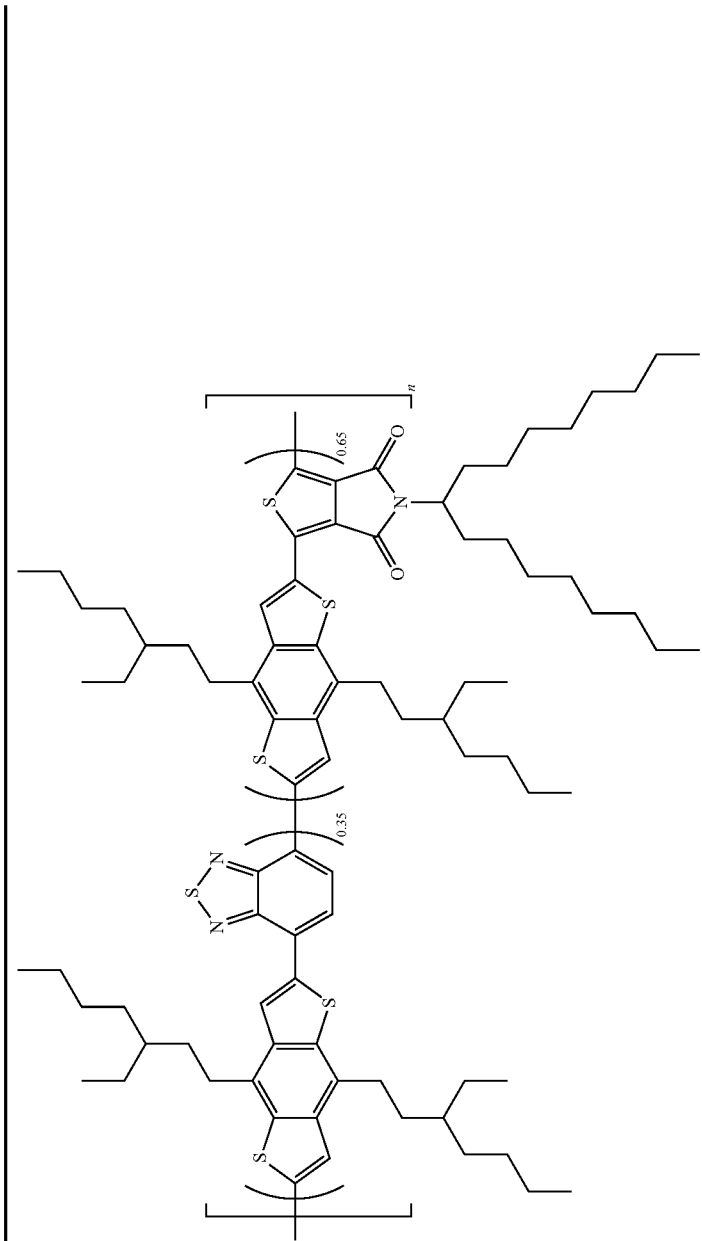 |

| Identifier | Polymer Structure |
|---|---|
| U | 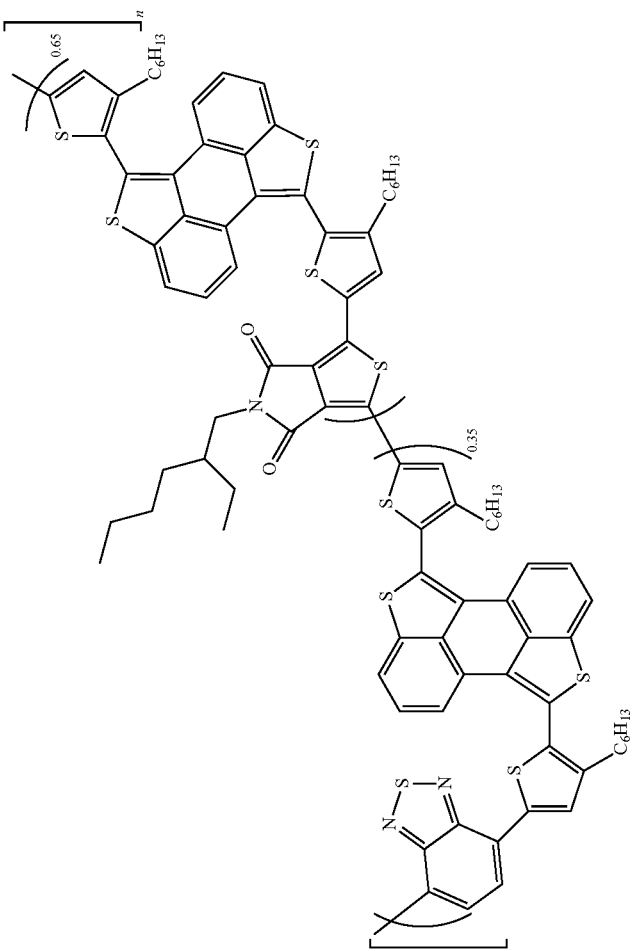 |

| Identifier | Polymer Structure |
|---|---|
| V | 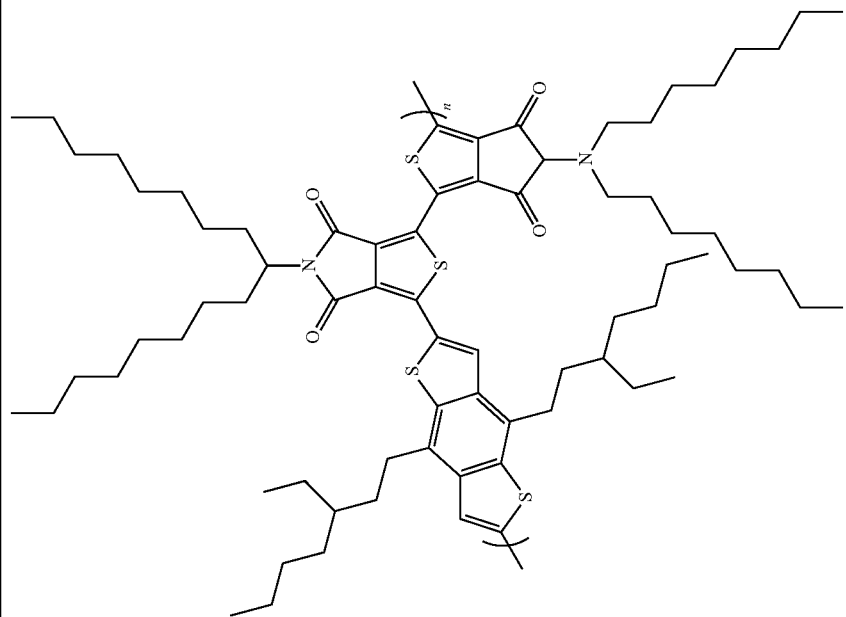 |

| Identifier | Polymer Structure |
|---|---|
| W | 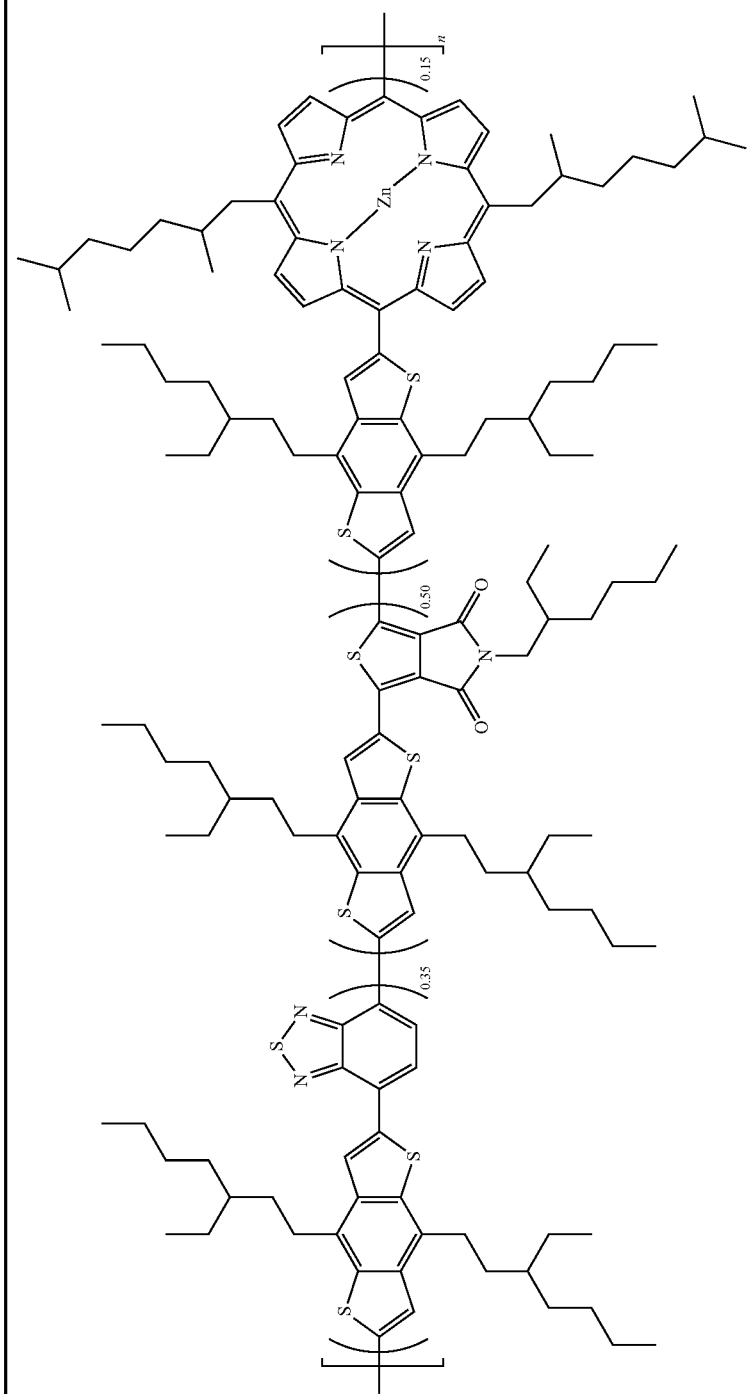 |

| Identifier | Polymer Structure |
|---|---|
| X | 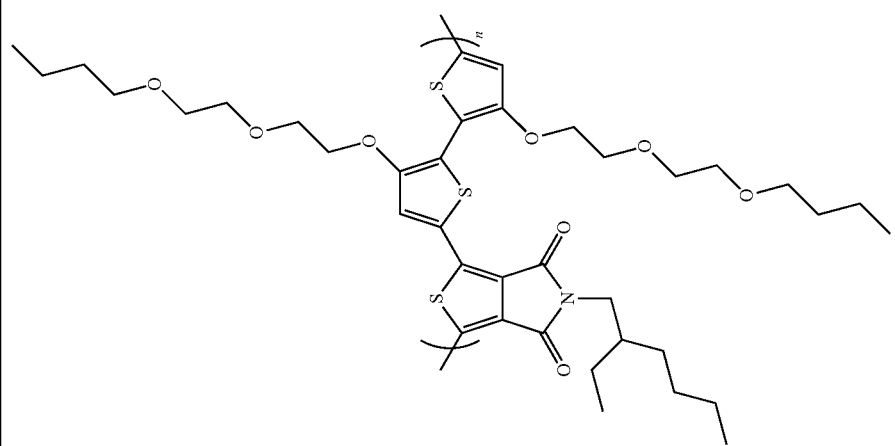 |

| Identifier | Polymer Structure |
|---|---|
| Y | 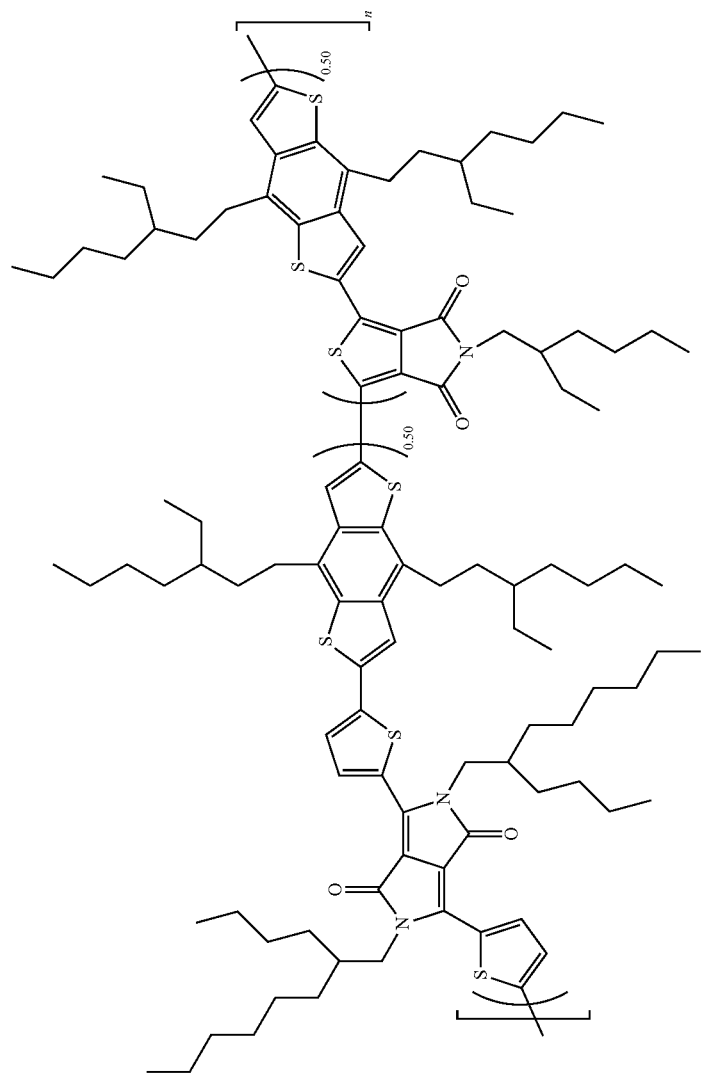 |

| Identifier | Polymer Structure |
|---|---|
| Z | 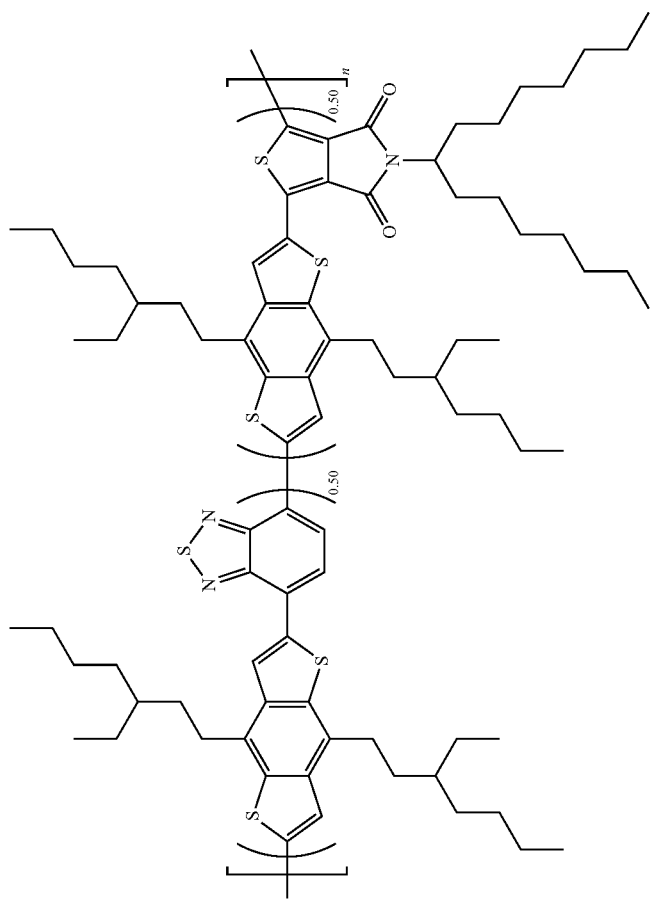 |

-continued
| Identifier | Polymer Structure |
|---|---|
| AA | 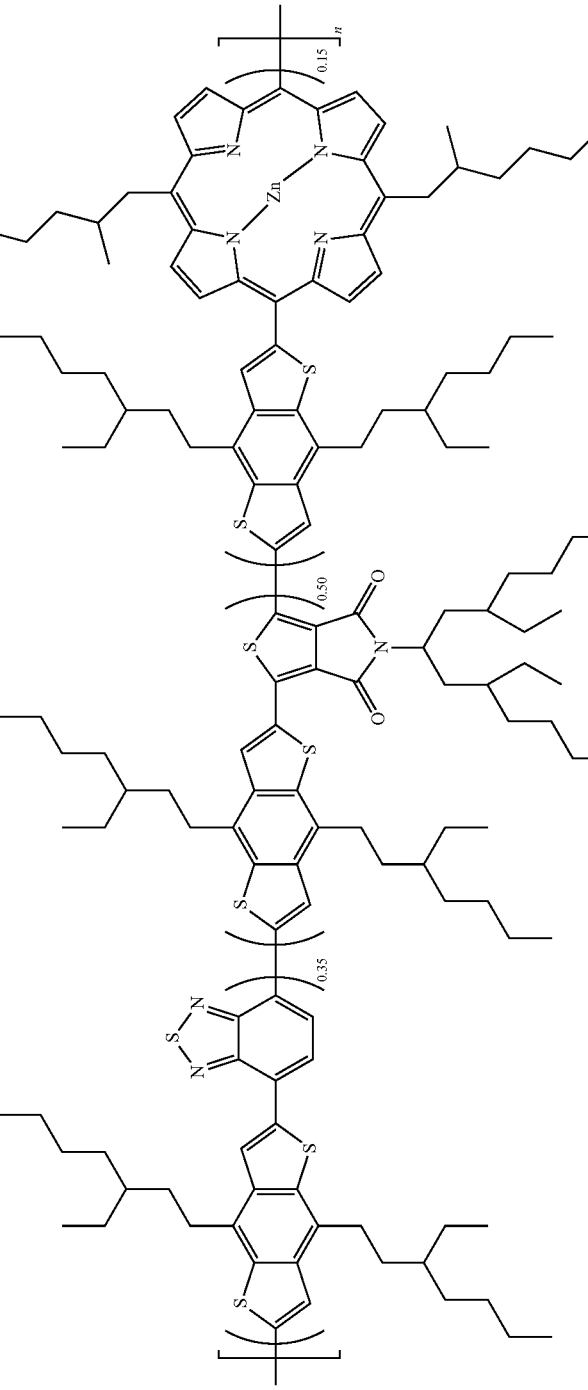 |

| Identifier | Polymer Structure |
|---|---|
| BB | -continued (structure) |

| Identifier | Polymer Structure |
|---|---|
| CC | 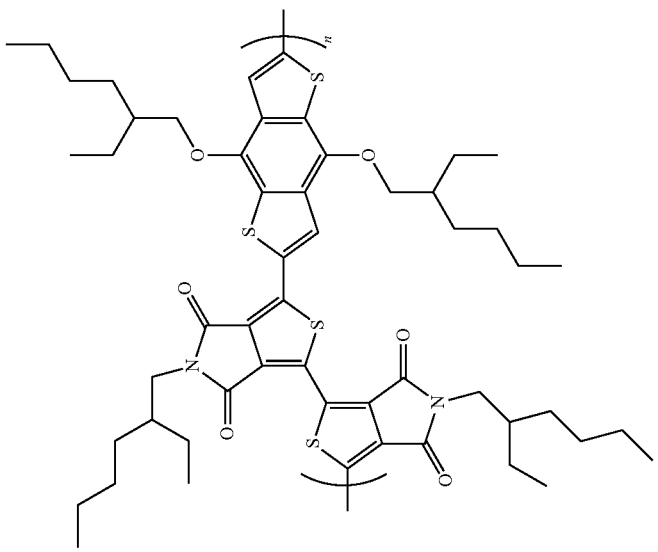 |

-continued
| Identifier | Polymer Structure |
|---|---|
| DD | 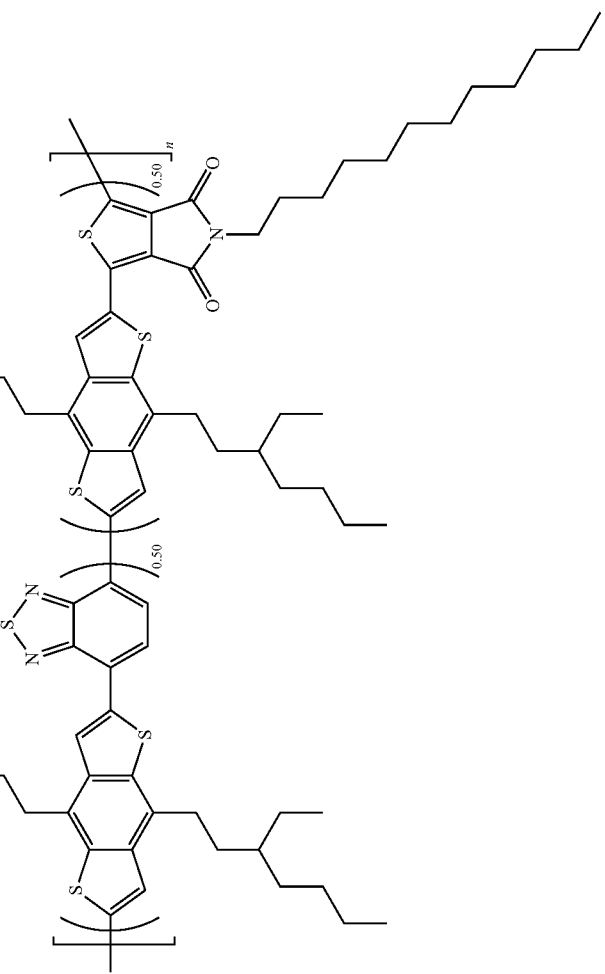 |

| Identifier | Polymer Structure |
|---|---|
| EE | 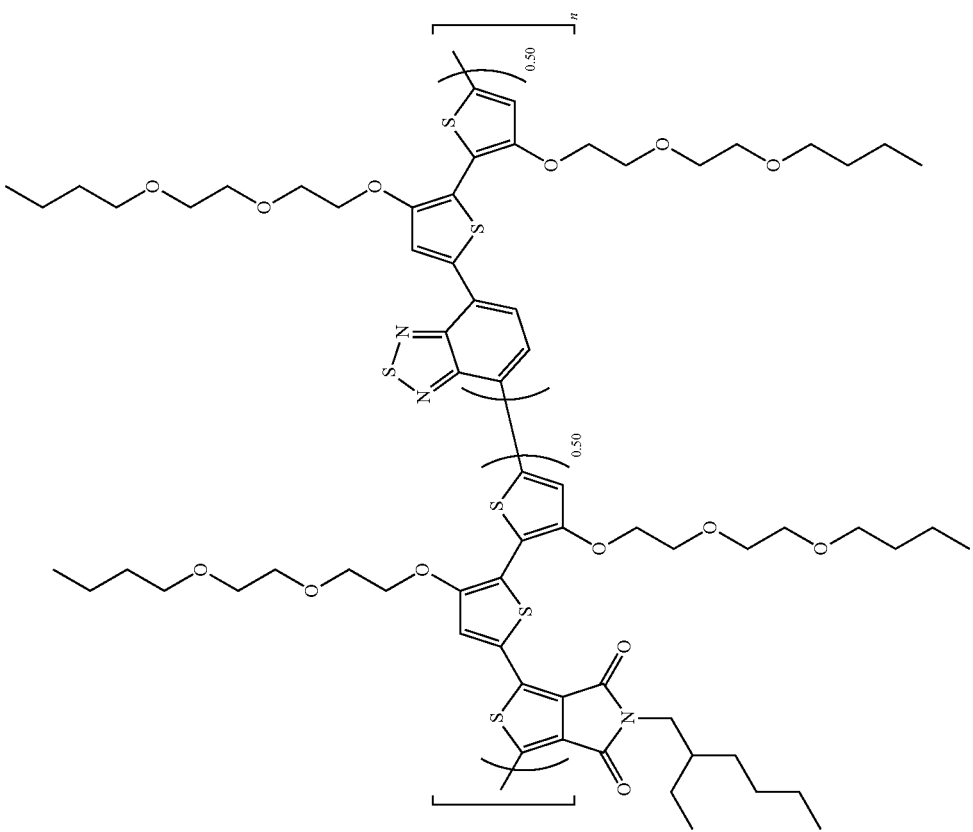 |

| Identifier | Polymer Structure |
|---|---|
| FF | 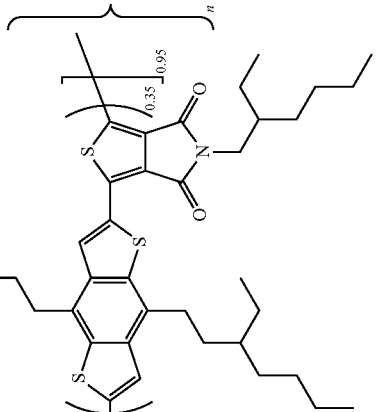 |

| Identifier | Polymer Structure |
|---|---|
| GG | 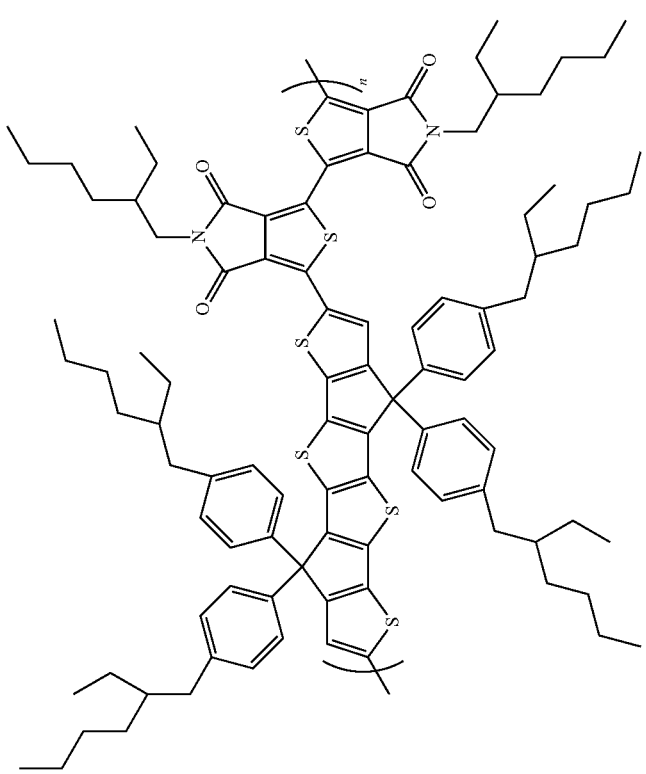 |

| Identifier | Polymer Structure |
|---|---|
| HH | 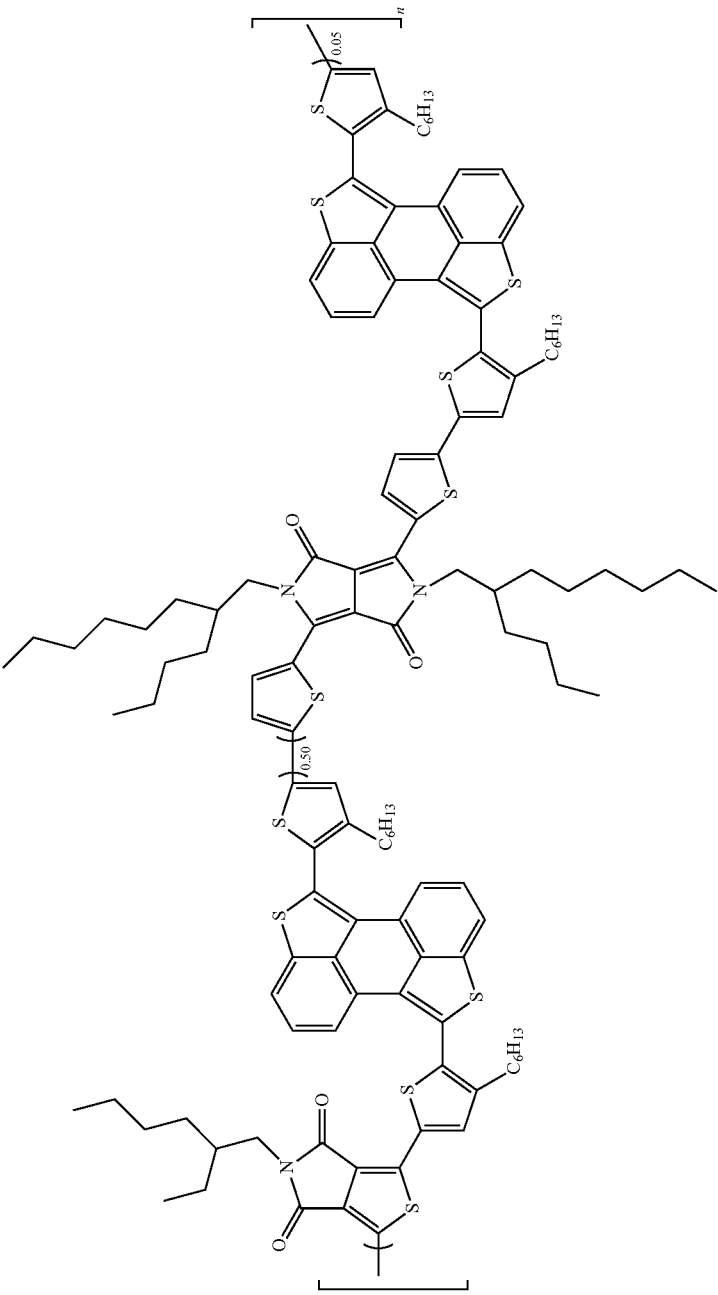 |

| Identifier | Polymer Structure |
|---|---|
| II | 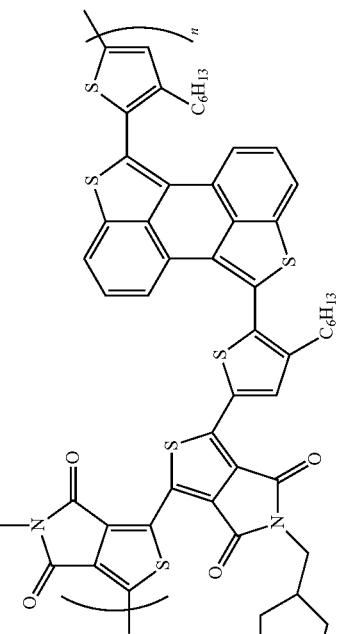 |
| JJ | |

| Identifier | Polymer Structure |
|---|---|
| KK | 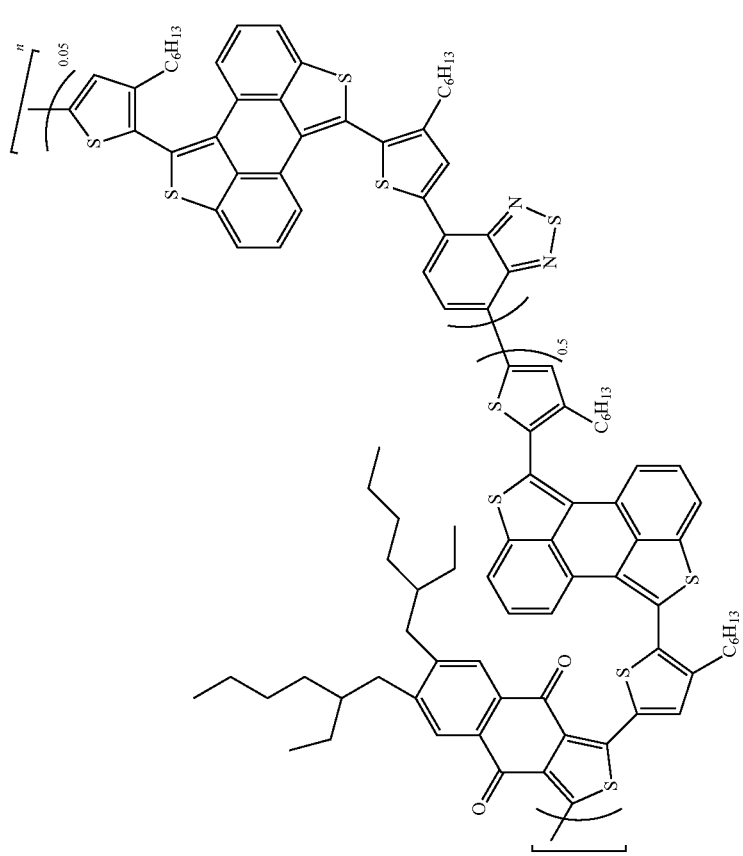 |

| Identifier | Polymer Structure |
|---|---|
| LL | 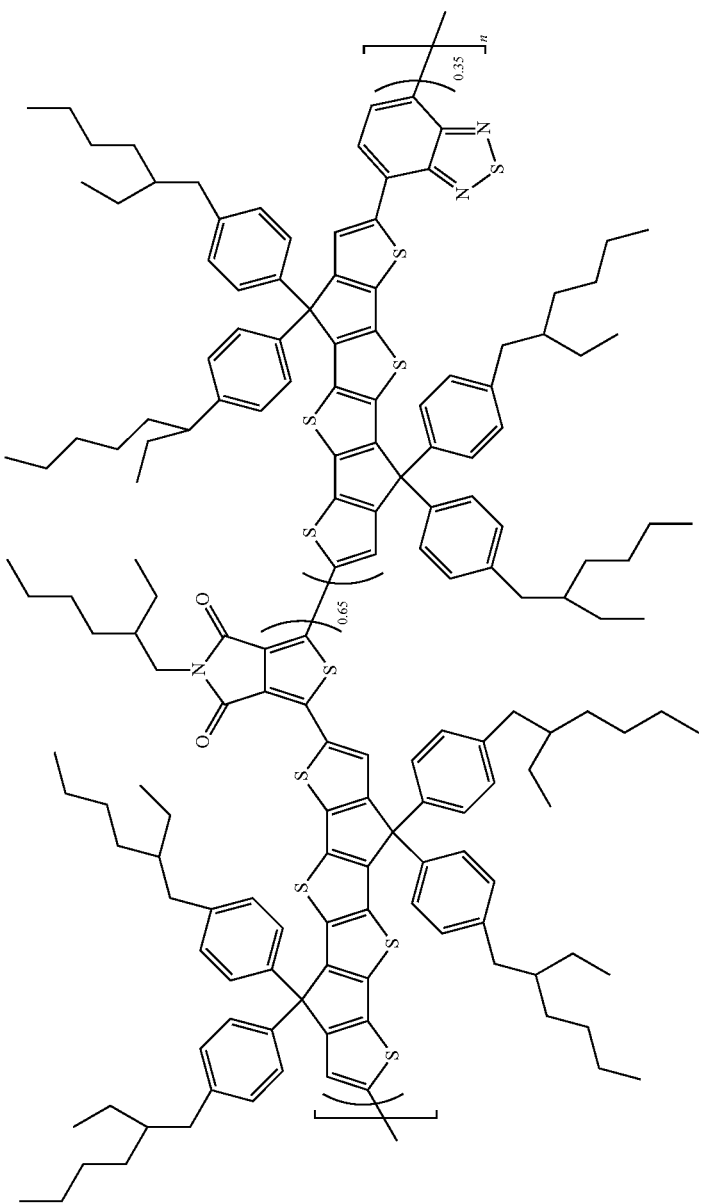 |

-continued
| Identifier | Polymer Structure |
|---|---|
| MM | 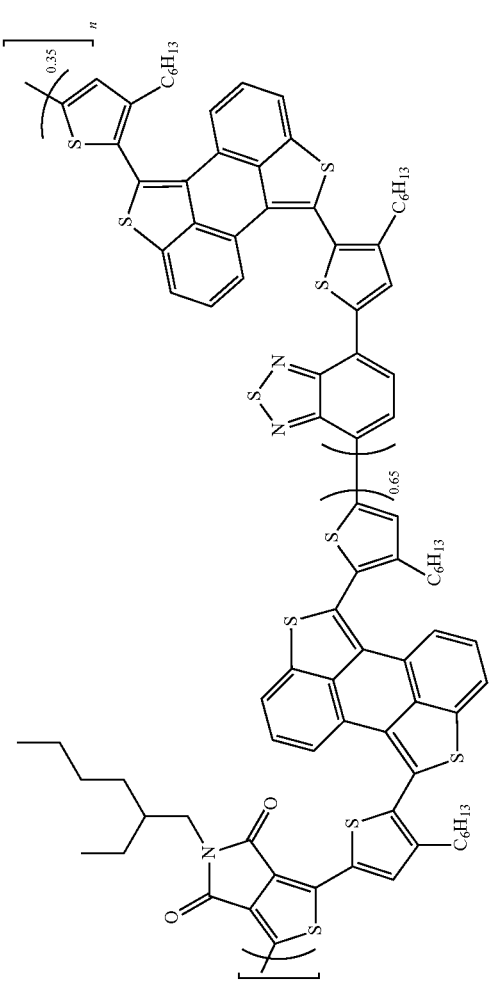 |

| Identifier | Polymer Structure |
|---|---|
| NN | 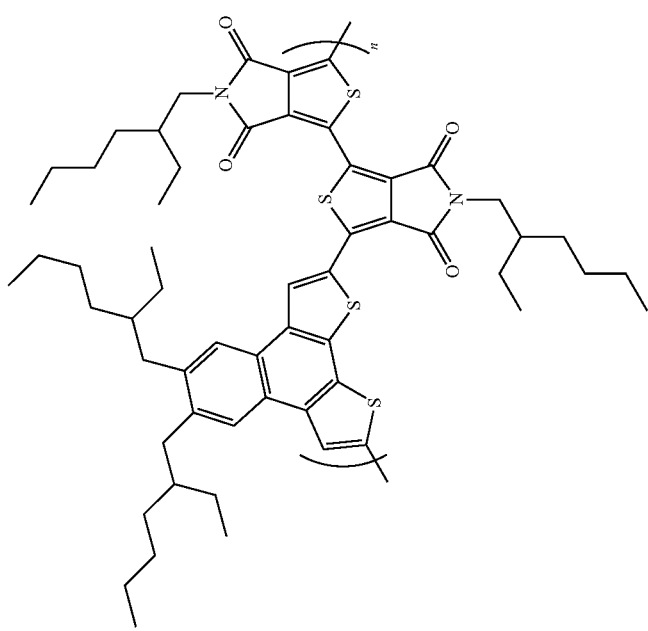 |

| Identifier | Polymer Structure |
|---|---|
| OO | 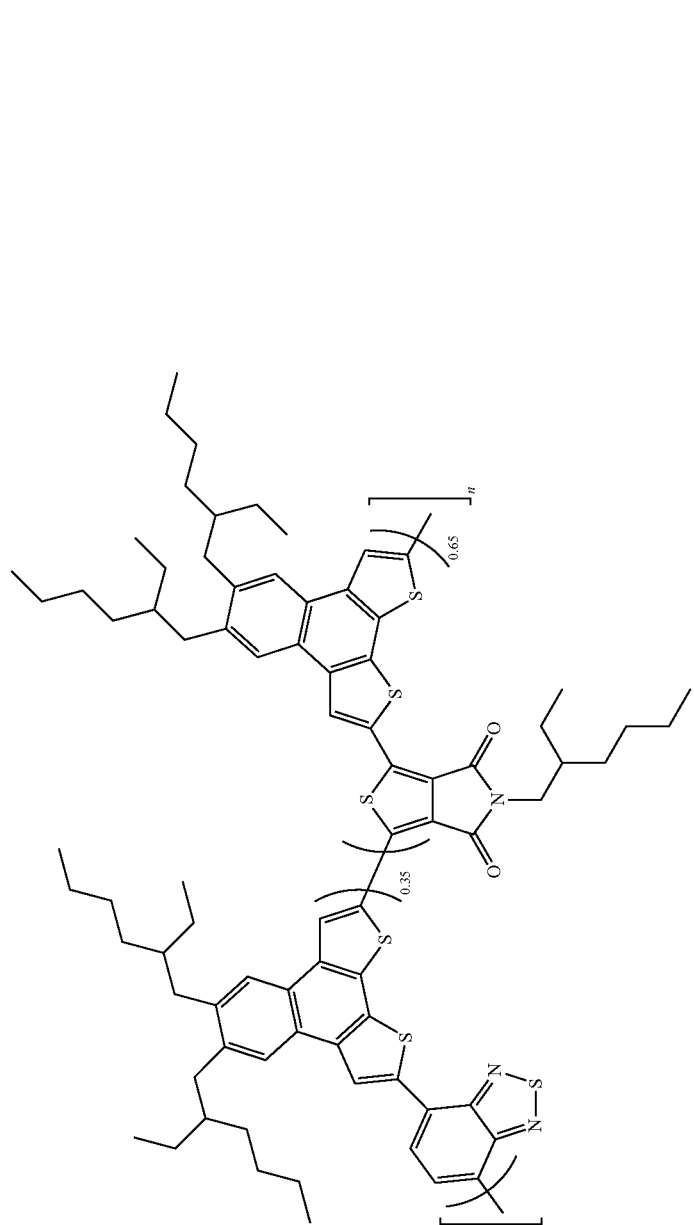 |

| Identifier | Polymer Structure |
|---|---|
| PP | 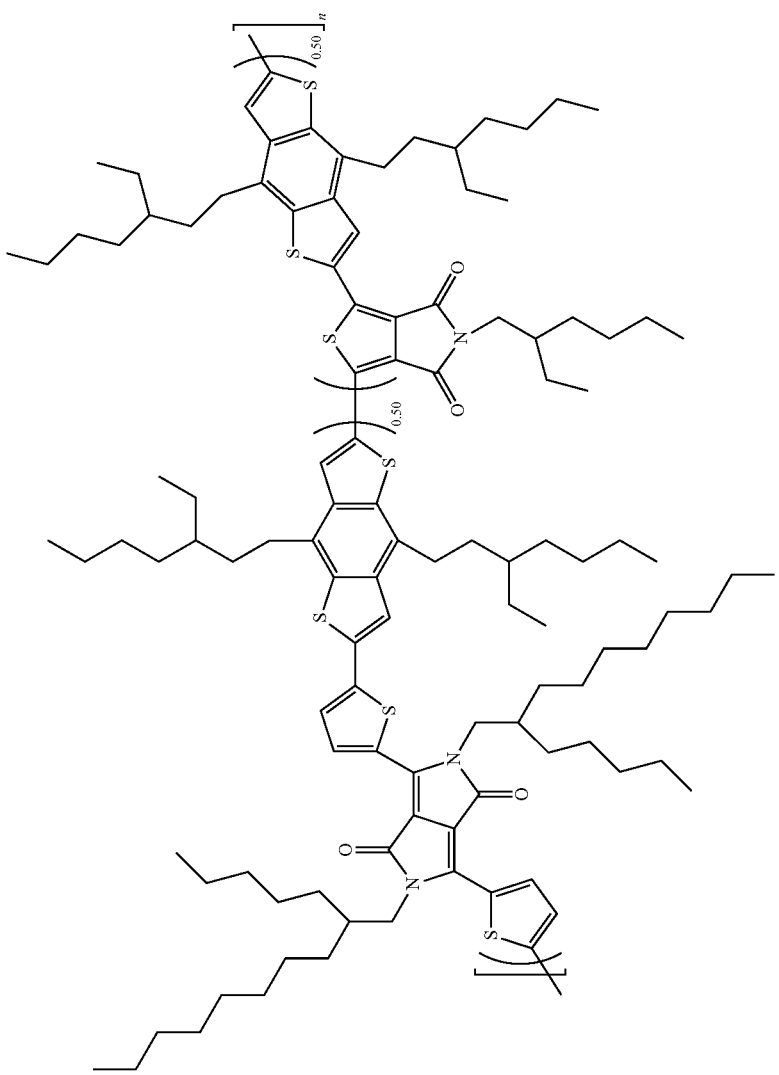 |

| Identifier | Polymer Structure |
|---|---|
| QQ | 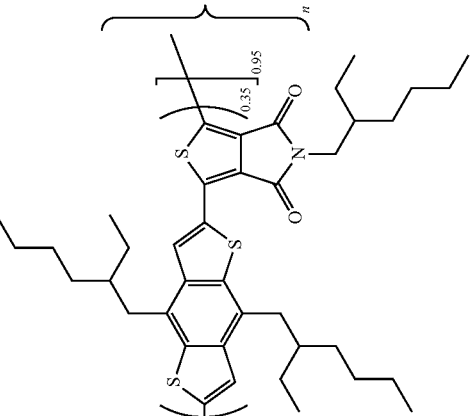 |

| Identifier | Polymer Structure |
|---|---|
| RR | *(chemical structure)* |

| Identifier | Polymer Structure |
|---|---|
| SS | 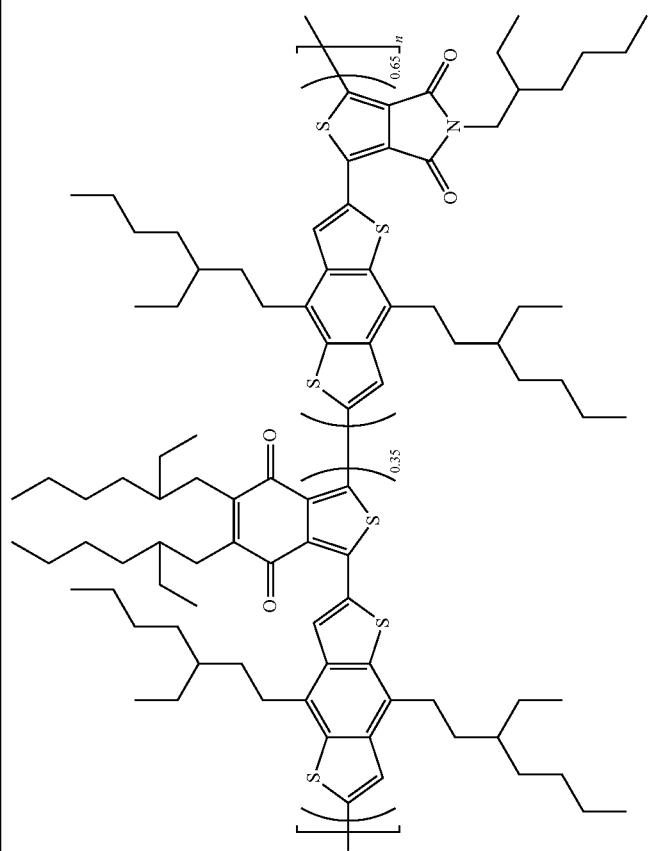 |

| Identifier | Polymer Structure |
|---|---|
| TT | 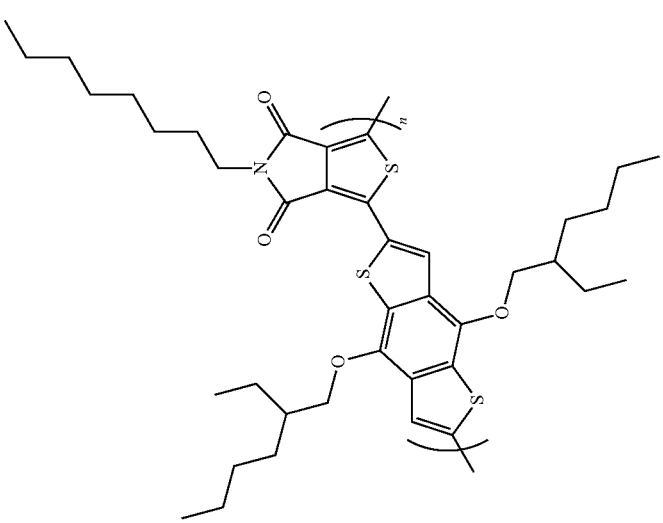 |

-continued
| Identifier | Polymer Structure |
|---|---|
| UU | 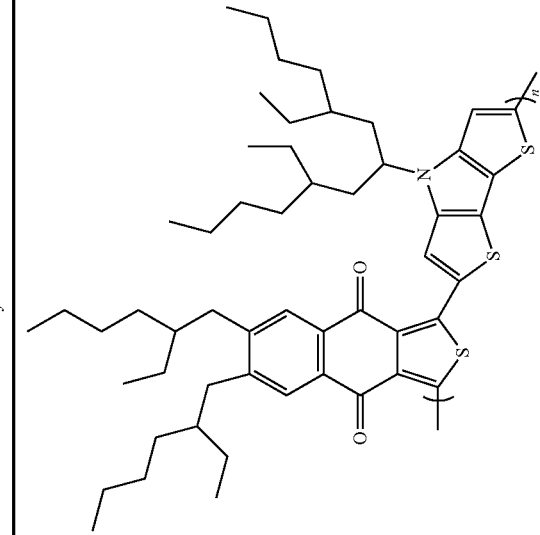 |

-continued
| Identifier | Polymer Structure |
|---|---|
| VV | 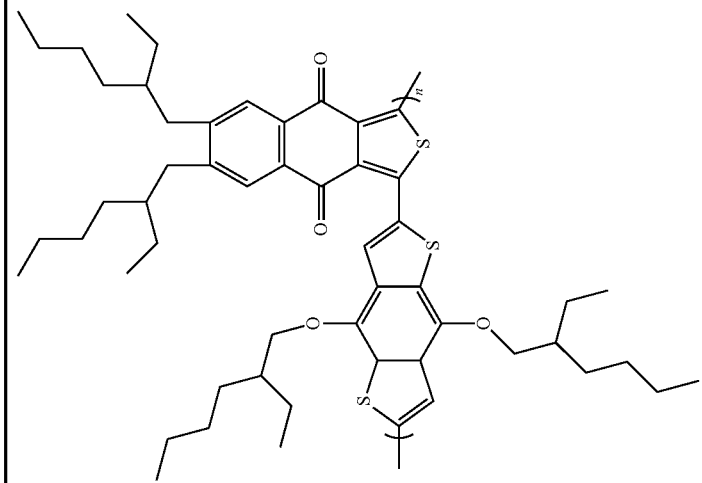 |

| Identifier | Polymer Structure |
|---|---|
| WW | 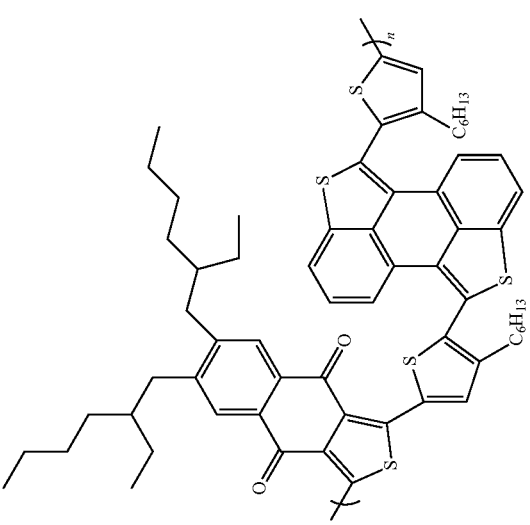 |

| Identifier | Polymer Structure |
|---|---|
| XX | 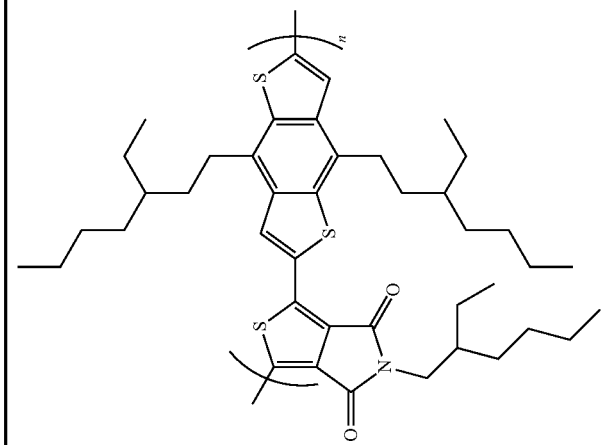 |

-continued
| Identifier | Polymer Structure |
|---|---|
| YY | 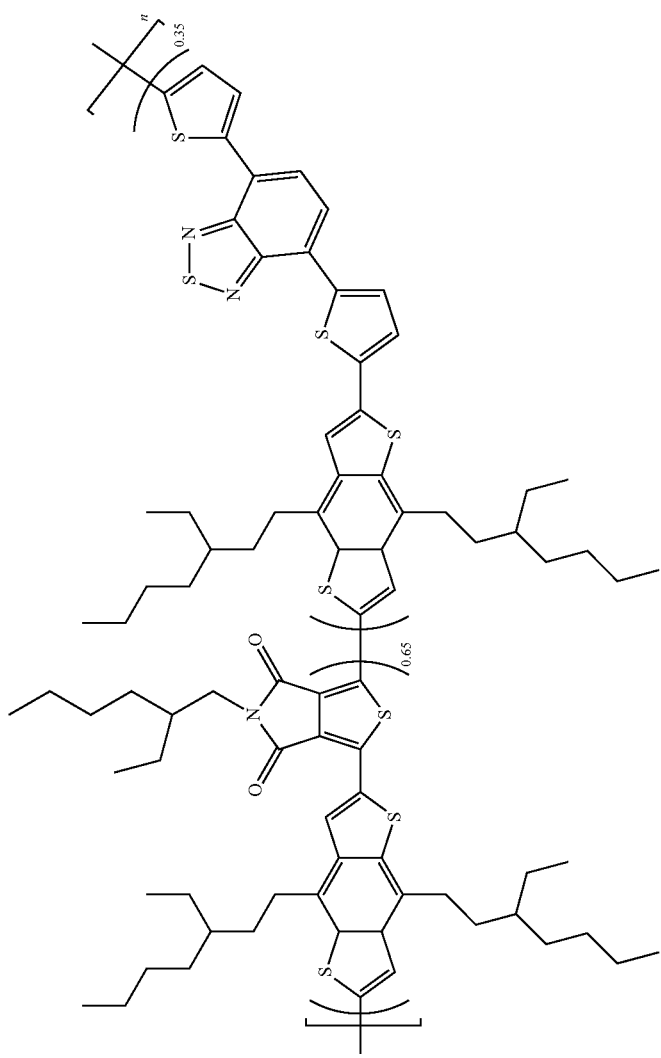 |

| Identifier | Polymer Structure |
|---|---|
| ZZ | 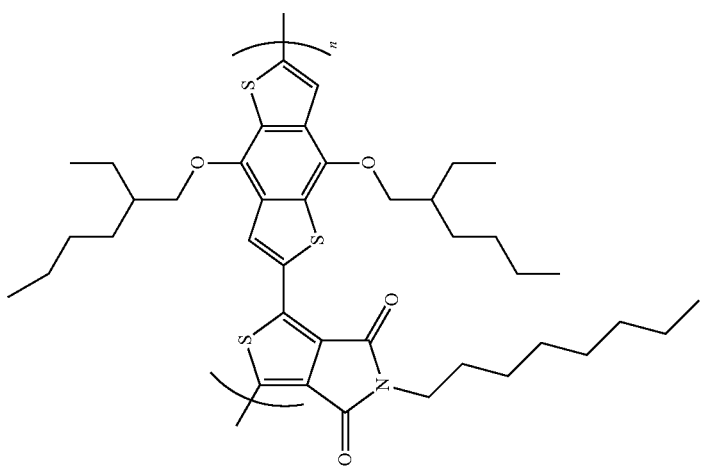 |

| Identifier | Polymer Structure |
|---|---|
| AAA | 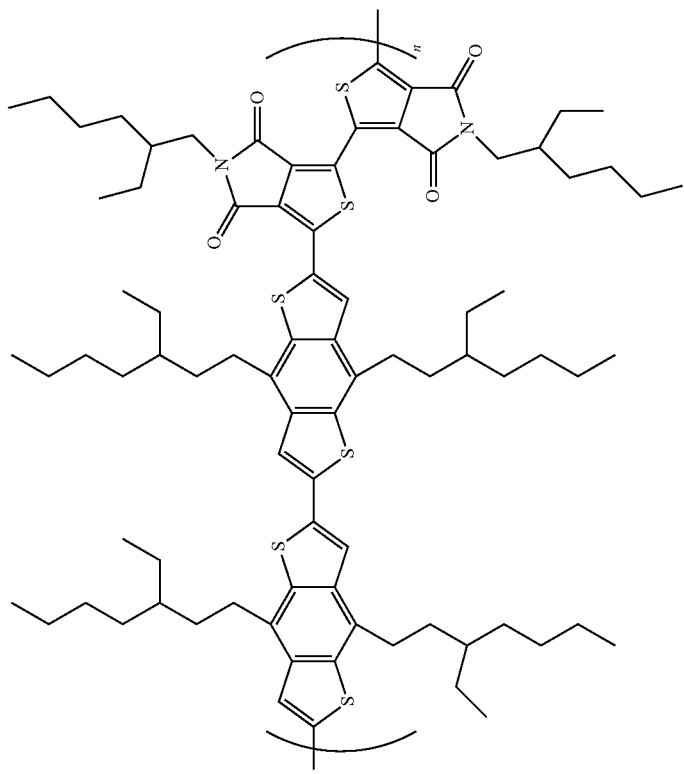 |

| Identifier | Polymer Structure |
|---|---|
| BBB | 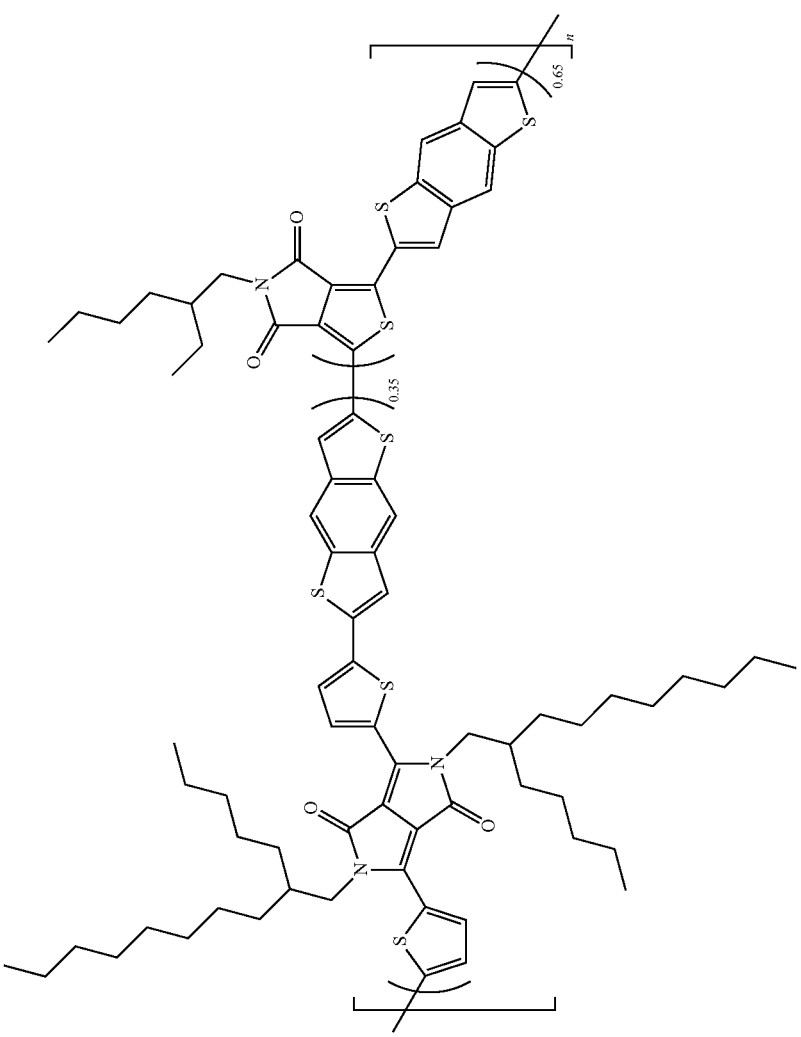 |

| Identifier | Polymer Structure |
|---|---|
| CCC | 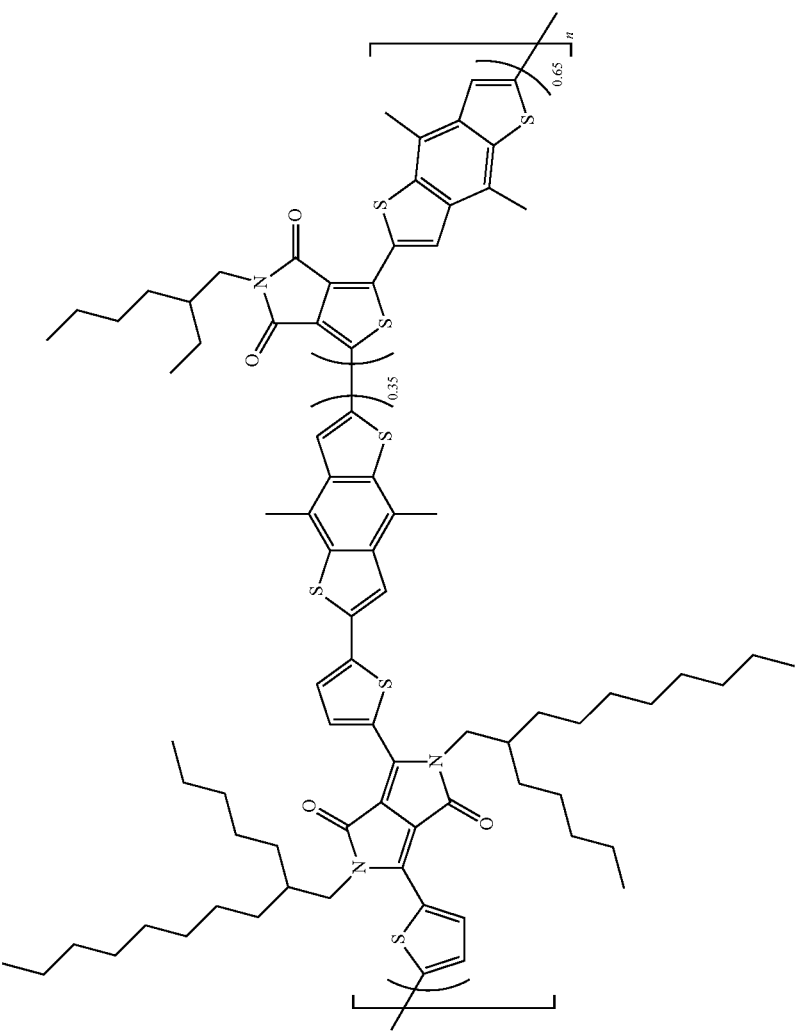 |

-continued
| Identifier | Polymer Structure |
|---|---|
| DDD | 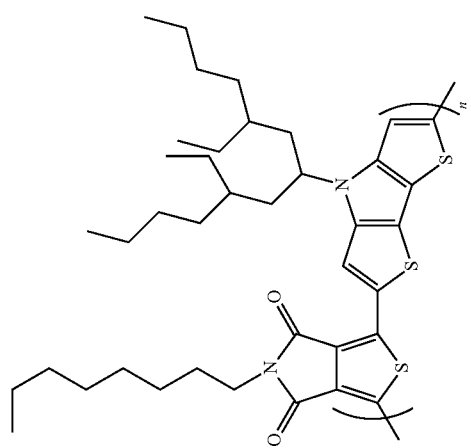 |

| Identifier | Polymer Structure |
|---|---|
| EEE | 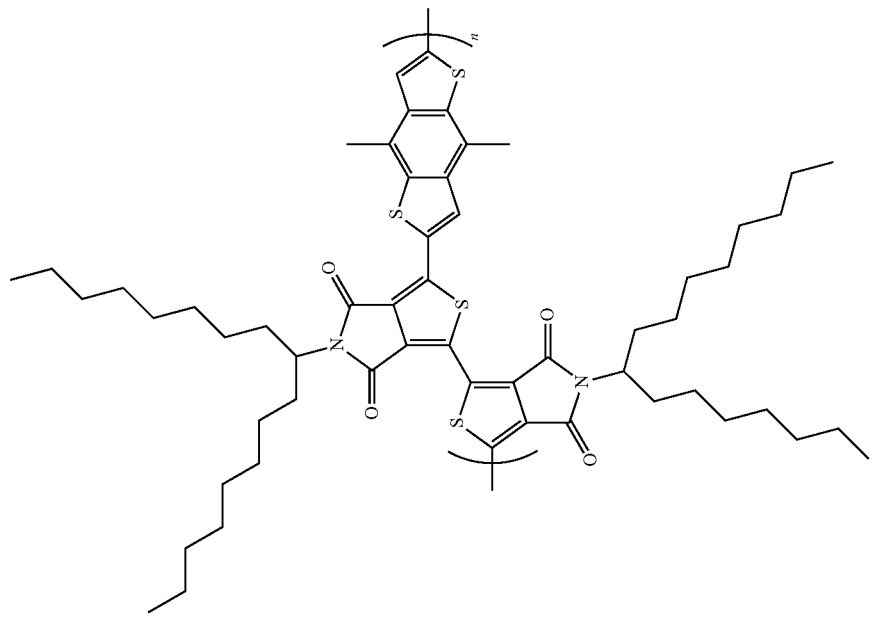 |

| Identifier | Polymer Structure |
|---|---|
| FFF | 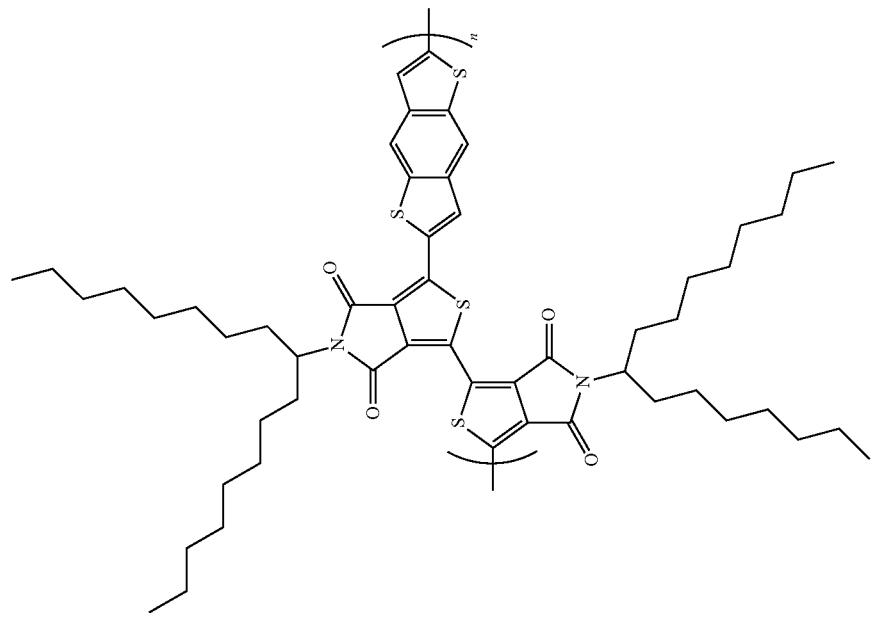 |

| Identifier | Polymer Structure |
|---|---|
| GGG | 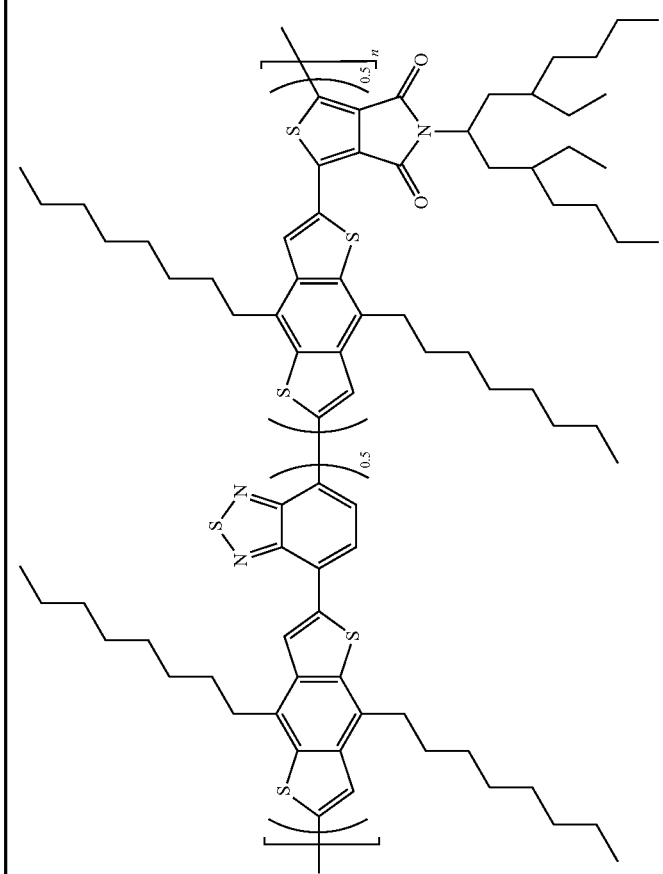 |

| Identifier | Polymer Structure |
|---|---|
| HHH | 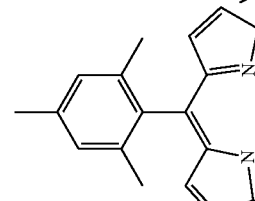 |

| Identifier | Polymer Structure |
|---|---|
| III | 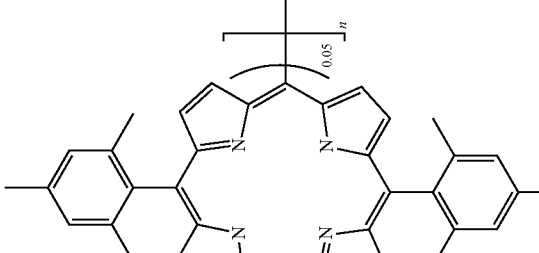 |

| Identifier | Polymer Structure |
|---|---|
| JJJ | 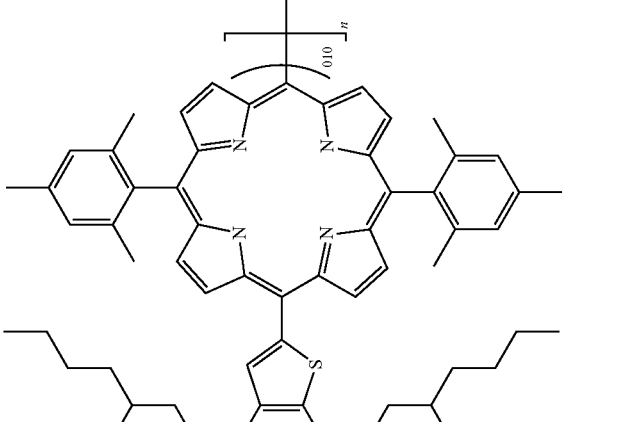 |

-continued

| Identifier | Polymer Structure |
|---|---|
| KKK | (structure with porphyrin, benzodithiophene, thienopyrrolodione, and benzothiadiazole units; subscripts 0.25, 0.65, 0.10) |

| Identifier | Polymer Structure |
|---|---|
| LLL | 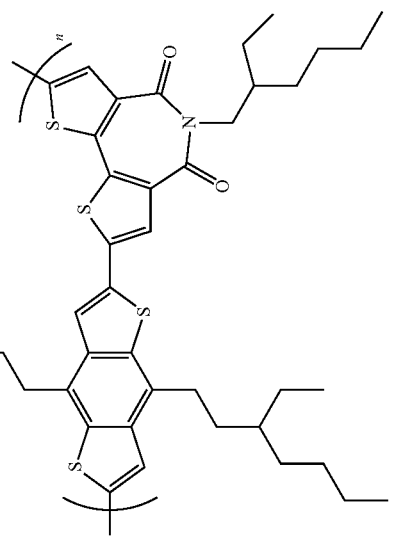 |

| Identifier | Polymer Structure |
|---|---|
| MMM | 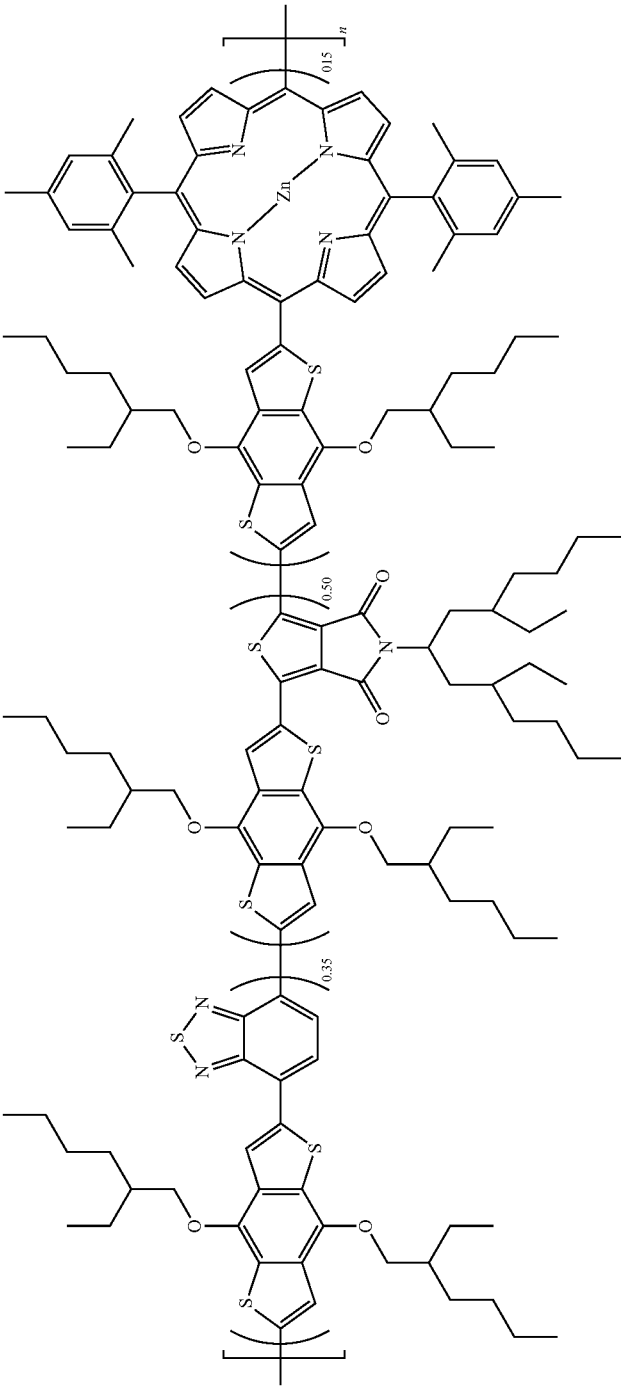 |

| Identifier | Polymer Structure |
|---|---|
| NNN | 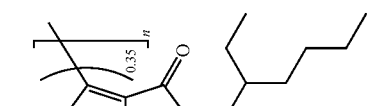 |

| Identifier | Polymer Structure |
|---|---|
| OOO | -continued |

| Identifier | Polymer Structure |
|---|---|
| PPP | 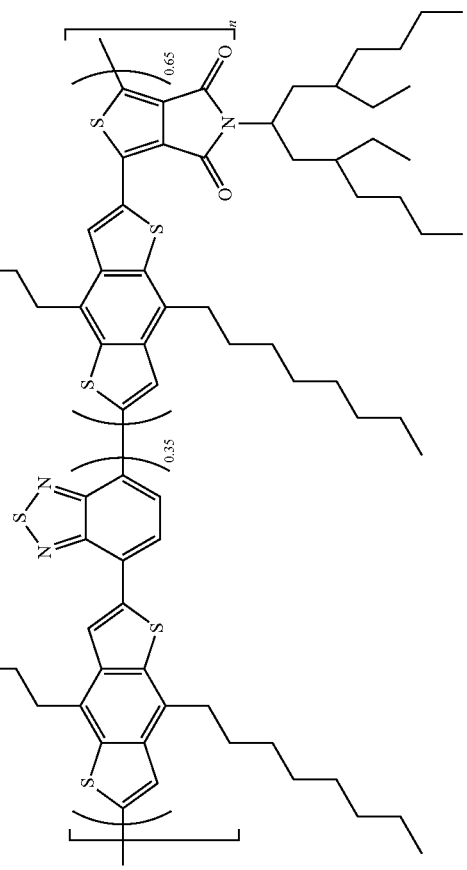 |

| Identifier | Polymer Structure |
|---|---|
| QQQ | (structure) |

| Identifier | Polymer Structure |
|---|---|
| RRR | 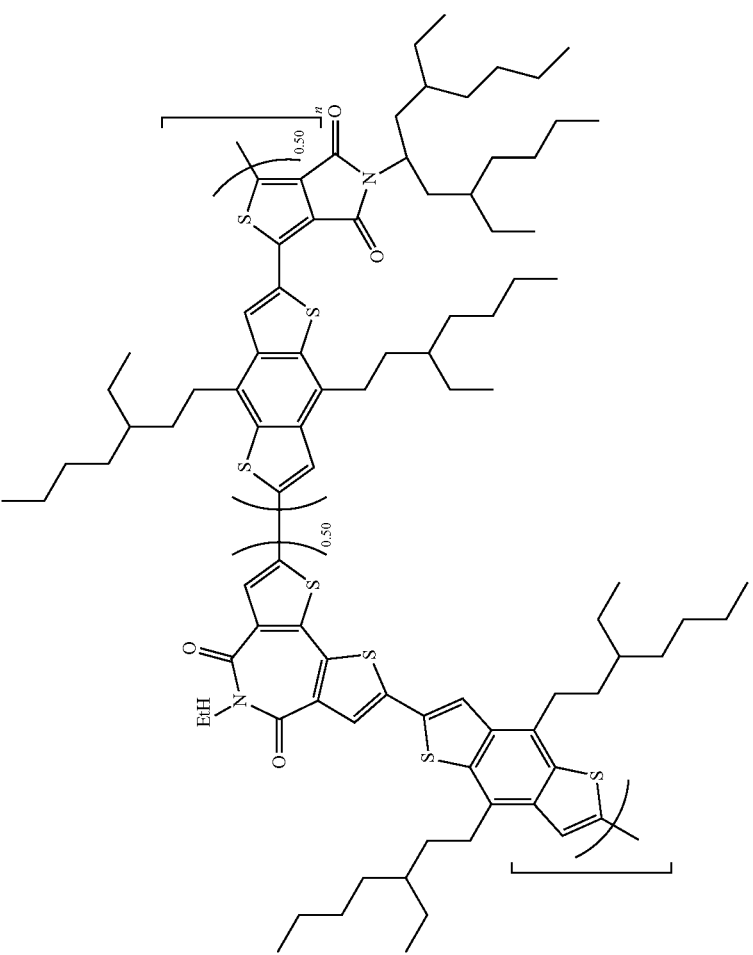 |

| Identifier | Polymer Structure |
|---|---|
| SSS | 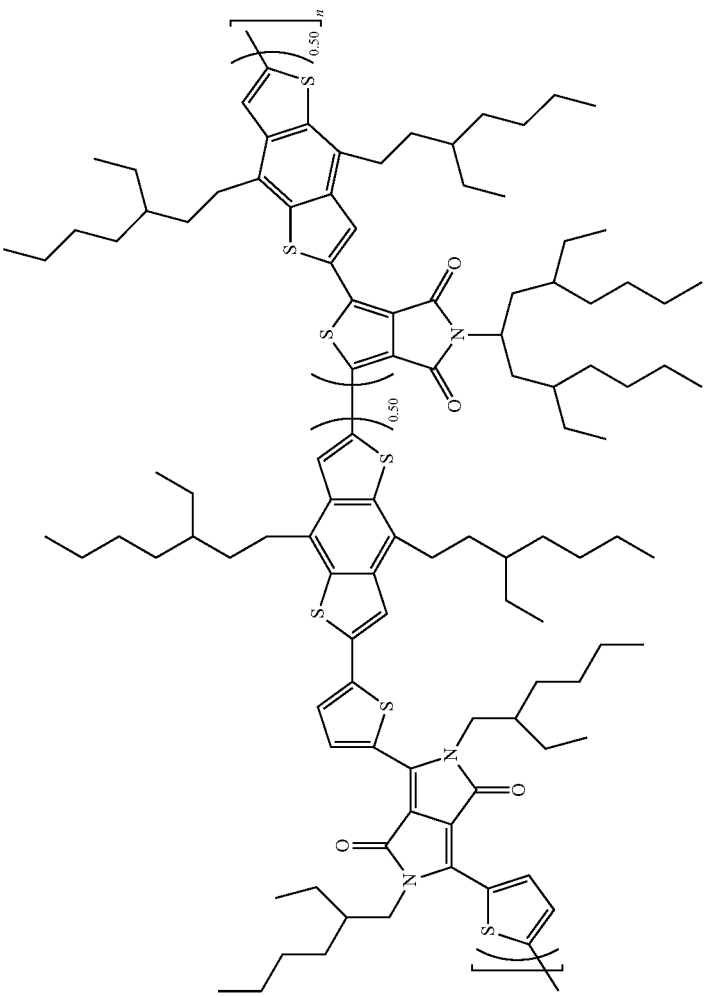 |

-continued
| Identifier | Polymer Structure |
|---|---|
| TTT | 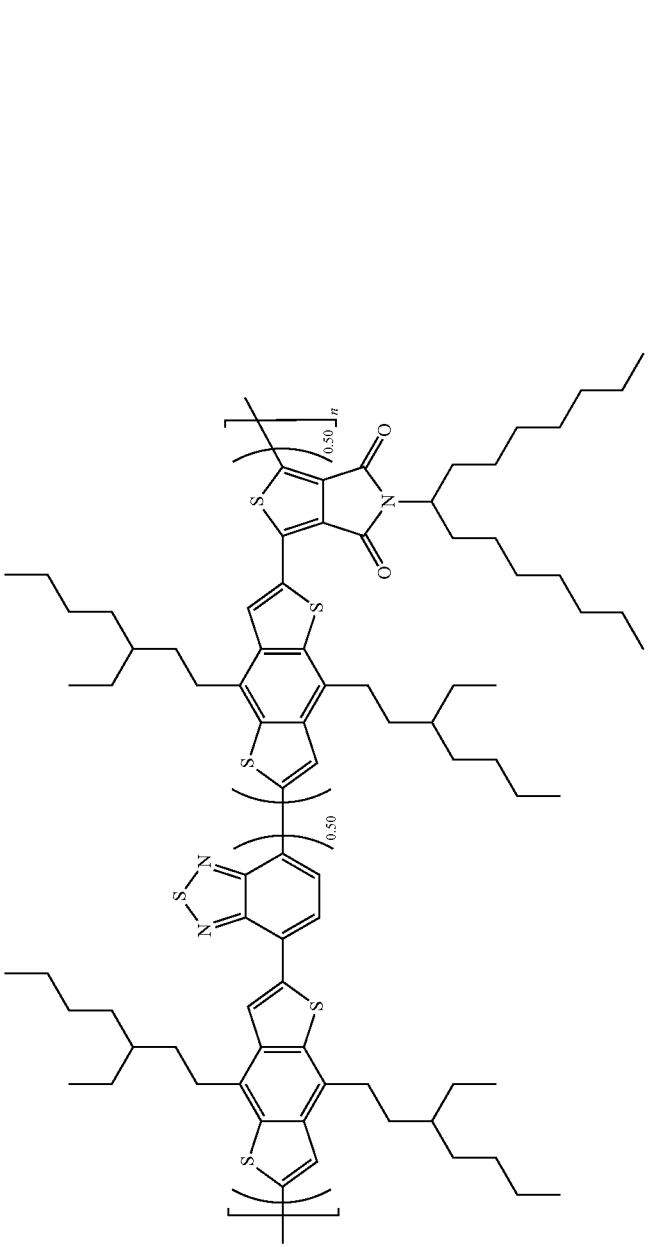 |

| Identifier | Polymer Structure |
|---|---|
| UUU | 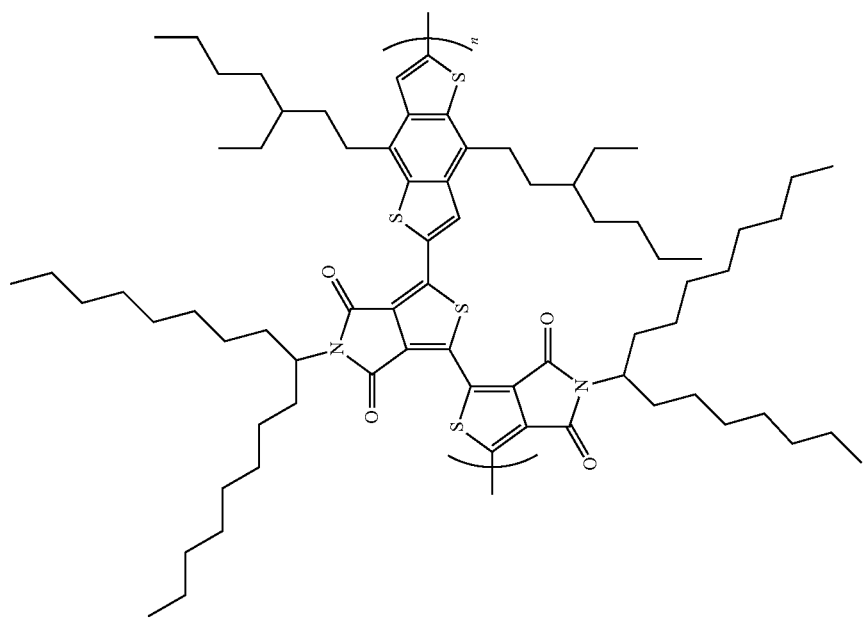 |

| Identifier | Polymer Structure |
|---|---|
| VVV | 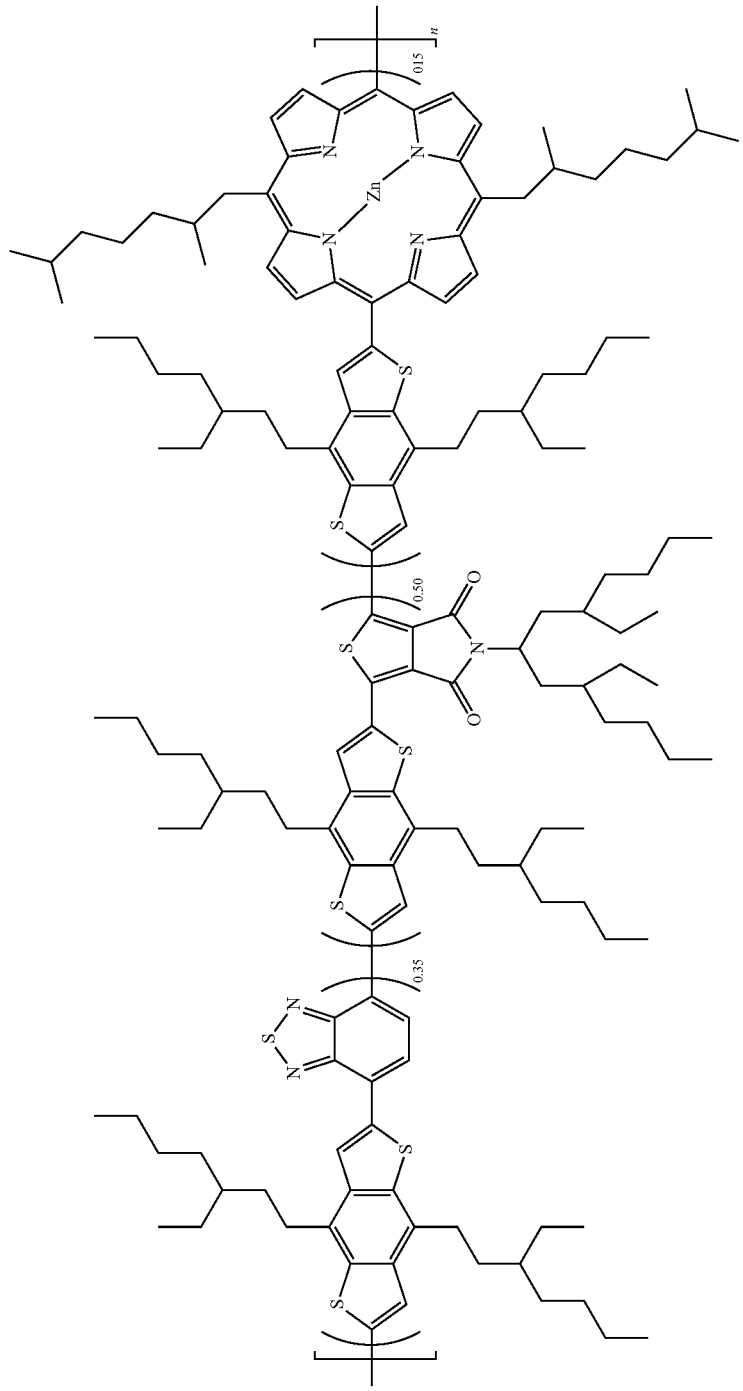 |

| Identifier | Polymer Structure |
|---|---|
| WWW | 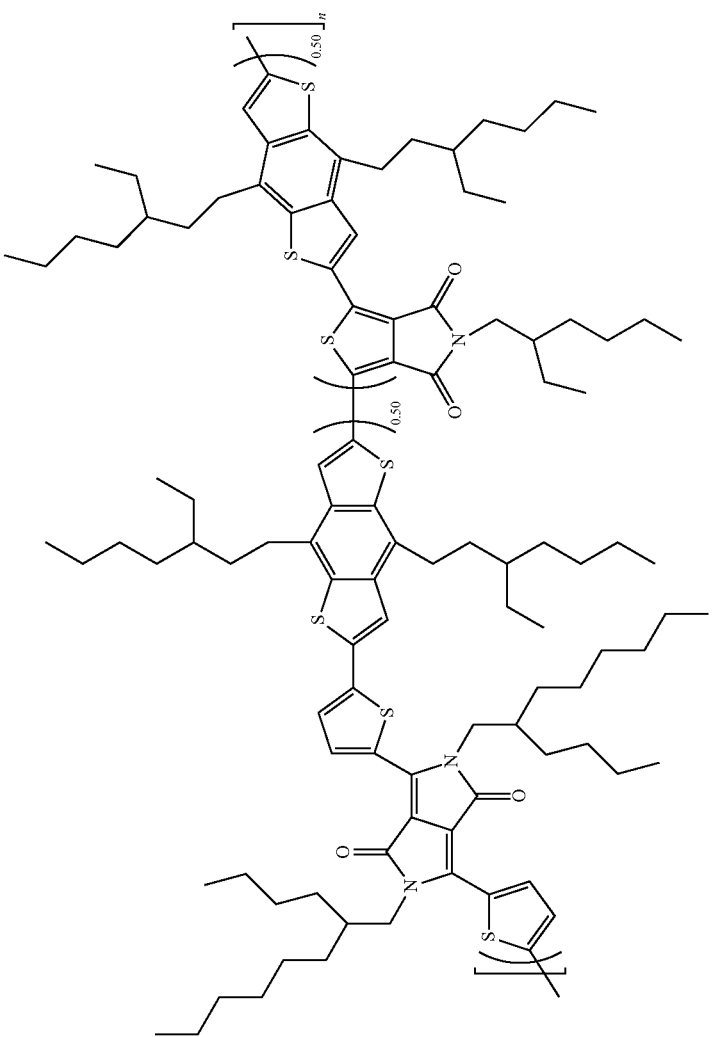 |

-continued
| Identifier | Polymer Structure |
|---|---|
| XXX | 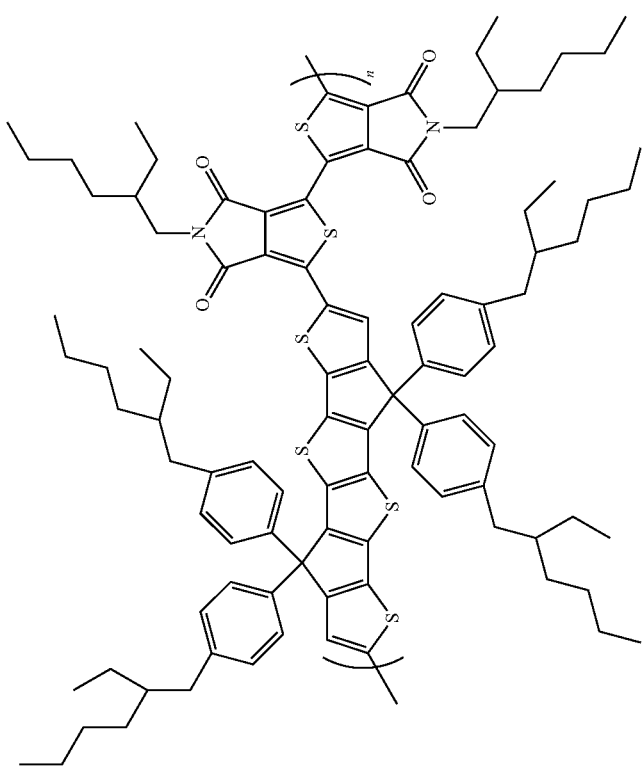 |

| Identifier | Polymer Structure |
|---|---|
| YYY | 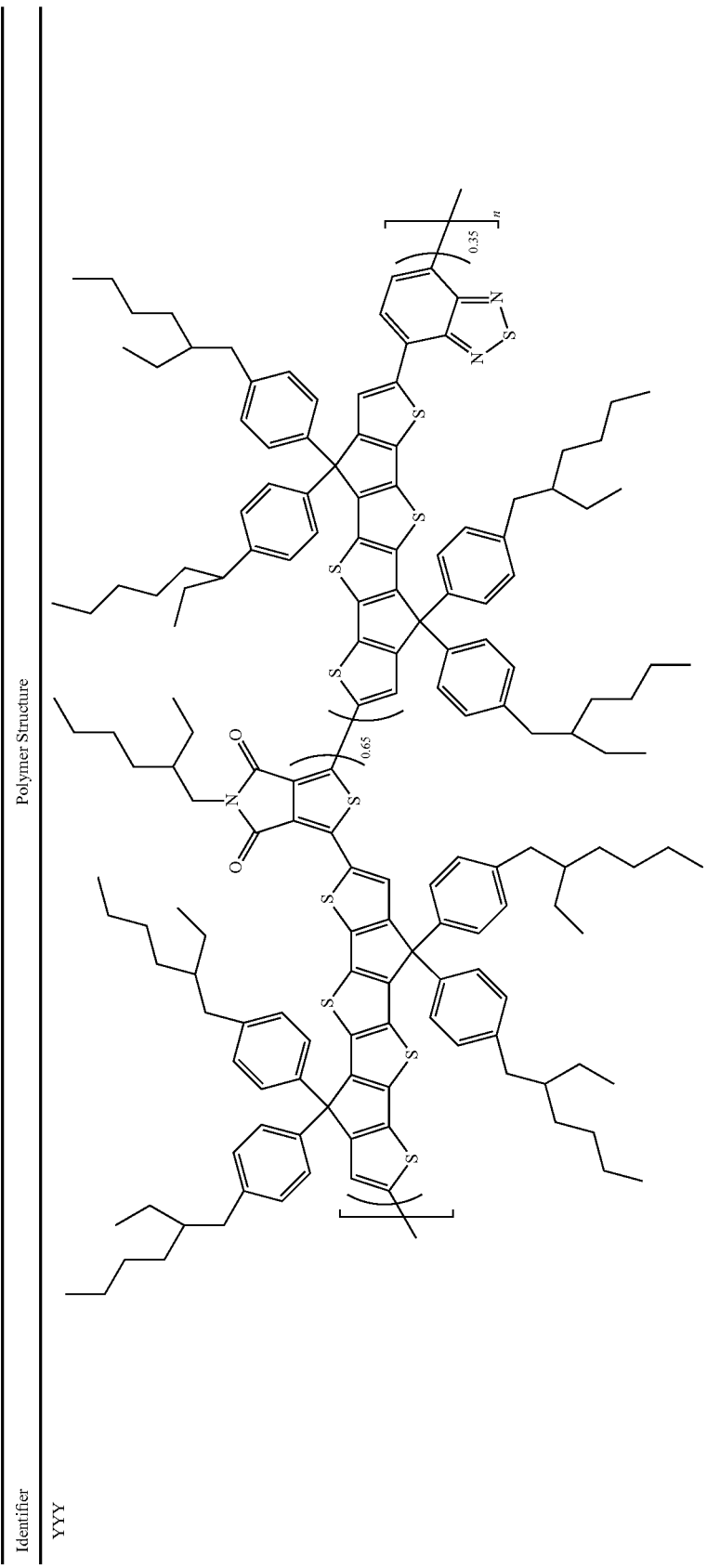 |

| Identifier | Polymer Structure |
|---|---|
| ZZZ | 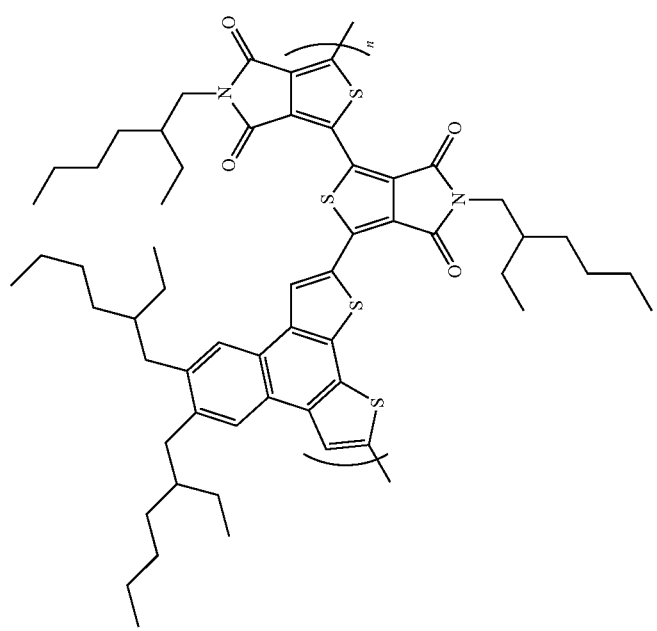 |

| Identifier | Polymer Structure |
|---|---|
| AAAA | 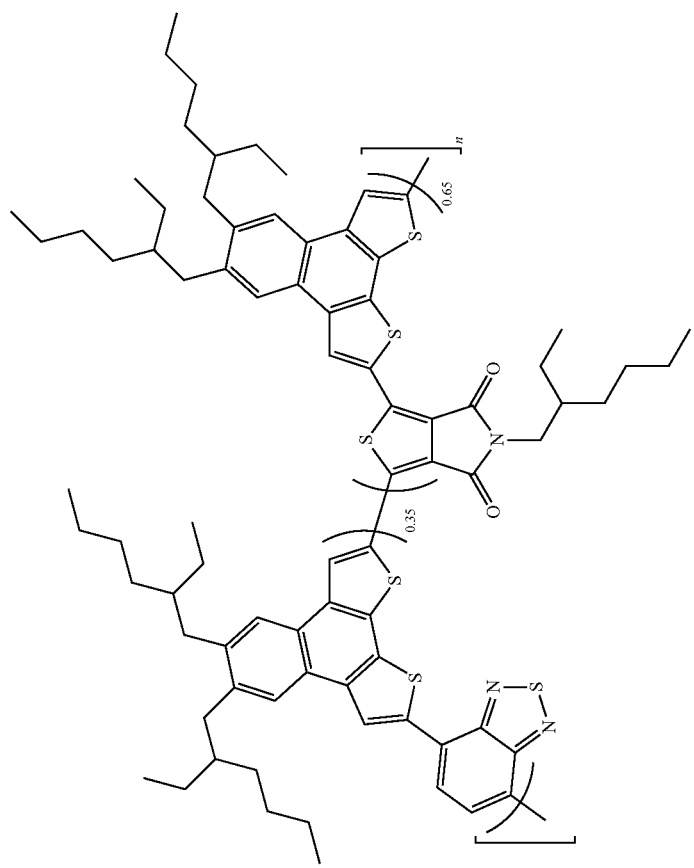 |

| Identifier | Polymer Structure |
|---|---|
| BBBB | 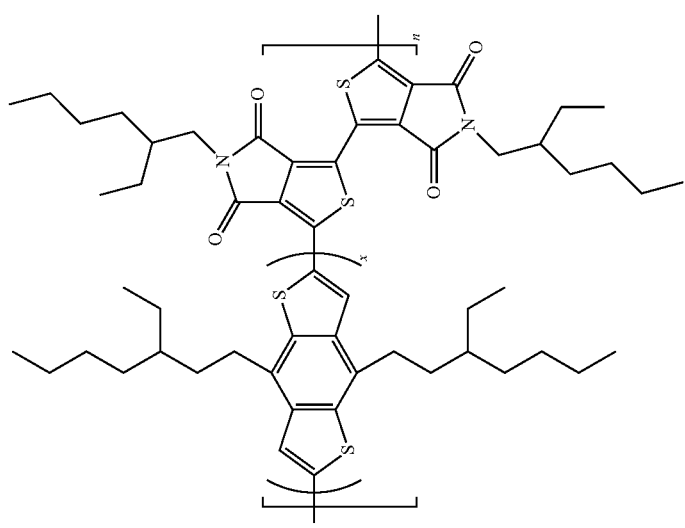 |

-continued

| Identifier | Polymer Structure |
|---|---|
| CCCC | (structure) |

| Identifier | Polymer Structure |
|---|---|
| DDDD | 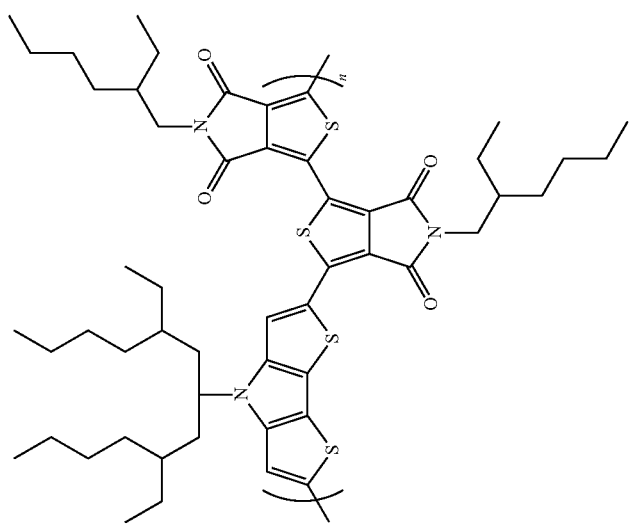 |

-continued
| Identifier | Polymer Structure |
|---|---|
| EEEE | 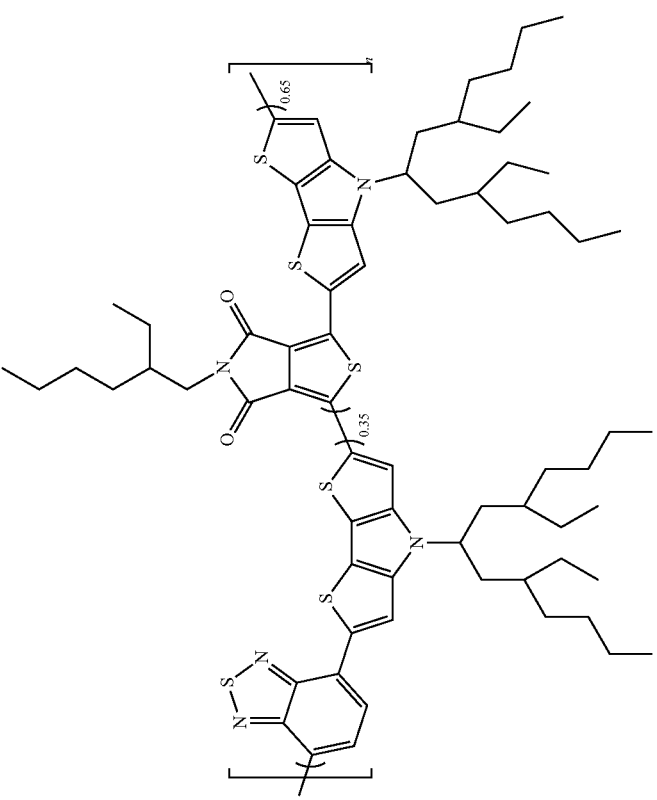 |

| Identifier | Polymer Structure |
|---|---|
| FFFF | 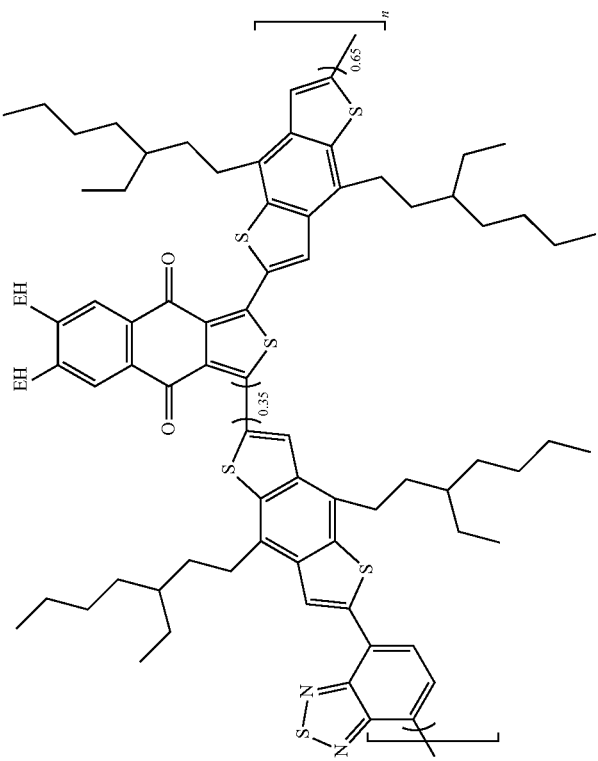 |

| Identifier | Polymer Structure |
|---|---|
| GGGG | 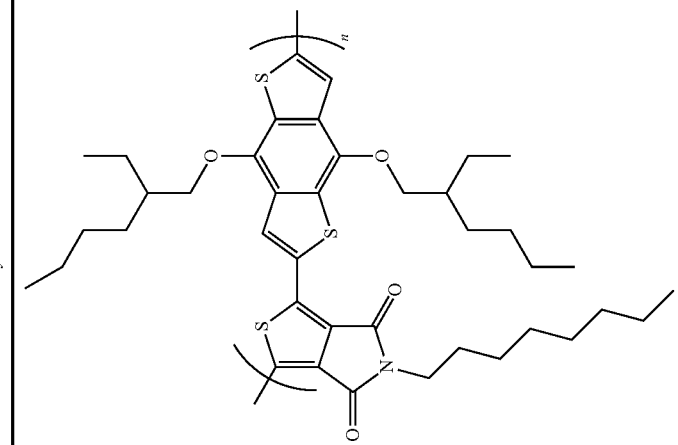 |

-continued
| Identifier | Polymer Structure |
|---|---|
| HHHH | 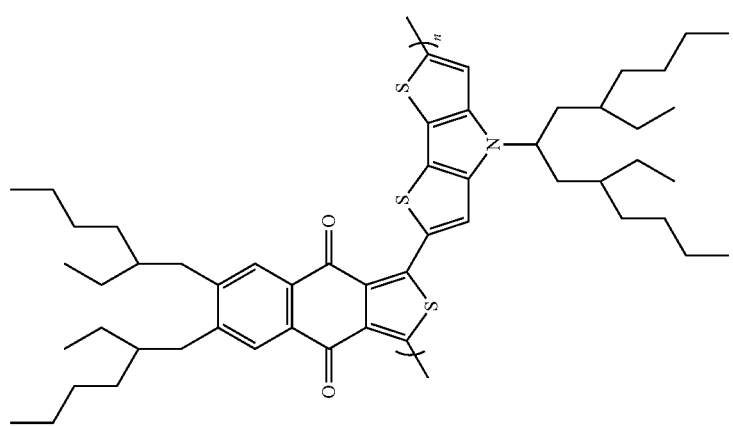 |

| Identifier | Polymer Structure |
|---|---|
| IIII | 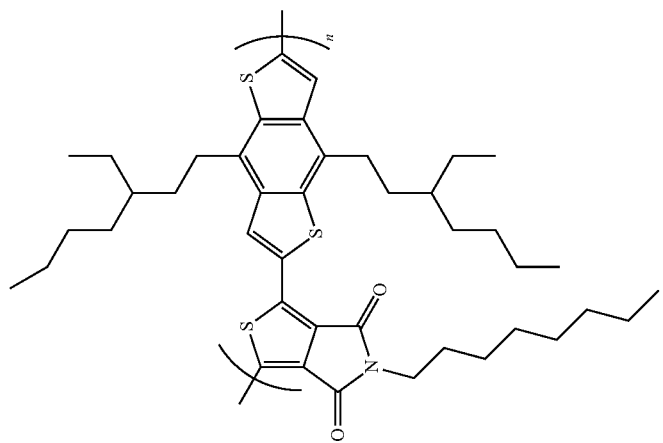 |

| Identifier | Polymer Structure |
|---|---|
| JJJJ | 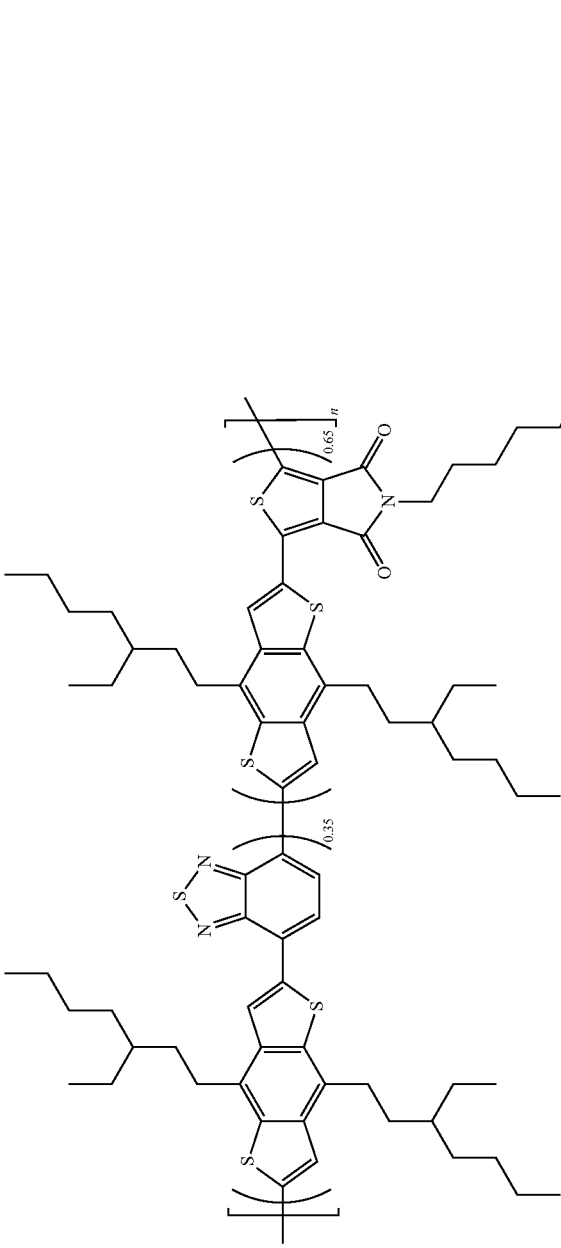 |

| Identifier | Polymer Structure |
|---|---|
| KKKK | 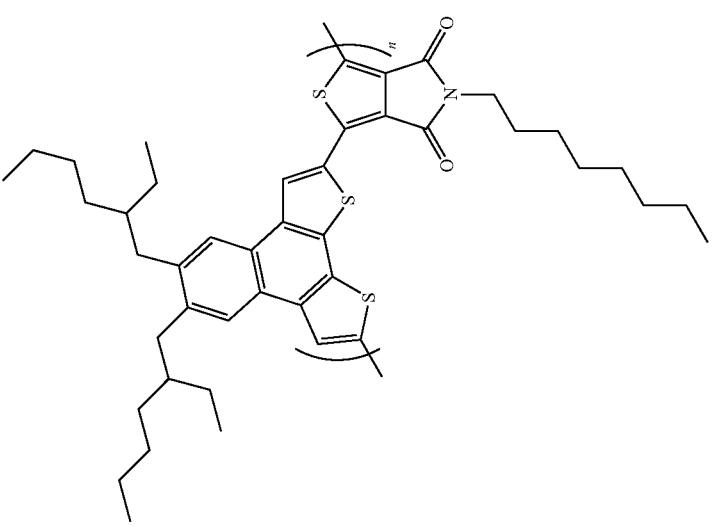 |

-continued
| Identifier | Polymer Structure |
|---|---|
| LLLL | 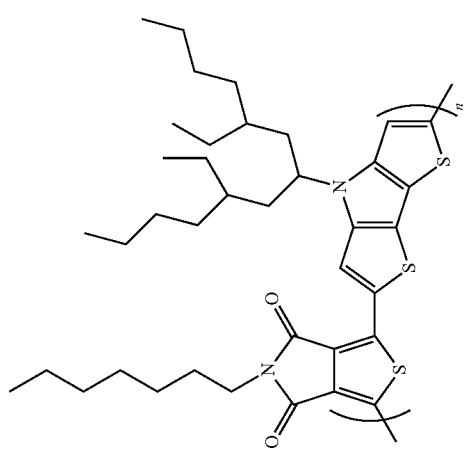 |

-continued
| Identifier | Polymer Structure |
|---|---|
| MMMM | 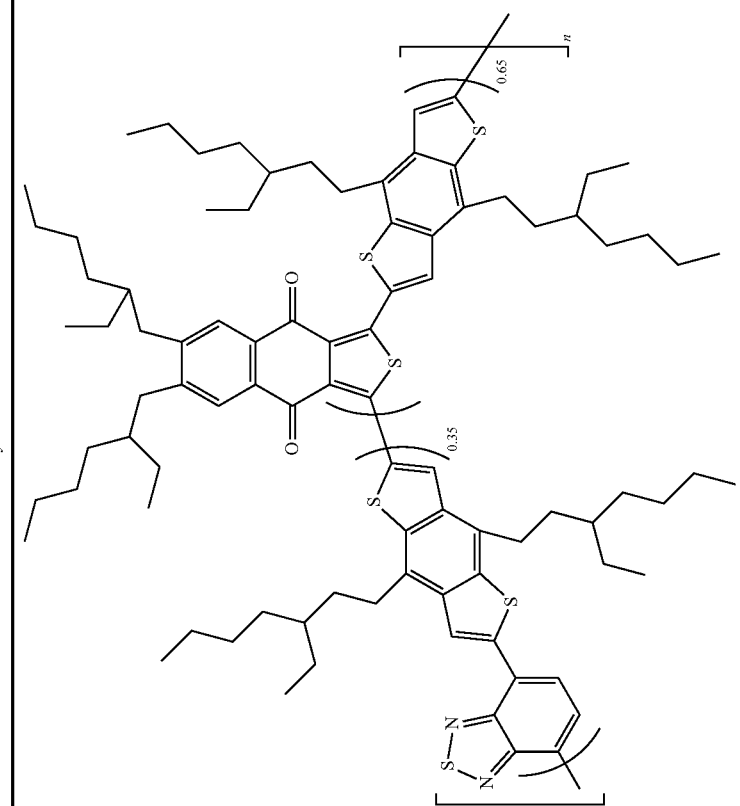 |

| Identifier | Polymer Structure |
|---|---|
| NNNN | 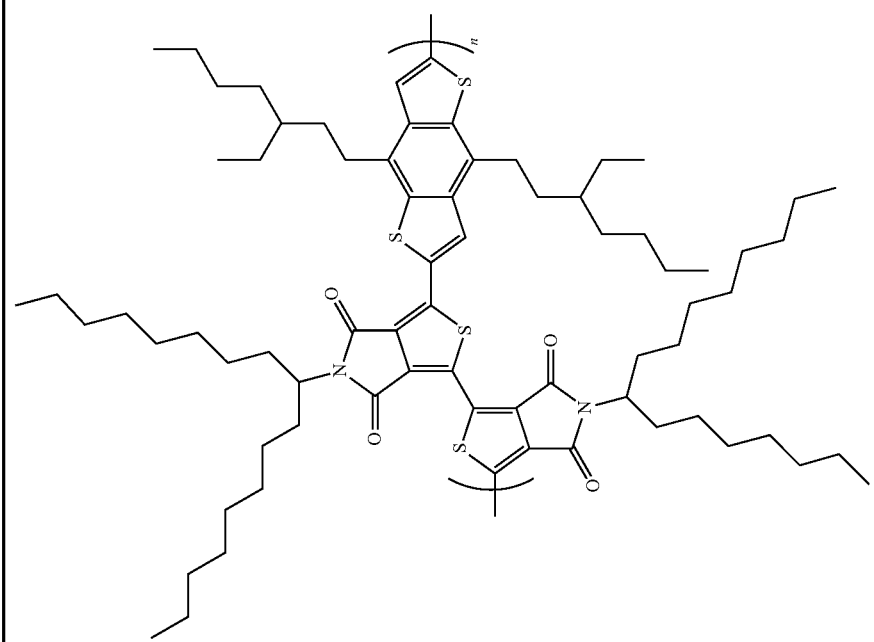 |

What is claimed is:

1. A device comprising:
at least one cathode;
at least one anode;
at least one photovoltaic active layer disposed between the cathode and anode and comprising at least one p-type material and at least one n-type material, wherein the p-type material comprises at least one polymer comprising a donor-acceptor structure, comprising a first acceptor backbone moiety:

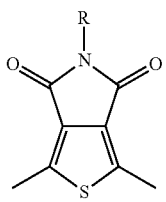

(I)

wherein R comprises optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy, and wherein the donor comprises at least one benzodithiophene structure, and the polymer comprises at least one second acceptor other than (I), wherein the second acceptor other than (I) comprises a benzothiadiazole structure, wherein the polymer is represented by:

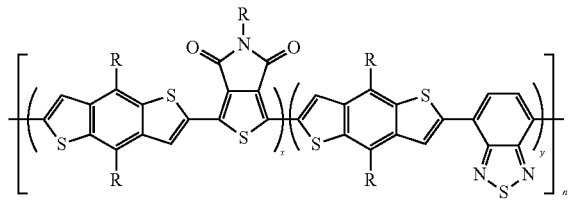

wherein the R groups of the benzodithiophene structures are alkyl groups, and wherein the R group of the formula (I) structure is as previously defined, and wherein n is adapted to provide the polymer with a number average molecular weight of at least 10,000, and wherein x and y are adapted to provide the polymer with a molar amount of 55-75% of the first acceptor having the formula (I) structure and a molar amount of 25-45% of the second acceptor having the benzothiadiazole structure relative to the total molar amount of the combined first and second structure.

2. The device of claim 1, wherein the molar amount of the first acceptor is about 65%, and the molar amount of the second acceptor is about 35%, relative to the total molar amount of the combined first and second acceptor structure.

3. The device of claim 1, wherein the benzodithiophene structure comprises at least one C6-C12 branched alkyl structure.

4. The device of claim 1, wherein the R group of Formula (I) is a C6-C12 branched alkyl structure.

5. The device of claim 1, wherein the polymer is a random polymer.

6. The device of claim 1, wherein the polymer is soluble in chloroform.

7. The device of claim 1, wherein the device has a power conversion efficiency of at least 6%.

8. The device of claim 1, wherein the device has an open circuit voltage of at least 0.9 V.

9. The device of claim 1, wherein the device has a power conversion efficiency of at least 6%, and an open circuit voltage of at least 0.9 V.

10. The device of claim 1, wherein the device has at least one hole transport layer disposed next to the active layer.

11. The device of claim 1, wherein the device has at least one hole transport layer disposed next to the active layer which comprises at least two polymers.

12. The device of claim 1, wherein the device has at least one hole transport layer disposed next to the active layer which comprises at least two polymers, wherein at least one polymer is a polythiophene and at least one polymer different from the other is a fluorinated polymer.

13. The device of claim 1, wherein the device has at least one hole transport layer disposed next to the active layer, wherein the hole transport layer comprises at least one sulfonated regioregular polythiophene.

14. The device of claim 1, wherein the active layer is annealed.

15. The device of claim 1, wherein the active layer is thermally annealed.

16. The device of claim 1, wherein the active layer is solvent annealed.

17. The device of claim 1, wherein the active layer is annealed with use of an electric field.

18. The device of claim 1, wherein the weight ratio of p-type and n-type material is about 1:1 to 1:3.

19. The device of claim 1, wherein the active layer is formed by deposition of an ink comprising at least one fluorinated solvent.

20. The device of claim 1, wherein the polymer is represented by:

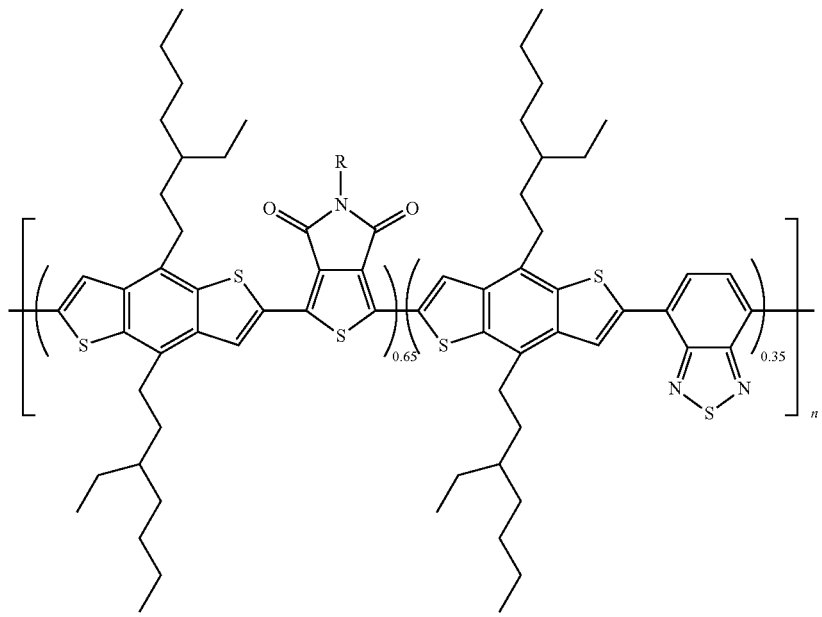

wherein R is defined as in claim 1.

21. A composition comprising at least one polymer comprising a donor-acceptor structure, comprising a first acceptor backbone moiety:

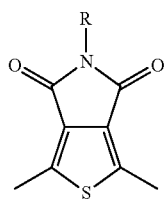

(I)

wherein R comprises optionally substituted alkyl, optionally substituted linear alkyl, optionally substituted branched alkyl, optionally substituted aryl, optionally substituted alkylaryl, optionally substituted arylalkyl, optionally substituted alkoxy, or optionally substituted aryloxy, and wherein the donor comprises at least one benzodithiophene structure, and the polymer comprises at least one second acceptor other than (I), wherein the second acceptor other than (I) is a benzothiadiazole, wherein the polymer is represented by:

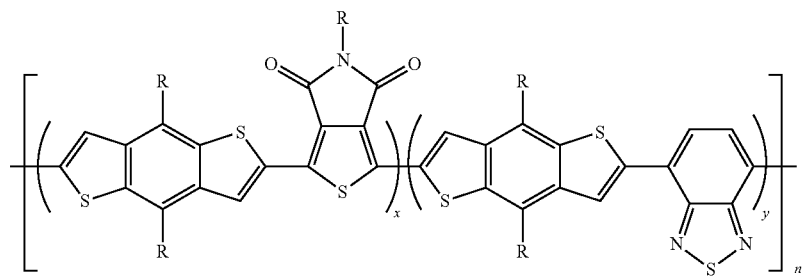

wherein the R groups of the benzodithiophene structures are alkyl groups, and wherein the R group of the formula (I) structure is as previously defined and wherein n is adapted to provide the polymer with a number average molecular weight of at least 10,000, and wherein x and y are adapted to provide the polymer with a molar amount of 55-75% of the first acceptor having the formula (I) structure and a molar amount of 25-45% of the second acceptor having the benzothiadiazole structure relative to the total molar amount of the combined first and second structure.

22. The composition of claim 21, wherein the composition further comprises at least one solvent.

23. The composition of claim 21, wherein the composition further comprises at least one n-type material.

24. The composition of claim 21, wherein the polymer is represented by:

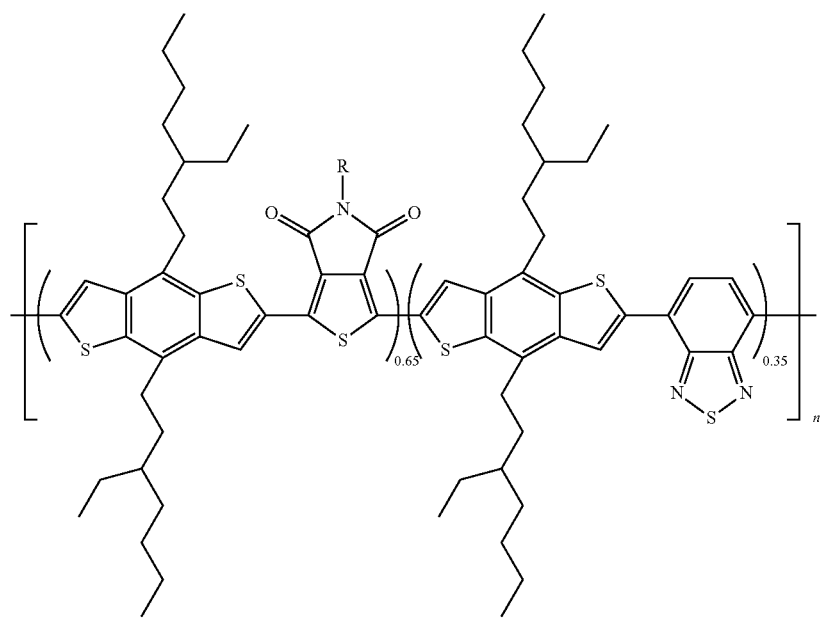

wherein R is defined as in claim 21.

25. The composition of claim 21, wherein the molar amount of the first acceptor is about 65%, and the molar amount of the second acceptor is about 35%, relative to the total molar amount of the combined first and second acceptor structure.

26. The composition of claim 21, wherein the benzodithiophene structure comprises at least one C6-C12 branched alkyl structure.

27. The composition of claim 21, wherein the R group of Formula (I) is a C6-C12 branched alkyl structure.

28. The composition of claim 21, wherein the polymer is a random polymer.

29. The composition of claim 21, wherein the polymer is soluble in chloroform.

30. The composition of claim 23, wherein the polymer is a p-type material, and the weight ratio of p-type and n-type material is about 1:1 to 1:3.

* * * * *